United States Patent
Osaka et al.

(10) Patent No.: US 9,564,597 B2
(45) Date of Patent: Feb. 7, 2017

(54) FLUORENE COMPOUND, LIGHT-EMITTING ELEMENT, LIGHT-EMITTING DEVICE, ELECTRONIC DEVICE, LIGHTING DEVICE, AND ORGANIC COMPOUND

(71) Applicant: Semiconductor Energy Laboratory Co., Ltd., Kanagawa-ken (JP)

(72) Inventors: Harue Osaka, Kanagawa (JP); Takako Takasu, Kanagawa (JP); Hiromi Nowatari, Kanagawa (JP); Satoko Shitagaki, Kanagawa (JP); Nobuharu Ohsawa, Kanagawa (JP); Satoshi Seo, Kanagawa (JP); Kyoko Takeda, Kanagawa (JP); Sachiko Kawakami, Kanagawa (JP); Tsunenori Suzuki, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 1 day.

(21) Appl. No.: 14/668,239

(22) Filed: Mar. 25, 2015

(65) Prior Publication Data
US 2015/0243899 A1 Aug. 27, 2015

Related U.S. Application Data

(62) Division of application No. 13/227,022, filed on Sep. 7, 2011, now Pat. No. 8,993,127.

(30) Foreign Application Priority Data

Sep. 8, 2010 (JP) .................................. 2010-200522
May 31, 2011 (JP) .................................. 2011-122811

(51) Int. Cl.
*H01L 51/54* (2006.01)
*C09K 11/06* (2006.01)
(Continued)

(52) U.S. Cl.
CPC ........... *H01L 51/0058* (2013.01); *C07C 25/02* (2013.01); *C07C 25/22* (2013.01); *C07C 31/36* (2013.01);
(Continued)

(58) Field of Classification Search
CPC ............... H01L 51/0032; H01L 51/005; H01L 51/0052; H01L 51/0054; H01L 51/0058; H01L 51/006; H01L 51/0062; H01L 51/0071; H01L 51/0072; H01L 51/0073; H01L 51/0074; H01L 51/0081; H01L 51/0085; H01L 51/50; H01L 51/5004; H01L 51/5012; H01L 51/5016; H01L 51/5056; H01L 51/5088; H01L 51/5092; H01L 51/5205; H01L 51/5221; H01L 2251/301; H01L 2251/308; H01L 2251/552; C07D 409/10; C07D 307/91; C07D 333/76; C09K 2211/1007; C09K 2211/1011; C09K 2211/1088; C09K 2211/1092; C09K 11/06; C07C 49/80; C07C 49/163; C07C 33/50; C07C 25/02; C07C 25/22; C07C 31/34; C07C 31/36; H05B 33/10; Y10S 428/917
(Continued)

(56) References Cited

U.S. PATENT DOCUMENTS 8,039,128 B2  10/2011 Watanabe et al.
8,075,796 B2  12/2011 Rao et al.
(Continued)

FOREIGN PATENT DOCUMENTS

EP    2 372 803 A1    10/2011
JP    2003-261472 A    9/2003
(Continued)

OTHER PUBLICATIONS

Kim et al. Macromol. Symp. 2000, 154, 171-176. Year of publication: 2000.*
(Continued)

*Primary Examiner* — Andrew K Bohaty
(74) *Attorney, Agent, or Firm* — Husch Blackwell LLP

(57) ABSTRACT

A substance having a hole-transport property and a wide band gap is provided. A fluorene compound represented by a general formula (G1) is provided. In the general formula (G1), $\alpha^1$ and $\alpha^2$ separately represent a substituted or unsubstituted arylene group having 6 to 13 carbon atoms; $Ar^1$ represents a substituted or unsubstituted aryl group having 6 to 18 carbon atoms, a substituted or unsubstituted 4-dibenzothiophenyl group, or a substituted or unsubstituted 4-dibenzofuranyl group; n and k separately represent 0 or 1; $Q^1$ represents sulfur or oxygen; and $R^1$ to $R^{15}$ separately represent hydrogen, an alkyl group having 1 to 12 carbon atoms, or an aryl group having 6 to 14 carbon atoms.

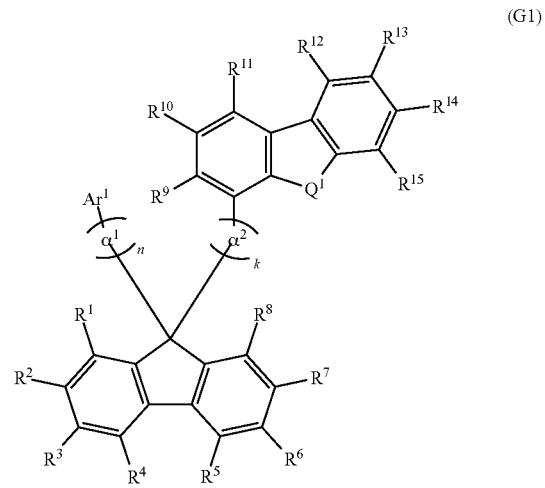

(G1)

12 Claims, 34 Drawing Sheets

(51) Int. Cl.
| | | |
|---|---|---|
| H01L 51/00 | (2006.01) | |
| C07C 25/02 | (2006.01) | |
| C07C 25/22 | (2006.01) | |
| C07C 33/50 | (2006.01) | |
| C07C 49/80 | (2006.01) | |
| C07D 307/91 | (2006.01) | |
| C07D 333/76 | (2006.01) | |
| C07D 409/10 | (2006.01) | |
| H05B 33/10 | (2006.01) | |
| C07C 31/36 | (2006.01) | |
| C07C 49/163 | (2006.01) | |
| H01L 51/50 | (2006.01) | |
| H01L 51/52 | (2006.01) | |

(52) U.S. Cl.
CPC ............ *C07C 33/50* (2013.01); *C07C 49/163* (2013.01); *C07C 49/80* (2013.01); *C07D 307/91* (2013.01); *C07D 333/76* (2013.01); *C07D 409/10* (2013.01); *C09K 11/06* (2013.01); *H01L 51/0052* (2013.01); *H01L 51/0073* (2013.01); *H01L 51/0074* (2013.01); *H05B 33/10* (2013.01); *C09K 2211/1007* (2013.01); *C09K 2211/1011* (2013.01); *C09K 2211/1088* (2013.01); *C09K 2211/1092* (2013.01); *H01L 51/006* (2013.01); *H01L 51/0054* (2013.01); *H01L 51/0072* (2013.01); *H01L 51/0081* (2013.01); *H01L 51/0085* (2013.01); *H01L 51/5004* (2013.01); *H01L 51/508* (2013.01); *H01L 51/5016* (2013.01); *H01L 51/5056* (2013.01); *H01L 51/5088* (2013.01); *H01L 51/5092* (2013.01); *H01L 51/5206* (2013.01); *H01L 51/5221* (2013.01); *H01L 2251/301* (2013.01); *H01L 2251/308* (2013.01); *H01L 2251/552* (2013.01); *Y10S 428/917* (2013.01)

(58) Field of Classification Search
USPC ....... 428/690, 691, 917, 411.4, 336; 427/58, 427/66; 257/40, 88–104, E51.001–E51.052; 313/500–512; 252/301.16–301.35
See application file for complete search history.

(56) References Cited

U.S. PATENT DOCUMENTS

| | | | |
|---|---|---|---|
| 8,496,846 B2 | 7/2013 | Rao et al. | |
| 8,815,114 B2 | 8/2014 | Rao et al. | |
| 2002/0016226 A1 | 2/2002 | Jin et al. | |
| 2006/0105199 A1 | 5/2006 | Gerlach et al. | |
| 2007/0026348 A1 | 2/2007 | Ohzeki et al. | |
| 2009/0058278 A1 | 3/2009 | Ushikubo et al. | |
| 2009/0159877 A1 | 6/2009 | Meng | |
| 2009/0160324 A1 | 6/2009 | Nomura et al. | |
| 2009/0167162 A1 | 7/2009 | Lin et al. | |
| 2009/0200918 A1 | 8/2009 | Seo et al. | |
| 2009/0284138 A1 | 11/2009 | Yasukawa et al. | |
| 2010/0072885 A1 | 3/2010 | Watanabe et al. | |
| 2010/0187978 A1 | 7/2010 | Yu et al. | |
| 2010/0230666 A1 | 9/2010 | Ohuchi et al. | |
| 2010/0283043 A1 | 11/2010 | Nishimura et al. | |
| 2010/0301744 A1* | 12/2010 | Osaka ................... | C07C 211/54 313/504 |
| 2011/0042655 A1 | 2/2011 | Kim et al. | |
| 2011/0095270 A1 | 4/2011 | Meng | |
| 2011/0095678 A1 | 4/2011 | Ogita et al. | |
| 2011/0105693 A1 | 5/2011 | Abdur-Rashid et al. | |
| 2011/0210316 A1 | 9/2011 | Kadoma et al. | |
| 2011/0248246 A1 | 10/2011 | Ogita et al. | |
| 2011/0285276 A1 | 11/2011 | Kadoma et al. | |
| 2011/0303901 A1 | 12/2011 | Cheng et al. | |
| 2011/0315965 A1 | 12/2011 | Takashima et al. | |
| 2012/0049768 A1 | 3/2012 | Seo et al. | |
| 2012/0056171 A1 | 3/2012 | Kim et al. | |
| 2012/0197020 A1 | 8/2012 | Osaka et al. | |

FOREIGN PATENT DOCUMENTS

| | | | | |
|---|---|---|---|---|
| JP | 2004-224723 A | 8/2004 | | |
| JP | 2007-001895 A | 1/2007 | | |
| JP | 2008-257097 A | 10/2008 | | |
| JP | 2009-256334 A | 11/2009 | | |
| KR | WO 2008120957 A1 * | 10/2008 | ............ | C07F 9/5325 |
| WO | WO 98/03596 A1 | 1/1998 | | |
| WO | WO 2007/126262 A1 | 11/2007 | | |
| WO | WO 2008/027594 A2 | 3/2008 | | |
| WO | WO 2008/120957 A1 | 10/2008 | | |
| WO | WO 2008/146825 A1 | 12/2008 | | |
| WO | WO 2009/066779 A1 | 5/2009 | | |
| WO | WO 2009/066808 A1 | 5/2009 | | |
| WO | WO 2009/132443 A1 | 11/2009 | | |
| WO | WO 2010/074087 A1 | 7/2010 | | |

OTHER PUBLICATIONS

Taiwanese Office Action re Application No. TW 100132100, dated Apr. 23, 2015.
Koene, B.E. et al., "Asymmetric Triaryldiamines as Thermally Stable Hole Transporting Layers for Organic Light-Emitting Devices," Chemistry of Materials, Jul. 21, 1998, vol. 10, No. 8, pp. 2235-2250, American Chemical Society.
Goldsmith, C.R. et al., "C—H Bond Activation by a Ferric Methoxide Complex: Modeling the Rate-Determining Step in the Mechanism of Lipoxygenase," Journal of the American Chemical Society, 2002, vol. 124, No. 1, pp. 83-96.
Onishi, T. et al., "A Method of Measuring an Energy Level," High Molecular EL Materials—Development of Light-Emitting High Molecular Compounds, Dec. 25, 2004, pp. 64-67, Kyoritsu Shuppan.
Ye, S. et al., "Phenyl-Substituted Fluorene-Dimer Cored Anthracene Derivatives: Highly Fluorescent and Stable Materials for High Performance Organic Blue-and White-Light-Emitting Diodes," Journal of Materials Chemistry, 2010, vol. 20, No. 16, pp. 3186-3194.
Suzuki, K. et al., "Studies on Fluorene Derivatives. XXIII. The Synthesis of 2'-Bromotribiphenylenepropane and Some Related Observation," Bulletin of the Chemical Society of Japan, 1964, vol. 37, No. 12, pp. 1833-1836.
Suzuki, K., "Fluorene Derivatives V. 2,2'-Dibromo-7,7'-dichlorodibiphenyleneethylene," Nippon Kagaku Zasshi, Jul. 1, 1954, vol. 75, No. 7, pp. 714-717.
Suzuki.K et al., "Fluorene derivatives IX. Tribiphenylenepropanes containing bromine atoms at the third position of the fluorene nucleus", Yuki Gosei Kagaku Kyoukaishi, 1958, vol. 16, No. 2, pp. 82-87.
Kajigaeshi, S. et al., "Rotational Isomerism in Fluorene Derivatives. III. The Conformation of 9-(9-Fluorenyl)-9-(2-substituted 9-fluorenyl)fluorene Derivatives," Bulletin of the Chemical Society of Japan, Dec. 1, 1979, vol. 52, No. 12, pp. 3569-3572.
Ye, S. et al., "Solution-Processed Solid Solution of a Novel Carbazole Derivative for High-Performance Blue Phosphorescent Organic Light-Emitting Diodes," Advanced Materials, 2010, vol. 22, No. 37, pp. 4167-4171.
Minabe, M. et al., "The Michael Reactions of Substituted 9,9'-Bifluorenylidenes with 2-Iodo-and 2,7-Diiodofluorene, and Some Other Reactions of Iodofluorenes," Bulletin of the Chemical Society of Japan, 1972, vol. 45, No. 10, pp. 3196-3201.
Minabe, M. et al., "Formation of 9,9':9',9"-Terfluorenyl Isomers Using Metalated Fluorenes as Synthetic Intermediates," Bulletin of the Chemical Society of Japan, Apr. 1, 1975, vol. 48, No. 4, pp. 1301-1303.

(56) References Cited

OTHER PUBLICATIONS

Suzuki, K. et al., "Fluorene derivatives. X. 4,4',4"-Tribromotribiphenylenepropane and 4'-bromotribiphenylenepropane," Yuki Gosei Kagaku Kyoukaishi, 1958, vol. 16, No. 6, pp. 304-309.

Minabe, M. et al., "The Michael Reactions of Chloro-substituted-9,9'-bifluorenylidenes with Fluorenes and a Comparison with Analogous Halogen Compounds," Bulletin of the Chemical Society of Japan, 1975, vol. 48, No. 2, pp. 586-590.

Suzuki, K., "Fluorene Derivatives. VI. 2,2',2"-Trichlorotribiphenylenepropane," Nippon Kagaku Zasshi, 1954, vol. 75, No. 8, pp. 793-795.

European Search Report re Application No. EP 11179794.0, dated Nov. 23, 2011.

Zhang, S. et al, "Tuning the Otpelectronic Properties of 4,4'-N,N'-Dicabazole-Biphenyl Through Heteroatom Linkage: New Host Materials for Phosphorescent Organic Light-Emitting Didoes," Organic Letters, Jun. 1, 2010, vol. 12, No. 15, pp. 3438-3441.

Clement, J.A. et al., "Synthesis and Characterization of Naphth-Annelated Thiophene Analogs," Tetrahedron, Mar. 27, 2010, vol. 66, No. 13, pp. 2340-2350.

Cameron, D.W. et al., "The Formation of Chromanone-type Systems via the Acylation of Derivatives of 2,6-Dihydroxyanthracene," Journal of the Chemical Society, 1967, pp. 95-99.

\* cited by examiner

FLUORENE COMPOUND, LIGHT-EMITTING ELEMENT, LIGHT-EMITTING DEVICE, ELECTRONIC DEVICE, LIGHTING DEVICE, AND ORGANIC COMPOUND

This application is a divisional of copending U.S. application Ser. No. 13/227,022, filed on Sep. 7, 2011 which is incorporated herein by reference.

BACKGROUND OF THE INVENTION

1. Field of the Invention

The present invention relates to a fluorene compound, a light-emitting element, a light-emitting device, an electronic device, a lighting device, and an organic compound.

2. Description of the Related Art

In recent years, research and development have been extensively conducted on light-emitting elements using electroluminescence (EL). In a basic structure of such a light-emitting element, a layer containing a light-emitting substance is interposed between a pair of electrodes. By applying voltage to this element, light emission from the light-emitting substance can be obtained.

Since such a light-emitting element is of self-light-emitting type, it is considered that the light-emitting element has advantages over a liquid crystal display in that visibility of pixels is high, backlight is not required, and so on and is therefore suitable as flat panel display elements. In addition, it is also a great advantage that the light-emitting element can be manufactured as a thin and lightweight element. Furthermore, very high speed response is also one of the features of such elements.

Furthermore, since such light-emitting elements can be formed in a film form, they make it possible to provide planar light emission. Therefore, large-area elements can be easily formed. This feature is difficult to obtain with point light sources typified by incandescent lamps and LEDs or linear light sources typified by fluorescent lamps. Thus, light-emitting elements also have great potential as planar light sources applicable to lighting devices and the like.

Such light-emitting elements utilizing EL can be broadly classified according to whether the light-emitting substance is an organic compound or an inorganic compound. In the case of an organic EL element in which a layer containing an organic compound used as the light-emitting substance is provided between a pair of electrodes, application of a voltage to the light-emitting element causes injection of electrons from the cathode and holes from the anode into the layer containing the organic compound having a light-emitting property, and thus a current flows. Light is emitted when the carriers (electrons and holes) are recombined and the organic compound returns to the ground state from the excited state where both the electrons and the holes are generated in organic molecules with a light-emitting property.

In improving element characteristics of such a light-emitting element, there are a lot of problems which depend on a substance, and in order to solve the problems, improvement of an element structure, development of a substance, and the like have been carried out.

A light-emitting element using organic EL has a plurality of layers, and a carrier-transport layer is generally provided between a light-emitting layer and an electrode. One of the reasons is that a carrier-transport layer can prevent energy transfer of excitation energy from the light-emitting layer to the electrode and occurrence of quenching. Further, a material (an exciton-blocking material) having higher excitation energy than a light-emitting layer is preferably used for a carrier-transport layer which is adjacent to the light-emitting layer so that excitation energy is not transferred from the light-emitting layer. In other words, a material having a wide band gap (Bg) between the highest occupied molecular orbital level (HOMO level) and the lowest unoccupied molecular orbital level (LUMO level) is considered preferable.

In a light-emitting element using organic EL, a carrier-transport layer provided between a light-emitting layer and an electrode may include a plurality of layers. One possible reason is to adjust a carrier-injection barrier between adjacent layers. It can be considered that with a higher injection barrier, carrier passage can be suppressed and this leads to more efficient recombination in the light-emitting layer.

In the case of an element which emits phosphorescence, excitation energy of a light-emitting substance would be lost unless the level of triplet excitation energy (T1 level) of a material in contact with the light-emitting substance is sufficiently higher than the T1 level of the light-emitting substance. Therefore, as a host material of a light-emitting layer of a phosphorescent light-emitting element or a material of a carrier-transport layer adjacent to the light-emitting layer, a material having a T1 level higher than that of a phosphorescent light-emitting material is used.

However, many of common materials having a wide band gap or a high T1 level have low molecular weights so as not to extend conjugation. Due to their low molecular weights, these materials have many problems such as significantly poor thermophysical properties (a low glass transition temperature (Tg), a strong tendency toward crystallization), poor film quality, and low stability during evaporation. Therefore, a material which can overcome these problems as well as having a wide band gap and a high T1 level is desired.

For example, Reference 1 discloses 4,4'-bis[N-(1-naphthyl)-N-phenylamino]biphenyl (abbreviation: NPB) as a material which can be used for a hole-transport layer of a light-emitting element.

[Reference 1] Chem. Mater., 1998, 10, pp. 2235-2250

SUMMARY OF THE INVENTION

However, NPB has absorption in the visible region. Therefore, when NPB is used for a light-emitting element, there is a problem in that NPB absorbs part of visible light emitted from a light-emitting layer and decreases light extraction efficiency. In addition, because NPB does not have a sufficiently wide band gap and has a low LUMO level, electrons may pass through a light-emitting layer into an adjacent NPB layer. Furthermore, in some cases, carrier balance cannot be optimized, and a decrease in efficiency and a change in color may be caused. Moreover, excitation energy may be transferred from the light-emitting layer to the adjacent NPB layer, which may result in quenching.

Thus, it is an object of one embodiment of the present invention to provide a substance having a hole-transport property and a wide band gap.

It is another object of one embodiment of the present invention to provide a light-emitting element having high emission efficiency by application of the above substance to the light-emitting element Another object is to provide a light-emitting element having a long lifetime by application of the above substance to the light-emitting element. It is still another object of one embodiment of the present invention to provide a light-emitting device including the light-emitting element, an electronic device including the light-emitting device, and a lighting device including the light-emitting device.

One embodiment of the present invention is a fluorene compound represented by a general formula (G1).

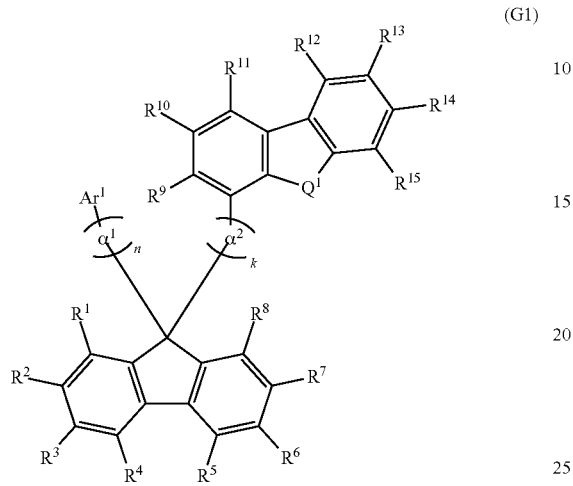

(G1)

In the formula, $\alpha^1$ and $\alpha^2$ separately represent a substituted or unsubstituted arylene group having 6 to 13 carbon atoms; $Ar^1$ represents a substituted or unsubstituted aryl group having 6 to 18 carbon atoms, a substituted or unsubstituted 4-dibenzothiophenyl group, or a substituted or unsubstituted 4-dibenzofuranyl group; n and k separately represent 0 or 1; $Q^1$ represents sulfur or oxygen; and $R^1$ to $R^{15}$ separately represent hydrogen, an alkyl group having 1 to 12 carbon atoms, or an aryl group having 6 to 14 carbon atoms.

In the above fluorene compound, it is preferable that substituents of $\alpha^1$, $\alpha^2$, and $Ar^1$ be separately an alkyl group having 1 to 12 carbon atoms or an aryl group having 6 to 14 carbon atoms.

Examples of $\alpha^1$ and $\alpha^2$ are separately a substituted or unsubstituted phenylene group, a substituted or unsubstituted biphenyldiyl group, a substituted or unsubstituted naphthalenediyl group, and the like.

Examples of $Ar^1$ are a substituted or unsubstituted phenyl group, a substituted or unsubstituted biphenyl group, a substituted or unsubstituted naphthyl group, a substituted or unsubstituted fluorenyl group, a substituted or unsubstituted 4-dibenzothiophenyl group, a substituted or unsubstituted 4-dibenzofuranyl group, and the like.

Examples of substituents of $\alpha^1$, $\alpha^2$, and $Ar^1$ and examples of $R^1$ to $R^{15}$ are separately a methyl group, an ethyl group, a propyl group, a pentyl group, a hexyl group, a heptyl group, an octyl group, a nonyl group, a decyl group, a dodecyl group, a tridecyl group, a phenyl group, a biphenyl group, a naphthyl group, a phenanthryl group, and the like.

In the above-described fluorene compound, it is preferable that $R^1$ to $R^{15}$ be separately represented by any one of structural formulae (R-1) to (R-14).

(R-1)

(R-2)

-continued

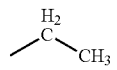

(R-3)

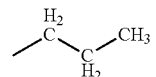

(R-4)

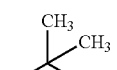

(R-5)

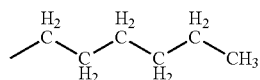

(R-6)

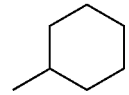

(R-7)

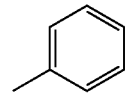

(R-8)

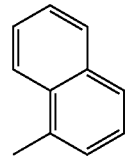

(R-9)

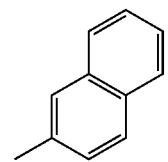

(R-10)

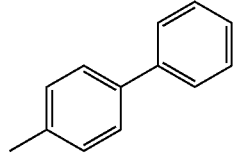

(R-11)

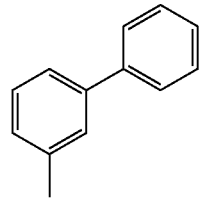

(R-12)

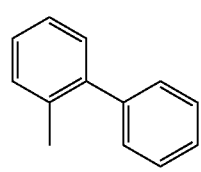

(R-13)

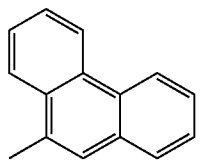
(R-14)

In the case where $\alpha^1$, $\alpha^2$, and $Ar^1$ have substituents, it is preferable that the substituents be separately represented by any one of the above structural formulae (R-2) to (R-14).

In the above-described fluorene compound, it is preferable that $\alpha^1$ and $\alpha^2$ be separately represented by any one of structural formulae ($\alpha$-1) to ($\alpha$-7).

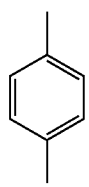
($\alpha$-1)

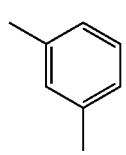
($\alpha$-2)

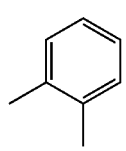
($\alpha$-3)

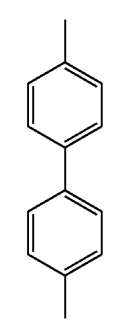
($\alpha$-4)

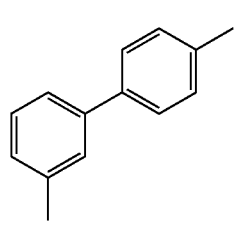
($\alpha$-5)

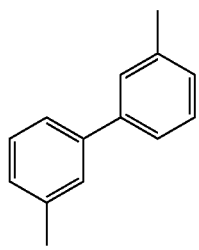
($\alpha$-6)

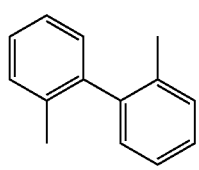
($\alpha$-7)

In the above-described fluorene compound, it is preferable that $Ar^1$ be represented by any one of structural formulae ($Ar^1$-1) to ($Ar^1$-21). In the structural formulae ($Ar^1$-15) to ($Ar^1$-19), $Q^2$ represents sulfur or oxygen.

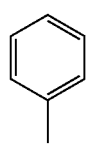
($Ar^1$-1)

($Ar^1$-2)

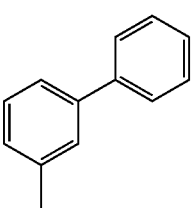
($Ar^1$-3)

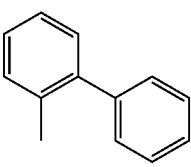
($Ar^1$-4)

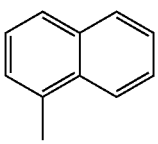
($Ar^1$-5)

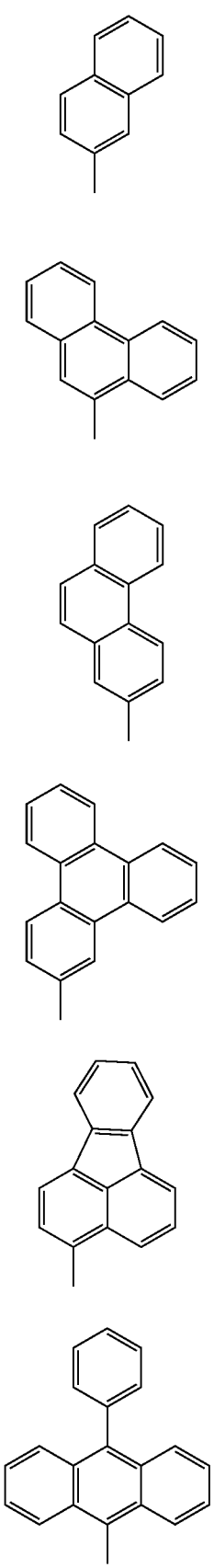
(Ar¹-6)
(Ar¹-7)
(Ar¹-8)
(Ar¹-9)
(Ar¹-10)
(Ar¹-11)
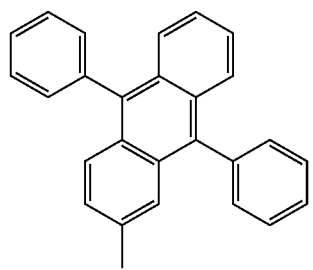
(Ar¹-12)
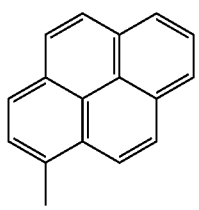
(Ar¹-13)
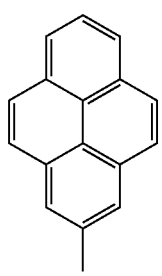
(Ar¹-14)
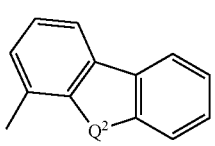
(Ar¹-15)
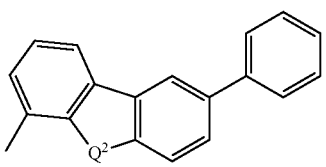
(Ar¹-16)
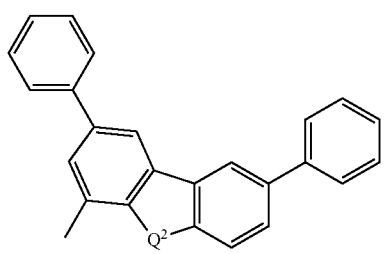
(Ar¹-17)
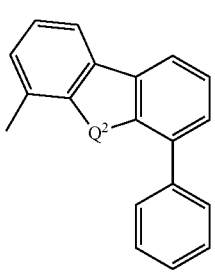
(Ar¹-18)

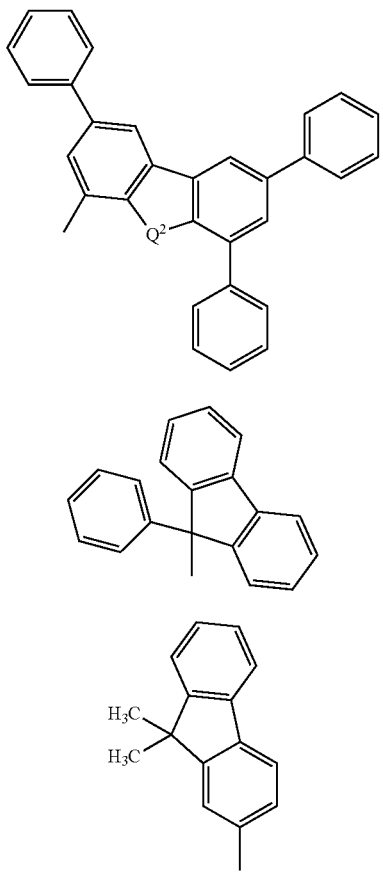

(Ar¹-19)

(Ar¹-20)

(Ar¹-21)

Another embodiment of the present invention is a light-emitting element including the above-described fluorene compound.

Another embodiment of the present invention is a light-emitting element having an anode, a cathode, a light-emitting layer between the anode and the cathode, and a layer including the above-described fluorene compound between the anode and the light-emitting layer.

In the above-described light-emitting element, the layer including the above-described fluorene compound may be in contact with the anode, or the layer including the above-described fluorene compound may be in contact with the light-emitting layer.

In particular, in the case where the layer including the above-described fluorene compound is in contact with the anode, it is preferable that the layer including the above-described fluorene compound further include a metal oxide, in particular, molybdenum oxide.

Another embodiment of the present invention is a light-emitting element having an anode, a cathode, and a light-emitting layer between the anode and the cathode, in which the light-emitting layer includes the above-described fluorene compound.

Another embodiment of the present invention is a light-emitting device including the above-described light-emitting element. Another embodiment of the present invention is an electronic device including the above-described light-emitting device. Another embodiment of the present invention is a lighting device including the above-described light-emitting device.

Note that the light-emitting device in this specification includes an image display device and a light source. In addition, the light-emitting device includes all the following modules: a module in which a connector, such as a flexible printed circuit (FPC), a tape automated bonding (TAB) tape, or a tape carrier package (TCP), is attached to a panel, a module in which a printed wiring board is provided at the end of a TAB tape or a TCP, and a module in which an integrated circuit (IC) is directly mounted on a light-emitting device by a chip-on-glass (COG) method.

According to one embodiment of the present invention, a substance having a hole-transport property and a wide band gap can be provided.

According to one embodiment of the present invention, a light-emitting element having high emission efficiency can be provided. Alternatively, a light-emitting element having a long lifetime can be provided. According to one embodiment of the present invention, a light-emitting device including the light-emitting element, an electronic device including the light-emitting device, and a lighting device including the light-emitting device can be provided.

DETAILED DESCRIPTION OF THE INVENTION

Figure 1A:
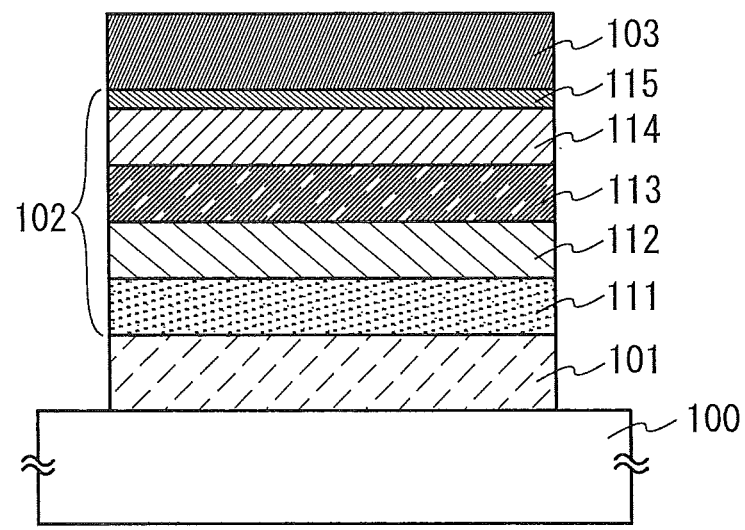
FIGS. 1A and 1B each illustrate a light-emitting element of one embodiment of the present invention.

Embodiments and examples will be described in detail with reference to the drawings. Note that the present invention is not limited to the following description and it will be readily appreciated by those skilled in the art that the modes and details of the present invention can be modified in various ways without departing from the spirit and scope thereof. Therefore, the present invention should not be interpreted as being limited to the description in the following embodiments and examples. Note that the same portions or portions having similar functions are commonly denoted by the same reference numerals in different drawings, and repetitive description thereof is omitted.

(Embodiment 1)

In this embodiment, a fluorene compound of one embodiment of the present invention will be described.

One embodiment of the present invention is a fluorene compound represented by the general formula (G1).

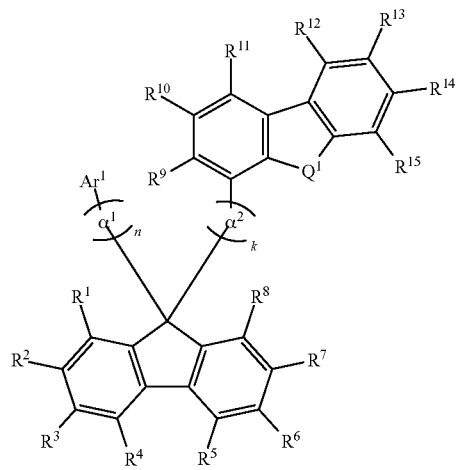

(G1)

In the general formula (G1), $\alpha^1$ and $\alpha^2$ separately represent a substituted or unsubstituted arylene group having 6 to 13 carbon atoms; $Ar^1$ represents a substituted or unsubstituted aryl group having 6 to 18 carbon atoms, a substituted or unsubstituted 4-dibenzothiophenyl group, or a substituted or unsubstituted 4-dibenzofuranyl group; n and k separately represent 0 or 1; $Q^1$ represents sulfur or oxygen; and $R^1$ to $R^{15}$ separately represent hydrogen, an alkyl group having 1 to 12 carbon atoms, or an aryl group having 6 to 14 carbon atoms.

In the general formula (G1), two substituents are bonded to the 9-position of a fluorene skeleton. These substituents are bonded by a sigma bond at the 9-position of the fluorene skeleton. Therefore, one of the substituents bonded to the 9-position of the fluorene skeleton does' not easily extend conjugation to the other substituent, and the fluorene compound represented by the general formula (G1) can have a wide band gap as well as a high molecular weight, which is preferable.

In the case where $\alpha^1$ in the above-described fluorene compound has one or more substituents, it is preferable that the one or more substituents be separately an alkyl group having 1 to 12 carbon atoms or an aryl group having 6 to 14 carbon atoms.

In the case where $\alpha^2$ in the above-described fluorene compound has one or more substituents, it is preferable that the one or more substituents be separately an alkyl group having 1 to 12 carbon atoms or an aryl group having 6 to 14 carbon atoms.

In the case where $Ar^1$ in the above-described fluorene compound has one or more substituents, it is preferable that the one or more substituents be separately an alkyl group having 1 to 12 carbon atoms or an aryl group having 6 to 14 carbon atoms.

It is preferable that $\alpha^1$ (n=1) and $\alpha^2$ (k=1) separately represent a substituted or unsubstituted phenylene group or a substituted or unsubstituted biphenyldiyl group. A phenylene group or a biphenyldiyl group is preferable because conjugation does not easily extend, a wide band gap can be obtained, and absorption in the visible region is unlikely to be observed. A phenylene group or a biphenyldiyl group is particularly preferable for use in a light-emitting element which emits shorter wavelength light such as blue or green fluorescence. A phenylene group is preferable because the level of triplet excitation energy (T1 level) is higher. A phenylene group is particularly preferable for use in a light-emitting element which emits shorter wavelength light such as blue or green phosphorescence. Note that the triplet excitation energy refers to an energy difference between a ground state and a triplet excited state.

It is preferable that $Ar^1$ be a substituted or unsubstituted phenyl group, a substituted or unsubstituted biphenyl group, a substituted or unsubstituted naphthyl group, a substituted or unsubstituted phenanthryl group, a substituted or unsubstituted triphenyl group, a substituted or unsubstituted fluoranthenyl group, a substituted or unsubstituted anthryl group, a substituted or unsubstituted pyrenyl group, a substituted or unsubstituted fluorenyl group, a substituted or unsubstituted 4-dibenzothiophenyl group, or a substituted or unsubstituted 4-dibenzofuranyl group. It is particularly preferable that $Ar^1$ be a naphthyl group, a phenanthryl group, or an anthryl group because it has a condensed ring and is capable of transporting more carriers. It is also preferable that $Ar^1$ be a phenyl group, a biphenyl group, a 4-dibenzothiophenyl group, or a 4-dibenzofuranyl group because a wide band gap can be obtained.

It is preferable that substituents of $\alpha^1$, $\alpha^2$, and $Ar^1$ and $R^1$ to $R^{15}$ be separately a methyl group, an ethyl group, a propyl group, a pentyl group, a hexyl group, a heptyl group, an octyl group, a nonyl group, a decyl group, a dodecyl group, a tridecyl group, a phenyl group, a biphenyl group, a naphthyl group, a phenanthryl group, or the like.

In the above-described fluorene compound, it is preferable that $R^1$ to $R^{15}$ be separately represented by any one of structural formulae (R-1) to (R-14).

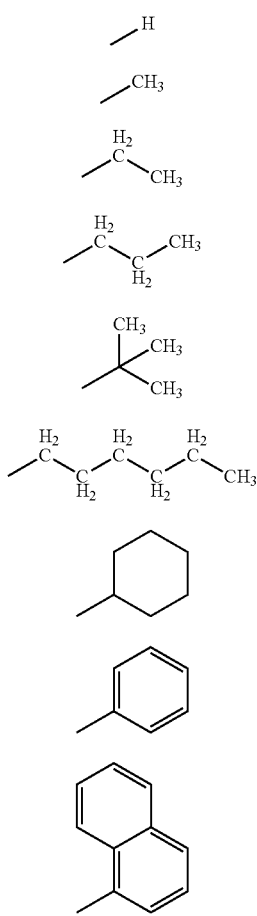

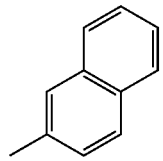

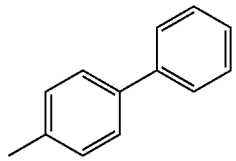

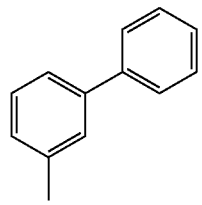

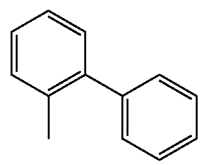

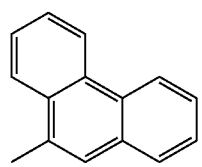

It is preferable that a substituent be provided at any position of $R^1$ to $R^{15}$ in the general formula (G1) because a material which is unlikely to be crystallized due to steric hindrance can be obtained. It is preferable that the substituent be an alkyl group as represented in the above structural formulae (R-2) to (R-6) because high solubility in an organic solvent can be obtained and easier purification and solution preparation can be achieved. It is preferable that the substituent be an alkyl group, or a phenyl group or a biphenyl group as represented in the above-described structural formulae (R-8) and (R-11) to (R-13) because a wide band gap can be obtained. It is preferable that the substituent be an aryl group as represented in the above-described structural formulae (R-8) to (R-14) because the carrier-transport property can be improved.

In particular, a fluorene compound having a substituent at the 2-position or the 8-position of a dibenzothiophene skeleton or a dibenzofuran skeleton (at the position of $R^{10}$ or $R^{13}$ in the general formula (G1)) is preferable because it can be easily synthesized. Note that in the case where the fluorene compound has a substituent, the number of synthetic steps may be increased and by-products or synthetic cost may be increased. In this respect, it is preferable that the fluorene compound do not have a substituent.

In the above-described fluorene compound, it is preferable that substituents of $\alpha^1$, $\alpha^2$, and $Ar^1$ be separately represented by any one of the structural formulae (R-2) to (R-14).

In the above-described fluorene compound, it is preferable that $\alpha^1$ and $\alpha^2$ be separately represented by any one of the structural formulae ($\alpha$-1) to ($\alpha$-7).

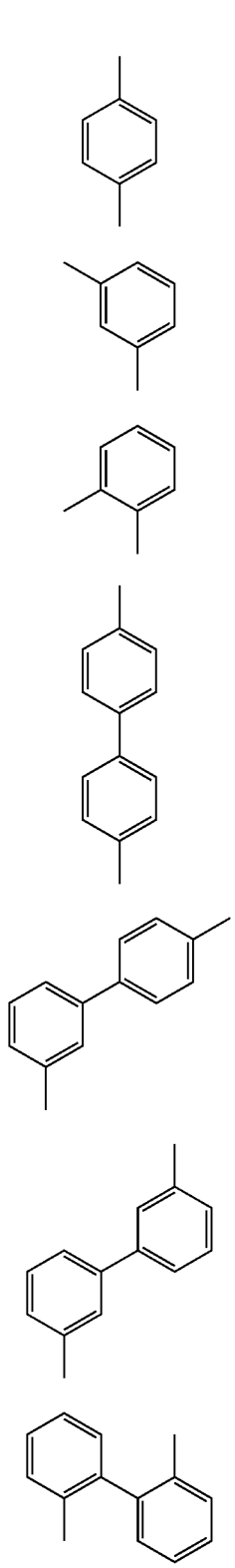

In the above-described fluorene compound, it is preferable that $Ar^1$ be represented by any one of the structural formulae ($Ar^1$-1) to ($Ar^1$-21). In the structural formulae ($Ar^1$-15) to ($Ar^1$-19), $Q^2$ represents sulfur or oxygen.

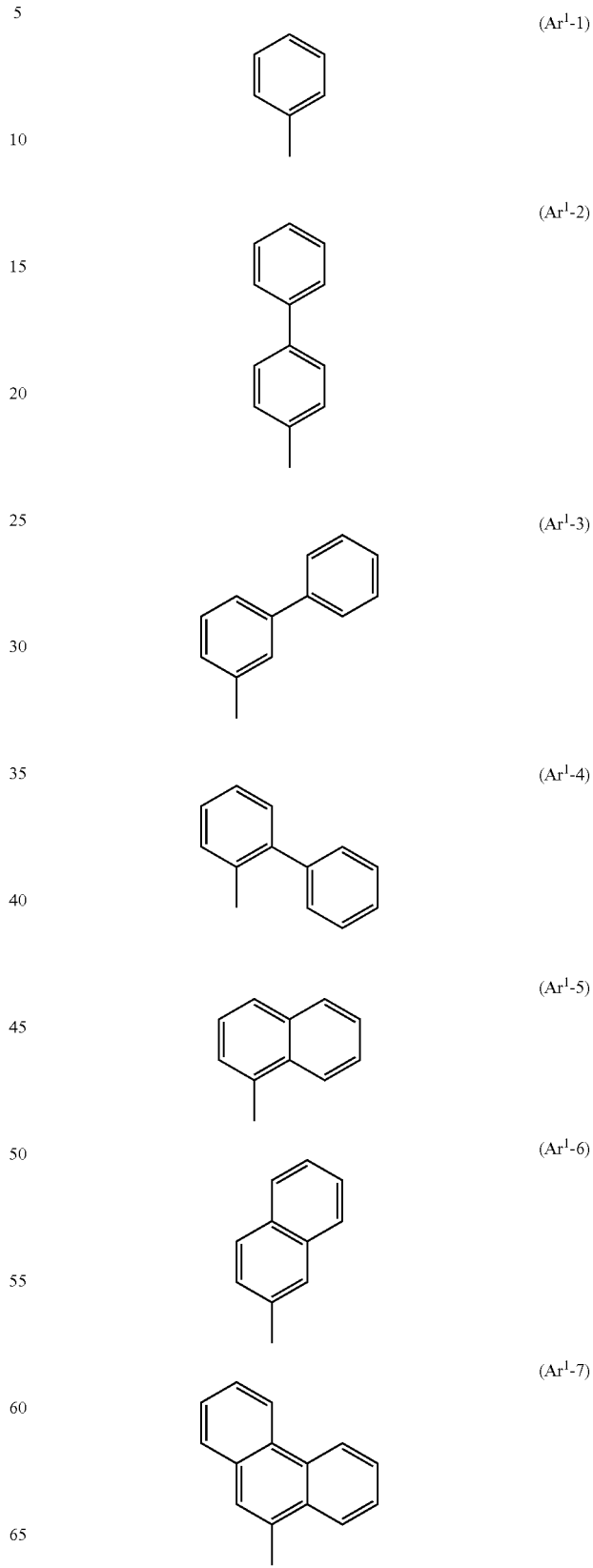

-continued
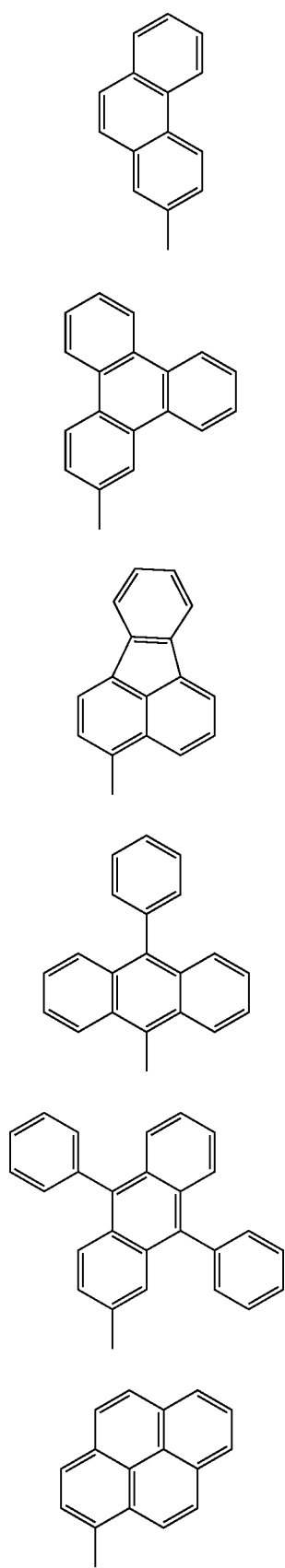
(Ar¹-8)
(Ar¹-9)
(Ar¹-10)
(Ar¹-11)
(Ar¹-12)
(Ar¹-13)
-continued
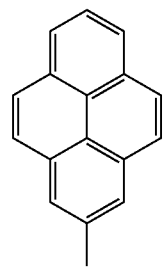
(Ar¹-14)
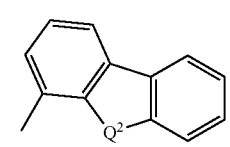
(Ar¹-15)
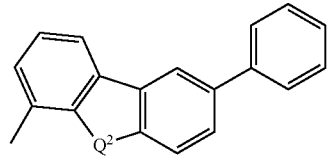
(Ar¹-16)
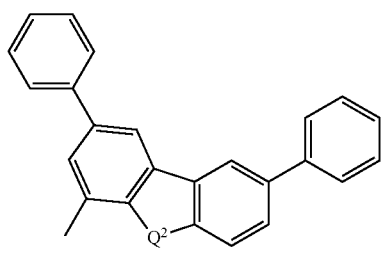
(Ar¹-17)
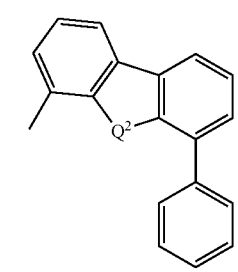
(Ar¹-18)
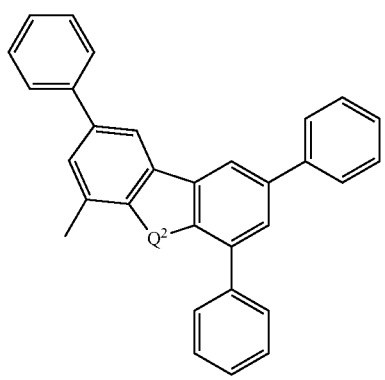
(Ar¹-19)

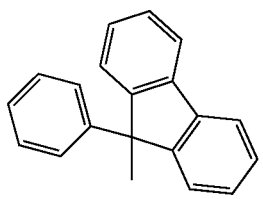
(Ar¹-20)

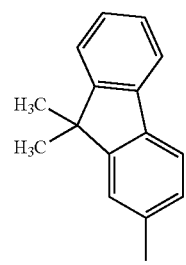
(Ar¹-21)

It is particularly preferable that Ar¹ have a condensed ring as in the above structural formulae (Ar¹-5) to (Ar¹-14) because the carrier-transport property can be improved.

It is further preferable that Ar¹ have an anthracene skeleton or a pyrene skeleton because excellent emission efficiency can be obtained. At this time, such a skeleton is bonded to the 9-position of the fluorene skeleton (Such a skeleton may be bonded to the 9-position of the fluorene skeleton through $\alpha^1$). Therefore, conjunction does not easily extend any farther (to a dibenzothiophene or dibenzofuran skeleton), and the fluorene compound can efficiently emit short-wavelength (shorter than blue-purple) light.

Specific structural formulae of a fluorene compound of one embodiment of the present invention are given in the following structural formulae (100) to (124), (130) to (154), (160) to (169), (170) to (179), (180) to (185), (190) to (201), (210) to (221), and (230) to (236). Note that the present invention is not limited to these structures.

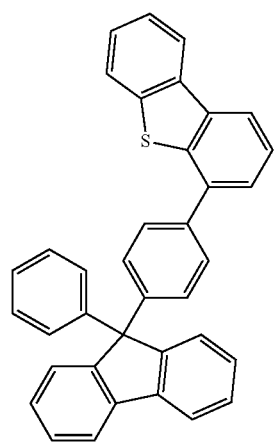
(100)

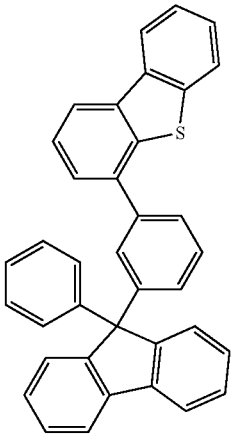
(101)

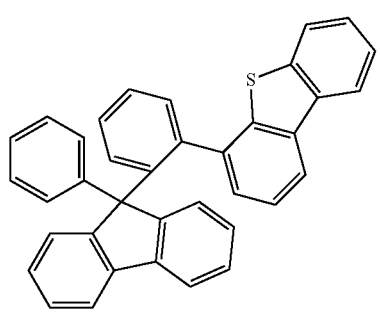
(102)

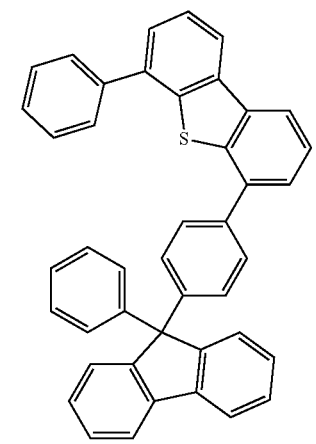
(103)

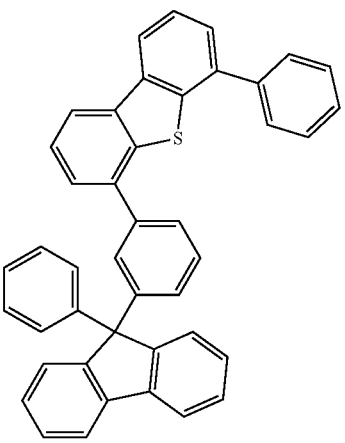
(104)

(105)
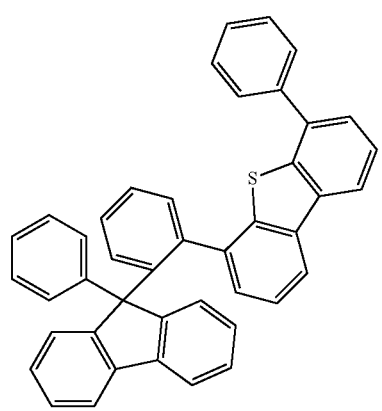
(106)
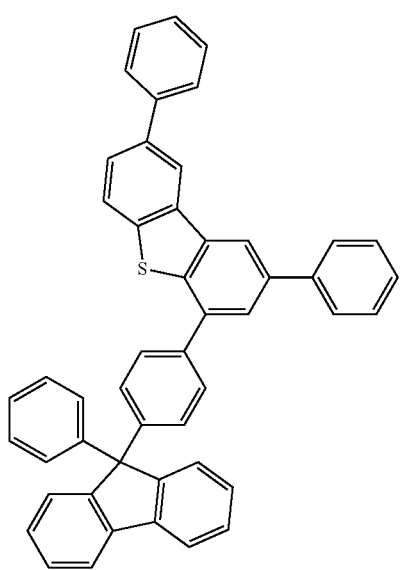
(107)
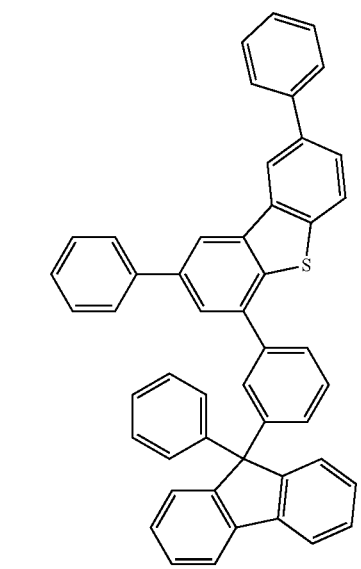
(108)
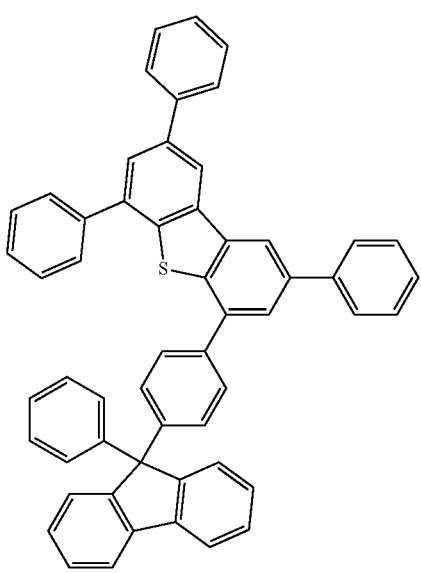
(109)
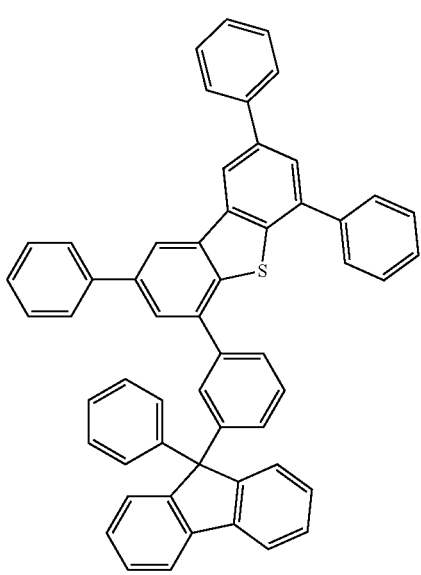
(110)
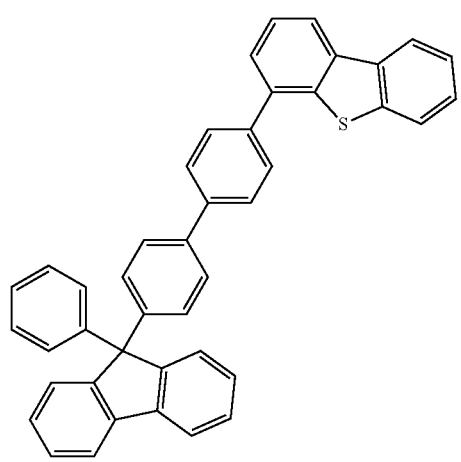

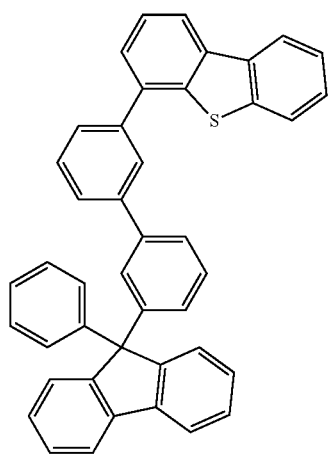
(111)
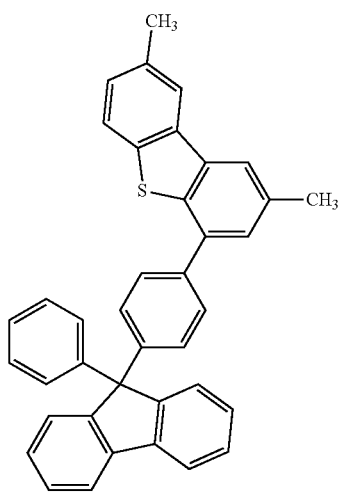
(114)
(112)
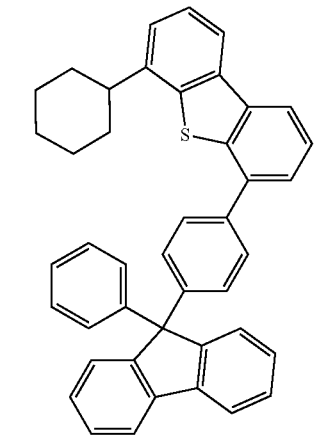
(115)
(113)
(116)

-continued
(117)
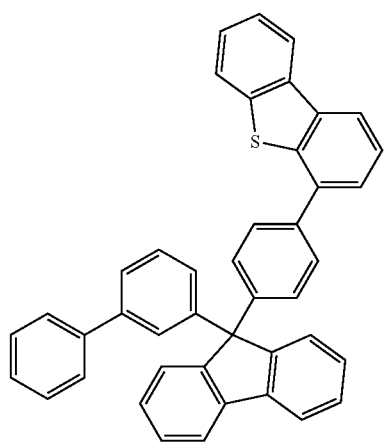
(118)
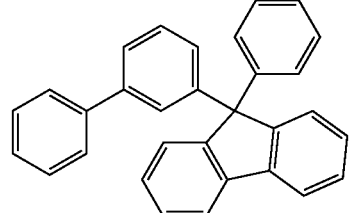
(119)
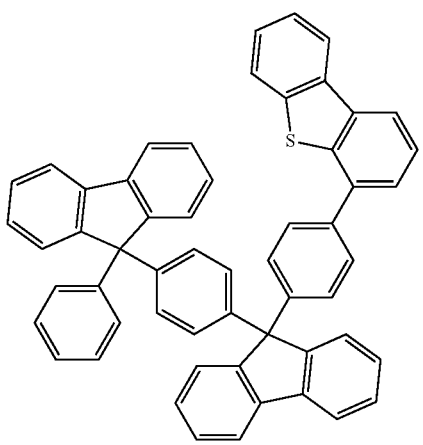
(120)
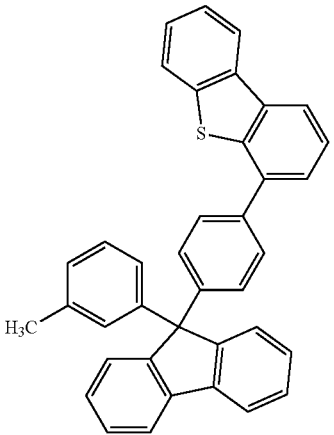
(121)
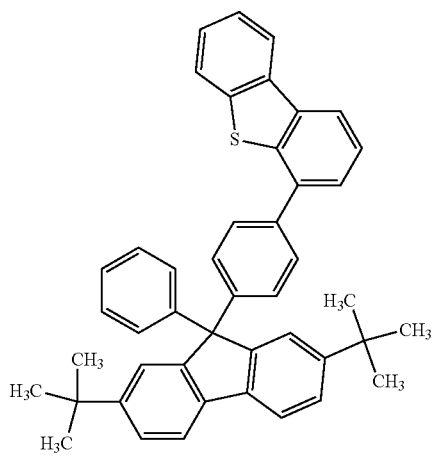
(122)
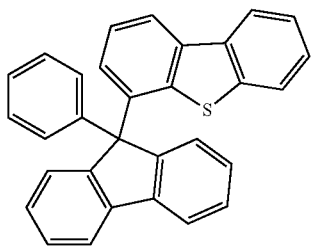
(123)
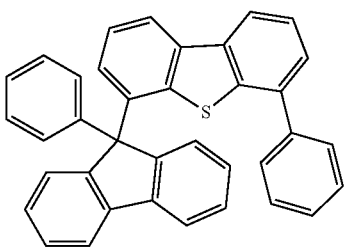

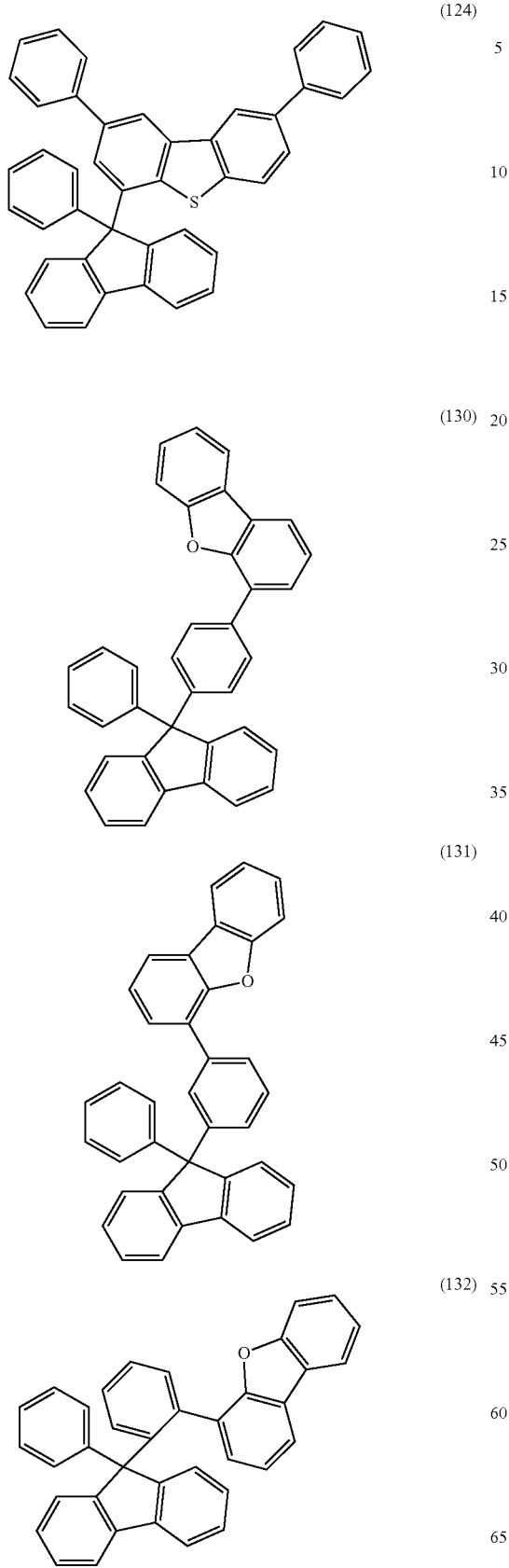
(124)
(130)
(131)
(132)
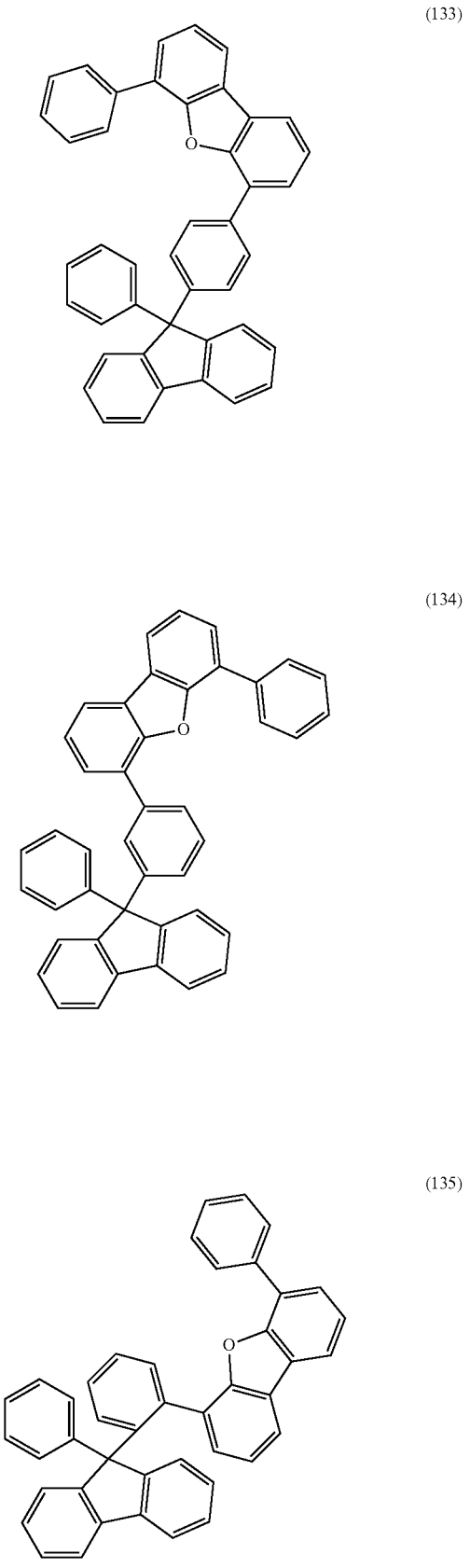
(133)
(134)
(135)

(136)
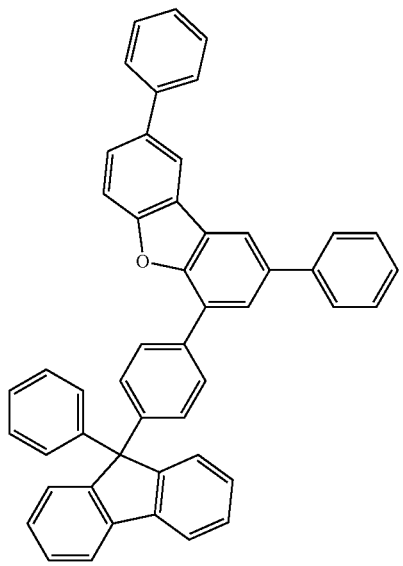
(137)
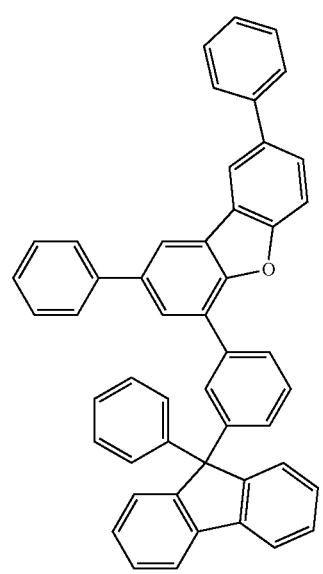
(138)
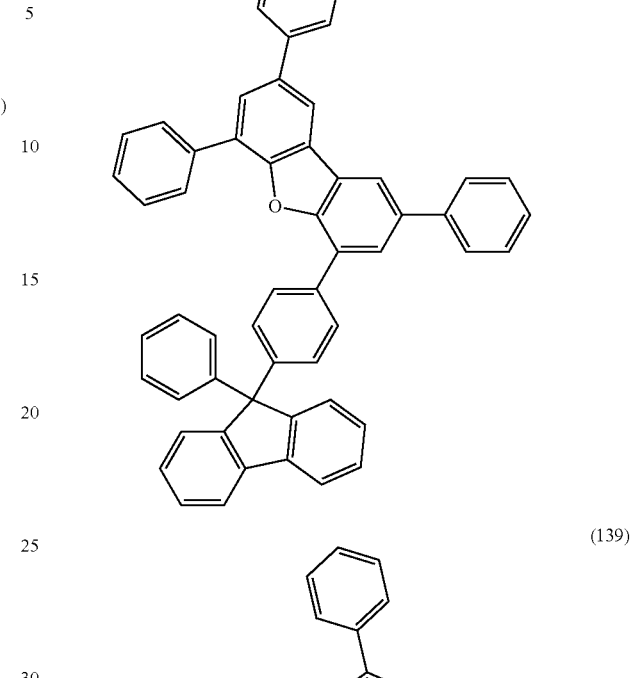
(139)
(140)
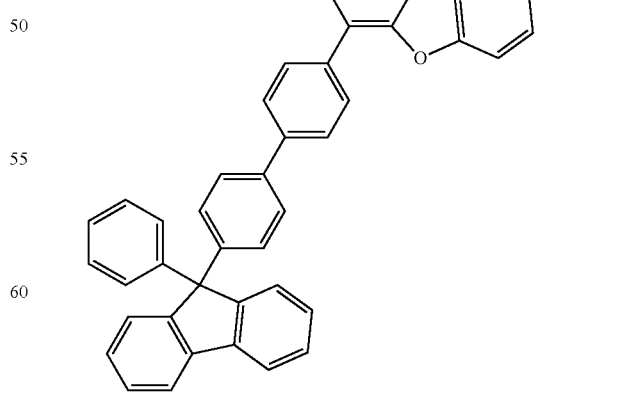

(141) 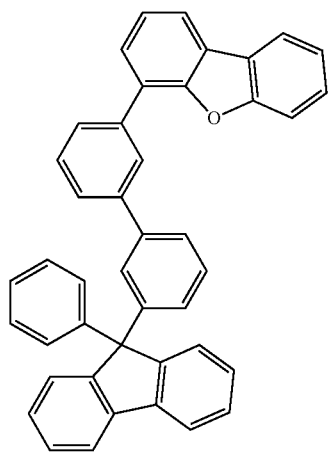
(142) 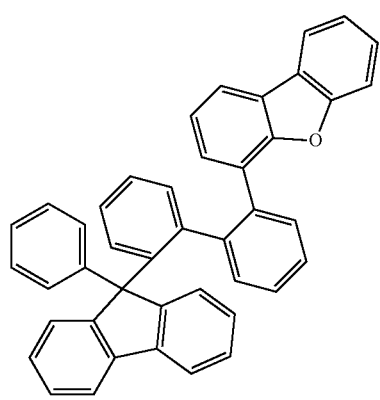
(143) 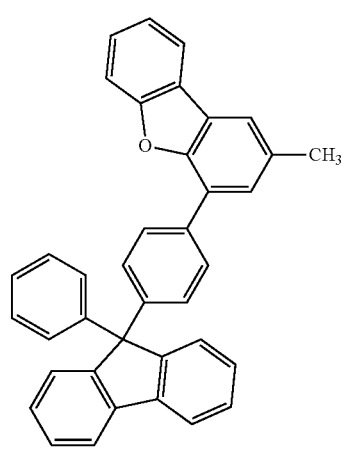
(144) 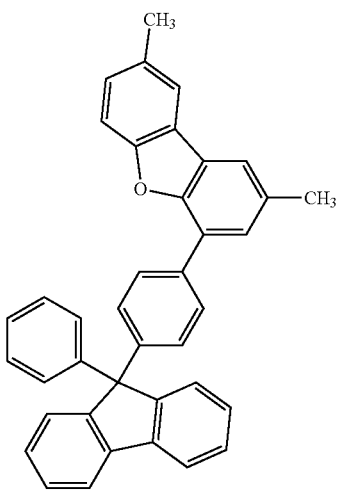
(145) 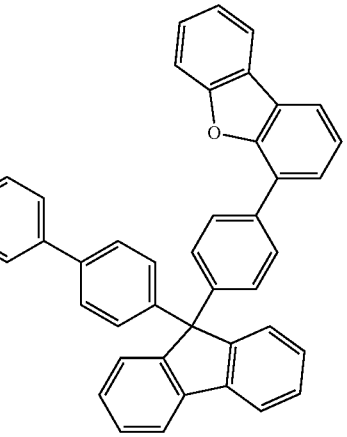
(146)

(147) 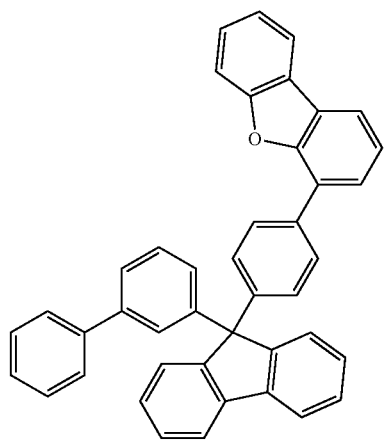
(148) 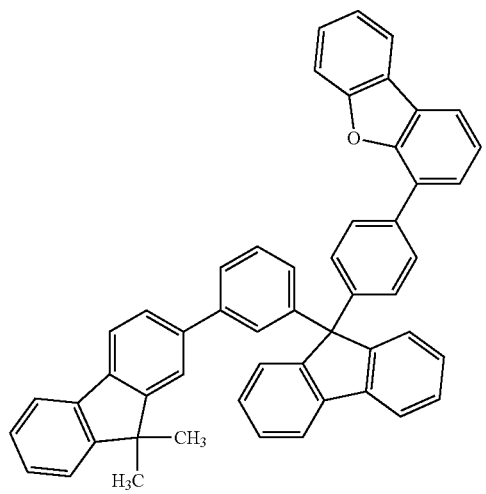
(149) 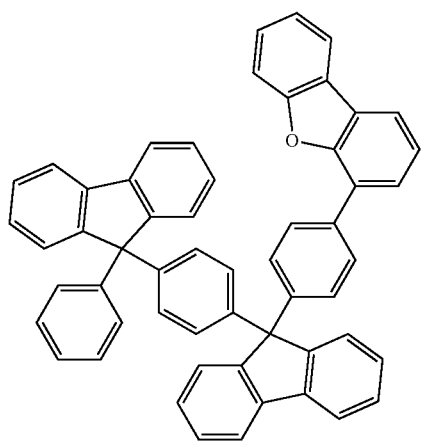
(150) 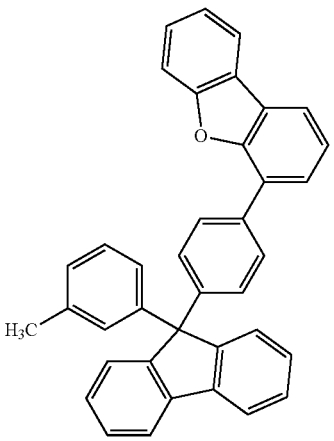
(151) 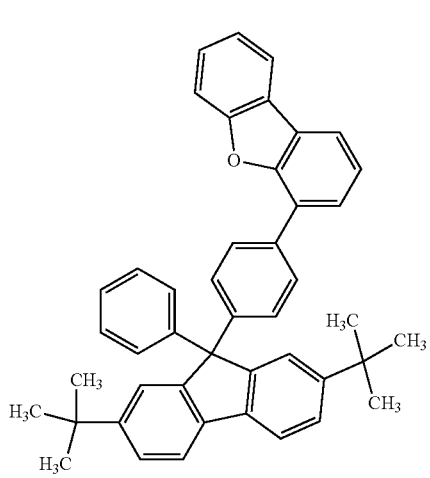
(152) 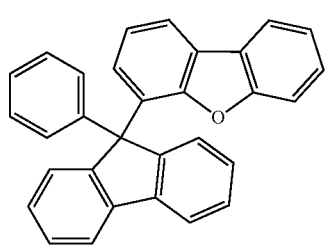
(153) 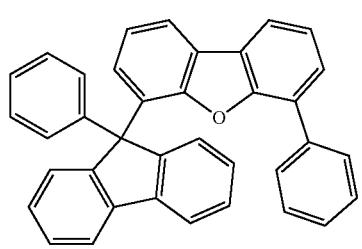

(154)
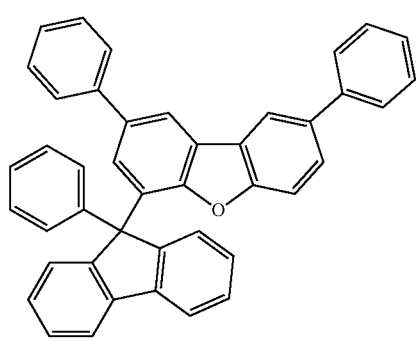
(160)
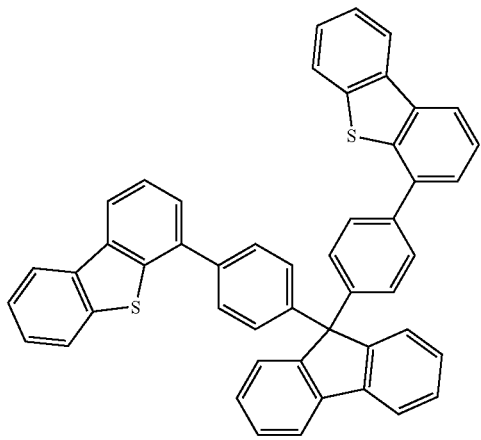
(161)
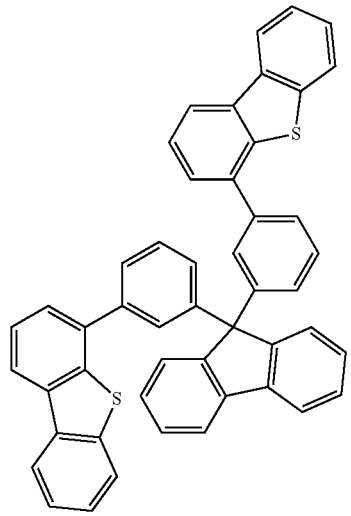
(162)
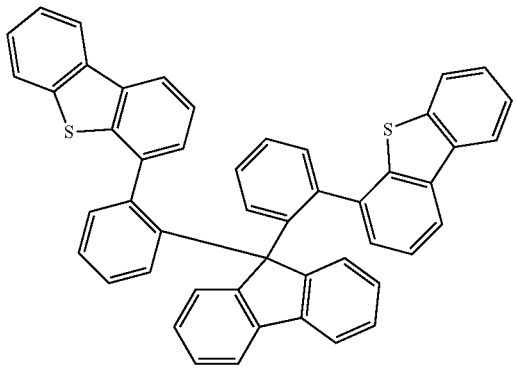
(163)
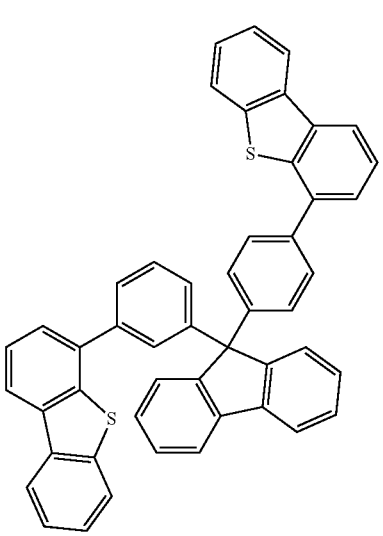
(164)
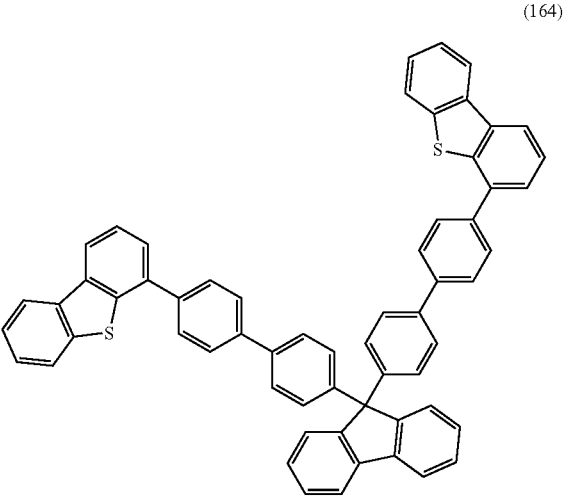

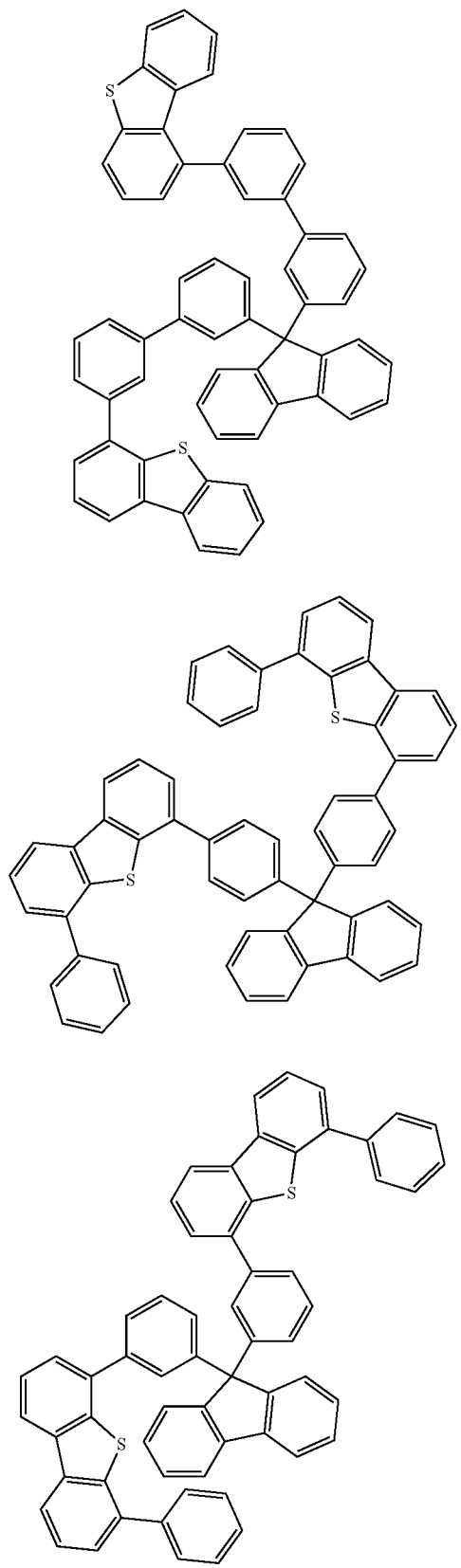
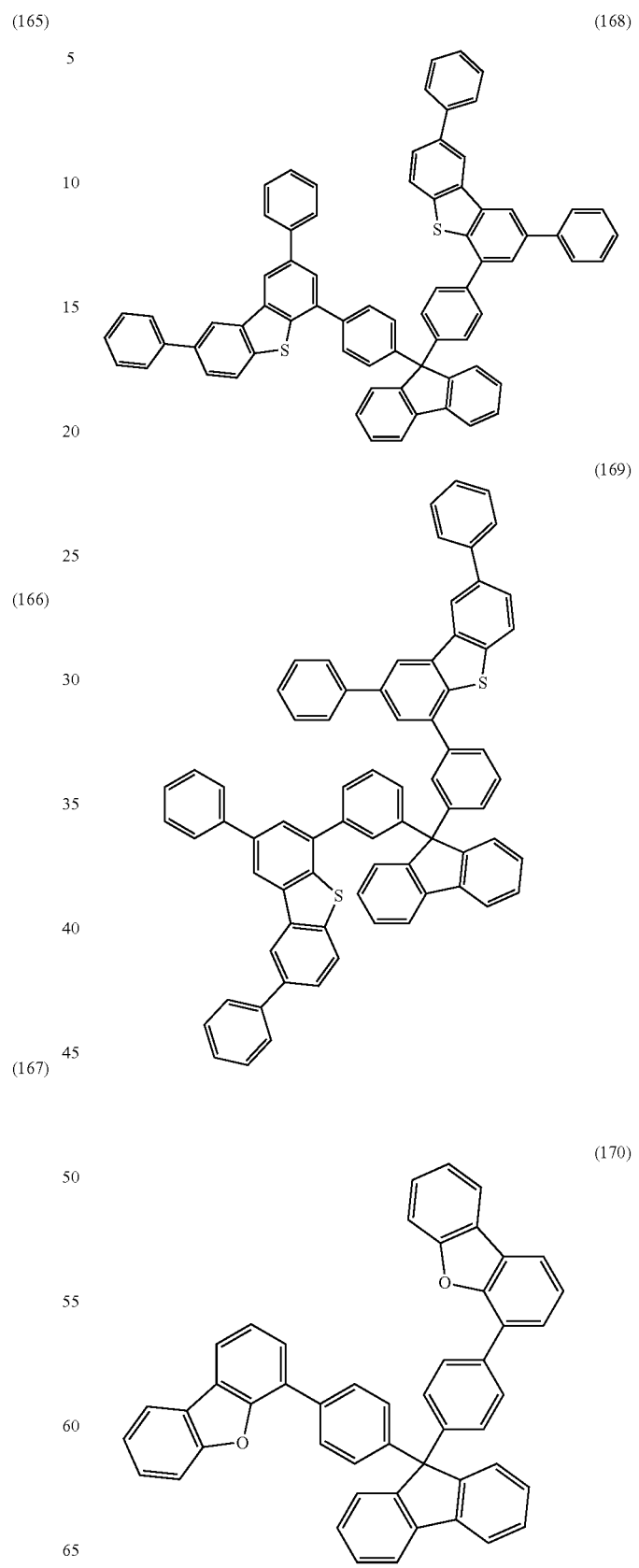

(171)
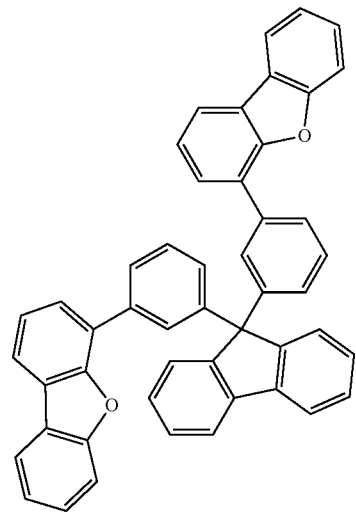
(172)
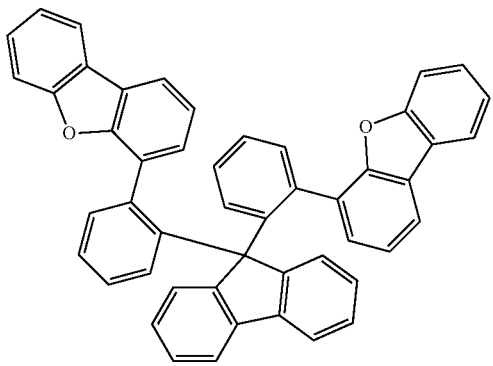
(173)
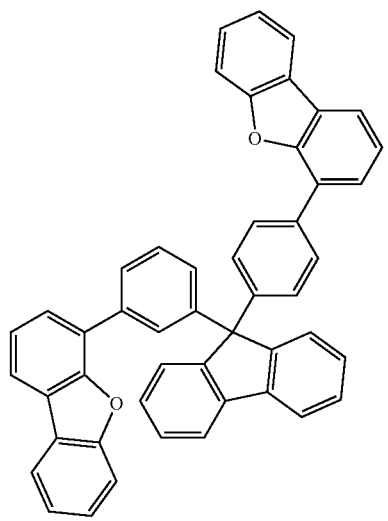
(174)
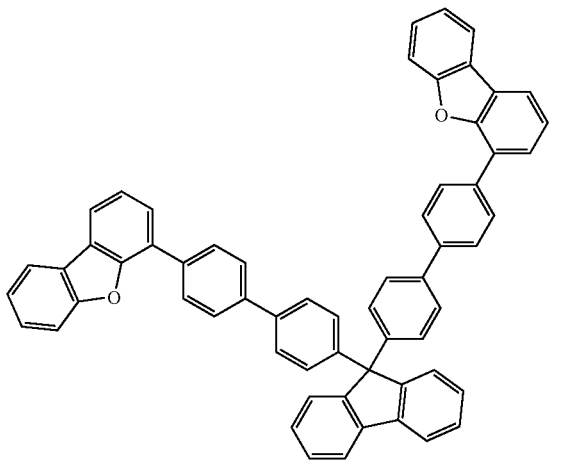
(175)
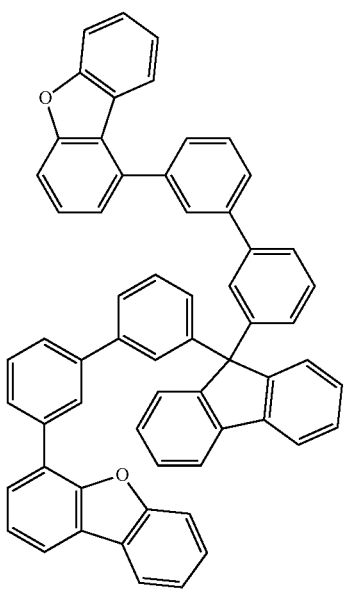
(176)
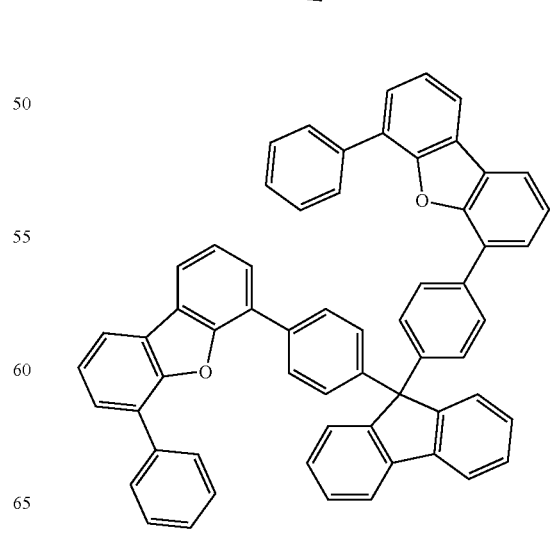

-continued
(177)
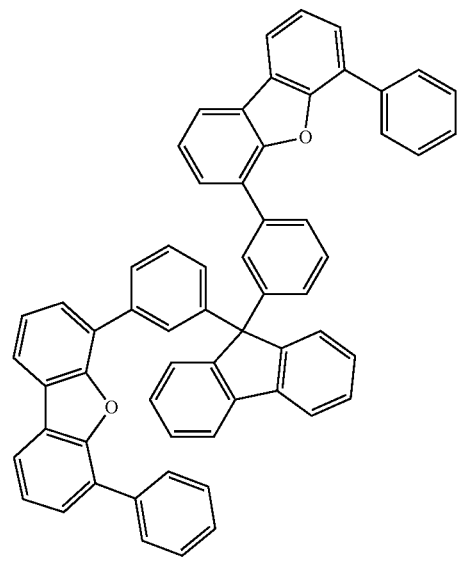
(178)
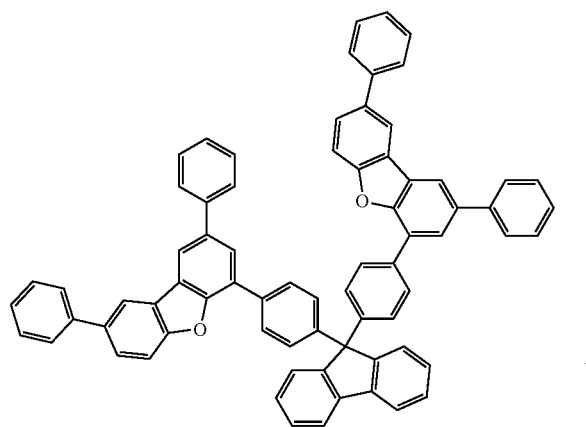
(179)
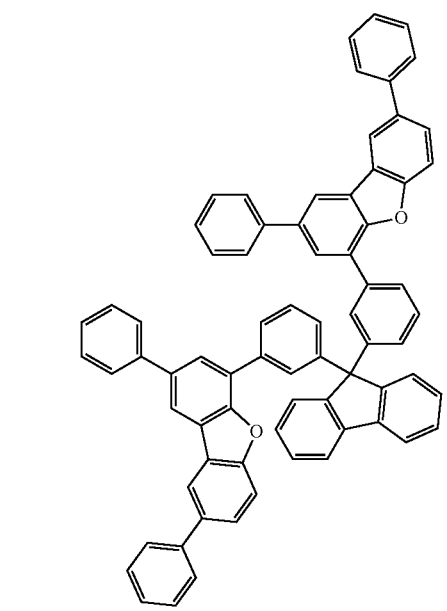
-continued
(180)
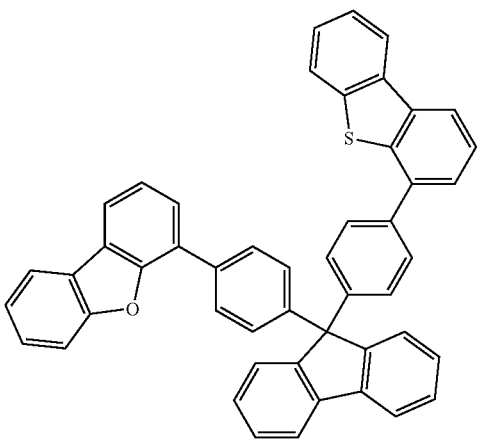
(181)
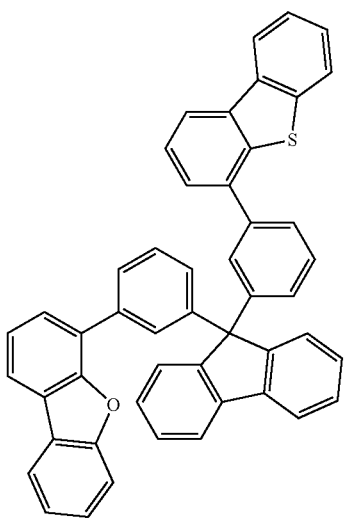
(182)
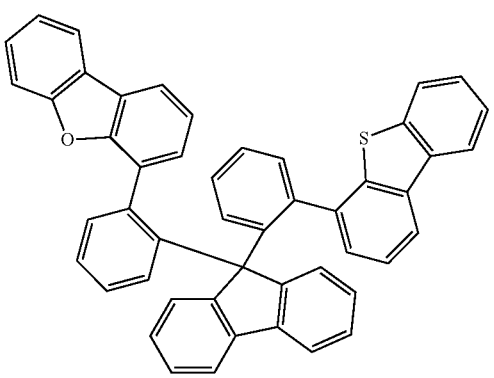

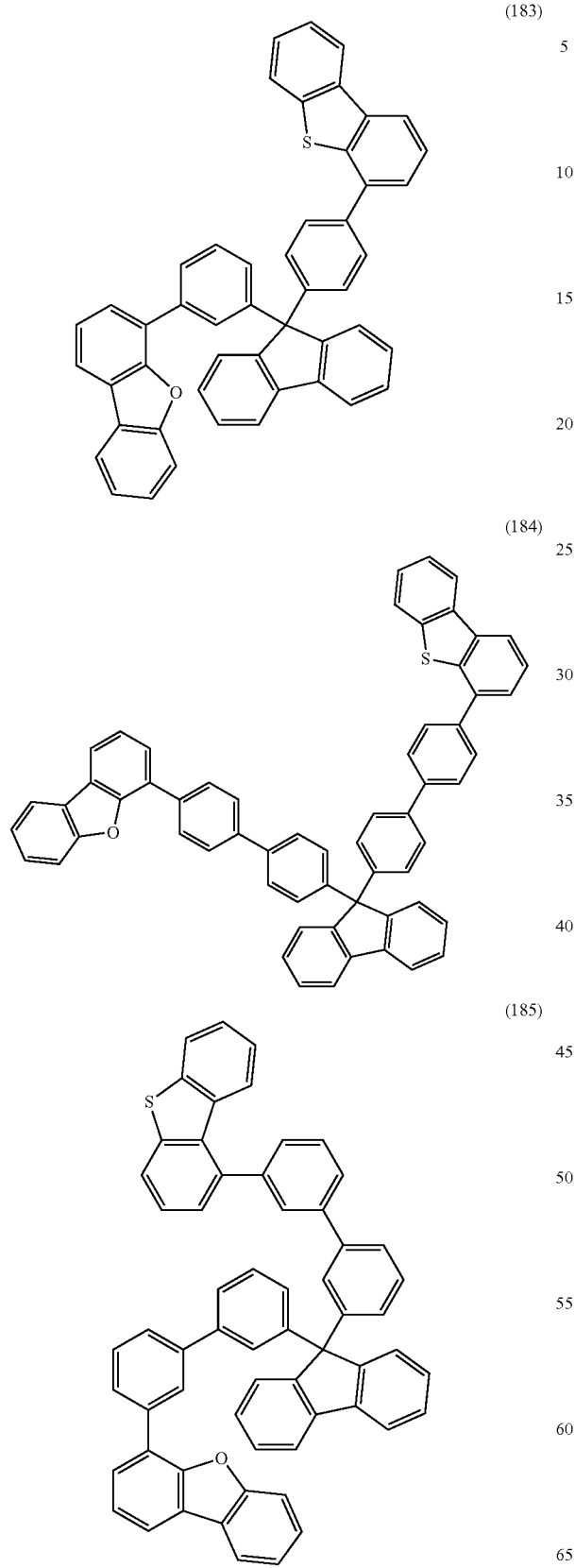
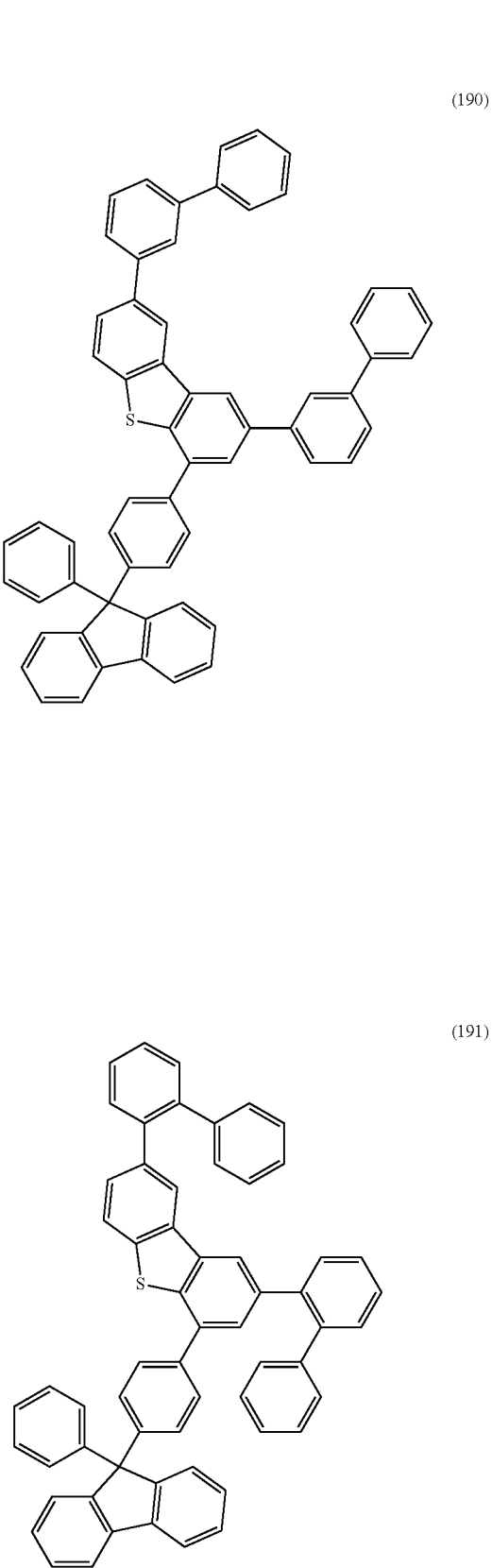

(192)
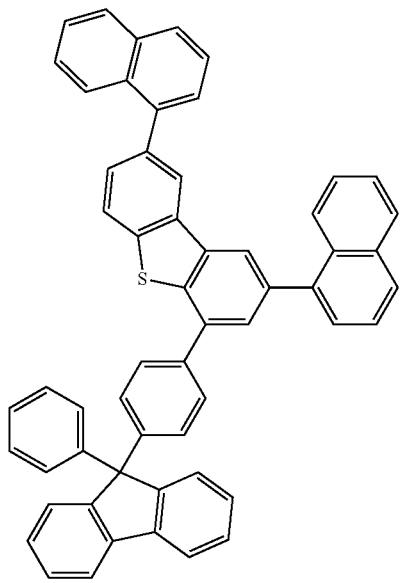
(193)
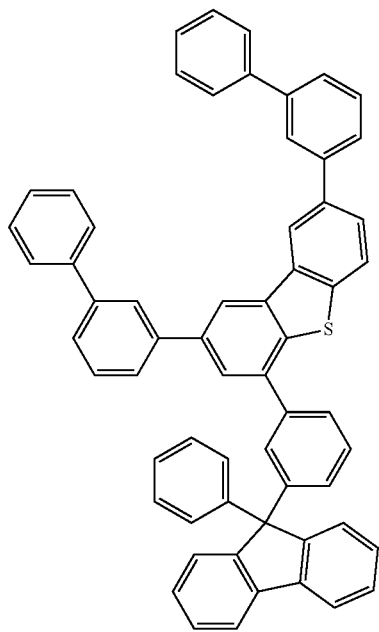
(194)
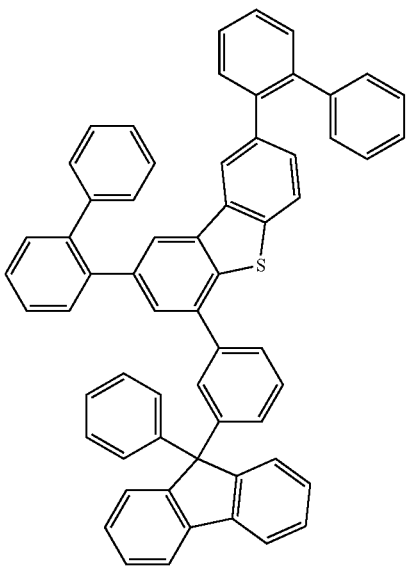
(195)
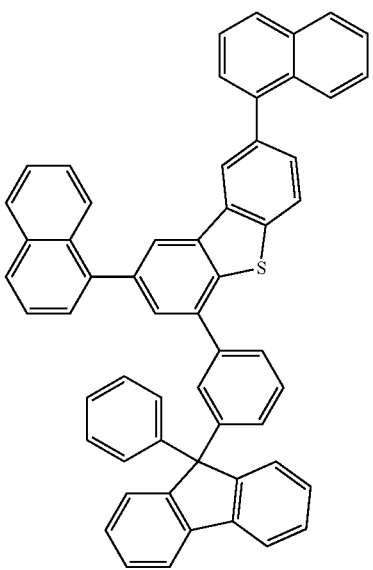

(196)
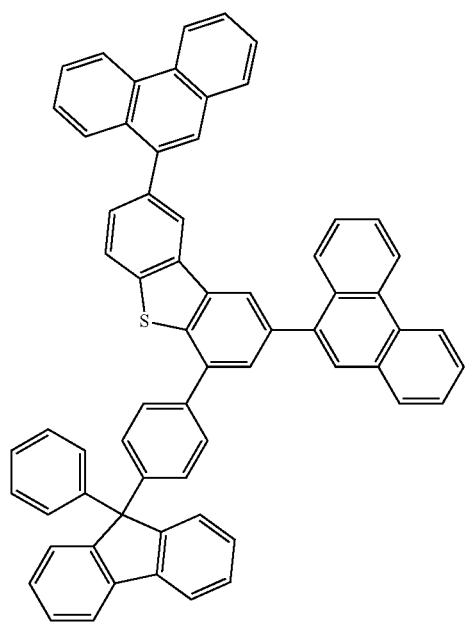
(197)
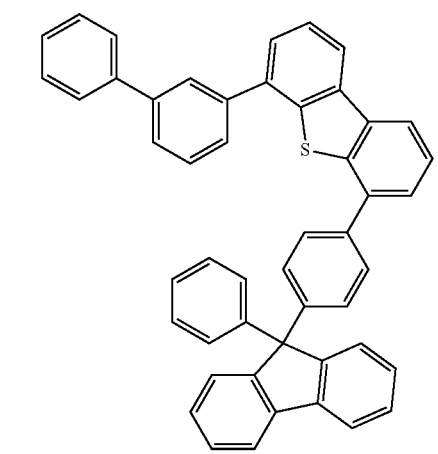
(198)
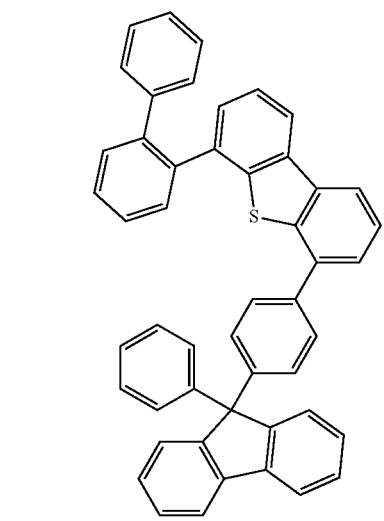
(199)
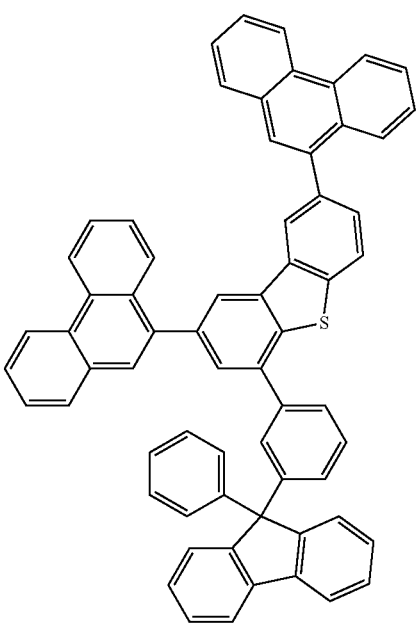
(200)
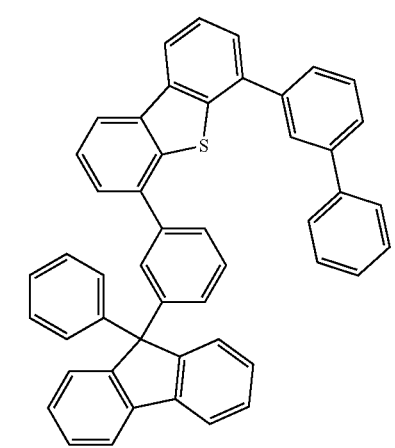
(201)
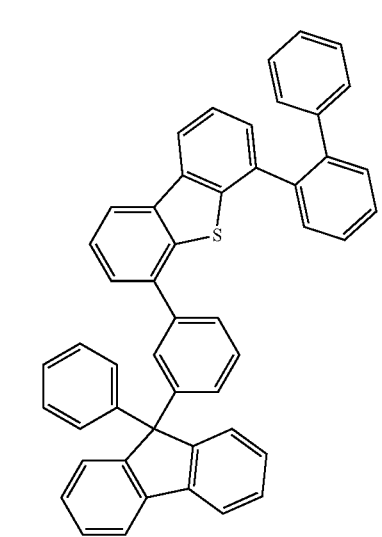

(210)
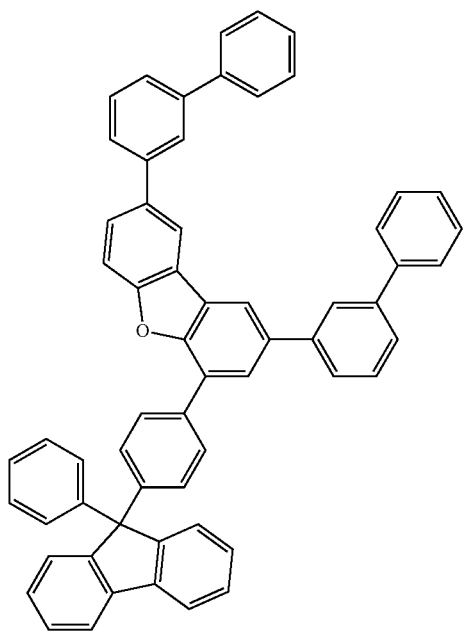
(211)
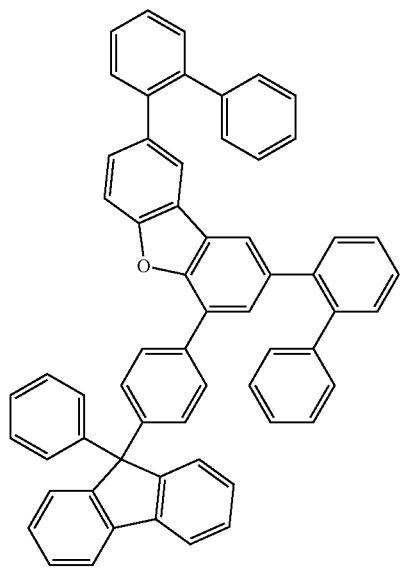
(212)
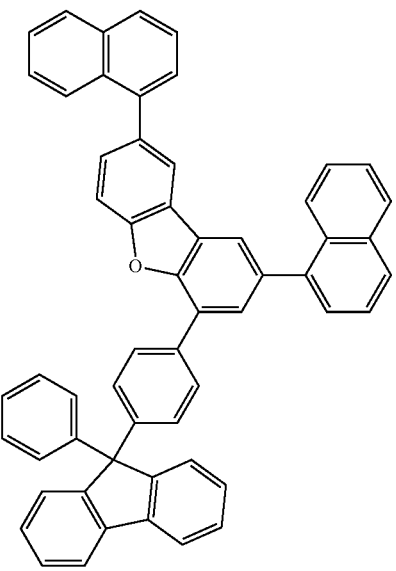
(213)
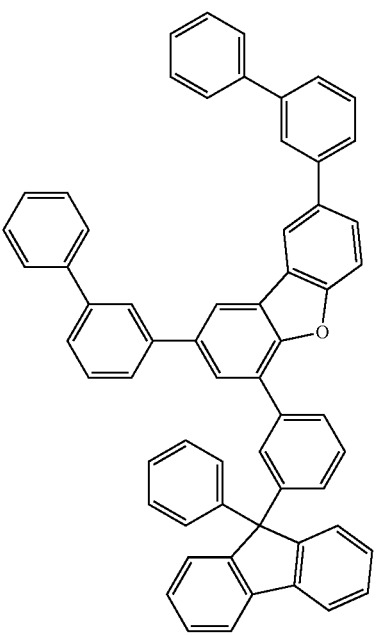

(214)
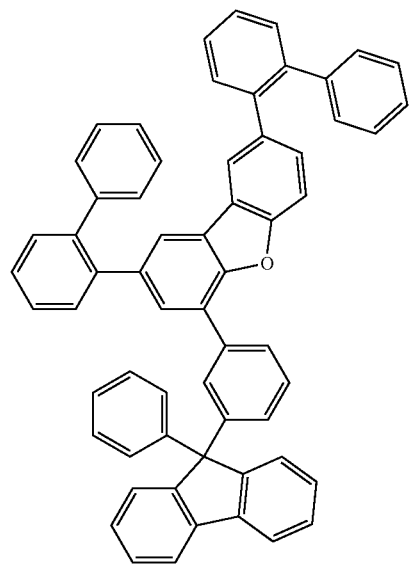
(215)
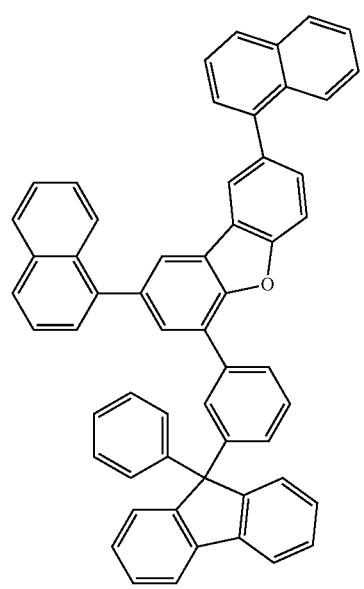
(216)
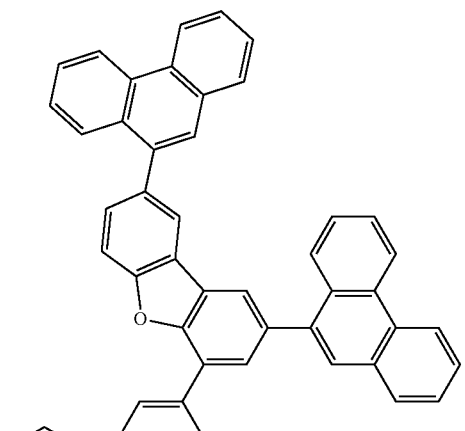
(217)
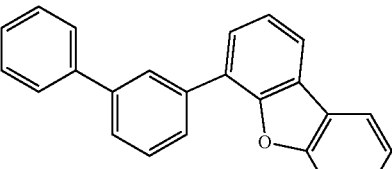
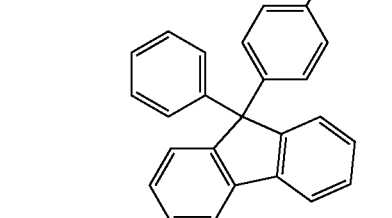
(218)
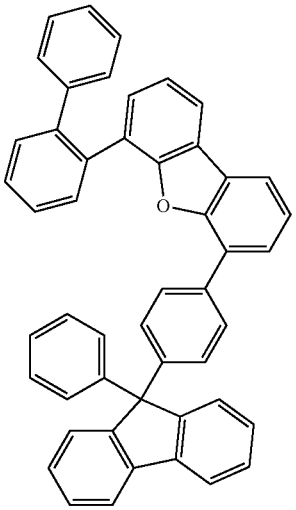

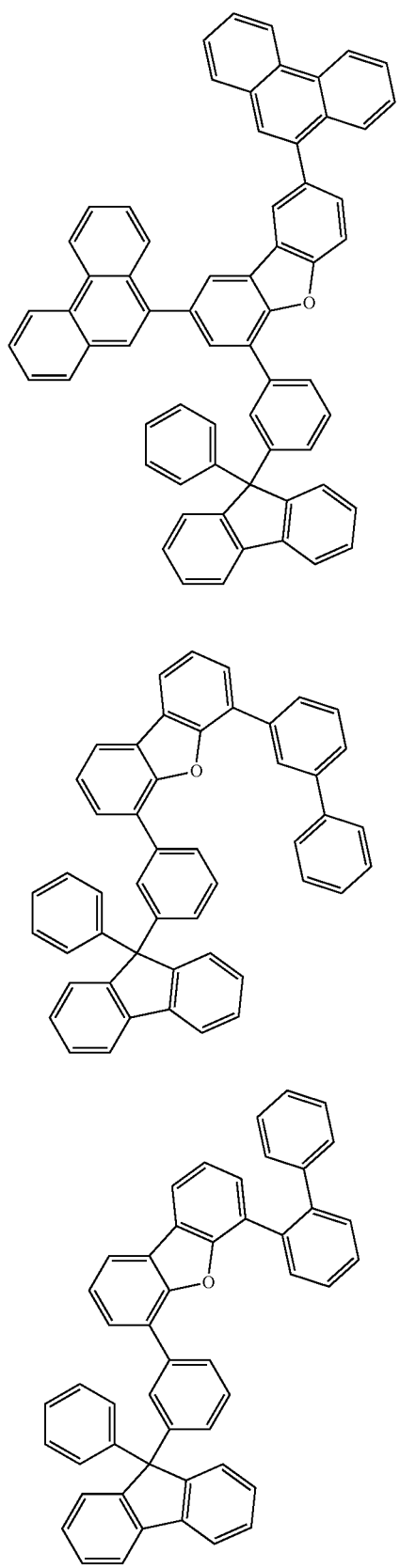
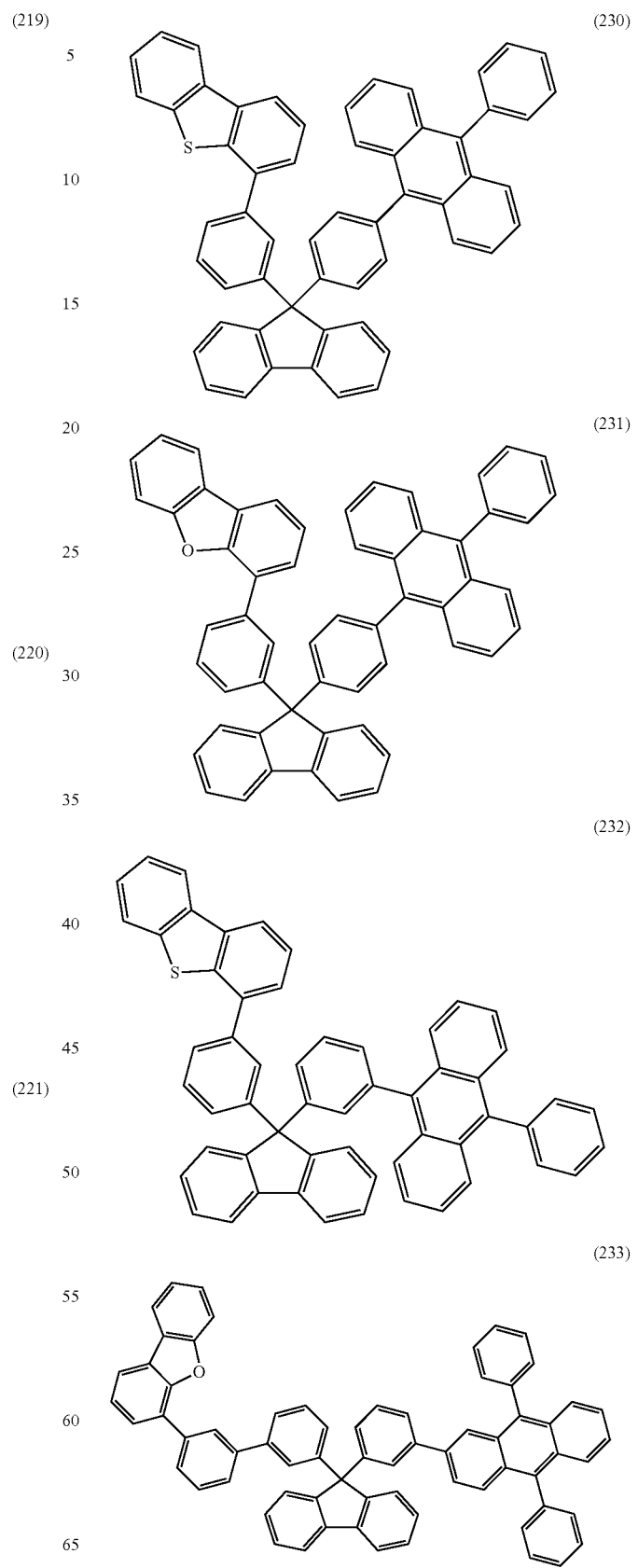

-continued (234)

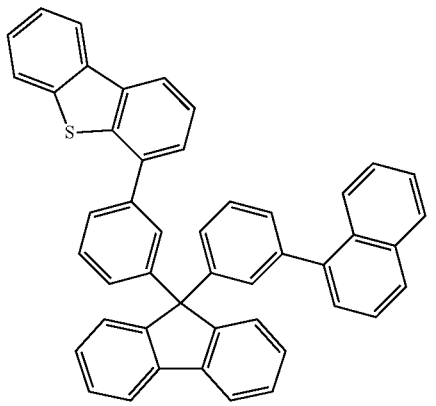

(235)

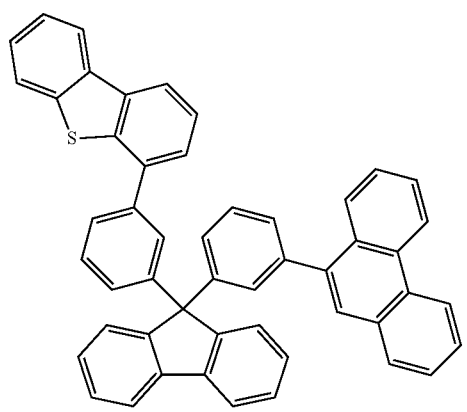

(236)

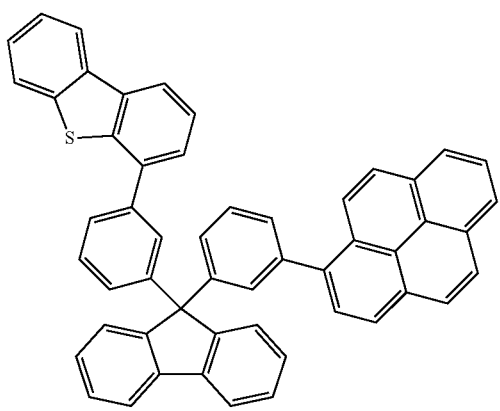

Furthermore, an organic compound used for the synthesis of a fluorene compound described in this embodiment is also a novel substance; therefore, the organic compound is also included in one embodiment of the present invention.

Thus, one embodiment of the present invention is an organic compound represented by a general formula (G2).

(G2)

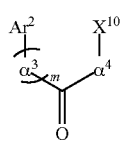

In the formula, $\alpha^3$ and $\alpha^4$ separately represent a substituted or unsubstituted arylene group having 6 to 13 carbon atoms; Ar² represents a substituted or unsubstituted aryl group having 7 to 18 carbon atoms, a substituted or unsubstituted 4-dibenzothiophenyl group, or a substituted or unsubstituted 4-dibenzofuranyl group; m represents 0 or 1; and $X^{10}$ represents chlorine, bromine, or iodine.

Another embodiment of the present invention is an organic compound represented by a general formula (G3).

(G3)

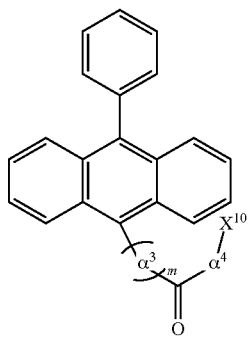

In the formula, $\alpha^3$ and $\alpha^4$ separately represent a substituted or unsubstituted arylene group having 6 to 13 carbon atoms; m represents 0 or 1; and $X^{10}$ represents chlorine, bromine, or iodine.

Another embodiment of the present invention is an organic compound represented by a structural formula (700).

(700)

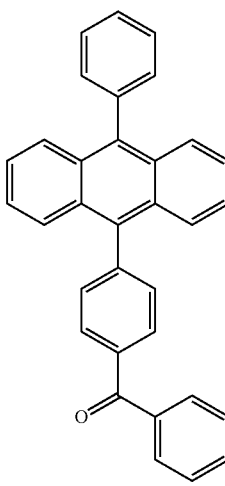

Another embodiment of the present invention is an organic compound represented by a general formula (G4).

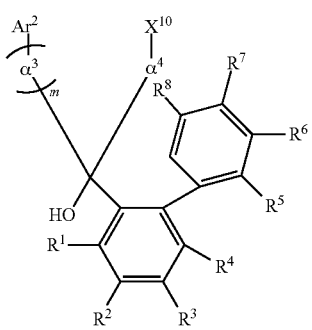

(G4)

In the formula, $\alpha^3$ and $\alpha^4$ separately represent a substituted or unsubstituted arylene group having 6 to 13 carbon atoms; $Ar^2$ represents a substituted or unsubstituted aryl group having 7 to 18 carbon atoms, a substituted or unsubstituted 4-dibenzothiophenyl group, or a substituted or unsubstituted 4-dibenzofuranyl group; m represents 0 or 1; $X^{10}$ represents chlorine, bromine, or iodine; and $R^1$ to $R^8$ separately represent hydrogen, an alkyl group having 1 to 12 carbon atoms, or an aryl group having 6 to 14 carbon atoms.

Another embodiment of the present invention is an organic compound represented by a general formula (G5).

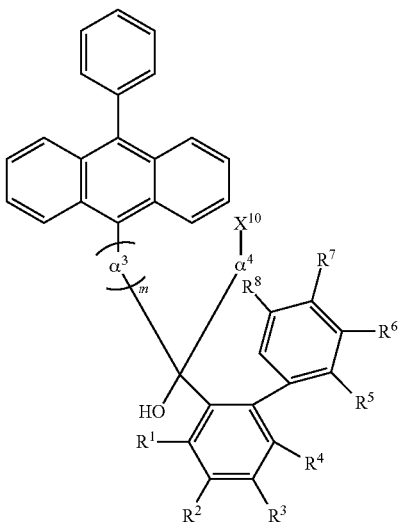

(G5)

In the formula, $\alpha^3$ and $\alpha^4$ separately represent a substituted or unsubstituted arylene group having 6 to 13 carbon atoms; m represents 0 or 1; $X^{10}$ represents chlorine, bromine, or iodine; and $R^1$ to $R^8$ separately represent hydrogen, an alkyl group having 1 to 12 carbon atoms, or an aryl group having 6 to 14 carbon atoms.

Another embodiment of the present invention is an organic compound represented by a structural formula (720).

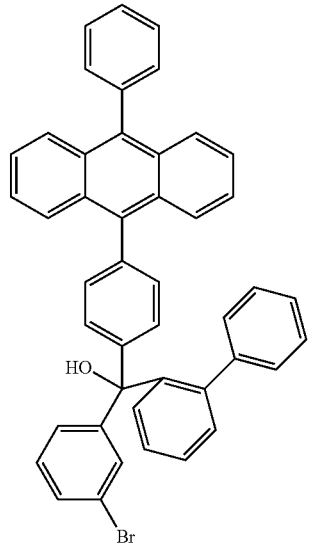

(720)

Thus, one embodiment of the present invention is an organic compound represented by a general formula (G6).

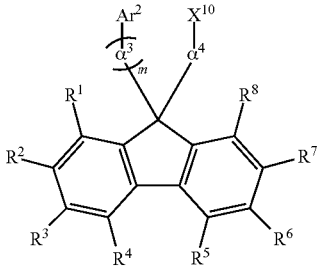

(G6)

In the formula, $\alpha^3$ and $\alpha^4$ separately represent a substituted or unsubstituted arylene group having 6 to 13 carbon atoms; $Ar^2$ represents a substituted or unsubstituted aryl group having 7 to 18 carbon atoms, a substituted or unsubstituted 4-dibenzothiophenyl group, or a substituted or unsubstituted 4-dibenzofuranyl group; m represents 0 or 1; $X^{10}$ represents chlorine, bromine, or iodine; and $R^1$ to $R^8$ separately represent hydrogen, an alkyl group having 1 to 12 carbon atoms, or an aryl group having 6 to 14 carbon atoms.

Another embodiment of the present invention is an organic compound represented by a general formula (G7).

(G7)

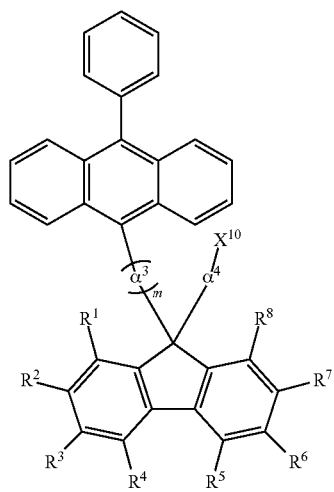

In the formula, $\alpha^3$ and $\alpha^4$ separately represent a substituted or unsubstituted arylene group having 6 to 13 carbon atoms; m represents 0 or 1; $X^{10}$ represents chlorine, bromine, or iodine; and $R^1$ to $R^8$ separately represent hydrogen, an alkyl group having 1 to 12 carbon atoms, or an aryl group having 6 to 14 carbon atoms.

Another embodiment of the present invention is an organic compound represented by a structural formula (740).

(740)

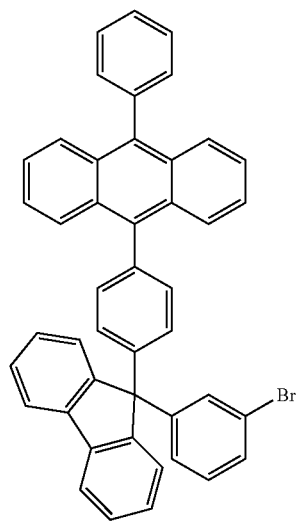

As an organic compound used in the synthesis of a fluorene compound of one embodiment of the present invention, an organic compound represented by any of structural formulae (700) to (710), (720) to (730), and (740) to (748) can be specifically given, for example. However, the present invention is not limited to these organic compounds.

(700)

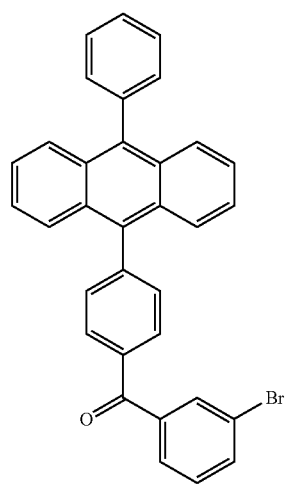

(701)

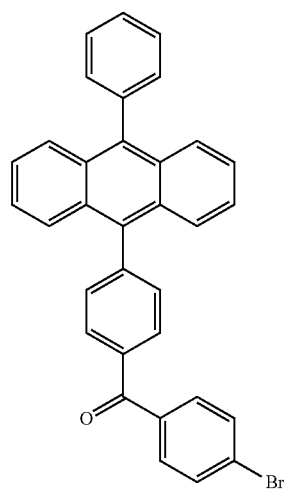

(702)

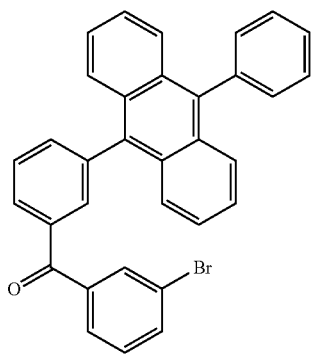

-continued
(703) 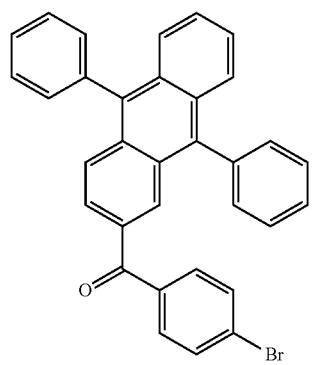
(704) 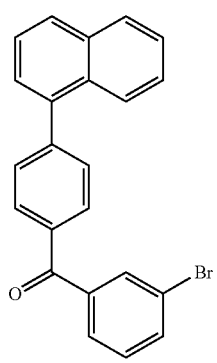
(705) 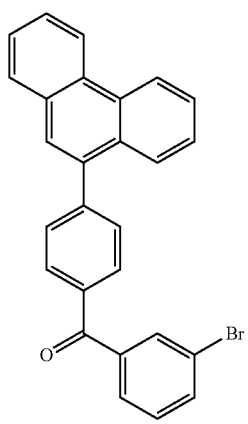
(706) 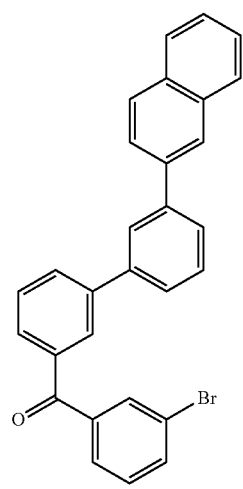
-continued
(707) 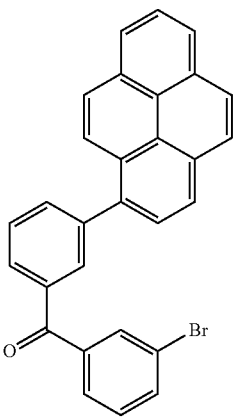
(708) 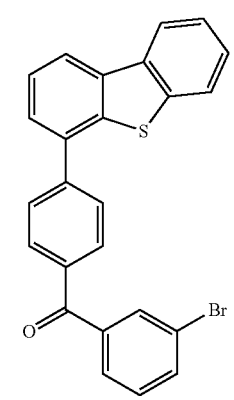
(709) 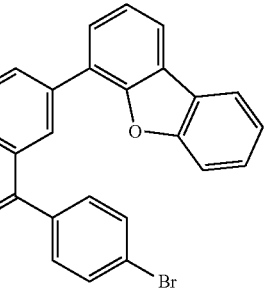
(710) 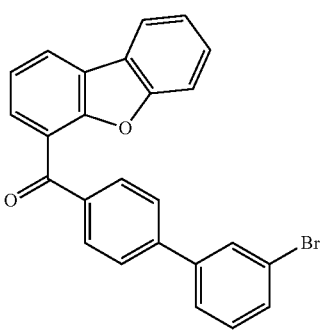

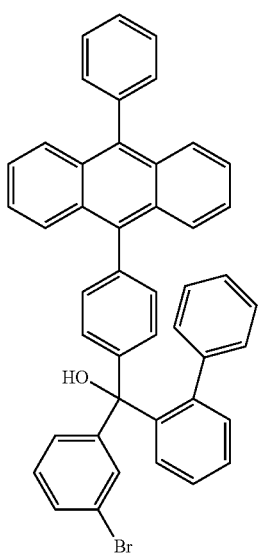
(720)
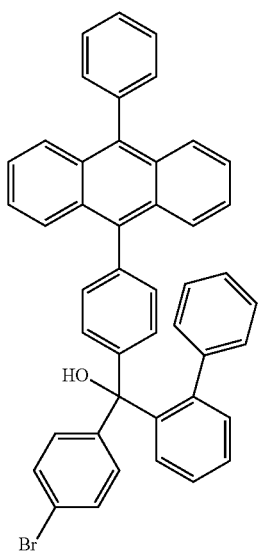
(721)
(722)
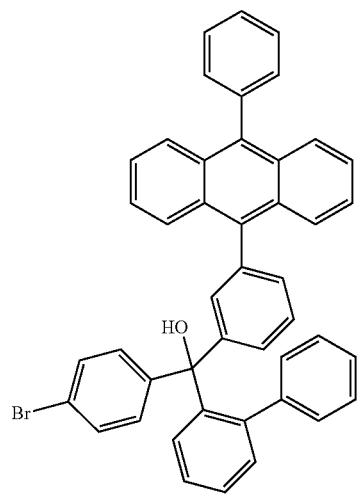
(723)
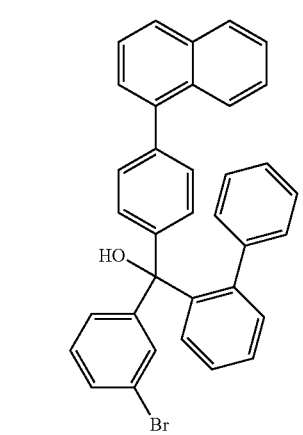
(724)
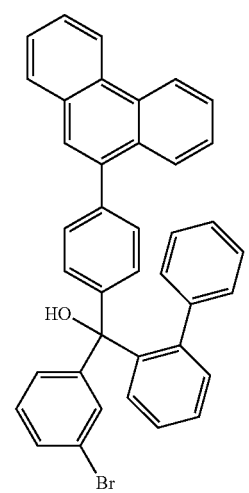
(725)

(726) 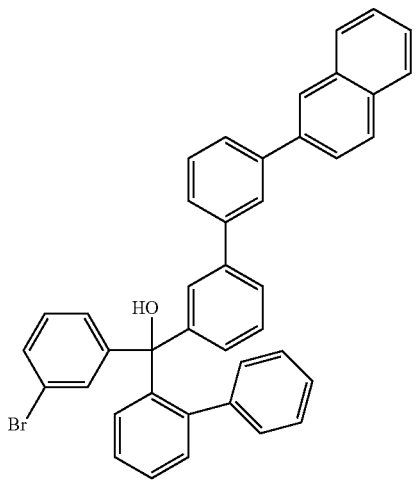
(727) 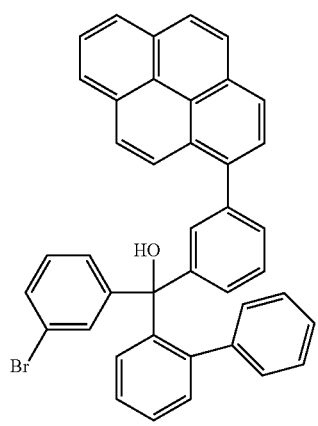
(728) 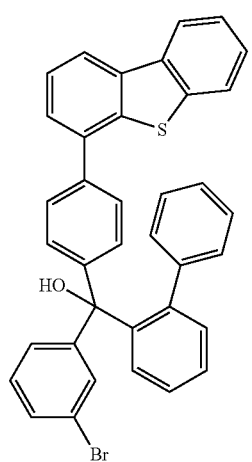
(729) 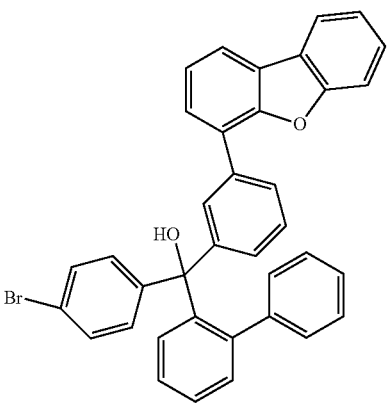
(730) 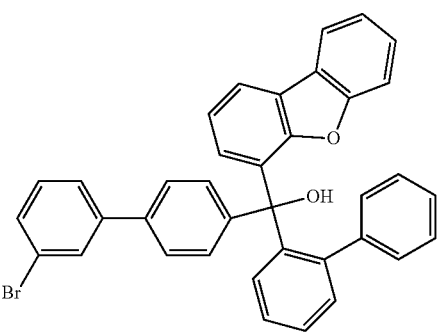
(740) 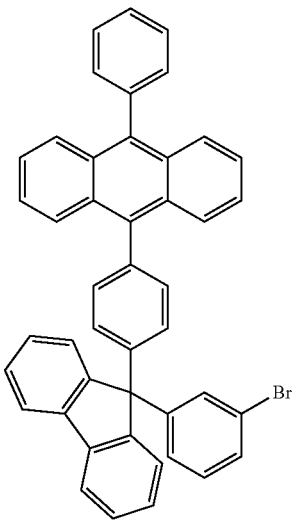
(741) 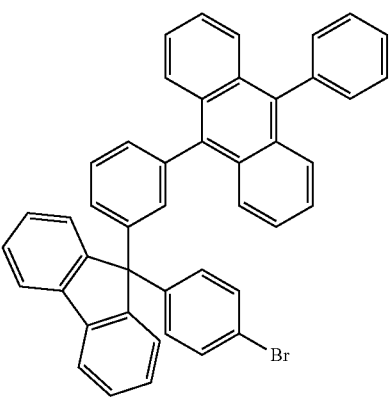

(742)

(743)

(744)

(745)

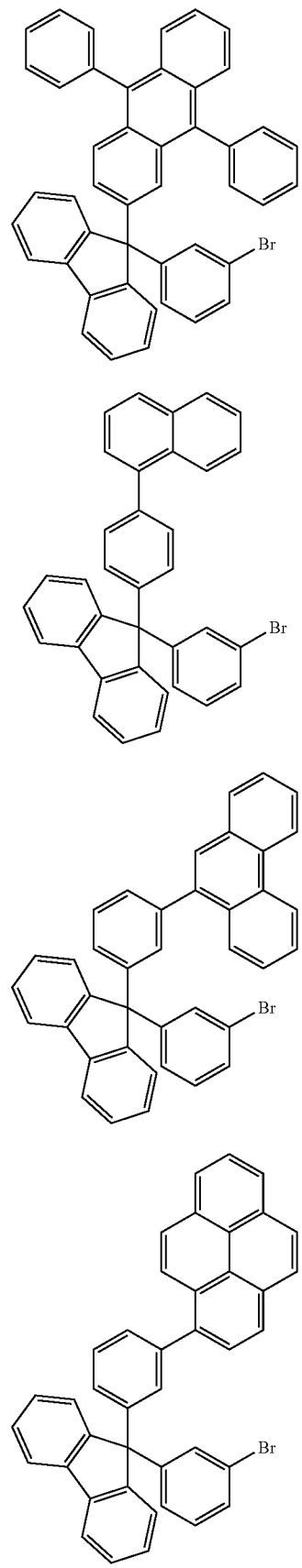

(746)

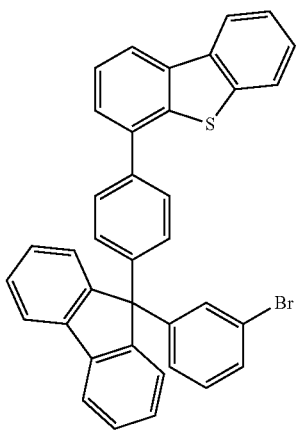

(747)

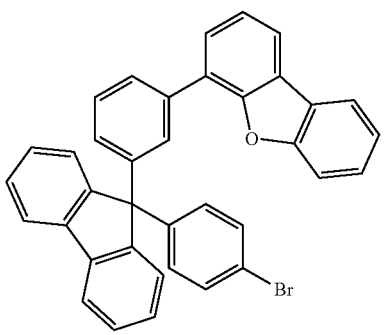

(748)

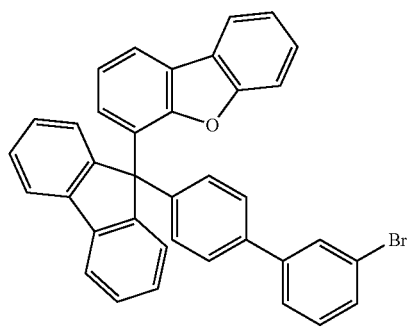

A variety of reactions can be applied to a method of synthesizing a fluorene compound of one embodiment of the present invention and to a method of synthesizing an organic compound used in the synthesis of the fluorene compound. For example, the fluorene compound of one embodiment of the present invention, represented by the general formula (G1), can be synthesized by synthesis methods described below. Note that a method of synthesizing a fluorene compound of one embodiment of the present invention is not limited to the synthesis methods described below.

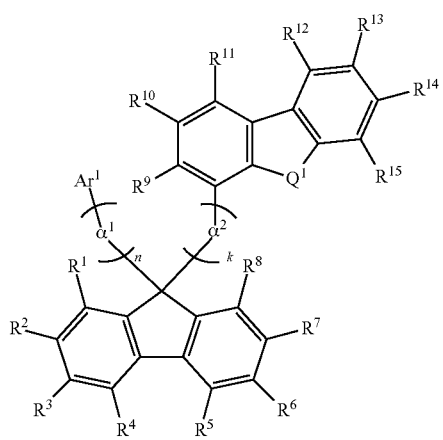

(G1)

In the general formula (G1), $\alpha^1$ and $\alpha^2$ separately represent a substituted or unsubstituted arylene group having 6 to 13 carbon atoms; $Ar^1$ represents a substituted or unsubstituted aryl group having 6 to 18 carbon atoms, a substituted or unsubstituted 4-dibenzothiophenyl group, or a substituted or unsubstituted 4-dibenzofuranyl group; n and k separately represent 0 or 1; $Q^1$ represents sulfur or oxygen; and $R^1$ to $R^{15}$ separately represent hydrogen, an alkyl group having 1 to 12 carbon atoms, or an aryl group having 6 to 14 carbon atoms.

<<Method 1 of Synthesizing Fluorene Compound Represented by General Formula (G1)>>

An example of a method of synthesizing the fluorene compound represented by the general formula (G1) will be described. Specifically, an example of a method of synthesizing a fluorene compound with k=1 in the general formula (G1) will be described.

<Step 1>

As illustrated in the following synthesis scheme A-1), after an aryl halide compound (a1) is lithiated or after a Grignard reagent is prepared from the aryl halide compound (a1), a reaction with an aryl carbonyl halogen compound (a2) is caused, whereby a diaryl ketone halide compound (a3) can be obtained.

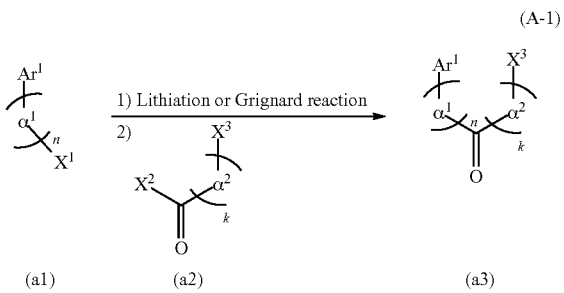

(A-1)

In the synthesis scheme (A-1), $\alpha^1$ and $\alpha^2$ separately represent a substituted or unsubstituted arylene group having 6 to 13 carbon atoms; $Ar^1$ represents a substituted or unsubstituted aryl group having 6 to 18 carbon atoms, a substituted or unsubstituted 4-dibenzothiophenyl group, or a substituted or unsubstituted 4-dibenzofuranyl group; n represents 0 or 1; k represents 1; and $X^1$, $X^2$, and $X^3$ separately represent a halogen. $X^1$ preferably represents bromine or iodine, which has high reactivity, more preferably iodine. $X^2$ preferably represents chlorine, which increases the stability of the compound (a2).

In the synthesis scheme (A-1), after an aryl compound having a halogen group is activated, a reaction with a carbonyl halogen compound is caused, whereby a diaryl ketone compound can be obtained.

Examples of the activation include a lithiation reaction with an alkyl lithium reagent and a reaction preparing a Grignard reagent with activated magnesium. As alkyl lithium, n-butyllithium, tert-butyllithium, methyllithium, and the like can be given. As a neutralizing acid, a hydrochloric acid or the like can be used. As a solvent, a dehydrated solvent can be used, and ethers such as diethyl ether and tetrahydrofuran (THF) can be used.

<Step 2>

Next, as illustrated in the following synthesis scheme (A-2), after a 1-biphenyl halide compound (a4) is lithiated or after a Grignard reagent is prepared from the 1-biphenyl halide compound (a4), a reaction with the diaryl ketone halide compound (a3) is caused, whereby a diaryl halide fluorene compound (a5) can be obtained.

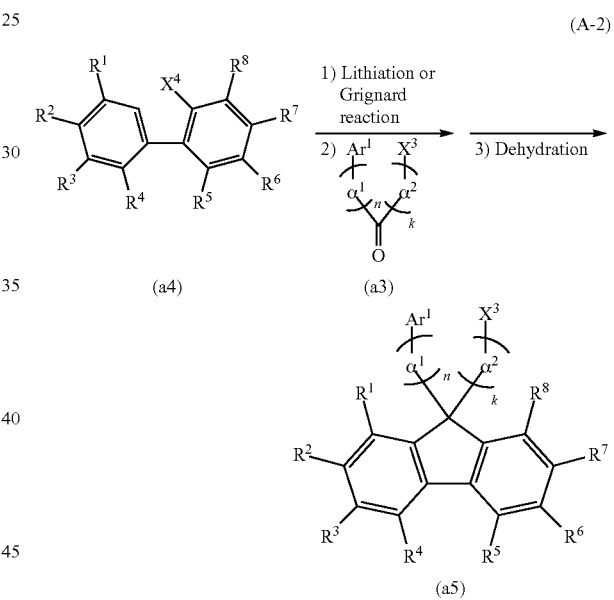

(A-2)

In the synthesis scheme (A-2), $\alpha^1$ and $\alpha^2$ separately represent a substituted or unsubstituted arylene group having 6 to 13 carbon atoms; $Ar^1$ represents a substituted or unsubstituted aryl group having 6 to 18 carbon atoms, a substituted or unsubstituted 4-dibenzothiophenyl group, or a substituted or unsubstituted 4-dibenzofuranyl group; $R^1$ to $R^8$ separately represent hydrogen, an alkyl group having 1 to 12 carbon atoms, or an aryl group having 6 to 14 carbon atoms; n represents 0 or 1; k represents 1; and $X^3$ and $X^4$ separately represent a halogen. $X^4$ preferably represents bromine or iodine, which has high reactivity, more preferably iodine.

In the synthesis scheme (A-2), an aryl compound having a halogen group is activated, the resulting substance is reacted with a ketone compound to give an aryl alcohol compound, and an acid is added to perform dehydration, whereby a fluorene compound can be prepared.

Examples of the activation include a lithiation reaction with an alkyl lithium reagent and a reaction preparing a Grignard reagent with activated magnesium. As alkyl lithium, n-butyllithium, tert-butyllithium, methyllithium, and the like can be given. As the acid, a hydrochloric acid or the like can be used. As the solvent, a dehydrated solvent can be used, and ethers such as diethyl ether and tetrahydrofuran (THF) can be used.

<Step 3>

Furthermore, as illustrated in the following synthesis scheme (A-3), the diaryl halide fluorene compound (a5) and a boron compound (a6) are coupled, whereby the fluorene compound represented by the general formula (G1) can be obtained.

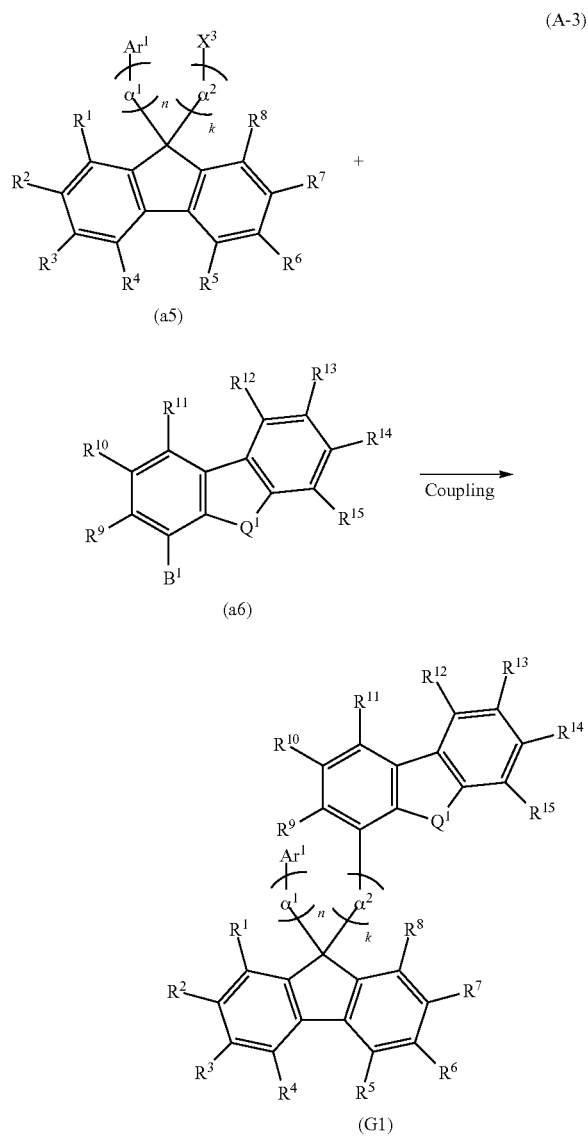

In the synthesis scheme (A-3), $\alpha^1$ and $\alpha^2$ separately represent a substituted or unsubstituted arylene group having 6 to 13 carbon atoms; $Ar^1$ represents a substituted or unsubstituted aryl group having 6 to 18 carbon atoms, a substituted or unsubstituted 4-dibenzothiophenyl group, or a substituted or unsubstituted 4-dibenzofuranyl group; $R^1$ to $R^{15}$ separately represent hydrogen, an alkyl group having 1 to 12 carbon atoms, or an aryl group having 6 to 14 carbon atoms; n represents 0 or 1; k represents 1; $Q^1$ represents sulfur or oxygen; $X^3$ represents a halogen; and $B^1$ represents a boronic acid or dialkoxyboron. $X^3$ preferably represents bromine or iodine, which has high reactivity, more preferably iodine.

Note that there are a variety of reaction conditions for the coupling reaction in the synthesis scheme (A-3). As an example, a synthesis method using a metal catalyst in the presence of a base can be employed.

In this embodiment, the case where a Suzuki-Miyaura reaction is performed in the synthesis scheme (A-3) is described. A palladium catalyst can be used as the metal catalyst, and a mixture of a palladium complex and a ligand thereof can be used as the palladium catalyst. As the palladium complex, palladium(II) acetate, tetrakis(triphenylphosphine)palladium(0), bis(triphenylphosphine)palladium(II) dichloride, and the like can be given. As the ligand, tri(ortho-tolyl)phosphine, triphenylphosphine, tricyclohexylphosphine, and the like can be given.

As a substance which can be used as the base, an organic base such as sodium tert-butoxide, an inorganic base such as potassium carbonate, and the like can be given. The reaction is preferably performed in a solution. Examples of a solvent that can be used are, but not limited to, the following solvents: a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and the like. However, the catalyst, base, and solvent which can be used are not limited thereto.

In the synthesis scheme (A-3), instead of the boron compound, aryl aluminum, aryl zirconium, aryl zinc, aryl tin, or the like may be used. In addition, the reaction in the synthesis scheme (A-3) is preferably performed under an inert atmosphere of nitrogen, argon, or the like.

In the scheme (A-3), the halogen group $X^3$ of the compound (a5) and the boron compound group $B^1$ of the compound (a6) are reacted. The fluorene compound represented by the general formula (G1) can also be obtained when the compound (a5) having the boron compound group $B^1$ and the compound (a6) having the halogen group $X^3$ are coupled (even when the reaction groups are exchanged).

Thus, the fluorene compound of this embodiment can be synthesized.

<<Method 2 of Synthesizing Fluorene Compound Represented by General Formula (G1)>>

Another example of a method of synthesizing the fluorene compound represented by the general formula (G1) will be described. Specifically, an example of a method of synthesizing a fluorene compound with n=1 in the general formula (G1) will be described.

<Step 1>

As illustrated in the following synthesis scheme (B-1), after an aryl dihalide compound (a7) is lithiated or after a Grignard reagent is prepared from the aryl dihalide compound (a7), a reaction with the aryl carbonyl halogen compound (a2) is caused, whereby a diaryl ketone dihalide compound (a8) can be obtained.

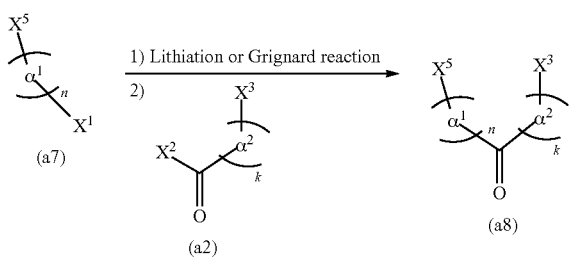

(B-1)

(a7) → (a2) → (a8)

In the synthesis scheme (B-1), $\alpha^1$ and $\alpha^2$ separately represent a substituted or unsubstituted arylene group having 6 to 13 carbon atoms; n represents 1; k represents 0 or 1; and $X^1$, $X^2$, $X^3$, and $X^5$ separately represent a halogen. $X^1$ preferably represents bromine or iodine, which has high reactivity, more preferably iodine. $X^2$ preferably represents chlorine, which increases the stability of the compound (a2).

In the synthesis scheme (B-1), as in the synthesis scheme (A-1), after an aryl compound having a halogen group is activated, a reaction with a carbonyl halogen compound is caused, whereby a diaryl ketone compound can be obtained. The synthesis scheme (A-1) can be referred to for details.

<Step 2>

Next, as illustrated in the following synthesis scheme (B-2), after the 1-biphenyl halide compound (a4) is lithiated or after a Grignard reagent is prepared from the 1-biphenyl halide compound (a4), a reaction with the diaryl ketone dihalide compound (a8) is caused, whereby a diaryl dihalide fluorene compound (a9) can be obtained.

In the synthesis scheme (B-2), $\alpha^1$ and $\alpha^2$ separately represent a substituted or unsubstituted arylene group having 6 to 13 carbon atoms; $R^1$ to $R^8$ separately represent hydrogen, an alkyl group having 1 to 12 carbon atoms, or an aryl group having 6 to 14 carbon atoms; n represents 1; k represents 0 or 1; and $X^3$, $X^4$, and $X^5$ separately represent a halogen. $X^4$ preferably represents bromine or iodine, which has high reactivity, more preferably iodine.

In the synthesis scheme (B-2), as in the synthesis scheme (A-2), an aryl compound having a halogen group is activated, the resulting substance is reacted with a ketone compound to give an aryl alcohol compound, and an acid is added to perform dehydration, whereby a fluorene compound can be prepared. The synthesis scheme (A-2) can be referred to for details.

<Step 3>

Next, as illustrated in the following synthesis scheme (B-3), the diaryl dihalide fluorene compound (a9) and the boron compound (a6) are coupled, whereby a diaryl halide fluorene compound (a10) can be obtained.

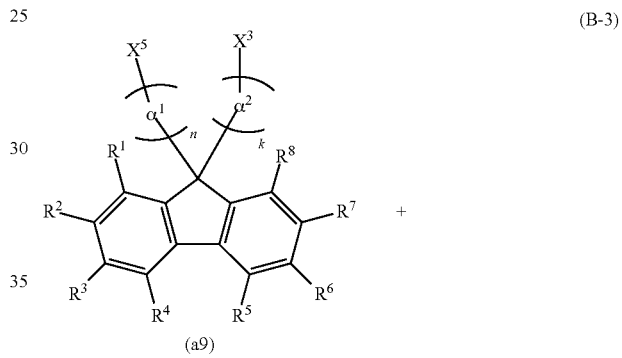

(B-3)

(a9) +

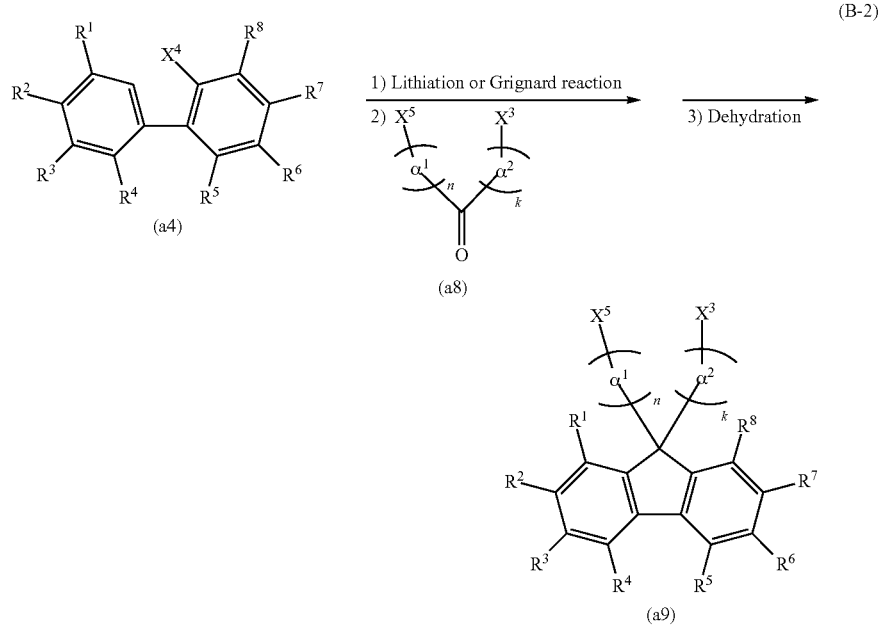

(B-2)

(a4) → (a8) → (a9)

Step 4

Next, as illustrated in the following synthesis scheme (B-4), the diaryl halide fluorene compound (a10) and a boron compound (a11) are coupled, whereby the fluorene compound represented by the general formula (G1) can be obtained.

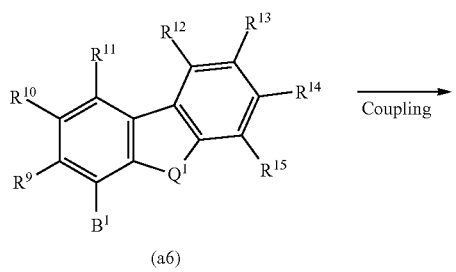

(a6)

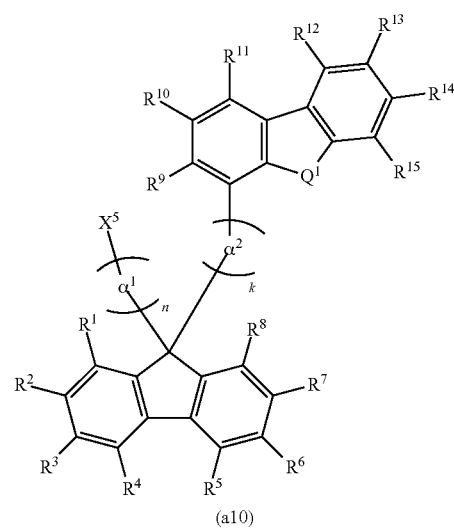

(a10)

In the synthesis scheme (B-3), $\alpha^1$ and $\alpha^2$ separately represent a substituted or unsubstituted arylene group having 6 to 13 carbon atoms; $R^1$ to $R^{15}$ separately represent hydrogen, an alkyl group having 1 to 12 carbon atoms, or an aryl group having 6 to 14 carbon atoms; n represents 1; k represents 0 or 1; $Q^1$ represents sulfur or oxygen; and $X^3$ and $X^5$ separately represent a halogen. $X^3$ and $X^5$ preferably represent bromine or iodine, which has high reactivity, more preferably iodine. In order to selectivlly react the compound (a6) with $X^3$ of the compound (a9), $X^3$ is preferably a halogen having higher reactivity than $X^5$ (for example, in the case where $X^5$ is chlorine, $X^3$ is preferably bromine or iodine, whereas in the case where $X^5$ is bromine, $X^3$ is preferably iodine). $B^1$ represents a boronic acid or dialkoxyboron.

Note that there are a variety of reaction conditions for the coupling reaction in the synthesis scheme (B-3). As an example, a synthesis method using a metal catalyst in the presence of a base can be employed. Since the synthesis can be performed under conditions similar to those in the synthesis scheme (A-3), the synthesis scheme (A-3) can be referred to for details.

(B-4)

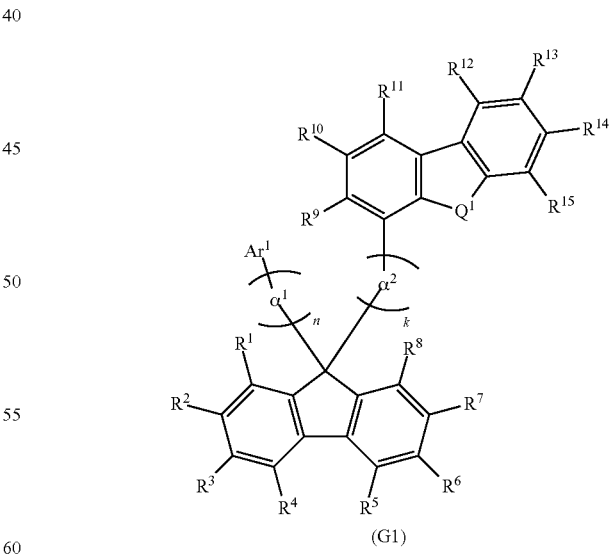

(a10)

(a11)

(G1)

In the synthesis scheme (B-4), $\alpha^1$ and $\alpha^2$ separately represent a substituted or unsubstituted arylene group having 6 to 13 carbon atoms; $Ar^1$ represents a substituted or unsubstituted aryl group having 6 to 18 carbon atoms, a substituted or unsubstituted 4-dibenzothiophenyl group, or a substituted or unsubstituted 4-dibenzofuranyl group; $R^1$ to $R^{15}$ separately represent hydrogen, an alkyl group having 1 to 12 carbon atoms, or an aryl group having 6 to 14 carbon atoms; n represents 1; k represents 0 or 1; $Q^1$ represents sulfur or oxygen; and $X^5$ represents a halogen. $X^5$ preferably represents bromine or iodine, which has high reactivity, more preferably iodine. $B^2$ represents a boronic acid or dialkoxyboron.

Note that there are a variety of reaction conditions for the coupling reaction in the synthesis scheme (B-4). As an example, a synthesis method using a metal catalyst in the presence of a base can be employed. Since the synthesis can be performed under conditions similar to those in the synthesis scheme (A-3), the synthesis scheme (A-3) can be referred to for details.

In the synthesis schemes (B-3) and (B-4), coupling reactions with the compound (a6) and the compound (a11) are caused in this order. The fluorene compound represented by the general formula (G1) can also be obtained by causing coupling reactions with the compound (a11) and the compound (a6) in this order.

In the case where the compound (a6) and the compound (a11) in the synthesis schemes (B-3) and (B-4) are the same compound (in the case where these compounds are identical except the reaction groups represented by $B^1$ and $B^2$), the fluorene compound represented by the general formula (G1) can also be obtained by causing a reaction using two or more equivalents of the compound (a6) with respect to the compound (a9) (or by adding both the compound (a6) and the compound (a11) to the compound (a9) at the same time). It is preferable to employ this reaction because the synthesis can be simplified.

As in the synthesis scheme (A-3), the fluorene compound represented by the general formula (G1) can also be obtained by coupling according to the synthesis schemes (B-3) and (B-4) with the reaction groups interchanged with each other.

Thus, the fluorene compound of this embodiment can be synthesized.

<<Method 3 of Synthesizing Fluorene Compound Represented by General Formula (G1)>>

Still another example of a method of synthesizing the fluorene compound represented by the general formula (G1) will be described.

<Step 1>

As illustrated in the following synthesis scheme (C-1), after the aryl halide compound (a1) is lithiated or after a Grignard reagent is prepared from the aryl halide compound (a1), a reaction with an aryl carbonyl halogen compound (a12) is caused, whereby a diaryl ketone compound (a13) can be obtained.

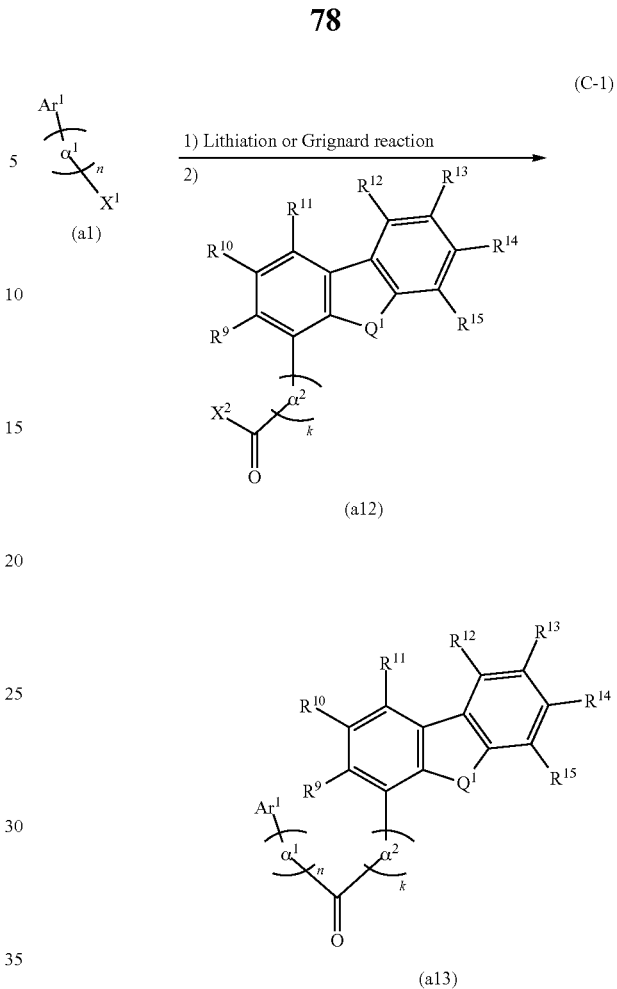

In the synthesis scheme (C-1), $\alpha^1$ and $\alpha^2$ separately represent a substituted or unsubstituted arylene group having 6 to 13 carbon atoms; $Ar'$ represents a substituted or unsubstituted aryl group having 6 to 18 carbon atoms, a substituted or unsubstituted 4-dibenzothiophenyl group; or a substituted or unsubstituted 4-dibenzofuranyl group; $R^9$ to $R^{15}$ separately represent hydrogen, an alkyl group having 1 to 12 carbon atoms, or an aryl group having 6 to 14 carbon atoms; n and k separately represent 0 or 1; $Q^1$ represents sulfur or oxygen; and $X^1$ and $X^2$ separately represent a halogen. $X^1$ preferably represents bromine or iodine, which has high reactivity, more preferably iodine. $X^2$ preferably represents chlorine, which increases the stability of the compound (a12).

In the synthesis scheme (C-1), as in the synthesis scheme (A-1), after an aryl compound having a halogen group is activated, a reaction with a carbonyl halogen compound is caused, whereby a diaryl ketone compound can be obtained. The synthesis scheme (A-1) can be referred to for details.

<Step 2>

Next, as illustrated in the following synthesis scheme (C-2), after the 1-biphenyl halide compound (a4) is lithiated or after a Grignard reagent is prepared from the 1-biphenyl halide compound (a4), a reaction with the diaryl ketone compound (a13) is caused, whereby the fluorene compound represented by the general formula (G1) can be obtained.

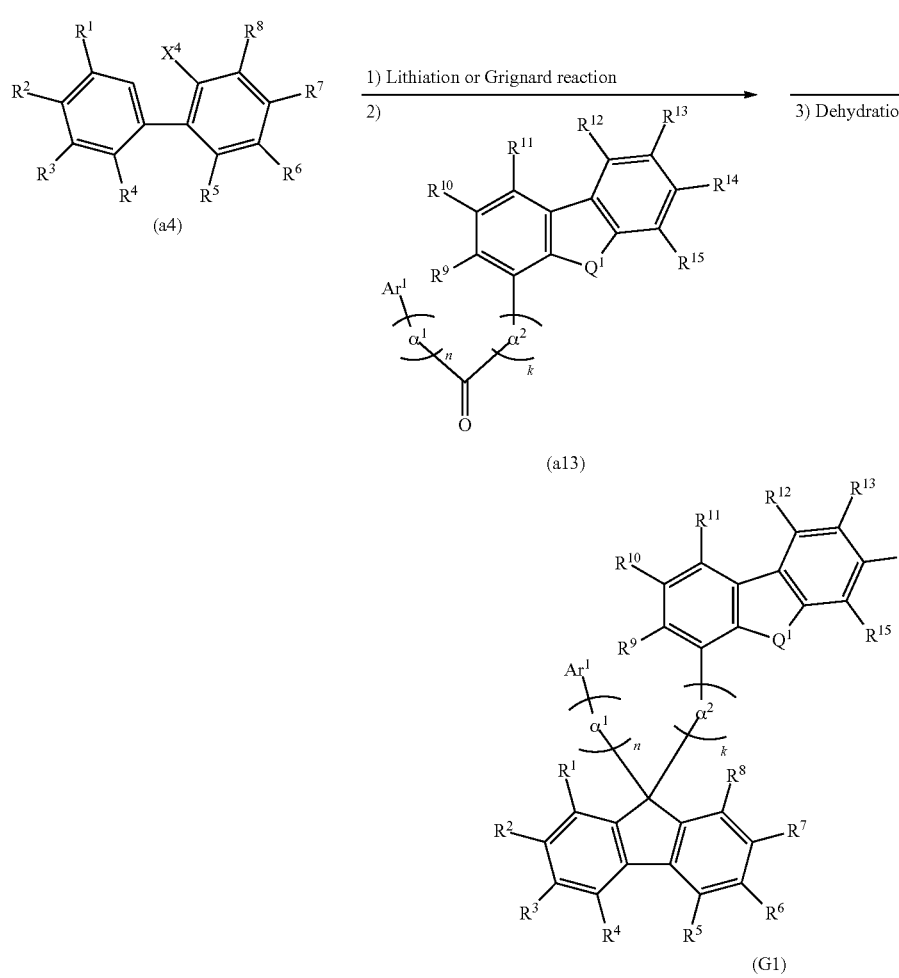

In the synthesis scheme (C-2), $\alpha^1$ and $\alpha^2$ separately represent a substituted or unsubstituted arylene group having 6 to 13 carbon atoms; $Ar^1$ represents a substituted or unsubstituted aryl group having 6 to 18 carbon atoms, a substituted or unsubstituted 4-dibenzothiophenyl group, or a substituted or unsubstituted 4-dibenzofuranyl group; $R^1$ to $R^{15}$ separately represent hydrogen, an alkyl group having 1 to 12 carbon atoms, or an aryl group having 6 to 14 carbon atoms; n and k separately represent 0 or 1; $Q^1$ represents sulfur or oxygen; and $X^4$ represents a halogen. $X^4$ preferably represents bromine or iodine, which has high reactivity, more preferably iodine.

In the synthesis scheme (C-2), as in the synthesis scheme (A-2), an aryl compound having a halogen group is activated, the resulting substance is reacted with a ketone compound to give an aryl alcohol compound, and an acid is added to perform dehydration, whereby a fluorene compound can be prepared. The synthesis scheme (A-2) can be referred to for details.

Thus, the fluorene compound of this embodiment can be synthesized.

The above-described fluorene compound of one embodiment of the present invention has a high hole-transport property. The fluorene compound of one embodiment of the present invention has a low highest occupied molecular orbital level (HOMO level). The fluorene compound of one embodiment of the present invention has a high lowest unoccupied molecular orbital level (LUMO level). The fluorene compound of one embodiment of the present invention has a wide band gap. The fluorene compound of one embodiment of the present invention has a high T1 level.

The fluorene compound of one embodiment of the present invention can be favorably used for a light-emitting element, and is particularly preferable for use for a hole-transport layer of a light-emitting element. A composite material formed by combining the fluorene compound of one embodiment of the present invention and an electron acceptor (an acceptor) can be used for a hole-injection layer of a light-emitting element.

This embodiment can be implemented in appropriate combination with any of the other embodiments.

Embodiment (2)

In this embodiment, a light-emitting element of one embodiment of the present invention, which includes the fluorene compound described in Embodiment 1 for a hole-transport layer, will be described with reference to FIGS. 1A and 1B.

In a light-emitting element of this embodiment, an EL layer having at least a hole-transport layer and a light-emitting layer is interposed between a pair of electrodes. The EL layer may have a plurality of layers in addition to the hole-transport layer and the light-emitting layer. The plurality of layers has a structure in which a layer containing a substance having a high carrier-injection property and a layer containing a substance having a high carrier-transport property are combined and stacked so that a light-emitting region is formed in a region away from the electrodes, that is, so that carriers recombine in a region away from the electrodes. The plurality of layers may include, for example, a hole-injection layer, an electron-injection layer, an electron-transport layer, and the like.

In the light-emitting element of this embodiment illustrated in FIG. 1A, an EL layer 102 having a hole-transport layer 112 and a light-emitting layer 113 is provided between a pair of electrodes, a first electrode 101 and a second electrode 103. The EL layer 102 includes a hole-injection layer 111, the hole-transport layer 112, the light-emitting layer 113, an electron-transport layer 114, and an electron-injection layer 115. The light-emitting element in FIG. 1A includes the first electrode 101 formed over a substrate 100, the hole-injection layer 111, the hole-transport layer 112, the light-emitting layer 113, the electron-transport layer 114, and the electron-injection layer 115 which are stacked over the first electrode 101 in this order, and the second electrode 103 provided thereover. Note that, in a light-emitting element described in this embodiment, the first electrode 101 functions as an anode and the second electrode 103 functions as a cathode.

The substrate 100 is used as a support of the light-emitting element. For the substrate 100, for example, glass, quartz, plastic, or the like can be used. A flexible substrate can also be used. The flexible substrate is a substrate that can be bent, such as a plastic substrate made of polycarbonate, polyarylate, or polyether sulfone, for example. A film (made of polypropylene, polyester, vinyl, polyvinyl fluoride, vinyl chloride, or the like), an inorganic film formed by evaporation, or the like can also be used. Note that materials other than these can be used as long as they can function as a support of the light-emitting element.

For the first electrode 101, any of metals, alloys, conductive compounds, mixtures thereof, and the like which has a high work function (specifically, a work function of 4.0 eV or more) is preferably used. Specific examples include indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like. Films of these conductive metal oxides are usually formed by sputtering, but may be formed by application of a sol-gel method or the like. For example, an IZO film can be found by a sputtering method using a target obtained by adding 1 wt % to 20 wt % of zinc oxide to indium oxide. Further, an IWZO film can be found by a sputtering method using a target obtained by adding 0.5 wt % to 5 wt % of tungsten oxide and 0.1 wt % to 1 wt % of zinc oxide to indium oxide. Other examples are gold, platinum, nickel, tungsten, chromium, molybdenum, iron, cobalt, copper, palladium, nitrides of metal materials (e.g., titanium nitride), and the like.

Note that when a layer included in the EL layer 102 and formed in contact with the first electrode 101 is formed using a later-described composite material formed by combining an organic compound and an electron acceptor (an acceptor), as a substance used for the first electrode 101, any of a variety of metals, alloys, and electrically conductive compounds, a mixture thereof, and the like can be used regardless of the work function; for example, aluminum, silver, an alloy containing aluminum (e.g., Al—Si), or the like can also be used.

The EL layer 102 formed over the first electrode 101 has at least the hole-transport layer 112 and the light-emitting layer 113, and the hole-transport layer 112 includes a fluorene compound which is one embodiment of the present invention. For part of the EL layer 102, a known substance can be used, and either a low molecular compound or a high molecular compound can be used. Note that substances forming the EL layer 102 may consist of organic compounds or may include an inorganic compound as a part.

Figure 1B:
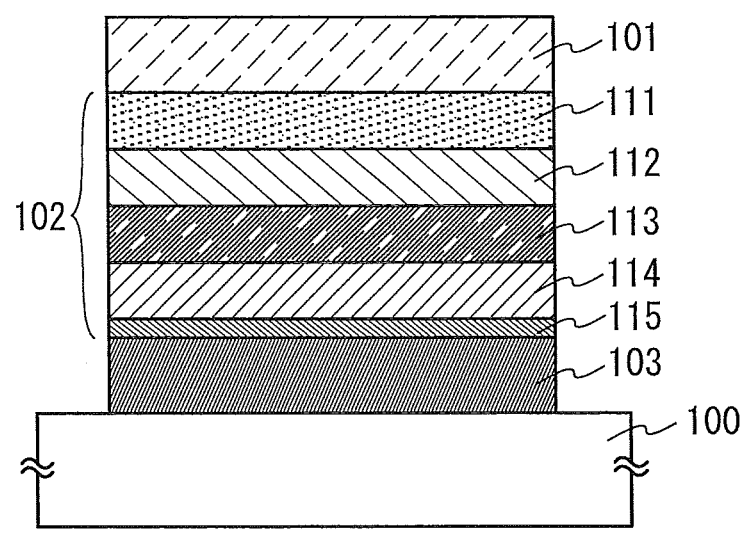

Further, as illustrated in FIGS. 1A and 1B, the EL layer 102 is formed by stacking an appropriate combination of the hole-injection layer 111, the electron-transport layer 114, the electron-injection layer 115, and the like in addition to the hole-transport layer 112 and the light-emitting layer 113.

The hole-injection layer 111 is a. layer containing a substance having a high hole-injection property. Examples of a substance having a high hole-injection property which can be used are metal oxides, such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide. Other examples of a substance that can be used are phthalocyanine-based compounds, such as phthalocyanine (abbreviation: $H_2Pc$) and copper(II) phthalocyanine (abbreviation: CuPc).

Other examples of a substance that can be used are aromatic amine compounds which are low molecular organic compounds, such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1).

Still other examples of a substance that can be used are high molecular compounds (e.g., oligomers, dendrimers, and polymers), such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacryla mide] (abbreviation: PTPDMA), and poly[N,N'-bis(4-butylphenyl)-N,N-bis(phenyl)benzidine] (abbreviation: Poly-TPD), and high molecular compounds to which acid is added, such as poly(3,4-ethylenedioxythiophene)/poly(styrenesulfonic acid) (PEDOT/PSS), or polyaniline/poly(styrenesulfonic acid) (PAni/PSS).

For the hole-injection layer 111, the composite material formed by combining an organic compound and an electron acceptor (an acceptor) may be used. Such a composite material, in which holes are generated in the organic compound by the electron acceptor, has high hole-injection and hole-transport properties. In this case, the organic compound is preferably a material excellent in transporting the generated holes (a substance having a high hole-transport property).

Examples of the organic compound used for the composite material are a variety of compounds, such as aromatic amine compounds, carbazole derivatives, aromatic hydrocarbons, and high molecular compounds (e.g., oligomers, dendrimers, and polymers). The organic compound used for the composite material is preferably an organic compound having a high hole-transport property, and specifically preferably a substance having a hole mobility of $10^{-6}$ cm$^2$/Vs or more. Note that other than these substances, any substance that has a property of transporting more holes than electrons may be used. Organic compounds that can be used for the composite material will be specifically described below.

A fluorene compound of one embodiment of the present invention is an organic compound having a high hole-transport property, and thus can be favorably used for the composite material. Other examples of an organic compound that can be used for the composite material are aromatic amine compounds, such as TDATA, MTDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), and 4-phenyl-4'-(9-phenylfluoren-9-yl)triphenylamine (abbreviation: BPAFLP), and carbazole derivatives, such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 9-phenyl-3-[4-(10-phenyl-9-anthryl)phenyl]-9H-carbazole (abbreviation: PCzPA), and 1,4-bis[4-(N-carbazolyl)phenyl]-2,3,5,6-tetraphenylbenzene.

Other examples of an organic compound that can be used are aromatic hydrocarbon compounds, such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, and 2,3,6,7-tetramethyl-9,10-di(1-naphthyl)anthracene.

Other examples of an organic compound that can be used are aromatic hydrocarbon compounds, such as 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl]anthracene (abbreviation: DPVPA).

Further, examples of the electron acceptor are organic compounds, such as 7,7,8,8-tetracyano-2,3,5,6-tetrafluoro-quinodimethane (abbreviation: F$_4$-TCNQ) and chloranil, oxides of transition metals, and oxides of metals that belong to Groups 4 to 8 in the periodic table, and the like. Specific preferred examples include vanadium oxide, niobium oxide, tantalum oxide, chromium oxide, molybdenum oxide, tungsten oxide, manganese oxide, and rhenium oxide because their electron-acceptor properties are high. Among these, molybdenum oxide is especially preferable since it is stable in the air, has low hygroscopic property, and is easily treated.

The composite material may be formed using the above-described electron acceptor and the above-described high molecular compound such as PVK, PVTPA, PTPDMA, or Poly-TPD, and may be used for the hole-injection layer 111.

The hole-transport layer 112 is a layer that contains a substance having a high hole-transport property. The hole-transport layer 112 of this embodiment includes a fluorene compound of one embodiment of the present invention.

The light-emitting layer 113 is a layer including a light-emitting substance. As the light-emitting substance, for example, a fluorescent compound, which emits fluorescence, or a phosphorescent compound, which emits phosphorescence, can be used.

A fluorene compound of one embodiment of the present invention is a material which emits fluorescence, and thus can be used as the light-emitting substance.

As a fluorescent compound that can be used for the light-emitting layer 113, the following light-emitting materials can be given, for example: materials that emit blue light, such as N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryptriphenylamine (abbreviation: YGAPA), and 4-(10-phenyl-9-anthryl)-4'-(9-phenyl-9H-carbazol-3-yl)triphenylamine (abbreviation: PCBAPA); materials that emit green light, such as N-(9,10-diphenyl-2-anthryl)-N,9-diphenyl-9H-carbazol-3-amine (abbreviation: 2PCAPA),
N-[9,10-bis(1,1'-biphenyl-2-yl)-2-anthryl]-N,9-diphenyl-9H-carbazol-3-amine (abbreviation: 2PCABPhA),
N-(9,10-diphenyl-2-anthryl)-N,N',N'-triphenyl-1,4-phenylenediamine (abbreviation: 2DPAPA),
N-[9,10-bis(1,1'-biphenyl-2-yl)-2-anthryl]-N,N,N-triphenyl-1,4-phenylenediamine (abbreviation: 2DPABPhA),
N-[9,10-bis(1,1'-biphenyl-2-yl)]-N-[4-(9H-carbazol-9-yl)phenyl]-N-phenylanthracen-2-amine (abbreviation: 2YGABPhA), and N,N,9-triphenylanthracen-9-amine (abbreviation: DPhAPhA); materials that emit yellow light, such as rubrene and 5,12-bis(1,1'-biphenyl-4-yl)-6,11-diphenyltetracene (abbreviation: BPT); and materials that emit red light, such as N,N,N',N'-tetrakis(4-methylphenyl)tetracene-5,11-diamine (abbreviation: p-mPhTD) and 7,14-diphenyl- N,N,N',N'-tetrakis(4-methylphenyl)acenaphtho[1,2-a]fluoranthene-3,10-d iamine (abbreviation: p-mPhAFD).

As a phosphorescent compound that can be used for the light-emitting layer 113, the following light-emitting materials can be given, for example: materials that emit blue light, such as bis[2-(4',6'-difluorophenyepyridinato-N,C$^{2'}$]iridium(III)tetrakis(1-pyrazolyl)borate (abbreviation: FIr6), bis[2-(4',6'-difluorophenyl)pyridinato-N,C$^{2'}$]iridium(III)picolinate (abbreviation: FIrpic), bis{2-[3',5'-bis(trifluoromethyl)phenyl]pyridinato-N,C$^{2'}$}iridium(III)picolinate (abbreviation: Ir(CF$_3$ppy)$_2$(pic)), and bis[2-(4',6'-difluorophenyl)pyridinato-N,C$^{2'}$]iridium(III)acetylacetonate (abbreviation: FIr(acac)); materials that emit green light, such as tris(2-phenylpyridinato-N,C$^{2'}$)iridium(III) (abbreviation: Ir(ppy)$_3$), bis(2-phenylpyridinato-N,C$^{2'}$)iridium(III) acetylacetonate (abbreviation: Ir(ppy)$_2$(acac)), bis(1,2-diphenyl-1H-benzimidazolato)iridium(III)acetylacetonate (abbreviation: Ir(pbi)$_2$(acac)), bis(benzo[h] quinolinato)iridium(III)acetylacetonate (abbreviation: Ir(bzq)$_2$(acac)), and tris(benzo[h]quinolinato)iridium(III) (abbreviation: Ir(bzq)$_3$); materials that emit yellow light, such as bis(2,4-diphenyl-1,3-oxazolato-N,C$^{2'}$)iridium(III)acetylacetonate (abbreviation: Ir(dpo)$_2$(acac)), bis[2-(4'-(perfluorophenylphenyl)pyridinato]iridium(III)acetylacetonate (abbreviation: Ir(p-PF-ph)$_2$(acac)), bis(2-phenylbenzothiazolato-N,C$^{2'}$)iridium(III)acetylacetonate (abbreviation: Ir(bt)$_2$(acac)), (acetylacetonato)bis[2,3-bis(4-fluorophenyl)-5-methylpyrazinato]iridium(III) (abbreviation: Ir(Fdppr-Me)$_2$(acac)), and (acetylacetonato)bis{2-(4-methoxyphenyl)-3,5-dimethylpyrazinato}iridium(III) (abbreviation: Ir(dmmoppr)$_2$(acac)); materials that emit orange light, such as tris(2-phenylquinolinato-N,C$^{2'}$)iridium(III) (abbreviation: Ir(pq)$_3$), bis(2-phenylquinolinato-N,C$^{2'}$)iridium(III)acetylacetonate (abbreviation: Ir(pq)$_2$(acac)), (acetylacetonato) bis(3,5-dimethyl-2-phenylpyrazinato)iridium(III) (abbreviation: Ir(mppr-Me)$_2$(acac)), and (ace tylacetonato)bis(5-isopropyl-3-methyl-2-phenylpyrazinato)iridium(III) (abbreviation: Ir(mppr-iPr)$_2$(acac)); and materials that emit red light, for example, organometallic complexes, such as bis[2-(2'-benzo[4,5-c]thienyl)pyridinato-N,C$^{3'}$)iridium(III) acetylacetonate (abbreviation: Ir(btp)$_2$(acac)), bis(1-phenylisoquinolinato-N,C$^{2'}$)iridium(III)acetylacetonate (abbreviation: Ir(piq)$_2$(acac), (acetylacetonato)bis[2,3-bis(4-fluorophenyl)quinoxalinato] iridium(III) (abbreviation: Ir(Fdpq)$_2$(acac)), (acetylacetonato)bis(2,3,5-triphenylpyrazinato)iridium(III) (abbreviation: Ir(tppr)$_2$(acac)), (dipivaloylmethanato)bis(2,3,5-triphenylpyrazinato)iridium (III) (abbreviation: Ir(tppr)$_2$(dpm)), and (2,3,7,8,12,13,17, 18-octaethyl-21H,23H-porphyrin)platinum(II) (abbreviation: PtOEP). Any of the following rare-earth metal complexes can be used as a phosphorescent compound: tris(acetylacetonato)(monophenanthroline)terbium(III) (abbreviation: Tb(acac)$_3$ (Phen)); tris(1,3-diphenyl-1,3-propanedionato)(monophenanthroline)europium(III) (abbreviation: Eu(DBM)$_3$(Phen)); and tris[1-(2-thenoyl)-3,3,3-trifluoroacetonato] (monophenanthroline)europium(III) (abbreviation: Eu(TTA)$_3$(Phen)), because their light emission is from a rare-earth metal ion (electronic transition between different multiplicities) in such a rare-earth metal complex.

As the light-emitting substance, a high molecular compound can be used. Specifically, the following light-emitting materials can be given, for example: materials that emit blue light, such as poly(9,9-diocVlfluorene-2,7-diyl) (abbreviation: PFO), poly[9,9-dioctylfluorene-2,7-diyl)-co-(2,5-dimethoxybenzene-1,4-diyl)] (abbreviation: PF-DMOP), and poly{(9,9-dioctylfluorene-2,7-diyl)-co-[N,N'-di-(p-butylphenyl)-1,4-diaminobenzene]} (abbreviation: TAB-PFH); materials that emit green light, such as poly(p-phenylenevinylene) (abbreviation: PPV), poly[(9,9-dihexylfluorene-2,7-diyl)-alt-co-(benzo[2,1,3]thiadiazole-4,7-diyl)] (abbreviation: PFBT), and poly[(9,9-dioctyl-2,7-divinylenefluorenylene)-alt-co-(2-methoxy-5-(2-ethylhexyloxy)-1,4-phenylene)]; and materials that emit orange to red light, such as poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-dihexyl-2,7-bis(1-cyanovinylene)fluorenylene]-alt-co-[2,5-bis(N,N'-diphenyl amino)-1,4-phenylene]}, and poly{[2-methoxy-5-(2-ethylhexyloxy)-1,4-bis (1-cyanovinylenephenylene)]-alt-co-[2,5-bis(N,N-diphenylamino)-1,4-phenylene]} (abbreviation: CN-PPV-DPD).

Note that the light-emitting layer 113 may have a structure in which any of the above-described light-emitting substances (guest material) is dispersed into another substance (host material). A variety of substances can be used as the host material, and it is preferable to use a substance having a LUMO level higher than that of a light-emitting substance and having a HOMO level lower than that of the light-emitting substance.

A fluorene compound of one embodiment of the present invention is a substance having a high LUMO level and a low HOMO level, and thus can be favorably used as the host material.

In the case where the light-emitting substance is a phosphorescent compound, a host material thereof is preferably a substance having a T1 level higher than that of the light-emitting substance. A fluorene compound of one embodiment of the present invention is a substance having a high T1 level, and thus can be favorably used as a host material of a phosphorescent light-emitting substance.

In the case where the light-emitting substance is a fluorescent compound, a host material thereof is preferably a substance having a level of singlet excitation enegy (Si level) higher than that of the light-emitting substance. A fluorene compound of one embodiment of the present invention is a substance having a high S1 level, and thus can be favorably used as a host material of a fluorescent light-emitting substance.

Specific examples of the host material that can be used are the following materials: metal complexes, such as tris(8-quinolinolato)aluminum(III) (abbreviation: Alq), tris(4-methyl-8-quinolinolato)aluminum(III) (abbreviation: Almq$_3$), bis(10-hydroxybenzo[h] quinolinato)beryllium(II) (abbreviation: BeBq$_2$), bis(2-methyl-8-quinolinolato)(4-phenylphenolato)aluminum(III) (abbreviation: BAlq), bis (8-quinolinolato)zinc(II) (abbreviation: Znq), bis[2-(2-benzoxazolyl)phenolato] zinc(II) (abbreviation: ZnPBO), and bis[2-(2-benzothiazolyl)phenolato]zinc(II) (abbreviation: ZnBTZ); heterocyclic compounds, such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl] benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), bathophenanthroline (abbreviation: BPhen), and bathocuproine (BCP); condensed aromatic compounds, such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl) anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrene (abbreviation: TPB3), 9,10-diphenylanthracene (abbreviation: DPAnth), and 6,12-dimethoxy-5,11-diphenylchrysene; aromatic amine compounds, such as N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), NPB (or a-NPD), TPD, DFLDPBi, and BSPB; and the like.

Plural kinds of host materials can also be used. For example, in order to suppress crystallization, a substance such as rubrene which suppresses crystallization, may be further added. In addition, NPB, Alq, or the like may be further added in order to efficiently transfer energy to the guest material.

With a structure in which a guest material is dispersed in a host material, crystallization of the light-emitting layer 113 can be suppressed. In addition, concentration quenching due to high concentration of the guest material can also be suppressed.

The electron-transport layer 114 is a layer including a substance having a high electron-transport property. Examples of the substance having a high electron-transport property are metal complexes having a quinoline skeleton or a benzoquinoline skeleton, such as tris(8-quinolinolato)aluminum (abbreviation: Alq), tris(4-methyl-8-quinolinolato)

aluminum (abbreviation: Almq$_3$), bis(10-hydroxybenzo[h]quinolinato)beryilium (abbreviation: BeBq$_2$), and bis(2-methyl-8-quinolinolato)(4-phenylphenolato)aluminum (abbreviation: BAlq). Other examples are metal complexes having an oxazole-based or thiazole-based ligand, such as bis[2-(2-hydroxyphenyl)benzoxazolato]zinc (abbreviation: Zn(BOX)$_2$) and bis[2-(2-hydroxyphenyl)benzothiazolato]zinc (abbreviation: Zn(BTZ)$_2$). Other than metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can be used. The substances described here are mainly substances having an electron mobility of 10$^{-6}$ cm$^2$/Vs or more. Further, the electron-transport layer is not limited to a single layer, and may be a stack of two or more layers containing any of the above substances.

The electron-injection layer 115 is a layer that contains a substance having a high electron-injection property. Examples of the substance that can be used for the electron-injection layer 115 are alkali metals, alkaline earth metals, and compounds thereof, such as lithium, cesium, calcium, lithium fluoride, cesium fluoride, calcium fluoride, and lithium oxide, rare earth-metal compounds, such as erbium fluoride, and the above-mentioned substances for forming the electron-transport layer 114.

Alternatively, a composite material formed by combining an organic compound and an electron donor (a donor) may be used for the electron-injection layer 115. Such a composite material, in which electrons are generated in the organic compound by the electron donor, has high electron-injection and electron-transport properties. The organic compound here is preferably a material excellent in transporting the generated electrons, and specifically any of the above substances (such as metal complexes and heteroaromatic compounds) for the electron-transport layer 114 can be used. The electron donor can be a substance exhibiting an electron-donating property for the organic compound. Specific examples of the electron donor are alkali metals, alkaline earth metals, and rare earth-metals, such as lithium, cesium, magnesium, calcium, erbium, and ytterbium. Any of alkali metal oxides and alkaline earth metal oxides is preferable, examples of which are lithium oxide, calcium oxide, barium oxide, and the like, and a Lewis base such as magnesium oxide or an organic compound such as tetrathiafulvalene (abbreviation: TTF) can be used.

Note that the hole-injection layer 111, the hole-transport layer 112, the light-emitting layer 113, the electron-transport layer 114, and the electron-injection layer 115 which are described above can each be formed by a method, such as an evaporation method (e.g., a vacuum evaporation method), an inkjet method, or a coating method.

When the second electrode 103 functions as a cathode, any of metals, alloys, conductive compounds, mixtures thereof, and the like which has a low work function (specifically, a work function of 3.8 eV or less) is preferably used for the second electrode 103. Specific examples of the substance that can be used are elements that belong to Groups 1 and 2 in the periodic table, that is, alkali metals such as lithium and cesium, alkaline earth metals such as magnesium, calcium, and strontium, alloys thereof (e.g., Mg—Ag and Al—Li), rare earth-metals such as europium and ytterbium, alloys thereof, aluminum, silver, and the like.

When a layer included in the EL layer 102 and formed in contact with the second electrode 103 is formed using the composite material formed by combining the organic compound and the electron donor (the donor), which are described above, a variety of conductive materials, such as aluminum, silver, ITO, and indium oxide-tin oxide containing silicon or silicon oxide, can be used regardless of the work function.

Note that when the second electrode 103 is formed, a vacuum evaporation method or a sputtering method can be used. In the case of using a silver paste or the like, a coating method, an inkjet method, or the like can be used.

In the above-described light-emitting element, a current flows due to a potential difference generated between the first electrode 101 and the second electrode 103 and holes and electrons recombine in the EL layer 102, so that light is emitted. Then, this light emission is extracted outside through one or both of the first electrode 101 and the second electrode 103. Therefore, one or both of the first electrode 101 and the second electrode 103 are electrodes having a property of transmitting visible light.

Further, the structure of the layers provided between the first electrode 101 and the second electrode 103 is not limited to the above-described structure. A structure other than the above may alternatively be employed as long as a light-emitting region in which holes and electrons recombine is provided in a portion away from the first electrode 101 and the second electrode 103 so as to prevent quenching due to proximity of the light-emitting region to metal.

In other words, there is no particular limitation on a stack structure of the layers. A layer including a substance having a high electron-transport property, a substance having a high hole-transport property, a substance having a high electron-injection property, a substance having a high hole-injection property, a bipolar substance (a substance having a high electron-transport property and a high hole-transport property), a hole-blocking material, or the like may freely be combined with a light-emitting layer and a hole-transport layer including a fluorene compound of one embodiment of the present invention.

A fluorene compound of one embodiment of the present invention is a substance having a low HOMO level, and thus can be favorably used as a hole-blocking material.

In the light-emitting element illustrated in FIG. 1B, the EL layer 102 is provided between a pair of electrodes, the first electrode 101 and the second electrode 103, over the substrate 100. The EL layer 102 includes the hole-injection layer 111, the hole-transport layer 112, the light-emitting layer 113, the electron-transport layer 114, and the electron-injection layer 115. The light-emitting element in FIG. 1B includes the second electrode 103 serving as a cathode over the substrate 100, the electron-injection layer 115, the electron-transport layer 114, the light-emitting layer 113, the hole-transport layer 112, and the hole-injection layer 111 which are stacked over the second electrode 103 in this order, and the first electrode 101 provided thereover which serves as an anode.

Note that a light-emitting element of this embodiment includes a fluorene compound of one embodiment of the present invention in a hole-transport layer; however, a light-emitting element of the present invention is not limited to this structure.

For example, a fluorene compound of one embodiment of the present invention may be included in a hole-injection layer of a light-emitting element. In this case, a hole-transport layer may be formed using a fluorene compound of one embodiment of the present invention, or may be formed using another material having a high hole-transport property. In addition, as described above, a fluorene compound of one embodiment of the present invention may be used as a host material of a fluorescent light-emitting material or a phosphorescent light-emitting material which emits phosphorescence to green.

A fluorene compound of one embodiment of the present invention has a low HOMO level, a high LUMO level, and a wide band gap. Thus, it can be favorably used for a carrier-transport layer (such as a hole-transport layer, an electron-transport layer, or a hole-blocking layer) adjacent to a light-emitting layer. Accordingly, a highly efficient element can be obtained.

A method of forming the light-emitting element will now be specifically described.

In a light-emitting element of this embodiment, the EL layer is interposed between the pair of electrodes. The EL layer includes at least a hole-transport layer and a light-emitting layer, and the hole-transport layer includes a fluorene compound of one embodiment of the present invention. Further, the EL layer may include a hole-injection layer, an electron-transport layer, or an electron-injection layer in addition to the light-emitting layer and the hole-transport layer. The electrodes (the first electrode and the second electrode) and the EL layer may be formed by any of a wet process such as a droplet discharging method (an inkjet method), a spin coating method, or a printing method, or by a dry process such as a vacuum evaporation method, a CVD method, or a sputtering method. A wet process allows formation at atmospheric pressure with a simple apparatus and by a simple process, which gives the effects of simplifying the process and improving productivity. In contrast, a dry process does not need dissolution of a material and enables use of a material that has low solubility in a solution, which expands the range of material choices.

All the thin films included in the light-emitting element may be formed by a wet process. In this case, the light-emitting element can be manufactured with only facilities needed for a wet process. Alternatively, the following method may be employed: formation of the stacked layers up to formation of the light-emitting layer is performed by a wet process whereas a functional layer, the first electrode, and the like which are stacked over the light-emitting layer are formed by a dry process. Further alternatively, the following method may be employed: the second electrode and a functional layer are formed by a dry process before the formation of the light-emitting layer whereas the light-emitting layer, a functional layer stacked thereover, and the first electrode are formed by a wet process. Needless to say, this embodiment is not limited to these, and a light-emitting element can be fainted by appropriate selection from a wet process and a dry process depending on a material to be used, necessary film thickness, and the interface state.

In this embodiment, a light-emitting element is fabricated over a substrate made of glass, plastic, or the like. By forming a plurality of such light-emitting elements over one substrate, a passive matrix light-emitting device can be manufactured. Further, a light-emitting element may be fabricated in such a way that a thin film transistor (TFT), for example, is formed over a substrate made of glass, plastic, or the like and the light-emitting element is formed over an electrode electrically connected to the TFT. Thus, an active matrix light-emitting device in which the TFT controls the driving of the light-emitting element can be manufactured.

Note that there is no particular limitation on the structure of the TFT; a staggered TFT or an inverted staggered TFT may be employed. In addition, there is no particular limitation on the crystallinity of a semiconductor used for the TFT; an amorphous semiconductor or a crystalline semiconductor may be used. Furthermore, a driver circuit formed over a TFT substrate may be formed with both n-channel TFTs and p-channel TFTs or may be formed with either n-channel TFTs or p-channel TFTs.

In the above manner, a light-emitting element can be manufactured using a fluorene compound of one embodiment of the present invention. According to one embodiment of the present invention, a light-emitting element having high emission efficiency can be realized. In addition, a light-emitting element having a long lifetime can be realized.

Furthermore, a light-emitting device (an image display device) including a light-emitting element of one embodiment of the present invention which is obtained as above can realize low power consumption.

Note that by use of a light-emitting element described in this embodiment, a passive matrix light-emitting device or an active matrix light-emitting device in which driving of the light-emitting element is controlled by a thin film transistor (TFT) can be manufactured.

This embodiment can be implemented in appropriate combination with any of the other embodiments.

Embodiment (3)

In this embodiment, a mode of a light-emitting element having a structure in which a plurality of light-emitting units is stacked (hereinafter, referred to as a stacked-type element) will be described with reference to FIGS. 2A and 2B. This light-emitting element is a light-emitting element including a plurality of light-emitting units between a first electrode and a second electrode.

Figure 2A:
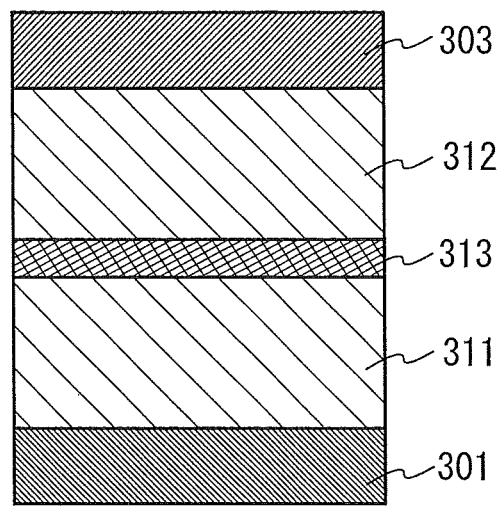
FIGS. 2A and 2B each illustrate a light-emitting element of one embodiment of the present invention.

In FIG. 2A, a first light-emitting unit 311 and a second light-emitting unit 312 are stacked between a first electrode 301 and a second electrode 303. In this embodiment, the first electrode 301 functions as an anode and the second electrode 303 functions as a cathode. Note that the first electrode 301 and the second electrode 303 can be similar to those in Embodiment 2. Further, the first light-emitting unit 311 and the second light-emitting unit 312 may have the same or different structures. The first light-emitting unit 311 and the second light-emitting unit 312 may have the same structure as in Embodiment 2, or either of the units may differ in structure from that in Embodiment 2.

Further, a charge-generation layer 313 is provided between the first light-emitting unit 311 and the second light-emitting unit 312. The charge-generation layer 313 has a function of injecting electrons into one of the light-emitting units and injecting holes into the other of the light-emitting units when a voltage is applied between the first electrode 301 and the second electrode 303. In the case of this embodiment, when a voltage is applied so that the potential of the first electrode 301 is higher than that of the second electrode 303, the charge-generation layer 313 injects electrons into the first light-emitting unit 311 and injects holes into the second light-emitting unit 312.

Note that the charge-generation layer 313 preferably has a property of transmitting visible light in terms of light extraction efficiency. Further, the charge-generation layer 313 functions even if it has lower conductivity than the first electrode 301 or the second electrode 303.

The charge-generation layer 313 may have a structure in which it includes the organic compound having a high hole-transport property and the electron acceptor (the acceptor) or a structure in which it includes an organic compound having a high electron-transport property and the electron donor (the donor), or may be a stack of both of these structures. Note that the electron acceptor or the electron donor is at least capable of providing and receiving electrons with the assistance of an electric field.

In the case of a structure in which the electron acceptor is added to an organic compound having a high hole-transport property, a fluorene compound of one embodiment of the present invention can be used as the organic compound having a high hole-transport property. Other examples are aromatic amine compounds, such as NPB, TPD, TDATA, MTDATA, and 4,4'-bis[N-(spiro-9,9'-bifluoren-2-yl)-N-phenylamino]biphenyl (abbreviation: BSPB), and the like. The substances mentioned here are mainly substances that have a hole mobility of $10^{-6}$ cm$^2$/Vs or more. Note that other than the above substances, any organic compound that has a property of transporting more holes than electrons may be used.

Examples of the electron acceptor are 7,7,8,8-tetracyano-2,3,5,6-tetrafluoroquinodimethane (abbreviation: $F_4$-TCNQ), chloranil, oxides of transition metals, and oxides of metals that belong to Groups 4 to 8 in the periodic table, and the like. Specific preferred examples include vanadium oxide, niobium oxide, tantalum oxide, chromium oxide, molybdenum oxide, tungsten oxide, manganese oxide, and rhenium oxide because their electron-acceptor properties are high. Among these, molybdenum oxide is especially preferable since it is stable in the air, has low hygroscopic property, and is easily treated.

In the case of the structure in which the electron donor is added to an organic compound having a high electron-transport property, any of the following substances can be used as the organic compound having a high electron-transport property, for example: metal complexes having a quinoline skeleton or a benzoquinoline skeleton such as Alq, Almq$_3$, BeBq$_2$, and BAlq; metal complexes having an oxazole-based ligand or a thiazole-based ligand, such as Zn(BOX)$_2$ and Zn(BTZ)$_2$; and the like. Examples other than the metal complexes are PBD, OXD-7, TAZ, BPhen, BCP, and the like. The substances described here are mainly substances having an electron mobility of $10^{-6}$ cm$^2$IVs or more. Note that other than the above substances, any organic compound that has a property of transporting more electrons than holes may be used.

Examples of the electron donor that can be used are alkali metals, alkaline-earth metals, rare-earth metals, metals that belong to Group 13 in the periodic table and oxides or carbonates thereof, and preferably specifically lithium, cesium, magnesium, calcium, ytterbium, indium, lithium oxide, cesium carbonate, and the like. An organic compound, such as tetrathianaphthacene, may be used as the electron donor.

By forming the charge-generation layer 313 with any of the above materials, it is possible to suppress an increase in driving voltage caused when the EL layers are stacked.

Figure 2B:
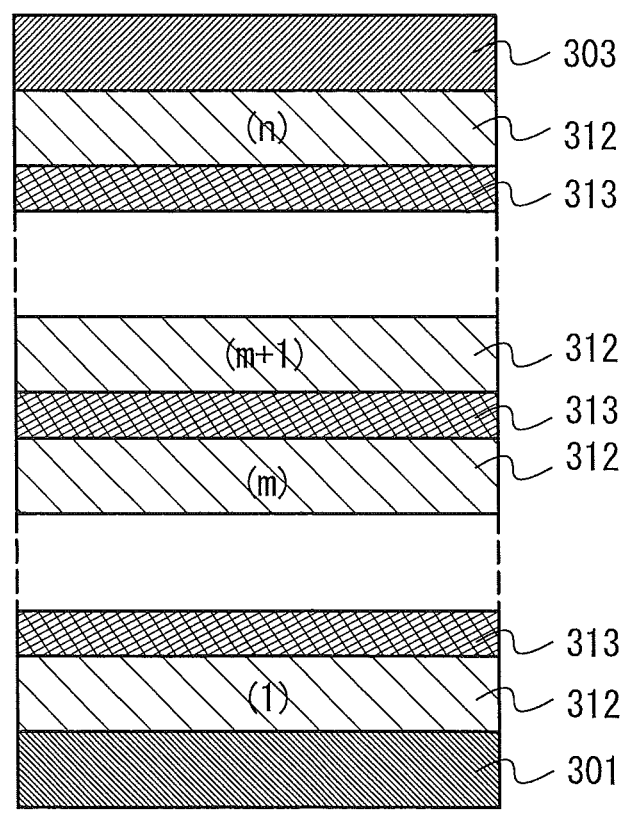

Although the light-emitting element having two light-emitting units is described in this embodiment, the embodiment can be applied to a light-emitting element in which three or more light-emitting units are stacked as illustrated in FIG. 2B. A plurality of light-emitting units which is partitioned by a charge-generation layer is arranged between a pair of electrodes, as in the light-emitting element according to this embodiment, whereby it is possible to realize an element having a long lifetime which can emit light with a high luminance while current density is kept low.

Furthermore, by making emission colors of the light-emitting units different, light having a desired color can be obtained from the light-emitting element as a whole. For example, the emission colors of first and second light-emitting units are complementary in a light-emitting element having the two light-emitting units, so that the light-emitting element can be made to emit white light as a whole. Note that the term "complementary" means color relationship in which an achromatic color is obtained when colors are mixed. That is, emission of white light can be obtained by mixture of light emitted from substances whose emission colors are complementary colors. Further, the same applies to a light-emitting element having three light-emitting units. For example, the light-emitting element as a whole can emit white light when the emission color of the first light-emitting unit is red, the emission color of the second light-emitting unit is green, and the emission color of the third light-emitting unit is blue.

Note that this embodiment can be implemented in appropriate combination with any of the other embodiments.

Embodiment (4)

In this embodiment, a light-emitting device including a light-emitting element of one embodiment of the present invention will be described with reference to FIGS. 3A and 3B. Note that FIG. 3A is a top view illustrating the light-emitting device, and FIG. 3B is a cross-sectional view taken along lines A-B and C-D of FIG. 3A.

Figure 3A:
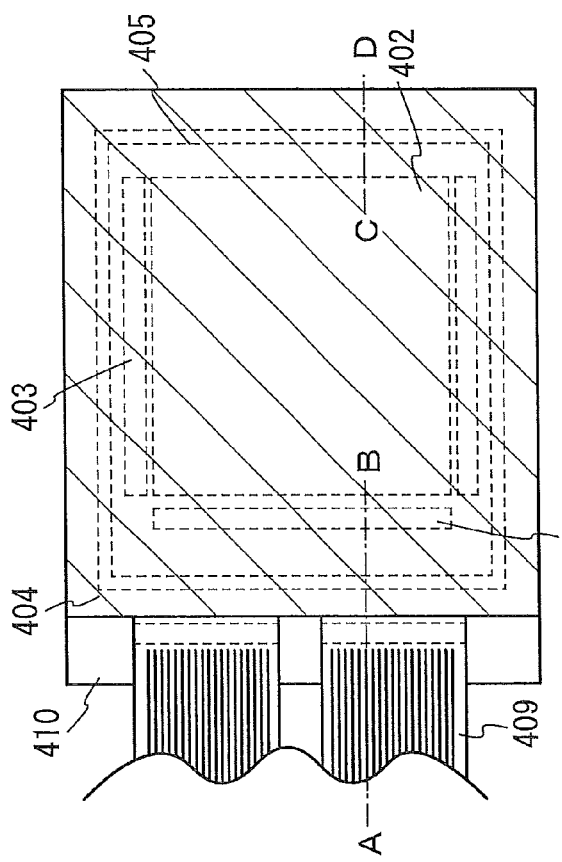
FIGS. 3A and 3B illustrate a light-emitting device of one embodiment of the present invention.
Figure 3B:
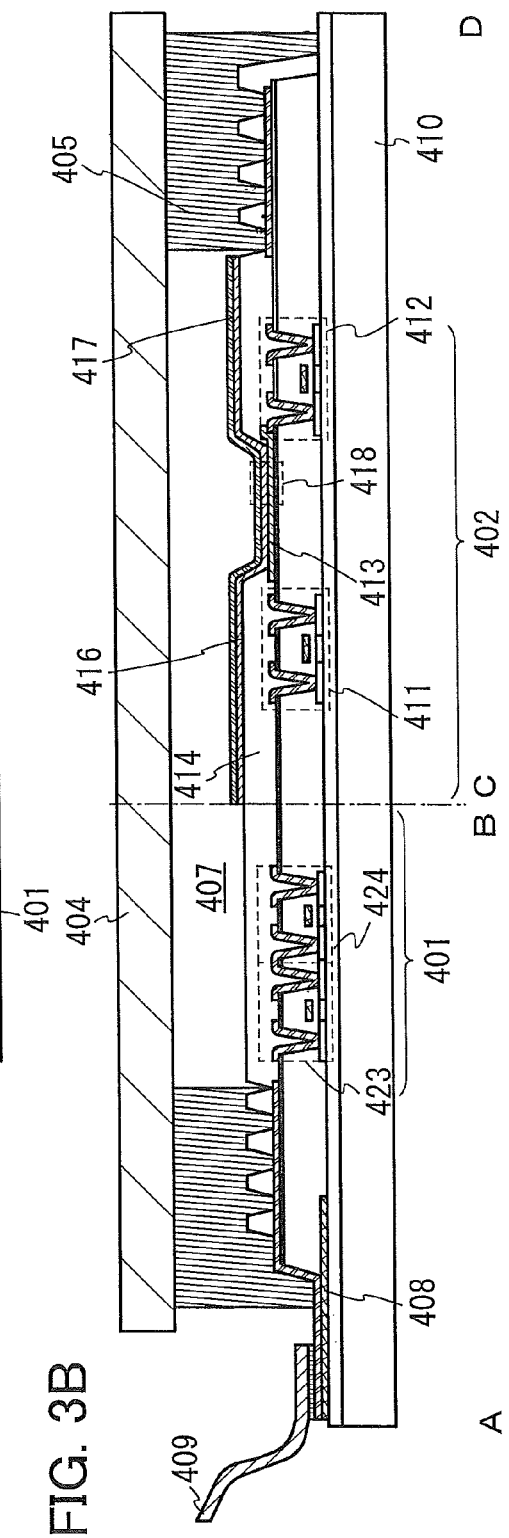

In FIG. 3A, reference numeral 401 denotes a driver circuit portion (a source side driver circuit), reference numeral 402 denotes a pixel portion, and reference numeral 403 denotes a driver circuit portion (a gate side driver circuit), which are each indicated by dotted lines. Reference numeral 404 denotes a sealing substrate, reference numeral 405 denotes a sealing material, and a portion enclosed by the sealing material 405 is a space 407.

Note that a lead wiring 408 is a wiring for transmitting signals that are to be input to the source side driver circuit 401 and the gate side driver circuit 403, and receives a video signal, a clock signal, a start signal, a reset signal, and the like from a flexible printed circuit (FPC) 409 which serves as an external input terminal. Although only the FPC is illustrated here, a printed wiring board (PWB) may be attached to the FPC. The light-emitting device in this specification includes not only a light-emitting device itself but also a light-emitting device to which an FPC or a PWB is attached.

Next, a cross-sectional structure will be described with reference to FIG. 3B. The driver circuit portion and the pixel portion are formed over an element substrate 410. Here, the source side driver circuit 401 which is the driver circuit portion and one pixel in the pixel portion 402 are illustrated.

Note that as the source side driver circuit 401, a CMOS circuit which includes an n-channel TFT 423 and a p-channel TFT 424 is formed. The driver circuit may be any of a variety of circuits formed with TFTs, such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 402 includes a plurality of pixels having a switching TFT 411, a current control TFT 412, and a first electrode 413 electrically connected to a drain of the current control TFT 412. Note that an insulator 414 is formed to cover an end portion of the first electrode 413. Here, the insulator 414 is formed by using a positive type photosensitive acrylic resin film.

In order to improve coverage, the insulator 414 is provided such that either an upper end portion or a lower end portion of the insulator 414 has a curved surface with a curvature. For example, when positive photosensitive acrylic is used as a material for the insulator 414, it is preferable that only an upper end portion of the insulator 414 have a curved surface with a radius of curvature (0.2 μm to 3 μm). For the insulator 414, it is also possible to use either a negative type that becomes insoluble in an etchant by light irradiation or a positive type that becomes soluble in an etchant by light irradiation.

An EL layer 416 and a second electrode 417 are faulted over the first electrode 413. Here, as a material for forming the first electrode 413 functioning as the anode, a material having a high work function is preferably used. For example, it is possible to use a single layer of an ITO film, an indium tin oxide film that includes silicon, an indium oxide film that includes 2 wt % to 20 wt % of zinc oxide, a titanium nitride film, a chromium film, a tungsten film, a Zn film, a Pt film, or the like, a stacked layer of a titanium nitride film and a film that mainly includes aluminum, a three-layer structure of a titanium nitride film, a film that mainly includes aluminum, and a titanium nitride film, or the like. Note that, when a stacked layer structure is employed, resistance of a wiring is low and an excellent ohmic contact is obtained.

In addition, the EL layer 416 is formed by any of various methods such as an evaporation method using an evaporation mask, a droplet discharging method like an inkjet method, a printing method, and a spin coating method. The EL layer 416 includes a fluorene compound described in Embodiment 1. Further, another material included in the EL layer 416 may be a low molecular material, an oligomer, a dendrimer, a high molecular material, or the like.

As a material used for the second electrode 417 which is formed over the EL layer 416 and serves as a cathode, it is preferable to use a material having a low work function (e.g., Al, Mg, Li, Ca, or an alloy or a compound thereof such as Mg—Ag, Mg—In, or Al—Li). In order that light generated in the EL layer 416 be transmitted through the second electrode 417, a stack of a metal thin film having a reduced thickness and a transparent conductive film (e.g., ITO, indium oxide containing 2 wt % to 20 wt % of zinc oxide, indium oxide-tin oxide that includes silicon or silicon oxide, or zinc oxide) is preferably used for the second electrode 417.

Further, the sealing substrate 404 is attached to the element substrate 410 with the sealing material 405, so that a light-emitting element 418 is provided in the space 407 enclosed by the element substrate 410, the sealing substrate 404, and the sealing material 405. The space 407 is filled with a filler, and may be filled with an inert gas (such as nitrogen or argon) or the sealing material 405.

Note that an epoxy-based resin is preferably used as the sealing material 405. Such a material preferably allows as little moisture and oxygen as possible to penetrate. As a material used for the sealing substrate 404, a plastic substrate formed of fiberglass-reinforced plastics (FRP), polyvinyl fluoride (PVF), polyester, acrylic, or the like can be used other than a glass substrate or a quartz substrate.

As described above, the active matrix light-emitting device including the light-emitting element of one embodiment of the present invention can be obtained.

Figure 4A:
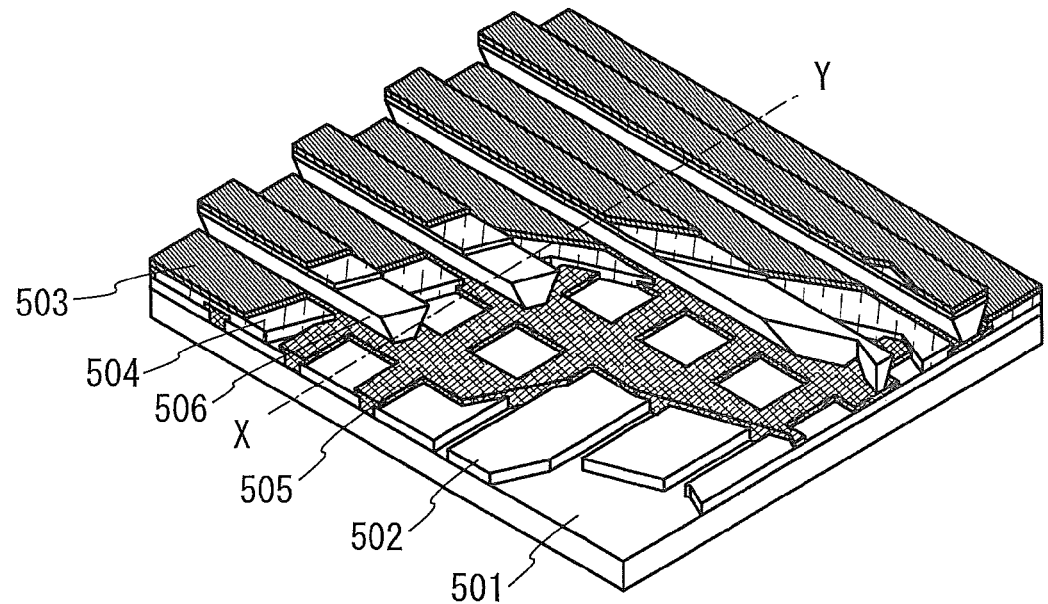
FIGS. 4A and 4B illustrate a light-emitting device of one embodiment of the present invention.
Figure 4B:
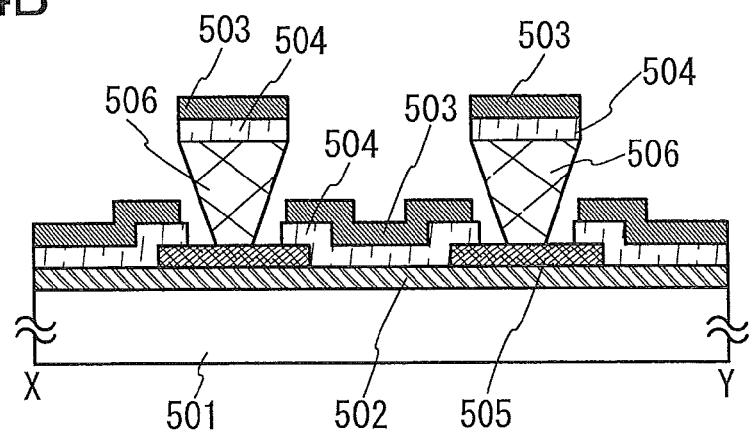

Further, a light-emitting element of the present invention can be used for a passive matrix light-emitting device as well as the above active matrix light-emitting device. FIGS. 4A and 4B illustrate a perspective view and a cross-sectional view of a passive matrix light-emitting device including a light-emitting element of the present invention. Note that FIG. 4A is a perspective view of the light-emitting device, and FIG. 4B is a cross-sectional view taken along line X-Y of FIG. 4A.

In FIGS. 4A and 4B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 slope so that a distance between both the sidewalls is gradually narrowed toward the surface of the substrate. In other words, a cross section taken along the direction of the short side of the partition layer 506 is trapezoidal, and the base (side in contact with the insulating layer 505) is shorter than the upper side (side not in contact with the insulating layer 505). With the partition layer 506 provided in such a way, a defect of a light-emitting element due to crosstalk or the like can be prevented.

Thus, the passive matrix light-emitting device including a light-emitting element of one embodiment of the present invention can be obtained.

The light-emitting devices described in this embodiment (the active matrix light-emitting device and the passive matrix light-emitting device) are both formed using a light-emitting element of one embodiment of the present invention, and accordingly, the light-emitting devices have low power consumption.

Note that this embodiment can be implemented in appropriate combination with any of the other embodiments.

Embodiment (5)

In this embodiment, with reference to FIGS. 5A to 5E and FIG. 6, description is given of examples of a variety of electronic devices and lighting devices that are each completed by using a light-emitting device which is one embodiment of the present invention.

Examples of the electronic devices to which the light-emitting device is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices and a lighting device are illustrated in FIGS. 5A to 5E.

Figure 5A:
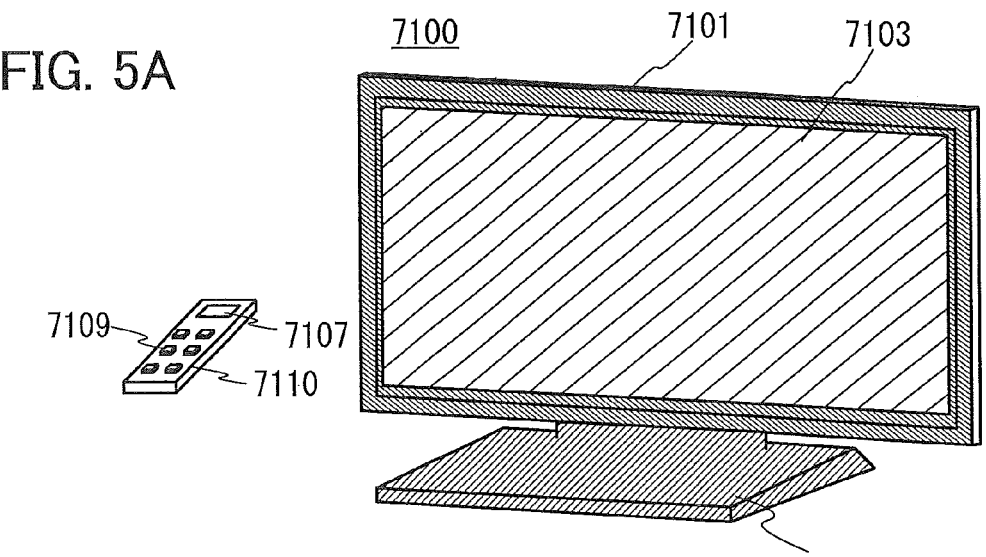
FIGS. 5A to 5E each illustrate an electronic device of one embodiment of the present invention.

FIG. 5A illustrates an example of a television device. In the television device 7100, a display portion 7103 is incorporated in a housing 7101. The display portion 7103 is capable of displaying images, and a light-emitting device can be used for the display portion 7103. In addition, here, the housing 7101 is supported by a stand 7105.

The television device 7100 can be operated with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television device 7100 is provided with a receiver, a modem, and the like. With the receiver, general television broadcasting can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 5B:
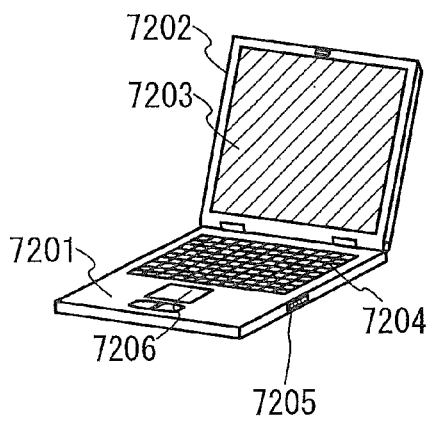

FIG. 5B illustrates a computer, which includes a main body 7201, a housing 7202, a display portion 7203, a keyboard 7204, an external connection port 7205, a pointing device 7206, and the like. This computer is manufactured by using a light-emitting device for the display portion 7203.

Figure 5C:
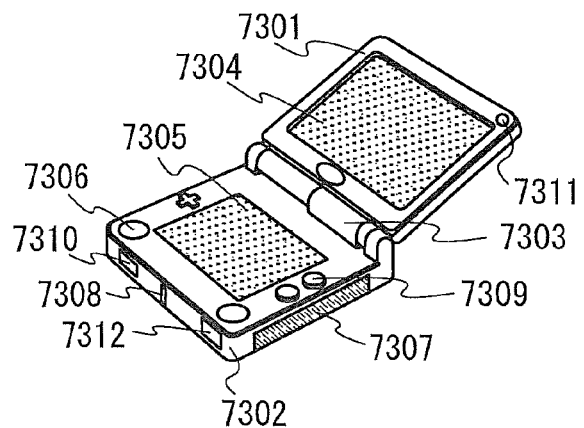

FIG. 5C illustrates a portable game machine, which includes two housings, a housing 7301 and a housing 7302, connected with a joint portion 7303 so that the portable game machine can be opened or closed. A display portion 7304 is incorporated in the housing 7301 and a display portion 7305 is incorporated in the housing 7302. In addition, the portable game machine illustrated in FIG. 5C includes a speaker portion 7306, a recording medium insertion portion 7307, an LED lamp 7308, an input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. It is needless to say that the structure of the portable game machine is not limited to the above as long as a light-emitting device is used for at least either the display portion 7304 or the display portion 7305, or both, and may include other accessories as appropriate. The portable game machine illustrated in FIG. 5C has a function of reading out a program or data stored in a storage medium to display it on the display portion, and a function of sharing information with another portable game machine by wireless communication. The portable game machine illustrated in FIG. 5C can have a variety of functions without limitation to the above.

Figure 5D:
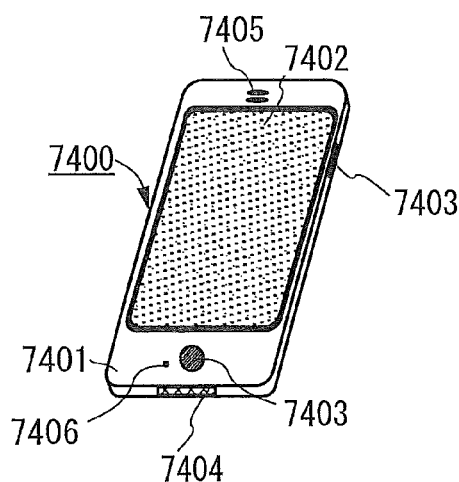

FIG. 5D illustrates an example of a cellular phone. The cellular phone 7400 is provided with operation buttons 7403, an external connection port 7404, a speaker 7405, a microphone 7406, and the like, in addition to a display portion 7402 incorporated in a housing 7401. Note that the cellular phone 7400 is manufactured using a light-emitting device for the display portion 7402.

When the display portion 7402 of the cellular phone 7400 illustrated in FIG. 5D is touched with a finger or the like, data can be input to the cellular phone 7400. Further, operations such as making a call and creating e-mail can be performed by touch on the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are mixed.

For example, in the case of making a call or creating e-mail, a character input mode mainly for inputting characters is selected for the display portion 7402 so that characters displayed on a screen can be input. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touch on the display portion 7402 or operation with the operation buttons 7403 of the housing 7401. Alternatively, the screen modes can be switched depending on kinds of images displayed on the display portion 7402. For example, when a signal for an image to be displayed on the display portion is data of moving images, the screen mode is switched to the display mode. When the signal is text data, the screen mode is switched to the input mode.

Moreover, in the input mode, if a signal detected by an optical sensor in the display portion 7402 is detected and the input by touch on the display portion 7402 is not performed during a certain period, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal identification can be performed. Furthermore, by provision of a backlight or a sensing light source emitting near-infrared light for the display portion, an image of a finger vein, a palm vein, or the like can also be taken.

Figure 5E:
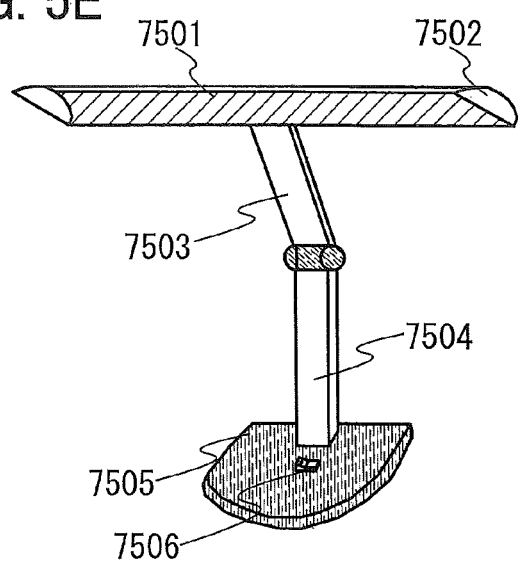

FIG. 5E illustrates a desk lamp, which includes a lighting portion 7501, a shade 7502, an adjustable arm 7503, a support 7504, a base 7505, and a power switch 7506. The desk lamp is manufactured using a light-emitting device for the lighting portion 7501. Note that the "lighting device" also includes ceiling lights, wall lights, and the like.

Figure 6:
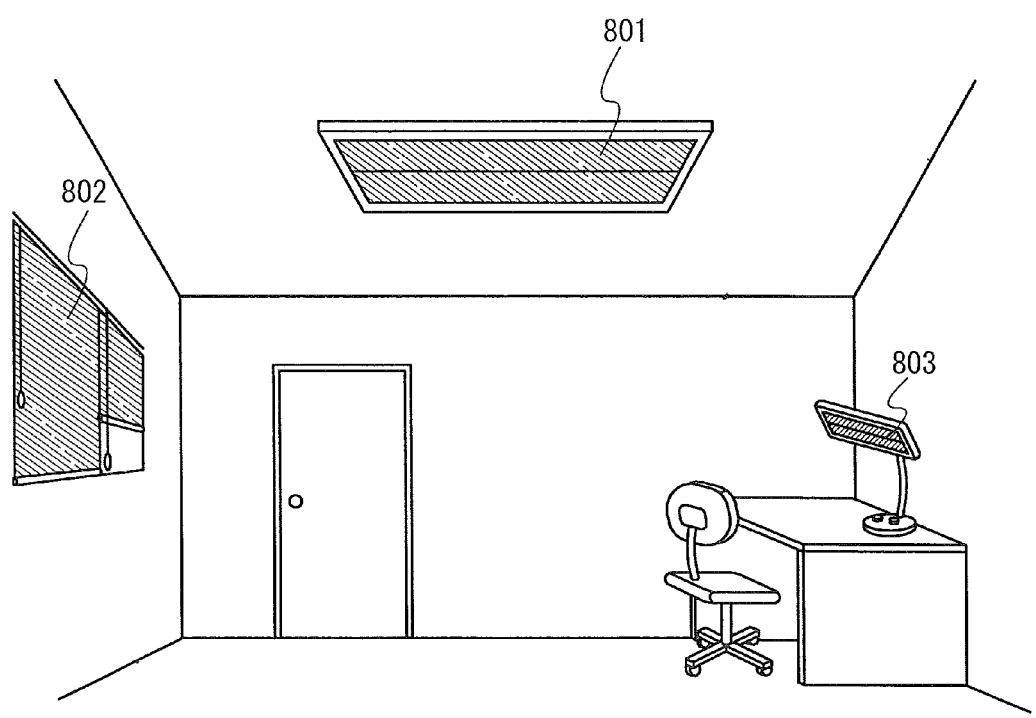
FIG. 6 illustrates a lighting device of one embodiment of the present invention.

FIG. 6 illustrates an example in which a light-emitting device is used for an interior lighting device 801. Since the light-emitting device can have a larger area, it can be used as a lighting device having a large area. Furthermore, the light-emitting device can be used as a roll-type lighting device 802. As illustrated in FIG. 6, a desk lamp 803 described with reference to FIG. 5E may also be used in a room provided with the interior lighting device 801.

In the above-described manner, electronic devices or lighting devices can be obtained by application of a light-emitting device. Application range of the light-emitting device is so wide that the light-emitting device can be applied to electronic devices in a variety of fields.

Note that the structure described in this embodiment can be combined with any of the structures described in Embodiments 1 to 4 as appropriate.

EXAMPLE 1

Synthesis Example 1

This example gives descriptions of a method of synthesizing 2,8-diphenyl-4-[4-(9-phenyl-9H-fluoren-9-yl)phenyl]dibenzothiophene (abbreviation: DBTFLP-III), which is a fluorene compound of one embodiment of the present invention, represented by the structural formula (106) in Embodiment 1.

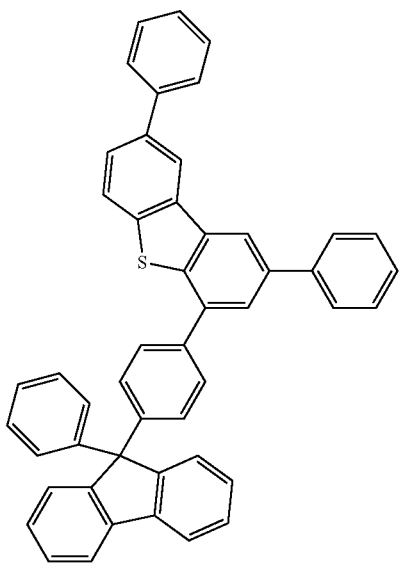

DBTFLP-III

To a 100 mL three-neck flask were added 1.6 g (4.0 mmol) of 9-(4-bromophenyl)-9-phenyl-9H-fluorene, 1.7 g (4.4 mmol) of 2,8-diphenyldibenzothiophene-4-boronic acid, 11 mg (0.1 mmol) of palladium(II) acetate, 30 mg (0.1 mmol) of tri(ortho-tolyl)phosphine, 30 mL of toluene, 3 mL of ethanol, and 5 mL of a 2 mol/L aqueous potassium carbonate solution. This mixture was degassed while being stirred under reduced pressure, and was then reacted by being heated and stirred under a nitrogen atmosphere at 90° C. for 6.5 hours.

After the reaction, 150 mL of toluene was added to this reaction mixture solution, and the organic layer was filtered through Florisil (produced by Wako Pure Chemical Industries, Ltd., Catalog No. 540-00135), alumina (produced by Merck & Co., Inc., neutral), and Celite (produced by Wako Pure Chemical Industries, Ltd., Catalog No. 531-16855) in this order to give a filtrate. The obtained residue was purified by silica gel column chromatography (with a developing solvent of toluene and hexane in a 1:3 ratio). The obtained fraction was concentrated, and acetone and methanol were added thereto. The mixture was irradiated with ultrasonic waves and then recrystallized to give 2.3 g of a white powder in a yield of 90%, which was the object of the synthesis. A reaction scheme of the above synthesis method is illustrated in the following (D-1).

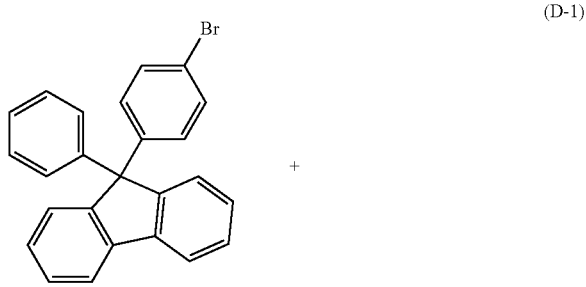

(D-1)

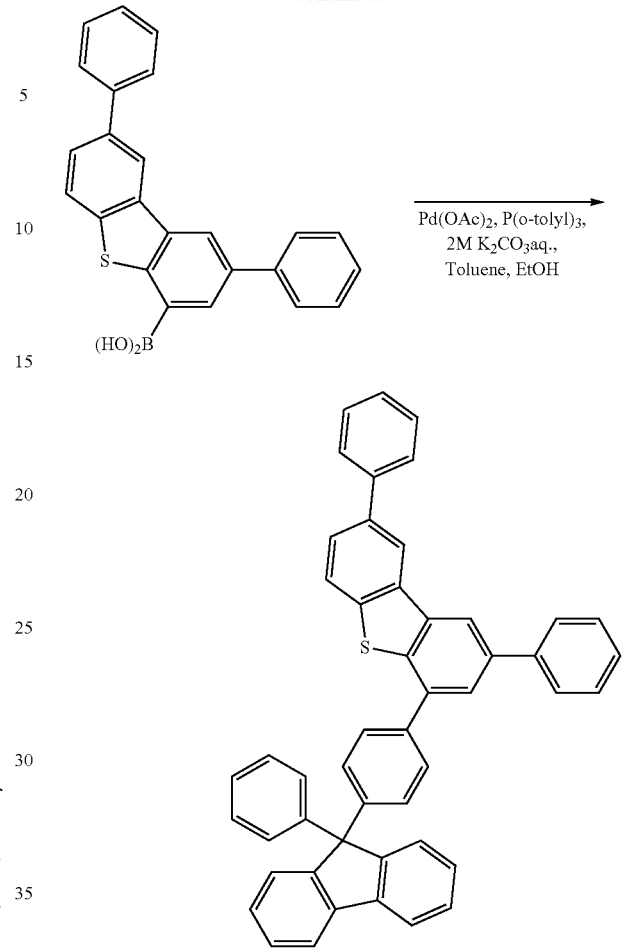

The Rf values of the substance that was the object of the synthesis and 9-(4-bromophenyl)-9-phenyl-9H-fluorene were respectively 0.33 and 0.60, which were found by silica gel thin layer chromatography (TLC) (with a developing solvent of ethyl acetate and hexane in a 1:10 ratio).

This compound was identified as DBTFLP-III, which was the object of the synthesis, by nuclear magnetic resonance (NMR) spectroscopy.

$^1$H NMR data of the obtained compound are as follows: $^1$H NMR (CDCl$_3$, 300 MHz): 7.23-7.52 (m, 20H), 7.65-7.76 (m, 8H), 7.81 (d, J=6.9 Hz, 1H), 7.88 (d, J=8.1 Hz, 1H), 8.40 (dd, J=11.7 Hz, 1.5 Hz, 2H).

Figure 7A:
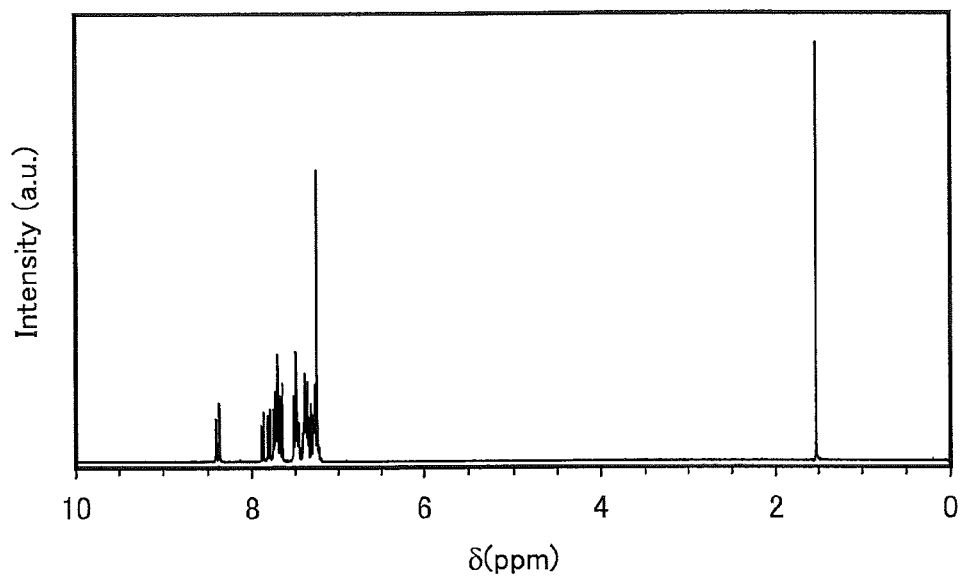
FIGS. 7A and 7B show $^1$H NMR charts of DBTFLP-III.
Figure 7B:
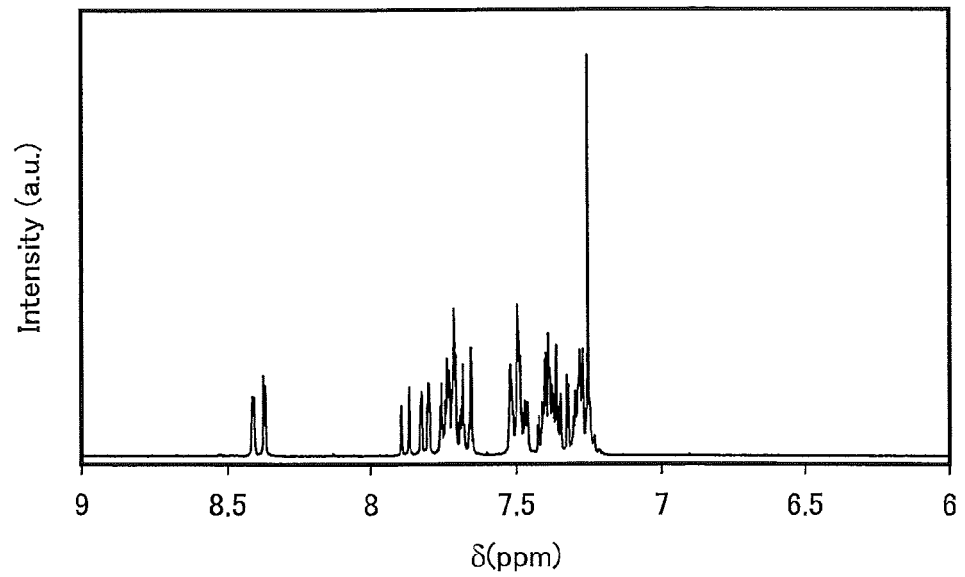

Further, the $^1$H NMR charts are shown in FIGS. 7A and 7B. Note that FIG. 7B is a chart where the range of from 6.0 ppm to 9.0 ppm in FIG. 7A is enlarged.

Figure 8A:
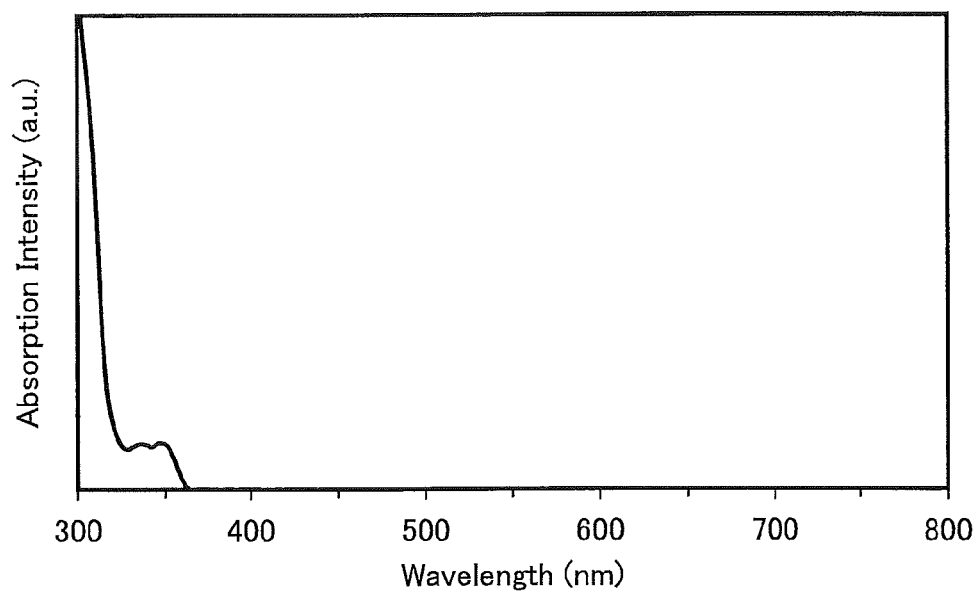
FIGS. 8A and 8B show an absorption spectrum and an emission spectrum of DBTFLP-III in a toluene solution of DBTFLP-III.
Figure 8B:
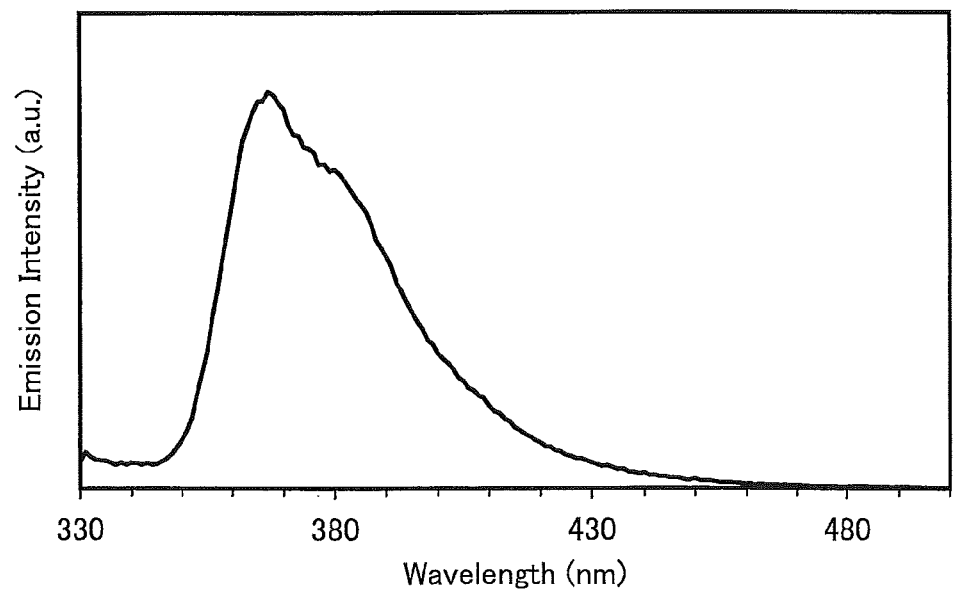
Figure 9A:
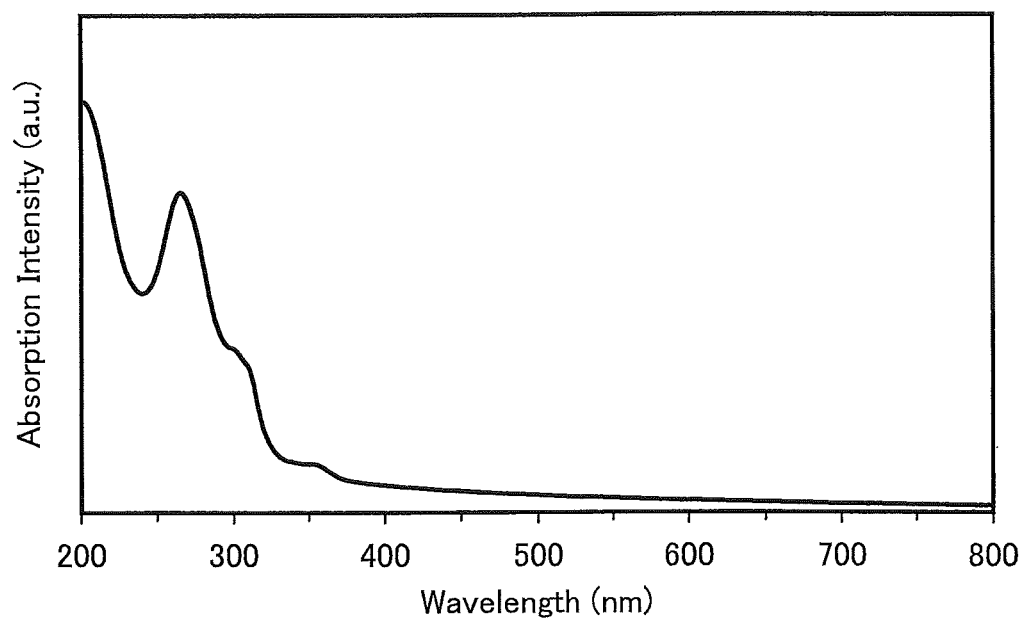
FIGS. 9A and 9B show an absorption spectrum and an emission spectrum of a thin film of DBTFLP-III.
Figure 9B:
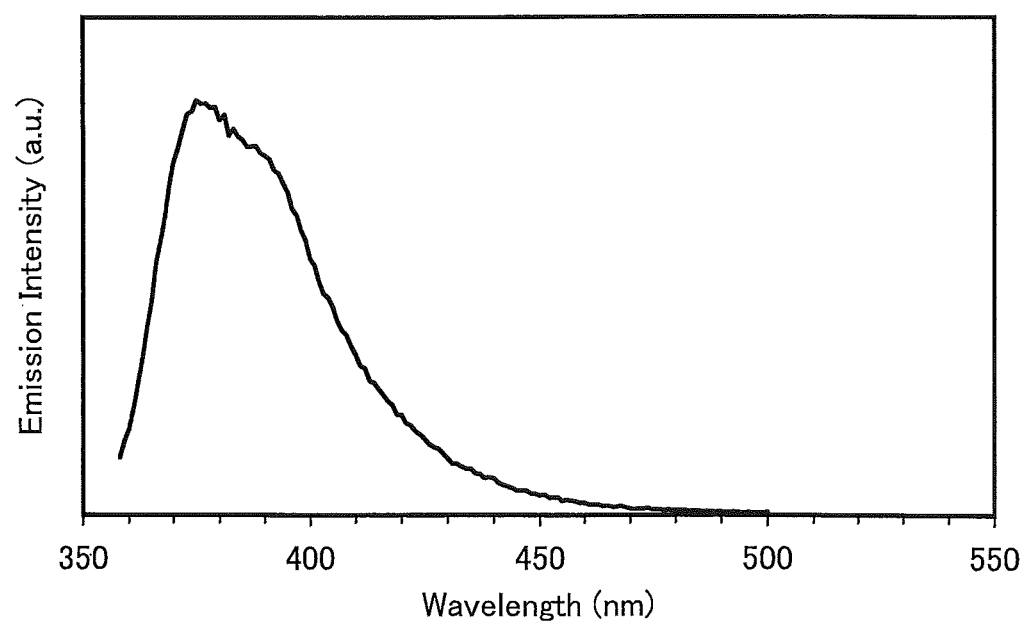

Further, FIG. 8A shows the absorption spectrum of DBTFLP-III in a toluene solution of DBTFLP-III, and FIG. 8B shows the emission spectrum thereof. In addition, FIG. 9A shows the absorption spectrum of a thin film of DBTFLP-III, and FIG. 9B shows the emission spectrum thereof. An ultraviolet-visible spectrophotometer (V-550, manufactured by JASCO Corporation) was used for the measurements. Samples were prepared in such a way that the solution was put in a quartz cell and the thin film was formed on a quartz substrate by evaporation. Here are shown the absorption spectrum for the solution which was obtained by subtracting the absorption spectra of quartz and toluene from those of quartz and the solution, and the absorption spectrum for the thin film which was obtained by subtracting the absorption spectrum of the quartz substrate from those of the quartz substrate and the thin film. In FIG. 8A and FIG. 9A, the horizontal axis represents wavelength (nm) and the vertical axis represents absorption intensity (arbitrary unit). In FIG. 8B and FIG. 9B, the horizontal axis represents wavelength (nm) and the vertical axis represents emission intensity (arbitrary unit). In the case of the toluene solution, absorption peaks were found at around 295 nm and 349 nm, and a peak of the emission wavelength was at 367 nm (at an excitation wavelength of 300 nm). In the case of the thin film, absorption peaks were found at around 266 nm, 299 nm, and 352 nm, and peaks of the emission wavelength were at 376 nm and 388 nm (at an excitation wavelength of 354 nm) FIG. 8A and FIG. 9A show that DBTFLP-III is a substance having weak absorption in the visible region. In other words, it is suggested that in the case where DBTFLP-III which is a fluorene compound of one embodiment of the present invention is used for a light-emitting element, visible light emitted from a light-emitting layer is unlikely to be absorbed by DBTFLP-III, and thus a decrease in light extraction efficiency of the element can be suppressed.

It is also found that DBTFLP-III has a peak of the emission spectrum at a very short wavelength and thus can be used for a host material of a light-emitting layer or used for a carrier-transport layer adjacent to the light-emitting layer in a fluorescent element which emits visible light.

The results of the measurement of the thin film by photoelectron spectrometry (AC-2, a product of Riken Keiki Co., Ltd.) in the air indicate that the HOMO level is −5.89 eV. From the Tauc plot of the absorption spectrum of the thin film, the absorption edge was 3.24 eV. Therefore, the energy gap in the solid state is estimated to be 3.24 eV, which means that the LUMO level is −2.65 eV. This indicates that DBTFLP-III has a relatively low HOMO level and a wide band gap.

Next, the oxidation-reduction characteristics were examined by cyclic voltammetry (CV) measurement. An electrochemical analyzer (ALS model 600A or 600C, manufactured by BAS Inc.) was used for the measurement.

For the measurement of the oxidation characteristics, the potential of the working electrode with respect to the reference electrode was scanned from 0.00 V to 1.25 V and then from 1.25 V to 0.00 V. As a result, the HOMO level was found to be −6.20 eV. In addition, the oxidation peak was at a similar value even after 100 cycles: This indicates that DBTFLP-III has properties effective against repetition of redox reactions between an oxidized state and a neutral state.

Note that a method for the measurement is described in detail below.

(Calculation of Potential Energy of Reference Electrode with Respect to Vacuum Level)

First, a potential energy (eV) of the reference electrode (Ag/Ag$^+$ electrode), which was used in this example, with respect to the vacuum level was calculated. That is, the Fermi level of the Ag/Ag$^+$ electrode was calculated. It is known that the oxidation-reduction potential of ferrocene in methanol is +0.610 [V vs. SHE] with respect to the normal hydrogen electrode (Reference: Christian R. Goldsmith et al., J. Am. Chem. Soc., Vol. 124, No. 1, 83-96, 2002). On the other hand, using the reference electrode used in this example, the oxidation-reduction potential of ferrocene in methanol was calculated to be+0.11 V [vs. Ag/Ag$^+$]. Therefore, it is found that the potential energy of the reference electrode used in this example was lower than that of the normal hydrogen electrode by 0.50 [eV].

Note that it is known that the potential energy of the normal hydrogen electrode from the vacuum level is −4.44 eV (Reference: Toshihiro Ohnishi and Tamami Koyama, Kobunshi EL Zaiiyou [*High Molecular EL Material*], Kyoritsu Shuppan, pp. 64-67). From the above, the potential energy of the reference electrode with respect to the vacuum level was calculated to be −4.44-0.50=−4.94 [eV].

(Conditions for CV Measurement of Objective Substance)

As for a solution used for the CV measurement, dehydrated dimethylformamide (DMF, manufactured by Sigma-Aldrich Inc., 99.8%, Catalog No. 22705-6) was used as a solvent, and tetra-n-butylammonium perchlorate (n-Bu$_4$NClO$_4$, manufactured by Tokyo Chemical Industry Co., Ltd., Catalog No. T0836), which was a supporting electrolyte, was dissolved in the solvent such that the concentration of tetra-n-butylammonium perchlorate was 100 mmol/L. Further, the object to be measured was dissolved in the solvent such that the concentration thereof was 2 mmol/L. In addition, a platinum electrode (PTE platinum electrode, manufactured by BAS Inc.) was used as a working electrode, a platinum electrode (Pt counter electrode for VC-3 (5 cm), manufactured by BAS Inc.) was used as an auxiliary electrode, and an Ag/Ag$^+$ electrode (RE-7 reference electrode for nonaqueous solvent, manufactured by BAS Inc.) was used as a reference electrode. Note that the measurement was conducted at room temperature (20° C. to 25° C.). In addition, the scan rate at the CV measurement was set to 0.1 V/sec in all the measurement.

Figure 14:
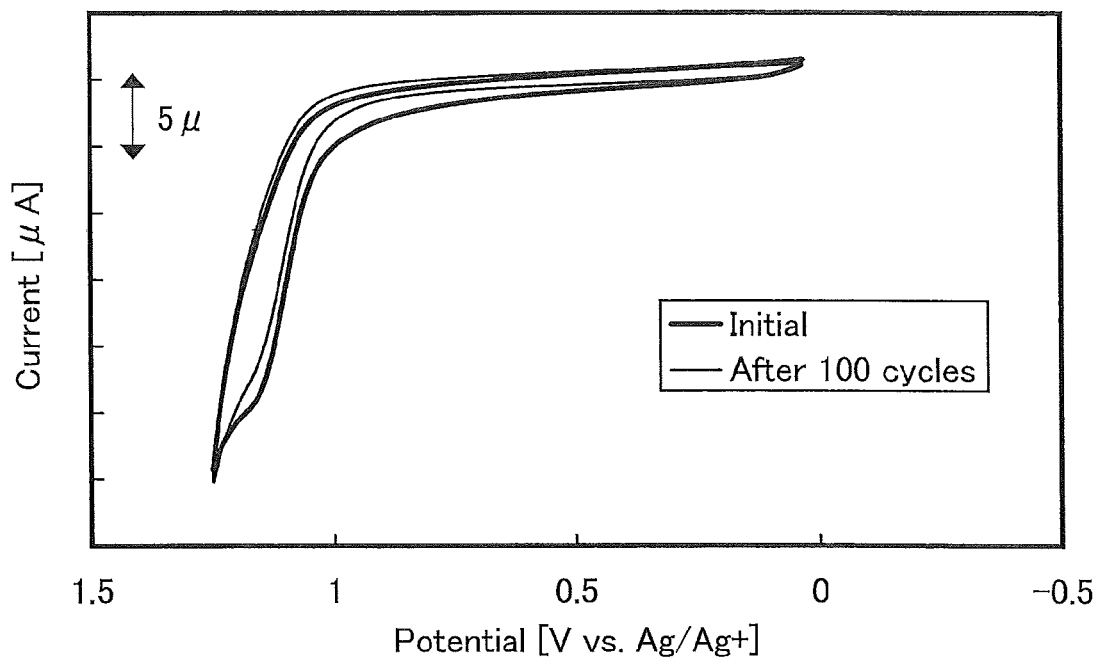
FIG. 14 show results of CV measurement of DBTFLP-III.

Next, the HOMO level was calculated from the CV measurement. FIG. 14 shows results of the CV measurement of the oxidation characteristics. As shown in FIG. 14, the oxidation peak potential (from the neutral state to the oxidation state) $E_{pa}$ was 1.18 V. In addition, the reduction peak potential (from the oxidation state to the neutral state) $E_{pc}$ was 1.04 V. Therefore, a half-wave potential (an intermediate potential between $E_{pa}$ and $E_{pc}$ ($E_{pa}+E_{pc}$)/2 [V]) can be calculated to be 1.11 V. This shows that DBTFLP-III is oxidized with an electrical energy of 1.11 [V vs. Ag/Ag$^+$]. Here, since the potential energy of the reference electrode, which was used above, with respect to the vacuum level is −4.94 eV as described above, the HOMO level of DBTFLP-III was calculated to be −4.94-1.11=−6.05 [eV].

A thin film of DBTFLP-III was formed by vacuum evaporation. This thin film was not a white and opaque film but a transparent film. This also suggests that DBTFLP-III is a substance which is unlikely to be crystallized.

EXAMPLE 2

Synthesis Example 2

This example gives descriptions of a method of synthesizing 4-[4-(9-phenyl-9H-fluoren-9-yl)phenyl]-6-phenyldibenzothiophene (abbreviation: DBTFLP-IV), which is a fluorene compound of one embodiment of the present invention, represented by the structural formula (103) in Embodiment 1.

101

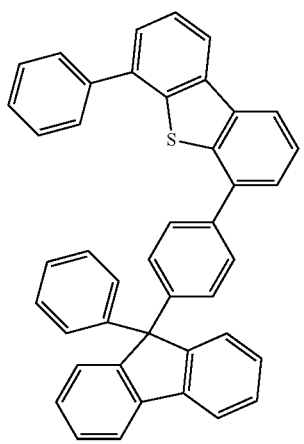

DBTFLP-IV

To a 100 mL three-neck flask were added 1.6 g (4.0 mmol) of 9-(4-bromophenyl)-9-phenyl-9H-fluorene, 1.2 g (4.0 mmol) of 4-phenyldibenzothiophene-6-boronic acid, 4.0 mg (20 μmol) of palladium(II) acetate, 12 mg (40 μmol) of tri(ortho-tolyl)phosphine, 30 mL of toluene, 3 mL of ethanol, and 3 mL of a 2 mol/L aqueous potassium carbonate solution. This mixture was degassed while being stirred under reduced pressure, and was then reacted by being heated and stirred under a nitrogen atmosphere at 90° C. for 6 hours.

After the reaction, 150 mL of toluene was added to this reaction mixture solution, and the organic layer was filtered through Florisil (produced by Wako Pure Chemical Industries, Ltd., Catalog No. 540-00135), alumina (produced by Merck & Co., Inc., neutral), and Celite (produced by Wako Pure Chemical Industries, Ltd., Catalog No. 531-16855) in this order to give a filtrate. The obtained residue was purified by silica gel column chromatography (with a developing solvent of toluene and hexane in a 1:3 ratio). The obtained fraction was concentrated, and acetone and methanol were added thereto. The mixture was irradiated with ultrasonic waves and then recrystallized to give 1.6 g of a white powder in a yield of 73%, which was the object of the synthesis. A reaction scheme of the above synthesis method is illustrated in the following (E-1).

(E-1)

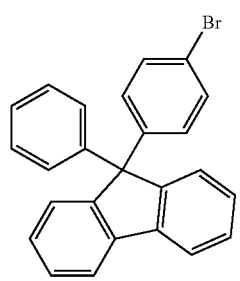

+

102

-continued

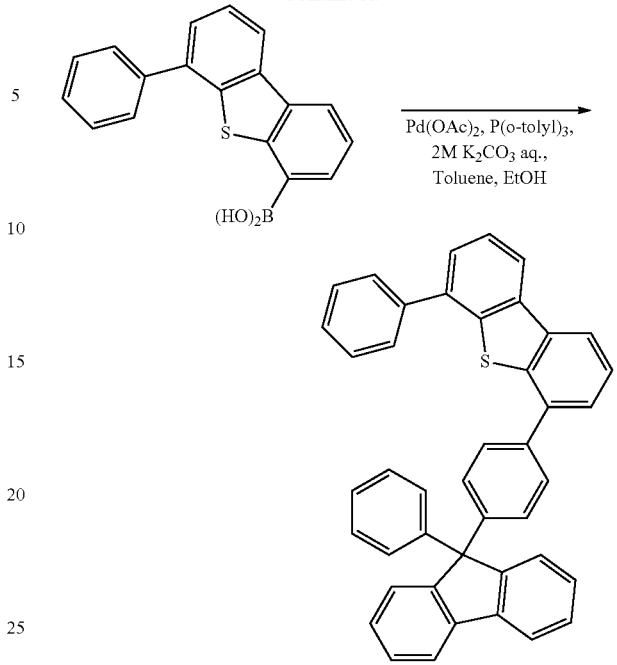

The Rf values of the substance that was the object of the synthesis and 9-(4-bromophenyl)-9-phenyl-9H-fluorene were respectively 0.40 and 0.48, which were found by silica gel thin layer chromatography (TLC) (with a developing solvent of ethyl acetate and hexane in a 1:10 ratio).

This compound was identified as DBTFLP-IV, which was the object of the synthesis, by nuclear magnetic resonance (NMR) spectroscopy.

$^1$H NMR data of the obtained compound are as follows: $^1$H NMR (CDCl$_3$, 300 MHz): 7.16-7.59 (m, 22H), 7.69-7.71 (m, 2H), 7.79 (d, J=7.5 Hz, 2H), 8.14-8.18 (m, 2H).

Figure 10A:
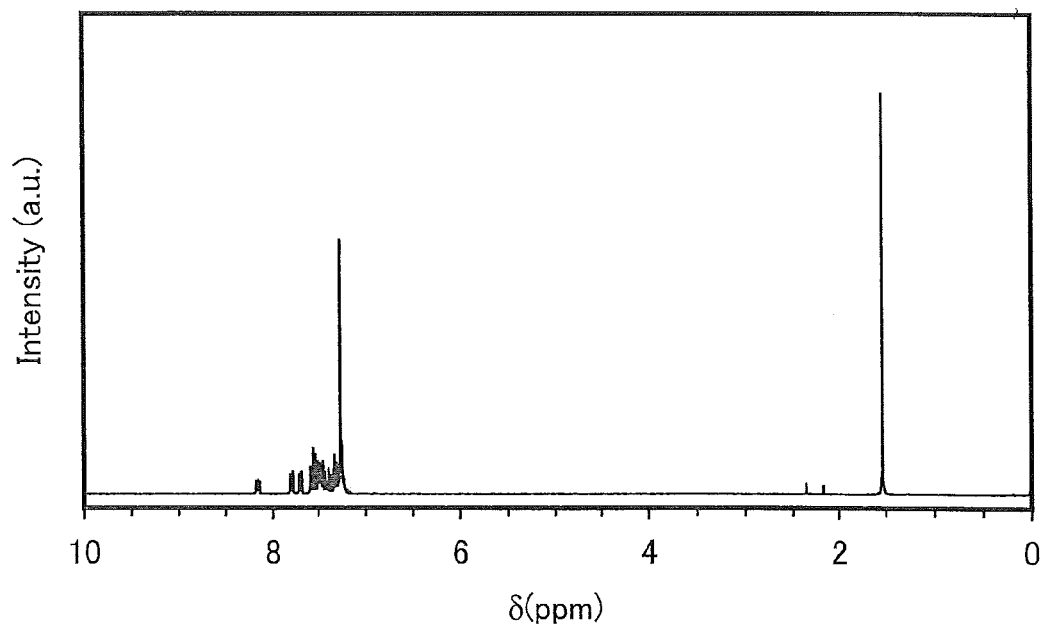
FIGS. 10A and 10B show $^1$H NMR charts of DBTFLP-IV.
Figure 10B:
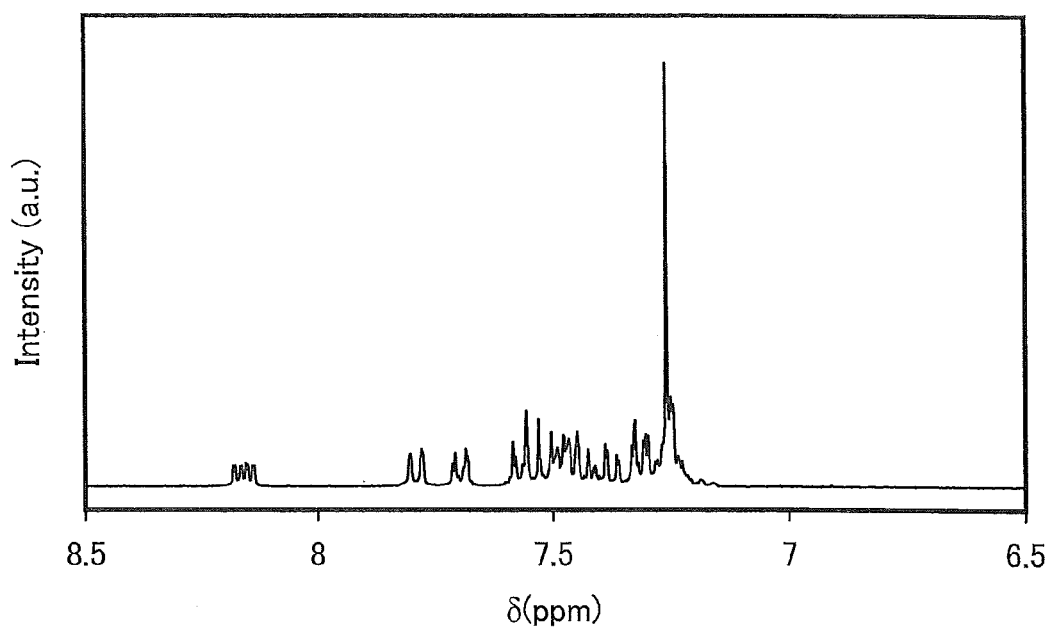

Further, the $^1$H NMR charts are shown in FIGS. 10A and 10B. Note that FIG. 10B is a chart where the range of from 6.5 ppm to 8.5 ppm in FIG. 10A is enlarged.

Figure 11A:
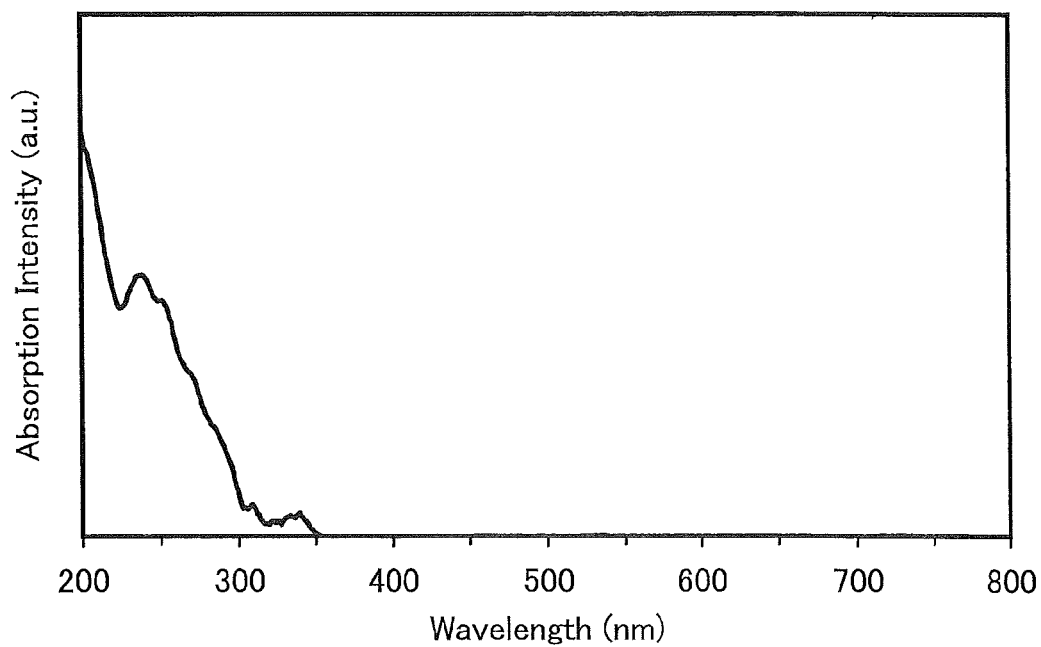
FIGS. 11A and 11B show an absorption spectrum of DBTFLP-IV in a hexane solution of DBTFLP-IV and an emission spectrum of DBTFLP-IV in a toluene solution of DBTFLP-IV.
Figure 11B:
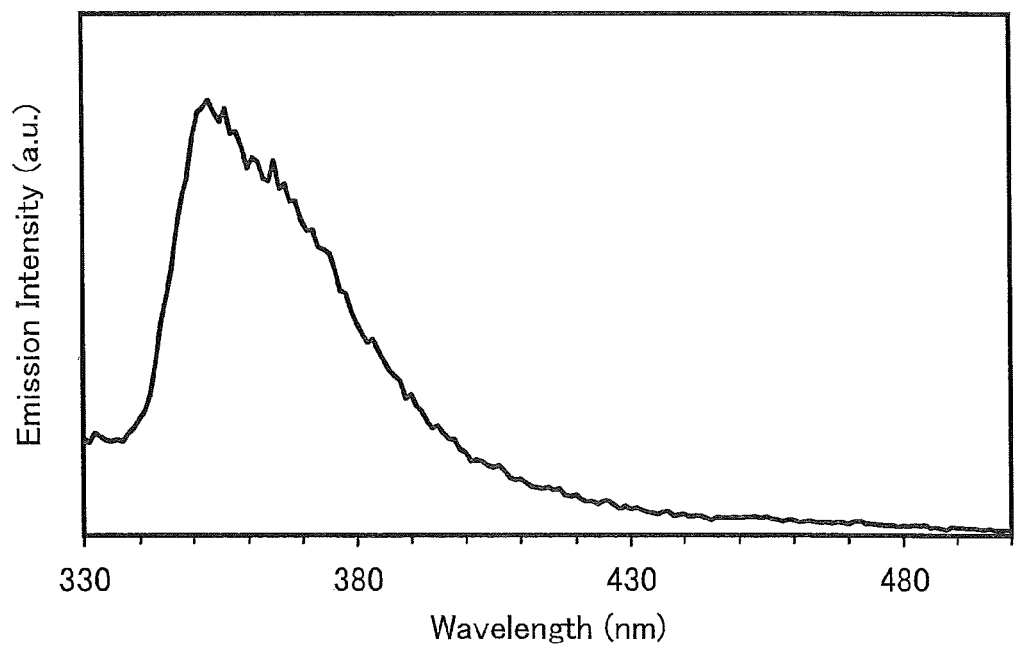
Figure 12A:
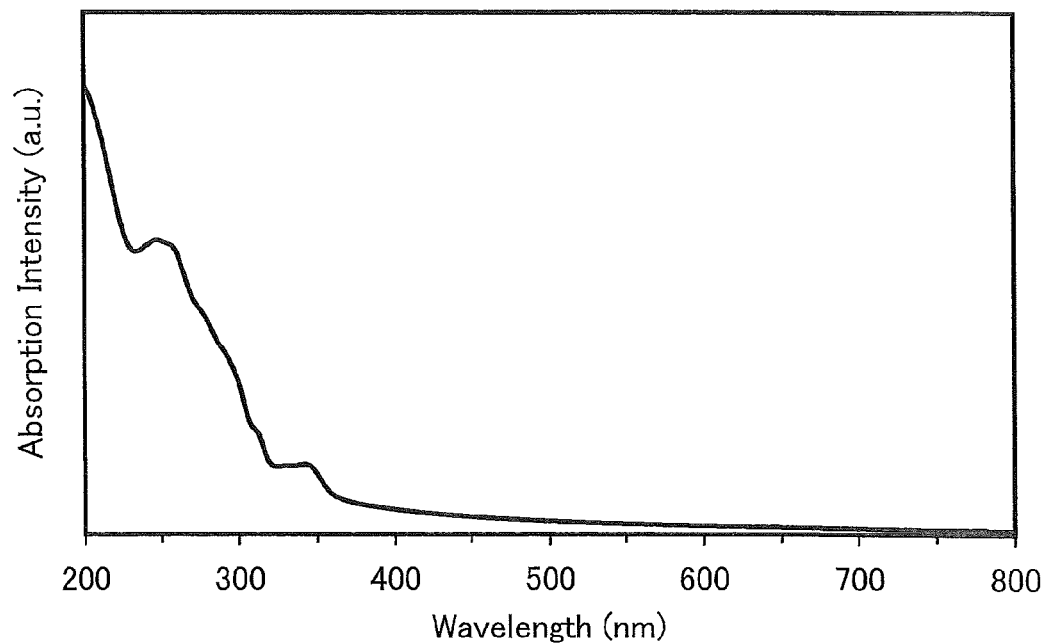
FIGS. 12A and 12B show an absorption spectrum and an emission spectrum of a thin film of DBTFLP-IV.
Figure 12B:
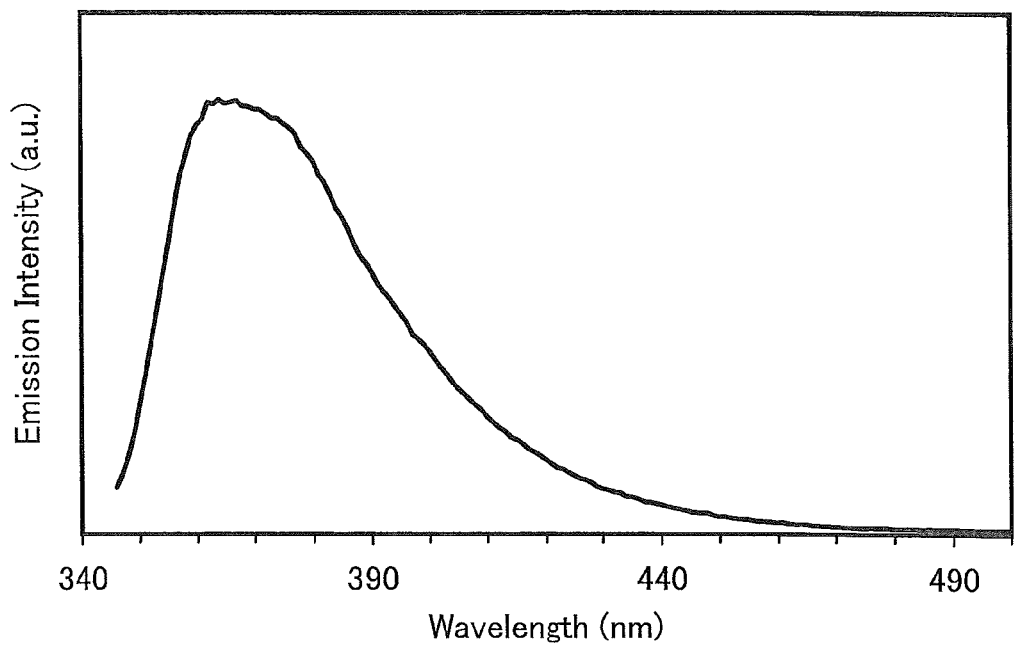

Further, FIG. 11A shows the absorption spectrum of DBTFLP-IV in a hexane solution of DBTFLP-IV, and FIG. 11B shows the emission spectrum of DBTFLP-IV in a toluene solution of DBTFLP-IV. In addition, FIG. 12A shows the absorption spectrum of a thin film of DBTFLP-IV, and FIG. 12B shows the emission spectrum thereof. An ultraviolet-visible spectrophotometer (V-550, manufactured by JASCO Corporation) was used for the measurements. Samples were prepared in such a way that the solution was put in a quartz cell and the thin film was formed on a quartz substrate by evaporation. Here are shown the absorption spectrum for the solution which was obtained by subtracting the absorption spectra of quartz and hexane from those of quartz and the solution, and the absorption spectrum for the thin film which was obtained by subtracting the absorption spectrum of the quartz substrate from those of the quartz substrate and the thin film. In FIG. 11A and FIG. 12A, the horizontal axis represents wavelength (nm) and the vertical axis represents absorption intensity (arbitrary unit). In FIG. 11B and FIG. 12B, the horizontal axis represents wavelength (nm) and the vertical axis represents emission intensity (arbitrary unit). In the case of the solution, absorption peaks were found at around 236 nm and 338 nm, and a peak of the emission wavelength was at 353 nm (at an excitation wavelength of 290 nm). In the case of the thin film, absorption peaks were found at around 247 nm and 343 nm, and a peak of the emission wavelength was at 365 nm (at an excitation wavelength of 343 nm). FIG. 11A and FIG. 12A show that DBTFLP-IV is a substance having weak absorption in the visible region. In other words, it is suggested that in the case where DBTFLP-IV which is a fluorene compound of one embodiment of the present invention is used for a light-emitting element, visible light emitted is unlikely to be reabsorbed, and thus the element is unlikely to have a decrease in light extraction efficiency.

It is also found that DBTFLP-IV has a peak of the emission spectrum at a very short wavelength and thus can be used as a host material of a light-emitting layer or used for a carrier-transport layer adjacent to the light-emitting layer in a fluorescent element which emits visible light.

The results of the measurement of the thin film by photoelectron spectrometry (AC-2, a product of Riken Keiki Co., Ltd.) in the air indicate that the HOMO level is −5.99 eV. From the Tauc plot of the absorption spectrum of the thin film, the absorption edge was 3.42 eV. Therefore, the energy gap in the solid state is estimated to be 3.42 eV, which means that the LUMO level is −2.57 eV. This indicates that DBTFLP-IV has a relatively low HOMO level and a wide band gap.

Next, the oxidation-reduction characteristics were examined by cyclic voltammetry (CV) measurement. An electrochemical analyzer (ALS model 600A or 600C, manufactured by BAS Inc.) was used for the measurement.

For the measurement of the oxidation characteristics, the potential of the working electrode with respect to the reference electrode was scanned from −0.40 V to 1.50 V and then from 1.50 V to −0.40 V. As a result, the HOMO level was found to be −6.20 eV. In addition, the oxidation peak was at a similar value even after 100 cycles. This indicates that DBTFLP-IV has properties effective against repetition of redox reactions between an oxidized state and a neutral state.

For the measurement of the reduction characteristics, the potential of the working electrode with respect to the reference electrode was scanned from −3.00 V to −1.18 V and then from −1.18 V to −3.00 V. As a result, the LUMO level was found to be −2.19 eV. In addition, the reduction peak was at a similar value even after 100 cycles. This indicates that DBTFLP-IV has properties effective against repetition of redox reactions between a neutral state and a reduced state.

Note that the measurement method is similar to that in Example 1; thus, Example 1 can be referred to for details.

Next, the glass transition temperature was measured with a differential scanning calorimeter (Pyris 1 DSC, manufactured by Perkin Elmer Co., Ltd.). According to the measurement results, it was found that the glass transition temperature was 154° C. In this manner, DBTFLP-IV has a high glass transition temperature and excellent heat resistance. In addition, the crystallization peak does not exist; thus, it is found that DBTFLP-IV is a substance which is unlikely to be crystallized. This can be attributed to a steric molecular structure and a sufficiently high molecular weight (576.7) of DBTFLP-IV.

A thin film of DBTFLP-IV was formed by vacuum evaporation. This thin film was not a white and opaque film but a transparent film. This also suggests that DBTFLP-IV is a substance which is unlikely to be crystallized.

Accordingly, DBTFLP-IV is found to be a material having a wide band gap and excellent thermophysical properties, and also an electrochemically stable material.

EXAMPLE 3

Figure 13A:
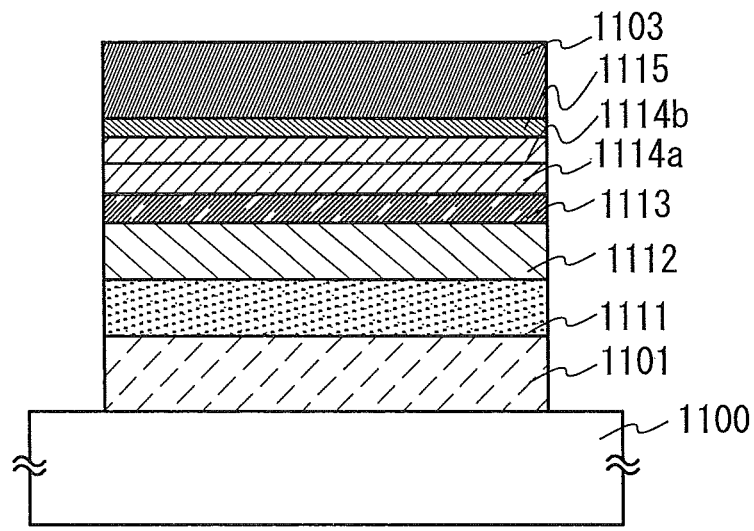
FIGS. 13A and 13B each illustrate a light-emitting element of an example.

In this example, a light-emitting element of one embodiment of the present invention will be described with reference to FIG. 13A. The chemical formulae of materials used in this example are illustrated below.

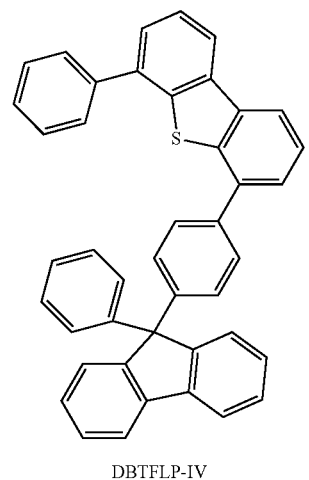

DBTFLP-IV

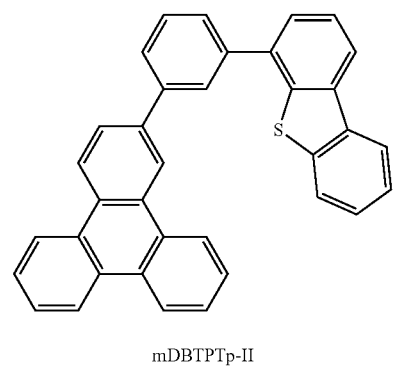

mDBTPTp-II

Ir(ppy)₃                Alq

BPhen

A method for manufacturing Light-Emitting Element 1 of this example will be described below.

(Light-Emitting Element 1)

First, a film of indium tin oxide containing silicon oxide (ITSO) was formed over a glass substrate 1100 by a sputtering method, so that a first electrode 1101 was formed.

Note that the thickness was set to 110 nm and the electrode area was set to 2 mm×2 mm.

In pretreatment for forming the light-emitting element over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about $10^{-4}$ Pa. Then, 4-[4-(9-phenyl-9H-fluoren-9-yl)phenyl]-6-phenyldibenzo thiophene (abbreviation: DBTFLP-IV) synthesized in Example 2 and molybdenum(VI) oxide were co-evaporated to form a hole-injection layer 1111 over the first electrode 1101. The thickness of the hole-injection layer 1111 was set to 50 nm, and the weight ratio of DBTFLP-IV to molybdenum(VI) oxide was adjusted to 4:2 (=DBTFLP-IV:molybdenum oxide). Note that the co-evaporation method refers to an evaporation method in which evaporation is carried out from a plurality of evaporation sources at the same time in one treatment chamber.

Next, over the hole-injection layer 1111, a DBTFLP-IV film was fainted to a thickness of 10 nm to form a hole-transport layer 1112.

Then, over the first electron-transport layer 1114a, a bathophenanthroline (abbreviation: BPhen) film was formed to a thickness of 15 nm to form a second electron-transport layer 1114b.

Further, over the second electron-transport layer 1114b, a lithium fluoride (LiF) film was formed by evaporation to a thickness of 1 nm to form an electron-injection layer 1115.

Lastly, an aluminum film was formed by evaporation to a thickness of 200 nm as a second electrode 1103 functioning as a cathode. Thus, Light-Emitting Element 1 of this example was fabricated.

Note that, in the above evaporation steps, evaporation was all performed by a resistance heating method.

Table 1 shows an element structure of Light-Emitting Element 1 obtained as described above.

TABLE 1

| | First electrode | Hole injection layer | Hole transport layer | Light-emitting layer | First electron transport layer | Second electron transport layer | Electron injection layer | Second electrode |
|---|---|---|---|---|---|---|---|---|
| Light emitting element 1 | ITSO 110 nm | DBTFLP-IV:MoOx (=4:2) 50 nm | DBTFLP-IV 10 nm | mDBTPTp-II:Ir(ppy)$_3$ (=1:0.06) 40 nm | Alq 15 nm | BPhen 15 nm | LiF 1 nm | Al 200 nm |

In a glove box containing a nitrogen atmosphere, Light-Emitting Element 1 was sealed so as not to be exposed to air. Then, operation characteristics of Light-Emitting Element 1 were measured. Note that the measurements were carried out at room temperature (in the atmosphere kept at 25° C.).

Figure 15:
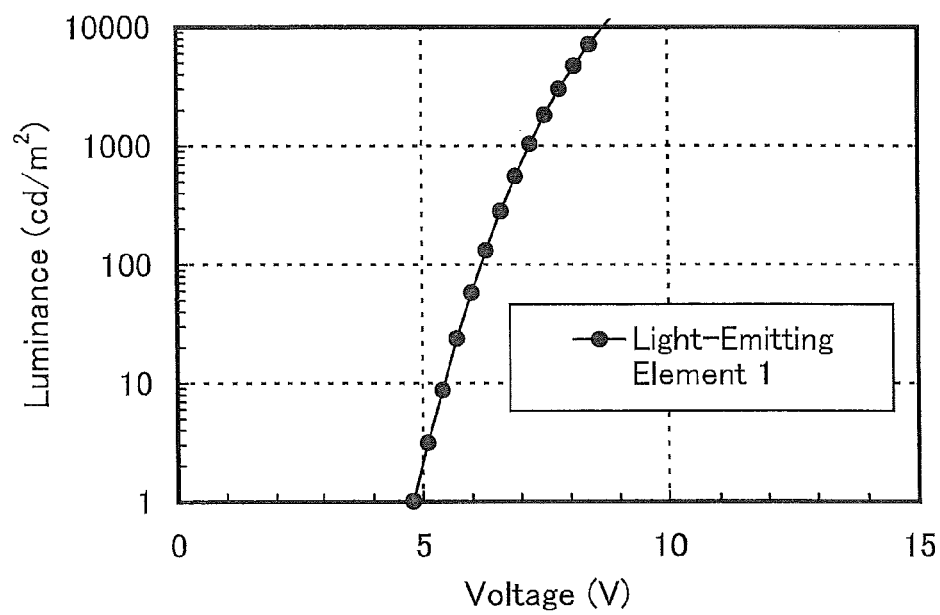
FIG. 15 shows voltage-luminance characteristics of a light-emitting element of Example 3.
Figure 16:
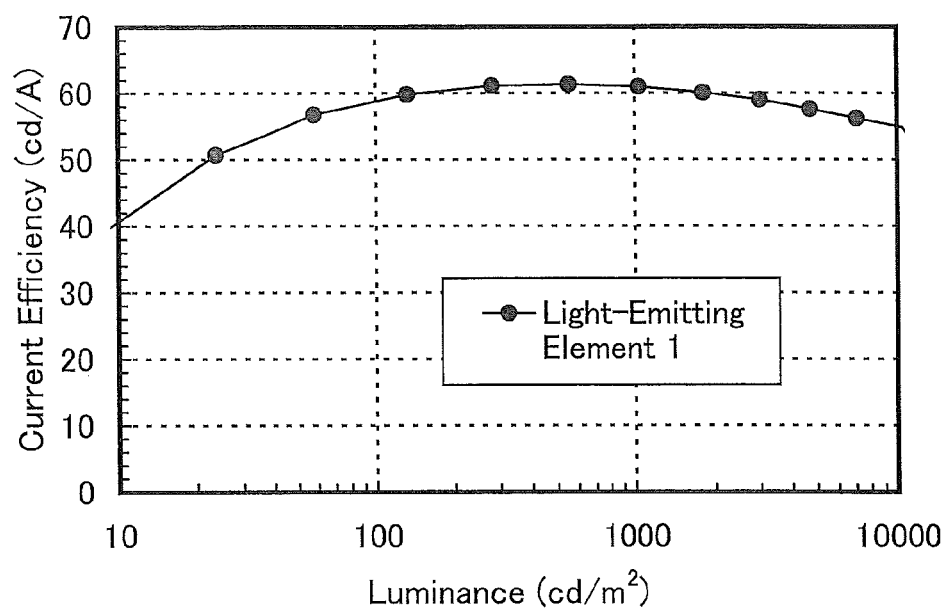
FIG. 16 shows luminance-current efficiency characteristics of a light-emitting element of Example 3.

FIG. 15 shows the voltage-luminance characteristics of Light-Emitting Element 1. In FIG. 15, the horizontal axis represents voltage (V) and the vertical axis represents luminance (cd/m$^2$). FIG. 16 shows the luminance-current efficiency characteristics. In FIG. 16, the horizontal axis represents luminance (cd/m$^2$) and the vertical axis represents current efficiency (cd/A). Further, Table 2 shows the voltage (V), current density (mA/cm$^2$), CIE chromaticity coordinates (x, y), current efficiency (cd/A), power efficiency (lm/W), and external quantum efficiency (%) of Light-Emitting Element 1 at a luminance of 1000 cd/m$^2$.

TABLE 2

| | Voltage | Current density | Chromaticity coordinate | | Current efficiency | Power efficiency | External quantum |
|---|---|---|---|---|---|---|---|
| | (V) | (mA/cm$^2$) | x | y | (cd/A) | (lm/W) | efficiency (%) |
| Light-emitting element 1 | 7.2 | 1.7 | 0.34 | 0.61 | 61 | 27 | 17 |

Further, 4-[3-(triphenylen-2-yl)phenyl]dibenzothiophene (abbreviation: mDBTPTp-II) and tris(2-phenylpyridinato-N,C$^{2'}$)iridium(III) (abbreviation: Ir(ppy)$_3$) were co-evaporated to form a light-emitting layer 1113 over the hole-transport layer 1112. Here, the weight ratio of mDBTPTp-II to Ir(ppy)$_3$ was adjusted to 1:0.06 (=mDBTPTp-II:Ir(ppy)$_3$). In addition, the thickness of the light-emitting layer 1113 was set to 40 nm.

Next, over the light-emitting layer 1113, a film of tris(8-quinolinolato)aluminum (abbreviation: Alq) was formed to a thickness of 15 nm to form a first electron-transport layer 1114a.

Figure 17:
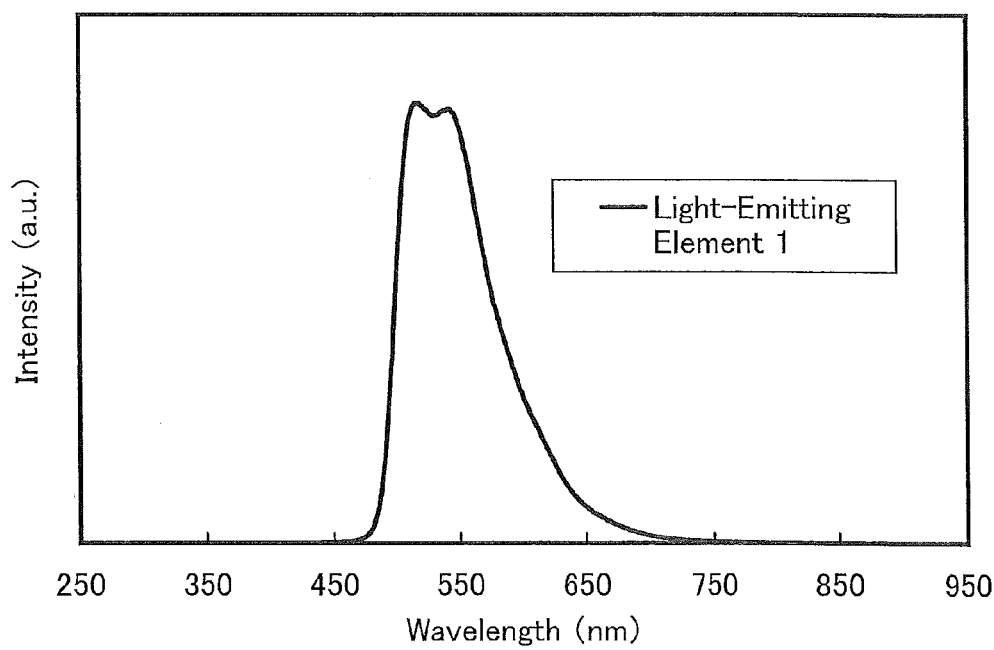
FIG. 17 shows an emission spectrum of a light-emitting element of Example 3.

FIG. 17 shows the emission spectrum of Light-emitting Element 1 which was obtained by applying a current at a current density of 0.1 mA/cm$^2$. In FIG. 17, the horizontal axis represents wavelength (nm) and the vertical axis represents intensity (arbitrary unit). As shown in FIG. 17, the emission spectrum of Light-Emitting Element 1 has a peak at 516 nm. In addition, as shown in Table 2, the CIE chromaticity coordinates of Light-Emitting Element 1 were (x, y)=(0.34, 0.61) at a luminance of 1000 cd/m$^2$. Light-Emitting Element 1 was found to provide green light emission originating from Ir(ppy)$_3$.

Figure 18:
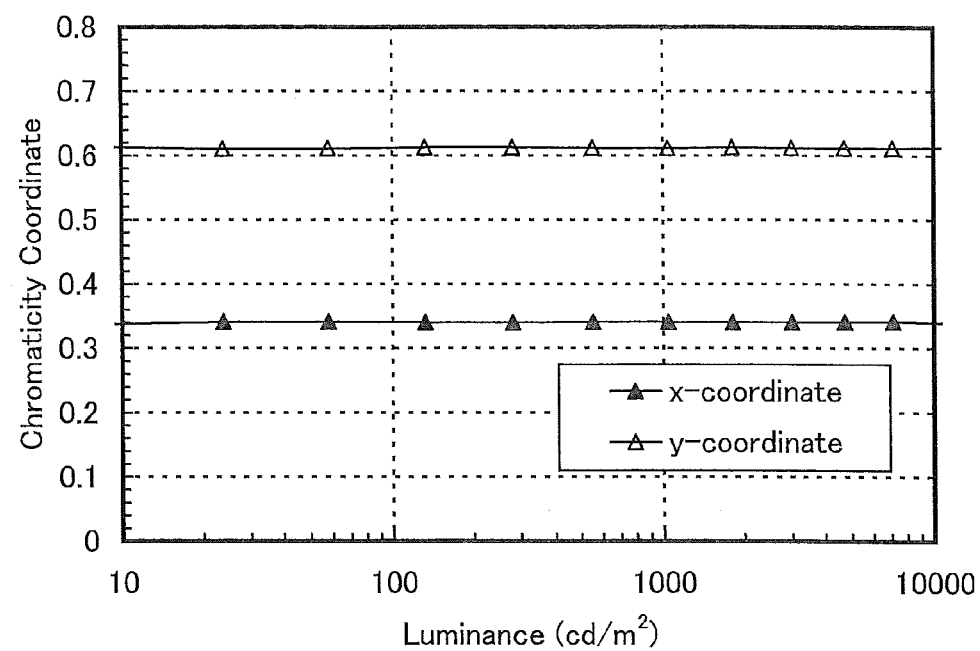
FIG. 18 shows luminance-chromaticity coordinate characteristics of a light-emitting element of Example 3.

FIG. 18 shows the luminance-chromaticity coordinate characteristics. In FIG. 18, the horizontal axis represents luminance (cd/m²) and the vertical axis represents chromaticity coordinate (the x-coordinate or the y-coordinate). As shown in FIG. 18, Light-Emitting Element 1 shows substantially no change in color over a range from low luminance to high luminance. It can be said from this result that Light-Emitting Element 1 is an element having excellent carrier balance.

In order to obtain highly efficient light emission from a light-emitting element including a light-emitting layer including a phosphorescent compound, such as Light-Emitting Element 1, it is preferable to use a substance having a sufficiently high T1 level for a hole-transport layer which is in contact with the light-emitting layer. In Light-Emitting Element 1, a layer including a fluorene compound of one embodiment of the present invention is in contact with a light-emitting layer which emits green light, and as shown in FIG. 16 and Table 2, Light-Emitting Element 1 is found to have high emission efficiency. Thus, a fluorene compound of one embodiment of the present invention is found to have a sufficiently high T1 level (which is at least higher than that of a green light-emitting material).

In addition, it is shown that an element having high emission efficiency can be realized by use of a fluorene compound of one embodiment of the present invention for a hole-transport layer. This can be attributed to a sufficiently high LUMO level of a fluorene compound of one embodiment of the present invention and suppressed passage of electrons through a light-emitting layer. It can also be attributed to a sufficiently low HOMO level and an excellent property of injecting holes into a light-emitting layer.

The above findings suggest that a fluorene compound of one embodiment of the present invention can be favorably used for a hole-transport layer of a light-emitting element which includes a green phosphorescent compound in a light-emitting layer. The findings also suggest that a composite material formed by combining a fluorene compound of one embodiment of the present invention and an electron acceptor (an acceptor) can be favorably used for a hole-injection layer. This can be attributed to a composite material including a fluorene compound of one embodiment of the present invention which is a material having a high hole-injection property and a high hole-transport property.

EXAMPLE 4

In this example, a light-emitting element of one embodiment of the present invention will be described with reference to FIG. 13A. The chemical formulae of materials used in this example are illustrated below.

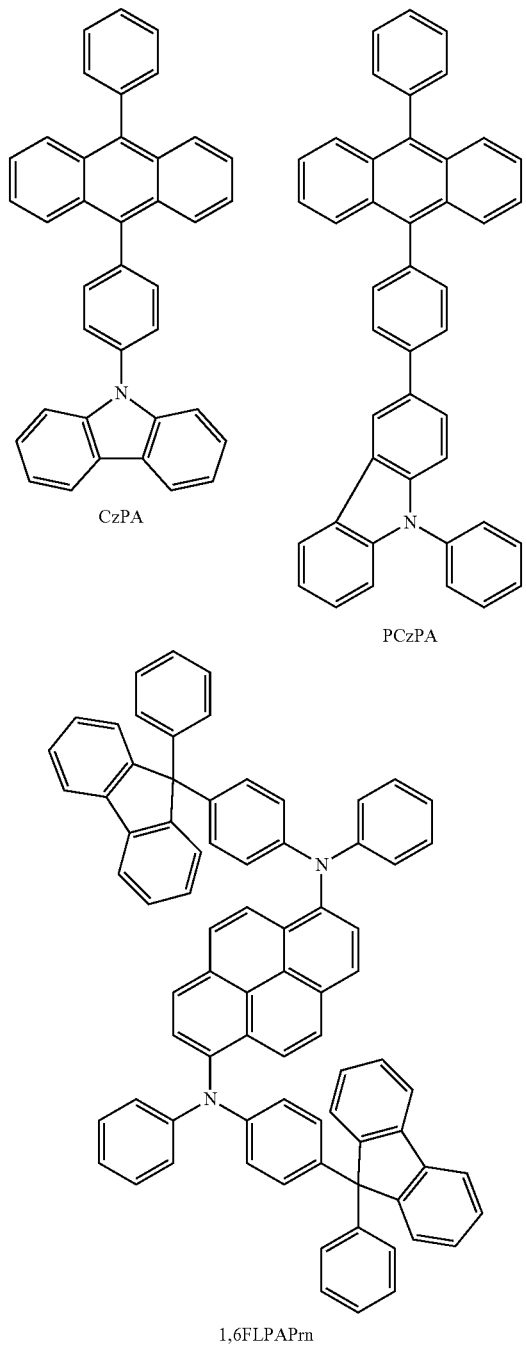

CzPA

PCzPA 1,6FLPAPrn

Methods for manufacturing Light-Emitting Element 2 and Comparative Light-Emitting Element 3 of this example will be described below.

(Light-Emitting Element 2)

First, a film of ITSO was formed over a glass substrate 1100 by a sputtering method, so that a first electrode 1101 was formed. Note that the thickness was set to 110 nm and the electrode area was set to 2 mm×2 mm.

In pretreatment for forming the light-emitting element over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately 10-4 Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about $10^{-4}$ Pa. Then, DBTFLP-IV synthesized in Example 2 and molybdenum(VI) oxide were co-evaporated to form a hole-injection layer 1111 over the first electrode 1101. The thickness of the hole-injection layer 1111 was set to 50 mn, and the weight ratio of DBTFLP-IV to molybdenum(VI) oxide was adjusted to 4:2 (=DBTFLP-IV:molybdenum oxide).

Next, over the hole-injection layer 1111, a DBTFLP-IV film was formed to a thickness of 10 nm to form a hole-transport layer 1112.

Furthermore, 9-[4-(N-carbazolyl)]phenyl-10-phenylanthracene (abbreviation: CzPA) and N,N'-bis[4-(9-phenyl-9H-fluoren-9-yl)phenyl]-N,N'-diphenylpyrene-1,6-diamine (abbreviation: 1,6FLPAPrn) were co-evaporated to form a light-emitting layer 1113 over the hole-transport layer 1112. Here, the weight ratio of CzPA to 1,6FLPAPrn was adjusted to 1:0.05 (=CzPA:1,6FLPAPrn). In addition, the thickness of the light-emitting layer 1113 was set to 30 nm.

Further, over the light-emitting layer 1113, a film of CzPA was formed to a thickness of 10 nm to form a first electron-transport layer 1114a.

Then, over the first electron-transport layer 1114a, a BPhen film was formed to a thickness of 15 nm to form a second electron-transport layer 1114b.

Further, over the second electron-transport layer 1114b, a LiF film was formed by evaporation to a thickness of 1 nm to form an electron-injection layer 1115.

Lastly, an aluminum film was formed by evaporation to a thickness of 200 nm as a second electrode 1103 functioning as a cathode. Thus, Light-Emitting Element 2 of this example was fabricated.

Note that, in the above evaporation steps, evaporation was all performed by a resistance heating method.

(Comparative Light-Emitting Element 3)

A hole-injection layer 1111 of Comparative Light-Emitting Element 3 was formed by co-evaporating 9-phenyl-3-[4-(10-phenyl-9-anthryl)phenyl]-9H-carbazole (abbreviation: PCzPA) and molybdenum(VI) oxide. The thickness of the hole-injection layer 1111 was set to 50 nm, and the weight ratio of PCzPA to molybdenum(VI) oxide was adjusted to 4:2 (=PCzPA:molybdenum oxide).

Further, a hole-transport layer 1112 of Comparative Light-Emitting Element 3 was formed by forming a film of PCzPA to a thickness of 10 nm. Components other than the hole-injection layer 1111 and the hole-transport layer 1112 were manufactured in a manner similar to those of Light-Emitting Element 2.

Table 3 shows element structures of Light-Emitting Element 2 and Comparative Light-Emitting Element 3 obtained as described above.

TABLE 3

| | First electrode | Hole injection layer | Hole transport layer | Light-emitting layer | First electron transport layer | Second electron transport layer | Electron injection layer | Second electrode |
|---|---|---|---|---|---|---|---|---|
| Light emitting element 2 | ITSO 110 nm | DBTFLP-IV:MoOx (=4:2) 50 nm | DBTFLP-IV 10 nm | CzPA:1,6FLPAPrn (=1:0.05) 30 nm | CzPA 10 nm | BPhen 15 nm | LiF 1 nm | Al 200 nm |
| Comparative light emitting element 3 | ITSO 110 nm | PCzPA:MoOx (=4:2) 50 nm | PCzPA 10 nm | CzPA:1,6FLPAPrn (=1:0.05) 30 nm | CzPA 10 nm | BPhen 15 nm | LiF 1 nm | Al 200 nm |

In a glove box containing a nitrogen atmosphere, these light-emitting elements were sealed so as not to be exposed to air. Then, operation characteristics of these light-emitting elements were measured. Note that the measurements were carried out at room temperature (in the atmosphere kept at 25° C.).

Note that Light-Emitting Element 2 and Comparative Light-Emitting Element 3 were formed over the same substrate. In addition, the first electrodes and the light-emitting layers to the second electrodes of the above-described two light-emitting elements were formed at the same respective times, and sealing was performed at the same time.

Figure 19:
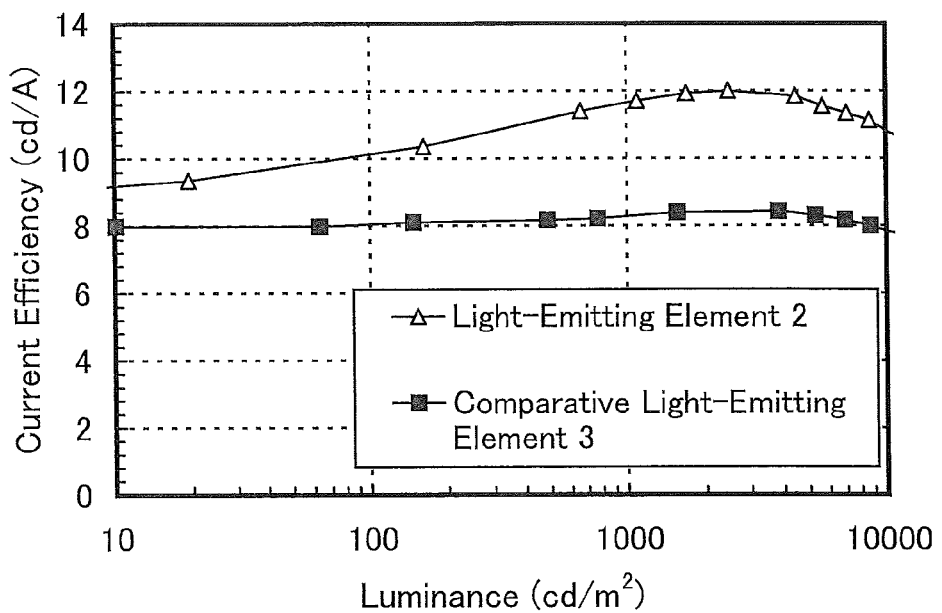
FIG. 19 shows luminance-current efficiency characteristics of a light-emitting element of Example 4.

FIG. 19 shows the luminance-current efficiency characteristics of Light-Emitting Element 2 and Comparative Light-Emitting Element 3. In FIG. 19, the horizontal axis represents luminance (cd/m$^2$) and the vertical axis represents current efficiency (cd/A). Further, Table 4 shows the voltage (V), current density (mA/cm$^2$), CIE chromaticity coordinates (x, y), luminance (cd/m$^2$), current efficiency (cd/A), power efficiency (lm/W), and external quantum efficiency (%) of each light-emitting element at a luminance of around 1000 cd/m$^2$.

TABLE 4

| | Voltage (V) | Current density (mA/cm$^2$) | Chromaticity coordinate x | Chromaticity coordinate y | Luminance (cd/m$^2$) | Current efficiency (cd/A) | Power efficiency (lm/W) | External quantum efficiency (%) |
|---|---|---|---|---|---|---|---|---|
| Light emitting element 2 | 3.6 | 9.3 | 0.15 | 0.23 | 1100 | 12 | 10 | 7.4 |

TABLE 4-continued

|  | Voltage (V) | Current density (mA/cm$^2$) | Chromaticity coordinate x | Chromaticity coordinate y | Luminance (cd/m$^2$) | Current efficiency (cd/A) | Power efficiency (lm/W) | External quantum efficiency (%) |
|---|---|---|---|---|---|---|---|---|
| Comparative light emitting element 3 | 3.0 | 9.3 | 0.15 | 0.21 | 800 | 8.2 | 8.6 | 5.7 |

Figure 20:
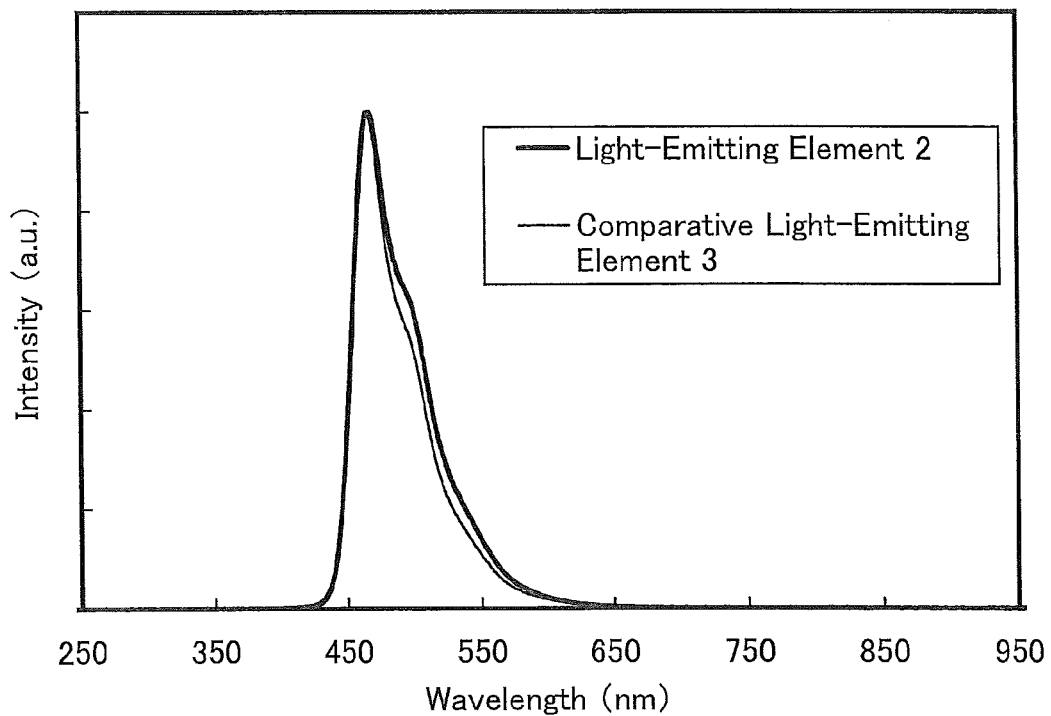
FIG. 20 shows an emission spectrum of a light-emitting element of Example 4.

FIG. 20 shows the emission spectra of these light-emitting elements which were obtained by applying a current at a current density of 0.1 mA/cm$^2$. In FIG. 20, the horizontal axis represents wavelength (nm) and the vertical axis represents intensity (arbitrary unit). As shown in FIG. 20, the emission spectra of Light-Emitting Element 2 and Comparative Light-Emitting Element 3 at around 1000 cd/m$^2$ each have a peak at around 466 nm and are similar to each other. In addition, as shown in Table 4, the CIE chromaticity coordinates of Light-Emitting Element 2 were (x, y)=(0.15, 0.23) and the CIE chromaticity coordinates of Comparative Light-Emitting Element 3 were (x, y)=(0.15, 0.21), each at a luminance of around 1000 cd/m$^2$. These results show that blue light emission originating from 1,6FLPAPm was obtained from Light-Emitting Element 2 and Comparative Light-Emitting Element 3.

PCzPA used in Comparative Light-Emitting Element 3 in this example is one of materials which can realize a highly efficient, long-life light-emitting element when used as a material for a hole-transport layer or a material for a hole-injection layer. As can be seen from FIG. 19, Light-Emitting Element 2 has higher emission efficiency than Comparative Light-Emitting Element 3.

The above results suggest that an element having high emission efficiency can be realized by use of a composite material formed by combining a fluorene compound of one embodiment of the present invention and an electron acceptor (an acceptor) for a hole-injection layer. This can be attributed to a composite material including a fluorene compound of one embodiment of the present invention which is a material having a high hole-injection property and a high hole-transport property.

In addition, it is shown that an element having high emission efficiency can be realized by use of a fluorene compound of one embodiment of the present invention for a hole-transport layer. This can be attributed to a sufficiently high LUMO level of a fluorene compound of one embodiment of the present invention and suppressed passage of electrons through a light-emitting layer. It can also be attributed to a sufficiently low HOMO level and an excellent property of injecting holes into a light-emitting layer.

In order to obtain highly efficient light emission from a light-emitting element including a light-emitting layer including a fluorescent compound, it is preferable to use a substance having a sufficiently high level of singlet excitation energy (Si level) for a hole-transport layer which is in contact with the light-emitting layer. In Light-Emitting Element 2, a layer including a fluorene compound of one embodiment of the present invention is in contact with a light-emitting layer which emits blue light, and as shown in FIG. 19 and Table 4, Light-Emitting Element 2 is found to have high emission efficiency. Thus, a fluorene compound of one embodiment of the present invention is found to have a sufficiently high S1 level. Note that the singlet excitation energy refers to an energy difference between a ground state and a singlet excited state.

Next, Light-Emitting Element 2 and Comparative Light-Emitting Element 3 were subjected to reliability tests. In the reliability tests, the two light-emitting elements of this example were each driven under the conditions where the initial luminance was set to 5000 cd/m$^2$ and the current density was constant.

Light-Emitting Element 2 and Comparative Light-Emitting Element 3 kept 65% of the initial luminance after the driving for 100 hours. As described above, PCzPA used in Comparative Light-Emitting Element 3 is one of materials which can realize a long-life light-emitting element when used as a material for a hole-transport layer or a material for a hole-injection layer. This result indicates that an element including a fluorene compound of one embodiment of the present invention can also achieve a long lifetime.

It is found from the above findings that Light-Emitting Element 2 including a fluorene compound of one embodiment of the present invention in a composite material of a hole-injection layer and in a hole-transport layer is an element which has comparably high reliability and extremely high emission efficiency as compared to Comparative Light-Emitting Element 3.

EXAMPLE 5

In this example, a light-emitting element of one embodiment of the present invention will be described with reference to FIG. 13A. The chemical formulae of materials used in this example are illustrated below.

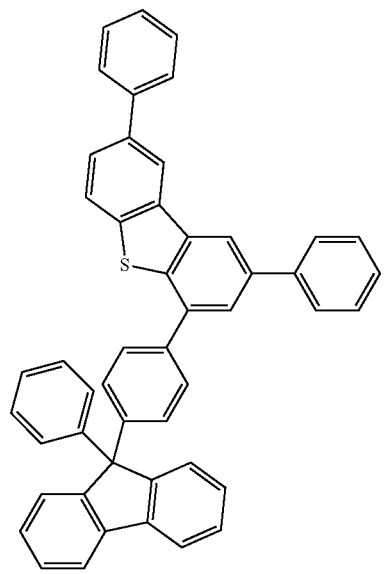

DBTFLP-III

Methods for manufacturing Light-Emitting Element 4 and Comparative Light-Emitting Element 5 of this example will be described below.

(Light-Emitting Element 4)

First, a film of ITSO was formed over a glass substrate 1100 by a sputtering method, so that a first electrode 1101 was formed. Note that the thickness was set to 110 nm and the electrode area was set to 2 mm×2 mm.

In pretreatment for forming the light-emitting element over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately 10-4 Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about $10^{-4}$ Pa. Then, 2,8-diphenyl-4-[4-(9-phenyl-9H-fluoren-9-yl)phenyl]dibenzothiophene (abbreviation: DBTFLP-III) synthesized in Example 1 and molybdenum(VI) oxide were co-evaporated to formed a hole-injection layer 1111 over the first electrode 1101. The thickness of the hole-injection layer 1111 was set to 50 nm, and the weight ratio of DBTFLP-III to molybdenum(VI) oxide was adjusted to 4:2 (=DBTFLP-III:molybdenum oxide).

Next, over the hole-injection layer 1111, a DBTFLP-III film was formed to a thickness of 10 nm to form a hole-transport layer 1112.

Furthermore, CzPA and 1,6FLPAPrn were co-evaporated to form a light-emitting layer 1113 over the hole-transport layer 1112. Here, the weight ratio of CzPA to 1,6FLPAPrn was adjusted to 1:0.05 (=CzPA:1, 6FLPAPrn). In addition, the thickness of the light-emitting layer 1113 was set to 30 nm.

Further, over the light-emitting layer 1113, a film of CzPA was formed to a thickness of 10 nm to form a first electron-transport layer 1114a.

Then, over the first electron-transport layer 1114a, a BPhen film was formed to a thickness of 15 nm to form a second electron-transport layer 1114b.

Further, over the second electron-transport layer 1114b, a LiF film was formed by evaporation to a thickness of 1 nm to form an electron-injection layer 1115.

Lastly, an aluminum film was formed by evaporation to a thickness of 200 nm as a second electrode 1103 functioning as a cathode. Thus, Light-Emitting Element 4 of this example was fabricated.

Note that, in the above evaporation steps, evaporation was all performed by a resistance heating method.

(Comparative Light-Emitting Element 5)

A hole-injection layer 1111 of Comparative Light-Emitting Element 5 was formed by co-evaporating PCzPA and molybdenum(VI) oxide. The thickness of the hole-injection layer 1111 was set to 50 nm, and the weight ratio of PCzPA to molybdenum(VI) oxide was adjusted to 4:2 (=PCzPA: molybdenum oxide).

Further, a hole-transport layer 1112 of Comparative Light-Emitting Element 5 was formed using PCzPA. The thickness was set to be 10 nm. Components other than the hole-injection layer 1111 and the hole-transport layer 1112 were manufactured in a manner similar to those of Light-Emitting Element 4.

Table 5 shows element structures of Light-Emitting Element 4 and Comparative Light-Emitting Element 5 obtained as described above.

TABLE 5

| | First electrode | Hole injection layer | Hole transport layer | Light-emitting layer | First electron transport layer | Second electron transport layer | Electron injection layer | Second electrode |
|---|---|---|---|---|---|---|---|---|
| Light emitting element 4 | ITSO 110 nm | DBTFLP-III:MoOx (=4:2) 50 nm | DBTFLP-III 10 nm | CzPA:1,6FLPAPrn (=1:0.05) 30 nm | CzPA 10 nm | BPhen 15 nm | LiF 1 nm | Al 200 nm |
| Comparative light emitting element 5 | ITSO 110 nm | PCzPA:MoOx (=4:2) 50 nm | PCzPA 10 nm | CzPA:1,6FLPAPrn (=1:0.05) 30 nm | CzPA 10 nm | BPhen 15 nm | LiF 1 nm | Al 200 nm |

In a glove box containing a nitrogen atmosphere, these light-emitting elements were sealed so as not to be exposed to air. Then, operation characteristics of these light-emitting elements were measured. Note that the measurements were carried out at room temperature (in the atmosphere kept at 25° C.).

Note that Light-Emitting Element 4 and Comparative Light-Emitting Element 5 were formed over the same substrate. In addition, the first electrodes and the light-emitting layers to the second electrodes of the above-described two light-emitting elements were formed at the same respective times, and sealing was performed at the same time.

Figure 21:
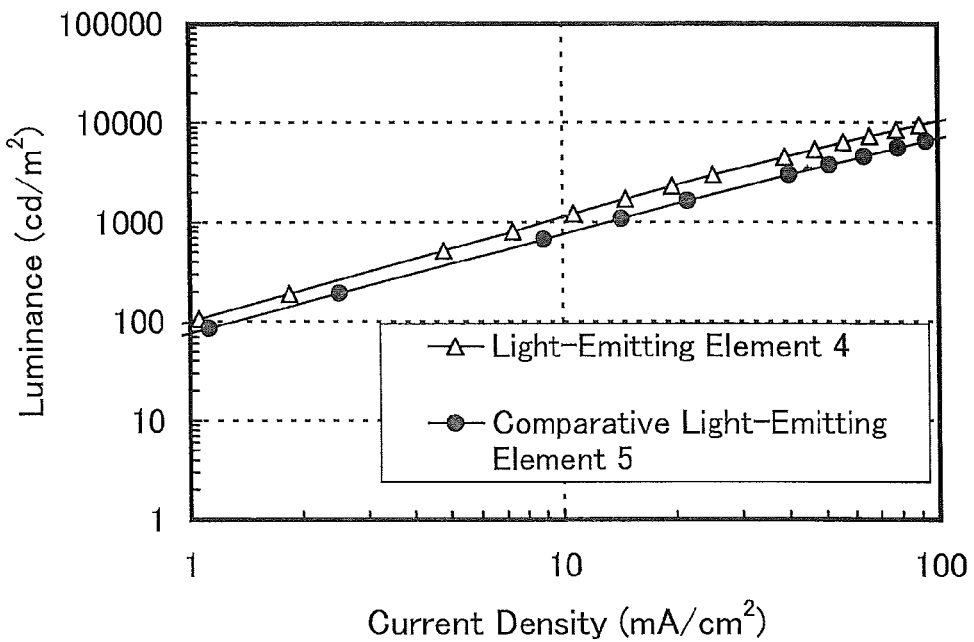
FIG. 21 shows current density-luminance characteristics of a light-emitting element of Example 5.
Figure 22:
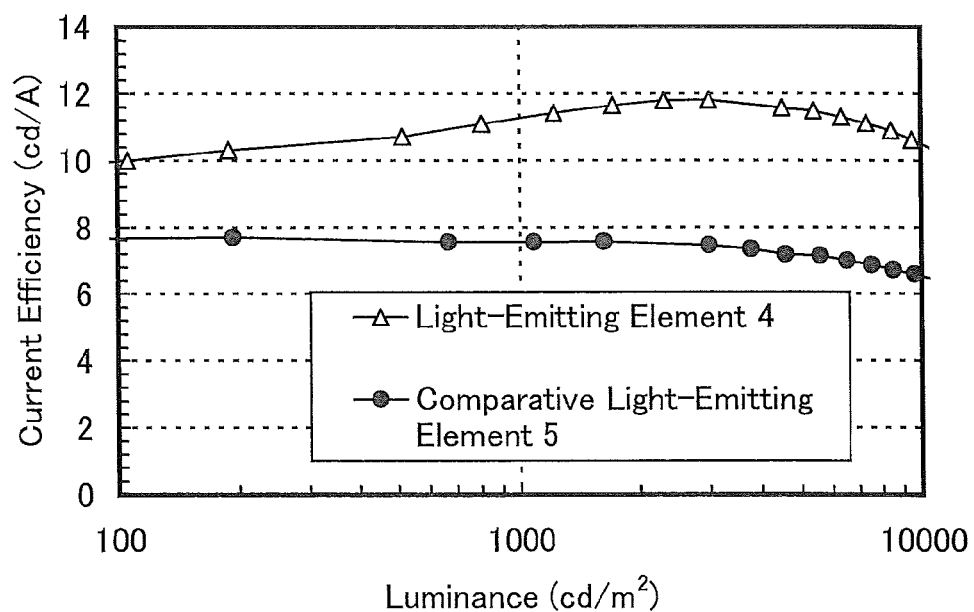
FIG. 22 shows luminance-current efficiency characteristics of a light-emitting element of Example 5.

FIG. 21 shows the current density-luminance characteristics of Light-Emitting Element 4 and Comparative Light-Emitting Element 5. In FIG. 21, the horizontal axis represents current density (mA/cm$^2$) and the vertical axis represents luminance (cd/m$^2$). FIG. 22 shows the luminance-current efficiency characteristics. In FIG. 22, the horizontal axis represents luminance (cd/m$^2$) and the vertical axis represents current efficiency (cd/A). Further, Table 6 shows the voltage (V), current density (mA/cm$^2$), CIE chromaticity coordinates (x, y), luminance (cd/m$^2$), current efficiency (cd/A), power efficiency (lm/W), and external quantum efficiency (%) of each light-emitting element at a luminance of around 1000 cd/m$^2$.

TABLE 6

| | Voltage (V) | Current density (mA/cm²) | Chromaticity coordinate | | Luminance (cd/m²) | Current efficiency (cd/A) | Power efficiency (lm/W) | External quantum efficiency (%) |
|---|---|---|---|---|---|---|---|---|
| | | | x | y | | | | |
| Light emitting element 4 | 3.3 | 7.3 | 0.15 | 0.23 | 1100 | 11 | 11 | 7.3 |
| Comparative light emitting element 5 | 3.1 | 14 | 0.15 | 0.21 | 800 | 7.6 | 7.8 | 5.3 |

Figure 23:
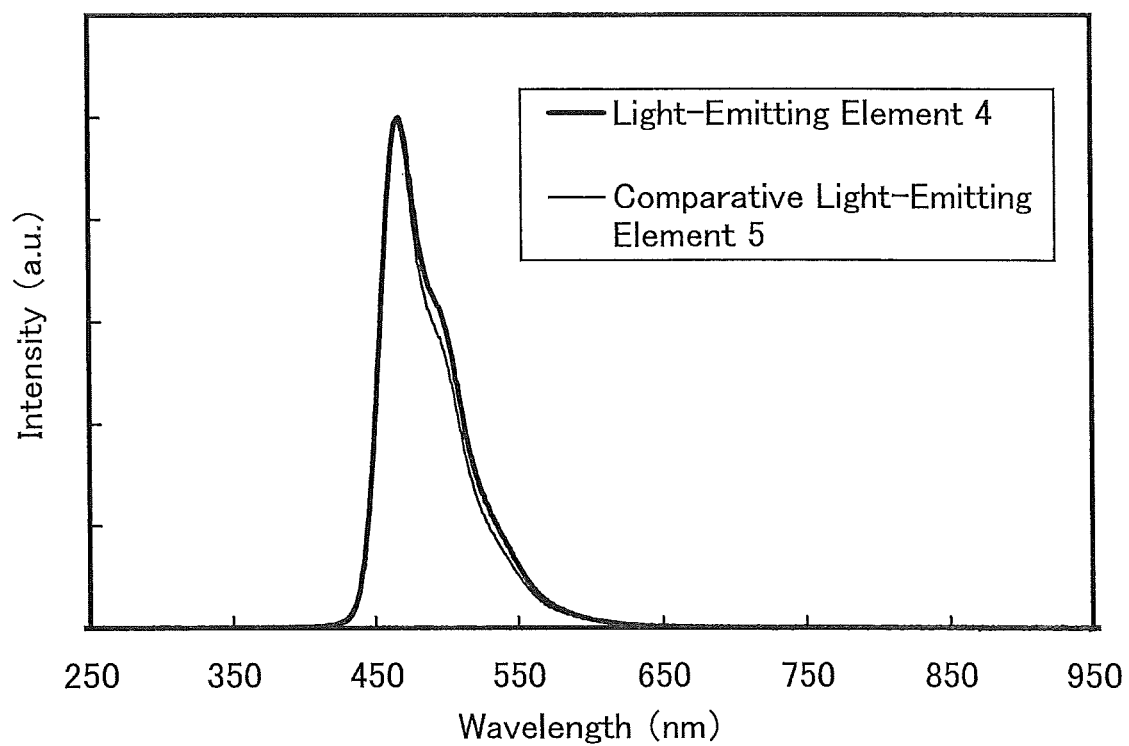
FIG. 23 shows an emission spectrum of a light emitting element of Example 5.

FIG. 23 shows the emission spectra of Light-Emitting Element 4 and Comparative Light-Emitting Element 5 which were obtained by applying a current at a current density of 0.1 mA/cm². In FIG. 23, the horizontal axis represents wavelength (nm) and the vertical axis represents intensity (arbitrary unit). As shown in FIG. 23, the emission spectra of Light-Emitting Element 4 and Comparative Light-Emitting Element 5 at around 1000 cd/m² each have a peak at around 466 nm and are similar to each other. In addition, as shown in Table 6, the CIE chromaticity coordinates of Light-Emitting Element 4 were (x, y)=(0.15, 0.23) and the CIE chromaticity coordinates of Comparative Light-Emitting Element 5 were (x, y)=(0.15, 0.21), each at a luminance of around 1000 cd/m². These results show that blue light emission originating from 1,6FLPAPrn was obtained from Light-Emitting Element 4 and Comparative Light-Emitting Element 5.

As can be seen from FIG. 21 and FIG. 22, Light-Emitting Element 4 exhibits higher emission efficiency than Comparative Light-Emitting Element 5.

The above results suggest that an element having high emission efficiency can be realized by use of a fluorene compound of one embodiment of the present invention for a composite material of a hole-injection layer and for a hole-transport layer. This can be attributed to a composite material including a fluorene compound of one embodiment of the present invention which is a material having a high hole-injection property and a high hole-transport property.

In addition, it is shown that an element having high emission efficiency can be realized by use of a fluorene compound of one embodiment of the present invention for a hole-transport layer. This can be attributed to a sufficiently high LUMO level of a fluorene compound of one embodiment of the present invention and suppressed passage of electrons through a light-emitting layer. It can also be attributed to a sufficiently low HOMO level and an excellent property of injecting holes into a light-emitting layer.

A layer including a fluorene compound of one embodiment of the present invention is in contact with a light-emitting layer which emits blue light, and as shown in FIG. 21, FIG. 22, and Table 6, Light-Emitting Element 4 is found to have high emission efficiency. Thus, a fluorene compound of one embodiment of the present invention is found to have a sufficiently high S1 level (which is at least higher than that of a blue light-emitting material).

EXAMPLE 6

Synthesis Example 3

This example gives descriptions of a method of synthesizing 4-{3-[3-(9-phenyl-9H-fluoren-9-yl)phenyl]phenyl}dibenzofuran (abbreviation: mmDBFFLBi-II), which is a fluorene compound of one embodiment of the present invention, represented by the structural formula (141) in Embodiment 1.

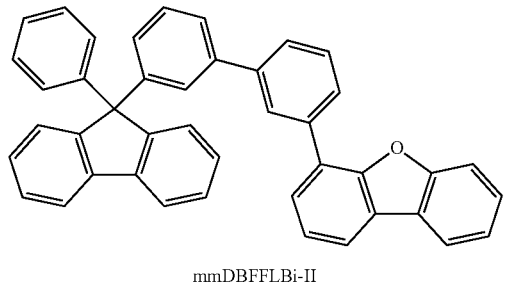 [SMILES: c1ccc(C2(c3cccc(-c4cccc(-c5cccc6c5sc5ccccc56)c4)c3)c3ccccc3-c3ccccc32)cc1]

mmDBFFLBi-II

In a 200 mL three-neck flask, a mixture of 3.5 g (8.9 mmol) of 9-(3-bromophenyl)-9-phenylfluorene, 2.8 g (9.8 mmol) of 3-(dibenzofuran-4-yl)phenylboronic acid, 22 mg (0.1 mmol) of palladium(II) acetate, 89.5 mg (0.3 mmol) of tri(ortho-tolyl)phosphine, 38 mL of toluene, 3.8 mL of ethanol, 12.7 mL of a 2 mol/L aqueous potassium carbonate solution was degassed while being stirred under reduced pressure, and was then reacted by being heated and stirred under a nitrogen atmosphere at 80° C. for 15.5 hours.

After the reaction, 300 mL of toluene was added to this reaction mixture solution, and the organic layer of this mixture solution was filtered through alumina (produced by Merck & Co., Inc., neutral) and Celite (produced by Wako Pure Chemical Industries, Ltd., Catalog No. 531-16855). The obtained filtrate was washed with water, and magnesium sulfate was added thereto so that moisture was adsorbed. This suspension was filtered to obtain a filtrate. The obtained filtrate was concentrated and purified by silica gel column chromatography. At this time, a mixed solvent of toluene and hexane (toluene:hexane=2:5) was used as a developing solvent for the chromatography. The obtained fraction was concentrated, and methanol was added thereto. The mixture was irradiated with ultrasonic waves and then recrystallized to give 3.0 g of a white powder in a yield of 60%, which was the object of the synthesis. A reaction scheme of the above synthesis method is illustrated in the following (F-1).

(F-1)

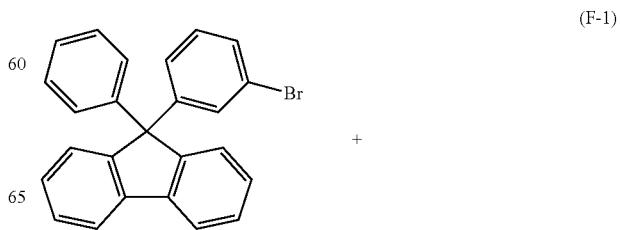

-continued

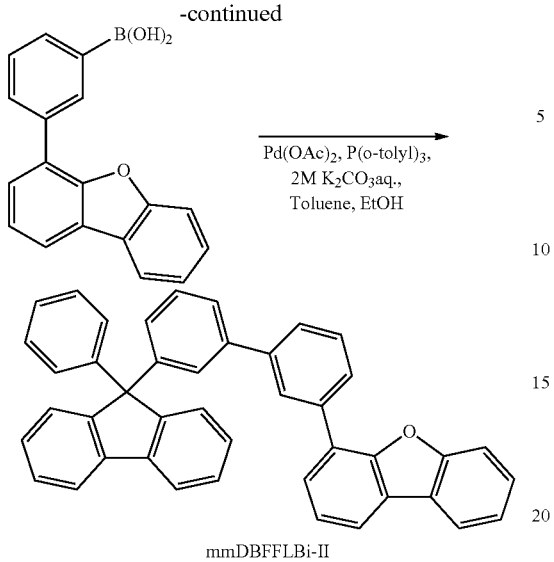

mmDBFFLBi-II

The Rf value of the substance that was the object of the synthesis was 0.33, which was found by silica gel thin layer chromatography (TLC) (with a developing solvent of ethyl acetate and hexane in a 1:10 ratio).

This compound was identified as mmDBFFLBi-II, which was the object of the synthesis, by nuclear magnetic resonance (NMR) spectroscopy.

$^1$H NMR data of the obtained compound are as follows: $^1$H NMR (CDCl$_3$, 300 MHz): δ (ppm)=7.18-7.60 (m, 22H), 7.78 (d, J=6.4 Hz, 2H), 7.85 (td, J=1.5 Hz, 7.3 Hz, 1H), 7.96 (dd, J=1.47 Hz, 7.81 Hz, 1H), 7.99-8.00 (m, 2H).

Figure 24A:
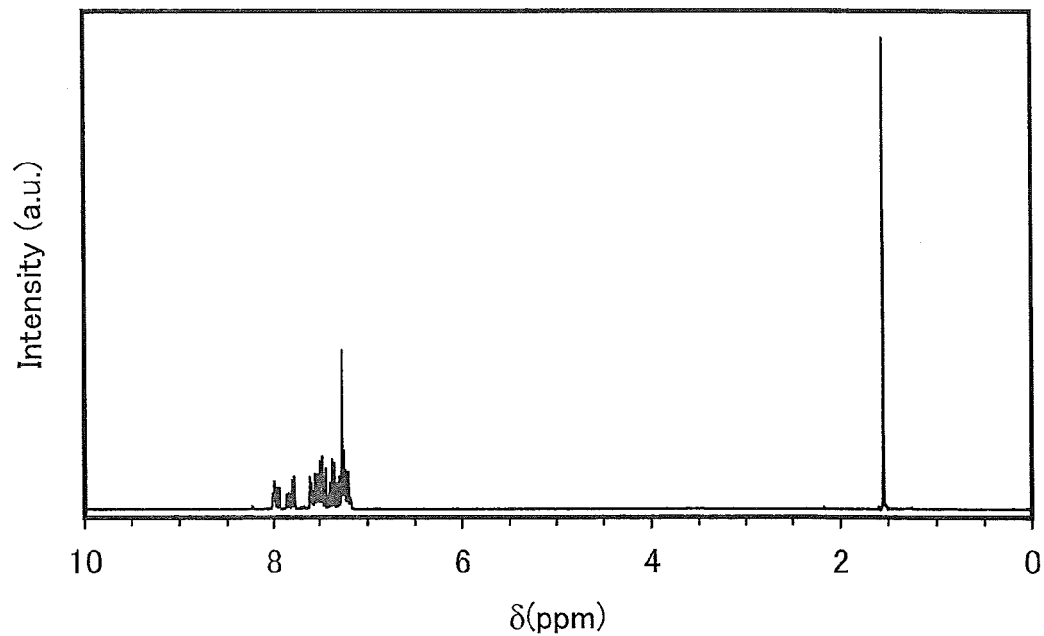
FIGS. 24A and 24B show $^1$H NMR charts of mmDBF-FLBi-II.
Figure 24B:
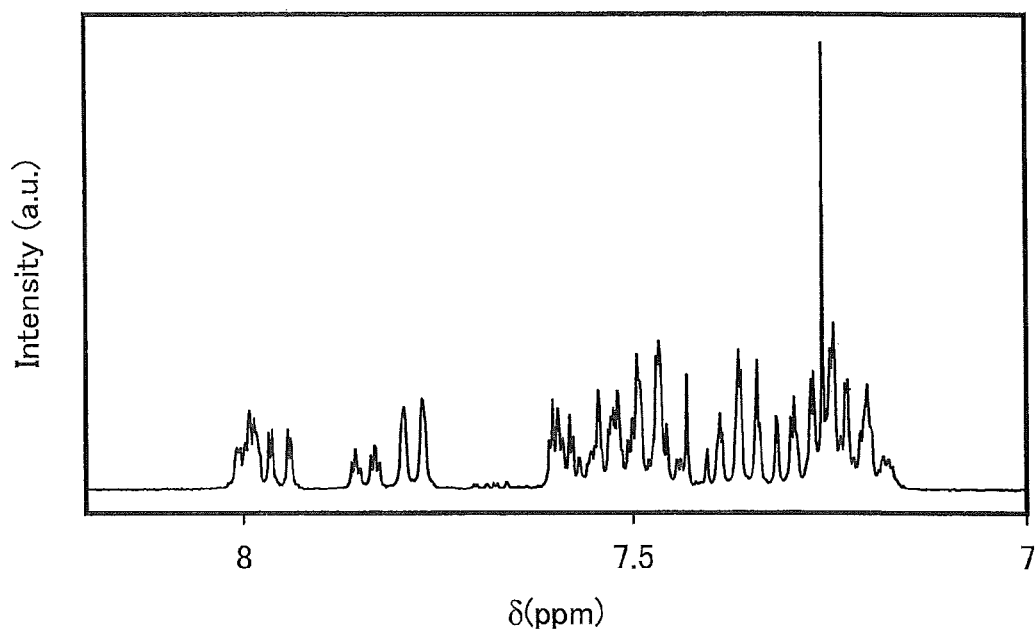

Further, the $^1$H NMR charts are shown in FIGS. 24A and 24B. Note that FIG. 24B is a chart where the range of from 7.0 ppm to 8.2 ppm in FIG. 24A is enlarged.

Figure 25A:
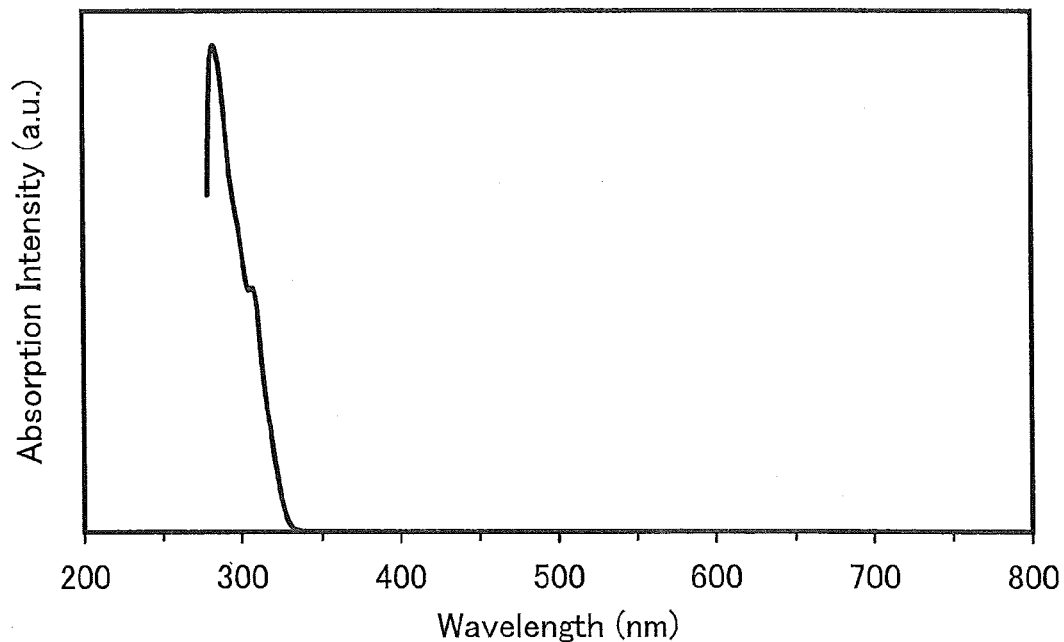
FIGS. 25A and 25B show an absorption spectrum and an emission spectrum of mmDBFFLBi-II in a toluene solution of mmDBFFLBi-II.
Figure 25B:
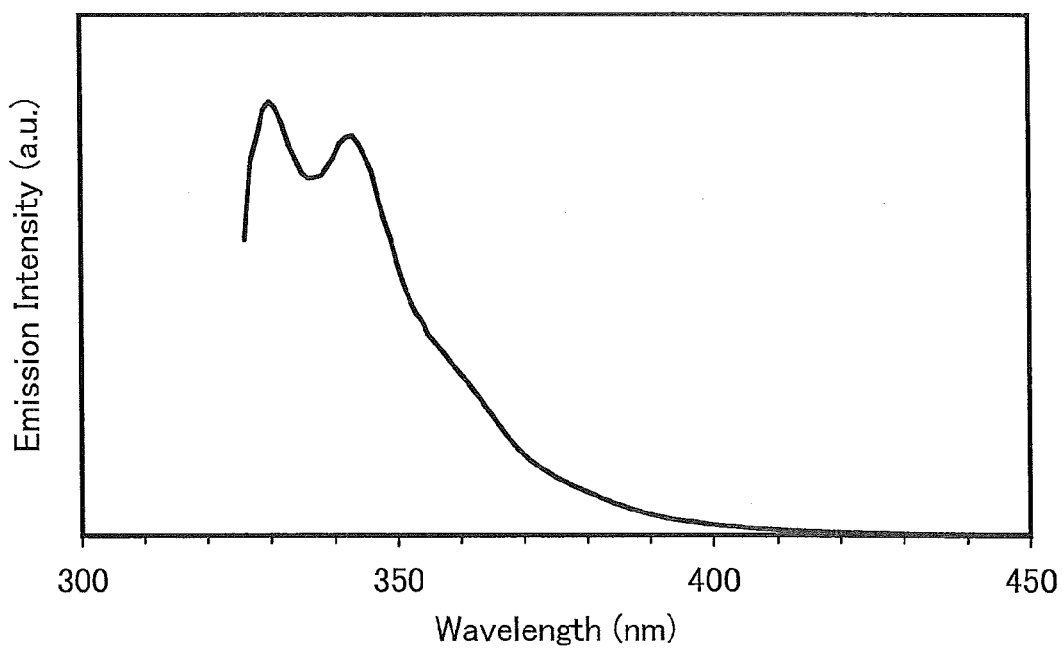

Further, FIG. 25A shows the absorption spectrum of mmDBFFLBi-II in a toluene solution of mmDBFFLBi-II, and FIG. 25B shows the emission spectrum thereof.

Figure 26A:
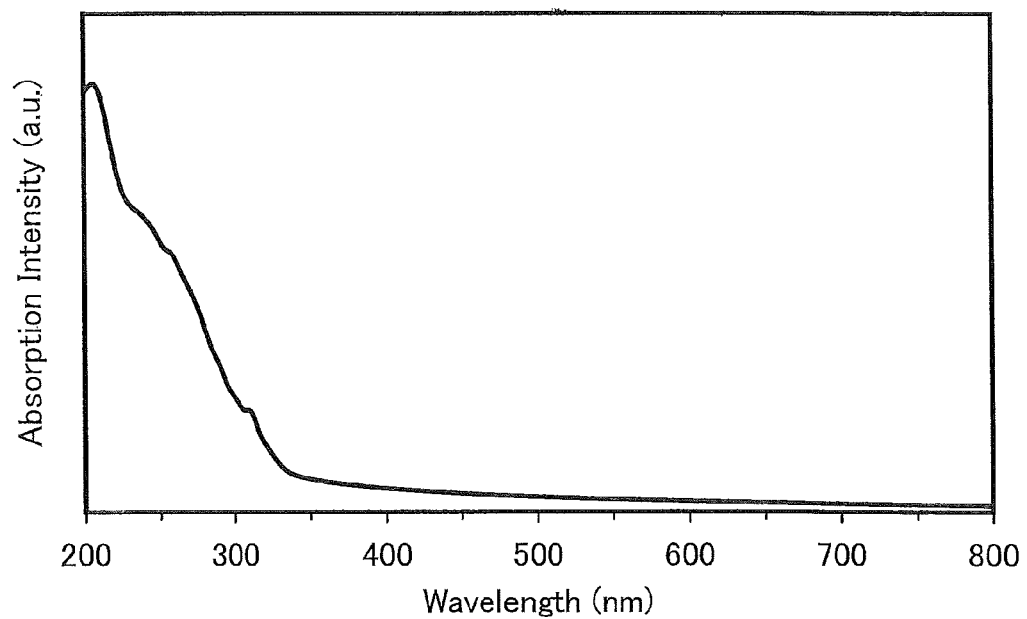
FIGS. 26A and 26B show an absorption spectrum and an emission spectrum of a thin film of mmDBFFLBi-II.
Figure 26B:
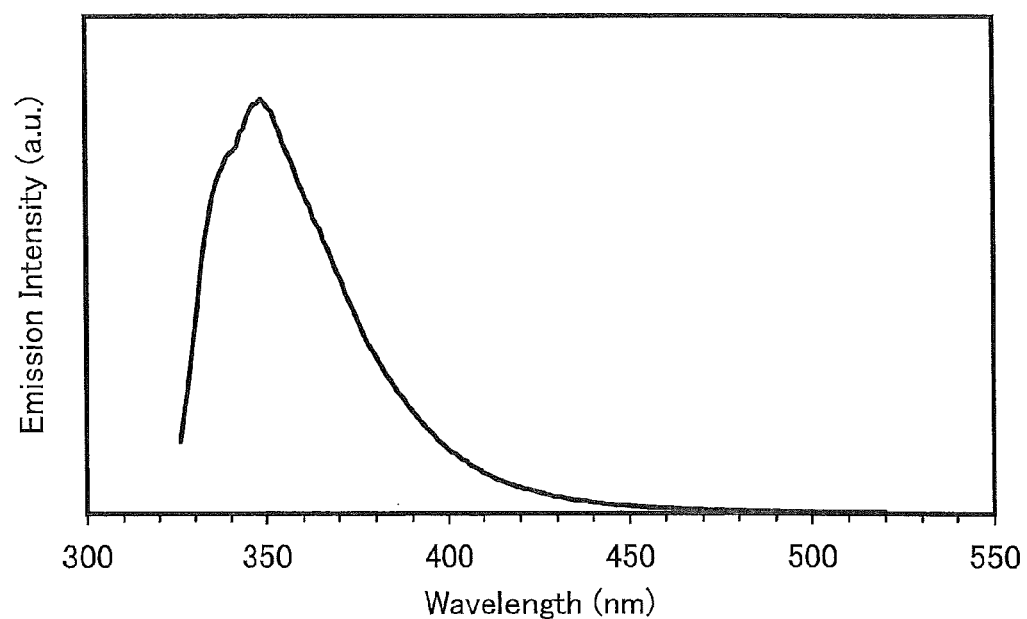

In addition, FIG. 26A shows the absorption spectrum of a thin film of mmDBFFLBi-II, and FIG. 26B shows the emission spectrum thereof. An ultraviolet-visible spectrophotometer (V-550, manufactured by JASCO Corporation) was used for the measurements. Samples were prepared in such a way that the solution was put in a quartz cell and the thin film was formed on a quartz substrate by evaporation. Here are shown the absorption spectrum for the solution which was obtained by subtracting the absorption spectra of quartz and toluene from those of quartz and the solution, and the absorption spectrum for the thin film which was obtained by subtracting the absorption spectrum of the quartz substrate from those of the quartz substrate and the thin film. In FIG. 25A and FIG. 26A, the horizontal axis represents wavelength (nm) and the vertical axis represents absorption intensity (arbitrary unit). In FIG. 25B and FIG. 26B, the horizontal axis represents wavelength (nm) and the vertical axis represents emission intensity (arbitrary unit). In the case of the solution, an absorption peak was found at around 304 nm and peaks of the emission wavelength were at 330 nm and 343 nm at an excitation wavelength of 310 nm). In the case of the thin film, an absorption peak was found at around 309 nm, and peaks of the emission wavelength were at 341 nm and 349 nm (at an excitation wavelength of 311 nm). FIG. 25A and FIG. 26A show that mmDBFFLBi-II is a substance having weak absorption in the visible region. In other words, it is suggested that in the case where mmD-BFFLBi-II which is a fluorene compound of one embodiment of the present invention is used for a light-emitting element, visible light emitted is unlikely to be reabsorbed, and thus the element is unlikely to have a decrease in light extraction efficiency.

It is also found that mmDBFFLBi-II has a peak of the emission spectrum at a very short wavelength and thus can be used as a host material of a light-emitting layer or used for a carrier-transport layer adjacent to the light-emitting layer in a fluorescent element which emits visible light.

A thin film of mmDBFFLBi-II was formed by vacuum evaporation. This thin film was not a white and opaque film but a transparent film. This also suggests that mmDBFFLBi-II is a substance which is unlikely to be crystallized.

EXAMPLE 7

Synthesis Example 4

This example gives descriptions of a method of synthesizing 4-{3-[3-(9-phenyl-9H-fluoren-9-yl)phenyl]phenyl}dibenzothiophene (abbreviation: mmDBTFLBi-II), which is a fluorene compound of one embodiment of the present invention, represented by the structural formula (111) in Embodiment 1.

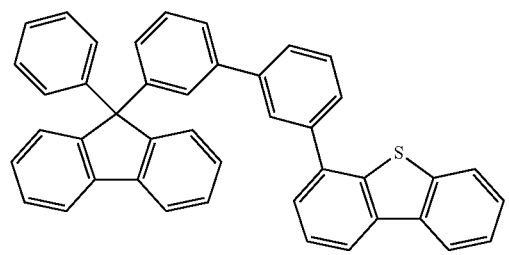

mmDBTFLBi-II

In a 200 mL three-neck flask, a mixture of 1.70 g (4.33 mmol) of 9-(3-bromophenyl)-9-phenyl-9H-fluorene, 1.40 g (4.73 mmol) of 3-(dibenzothiophen-4-yl)phenylboronic acid, 10.0 mg (0.04 mmol) of palladium(II) acetate, 36.5 mg (0.12 mmol) of tri(ortho-tolyl)phosphine, 20 mL of toluene, 2.0 mL of ethanol, 7.0 mL of a 2 mol/L aqueous potassium carbonate solution was degassed while being stirred under reduced pressure, and was then reacted by being heated and stirred under a nitrogen atmosphere at 80° C. for 11 hours.

After the reaction, 300 mL of toluene was added to this reaction mixture solution, and the organic layer of this mixture solution was filtered through alumina (produced by Merck & Co., Inc., neutral) and Celite (produced by Wako Pure Chemical Industries, Ltd., Catalog No. 531-16855). The obtained filtrate was washed with water, and magnesium sulfate was added thereto so that moisture was adsorbed. This suspension was filtered to obtain a filtrate. The obtained filtrate was concentrated and purified by silica gel column chromatography. At this time, a mixed solvent of toluene and hexane (toluene:hexane=1:5) was used as a developing solvent for the chromatography. The obtained fraction was concentrated to give 2.30 g of a white powder in a yield of 92%, which was the object of the synthesis. A reaction scheme of the above synthesis method is illustrated in the following (G-1).

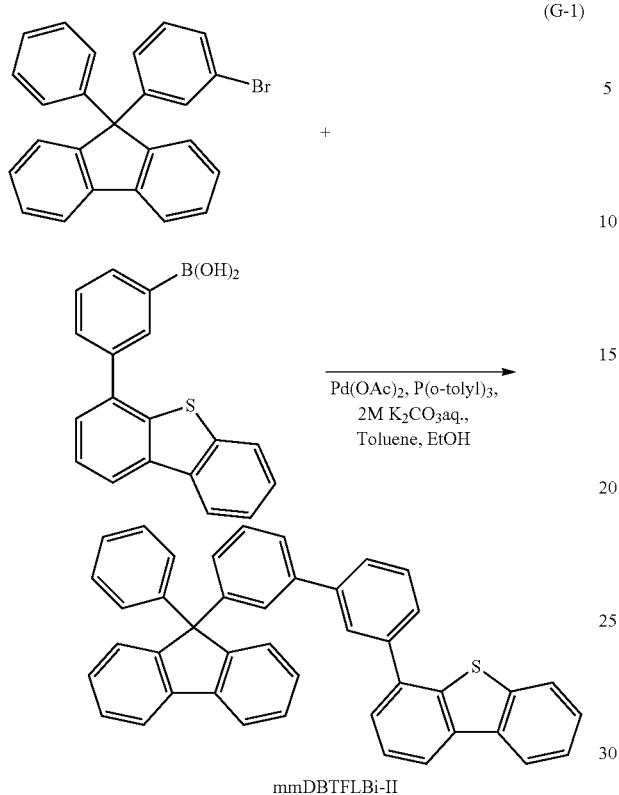

mmDBTFLBi-II

The Rf value of the substance that was the object of the synthesis was 0.25, which was found by silica gel thin layer chromatography (TLC) (with a developing solvent of ethyl acetate and hexane in a 1:10 ratio).

This compound was identified as mmDBTFLBi-II, which was the object of the synthesis, by nuclear magnetic resonance (NMR) spectroscopy.

$^1$H NMR data of the obtained compound are as follows: $^1$H NMR (CDCl$_3$, 300 MHz): δ (ppm)=7.18-7.39 (m, 11H), 7.47-7.59 (m, 11H), 7.63-7.67 (m, 1H), 7.78 (d, J=7.32, 2H), 7.81-7.88 (m, 2H), 8.15-8.21 (m, 2H).

Figure 27A:
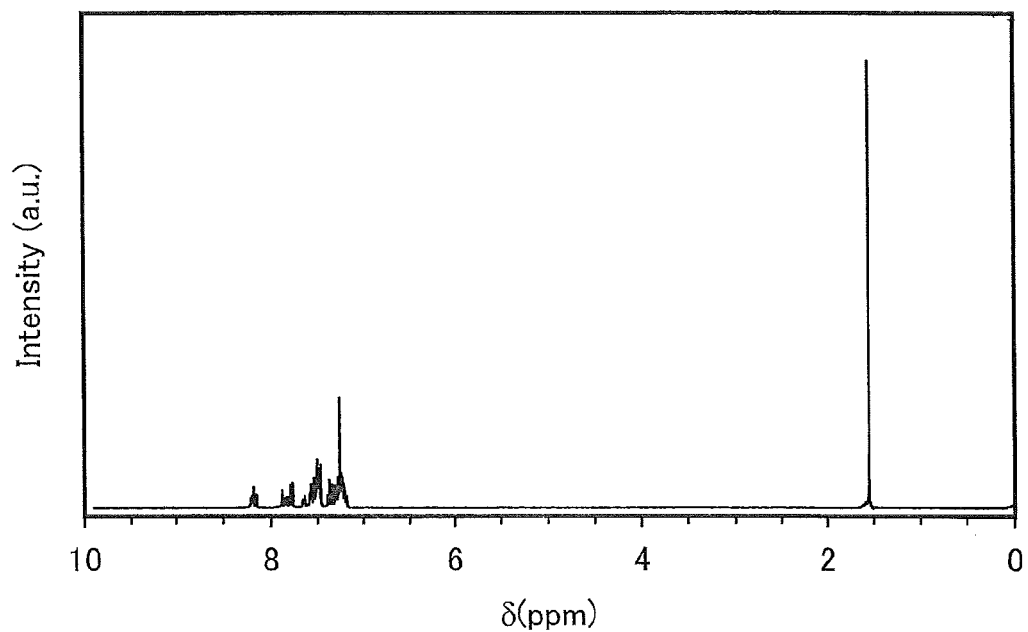
FIGS. 27A and 27B show $^1$H NMR charts of mmDBT-FLBi-II.
Figure 27B:
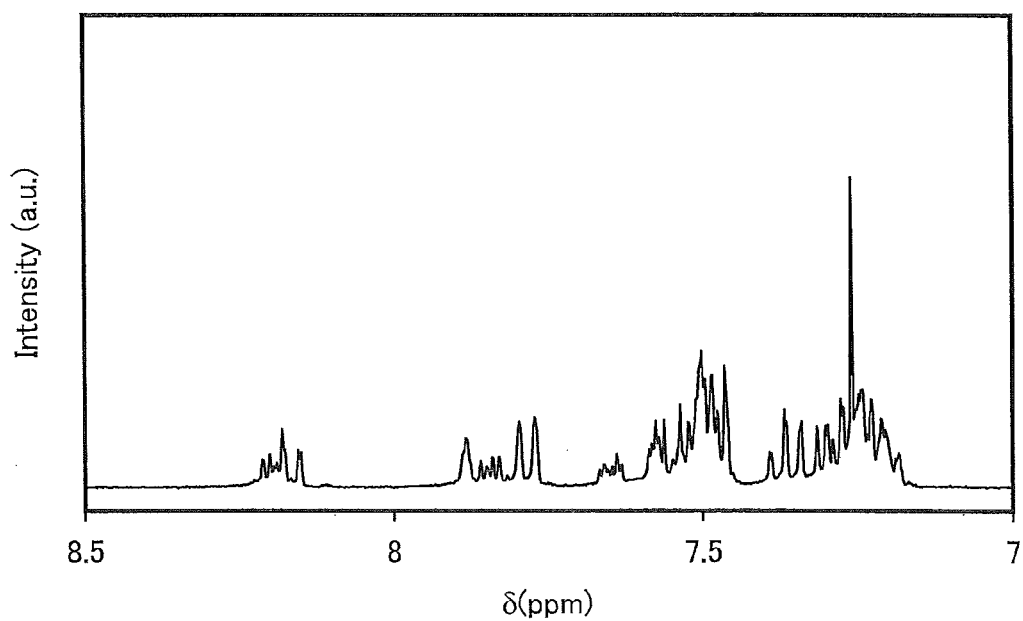

Further, the $^1$H NMR charts are shown in FIGS. 27A and 27B. Note that FIG. 27B is a chart where the range of from 7.0 ppm to 8.5 ppm in FIG. 27A is enlarged.

Figure 28A:
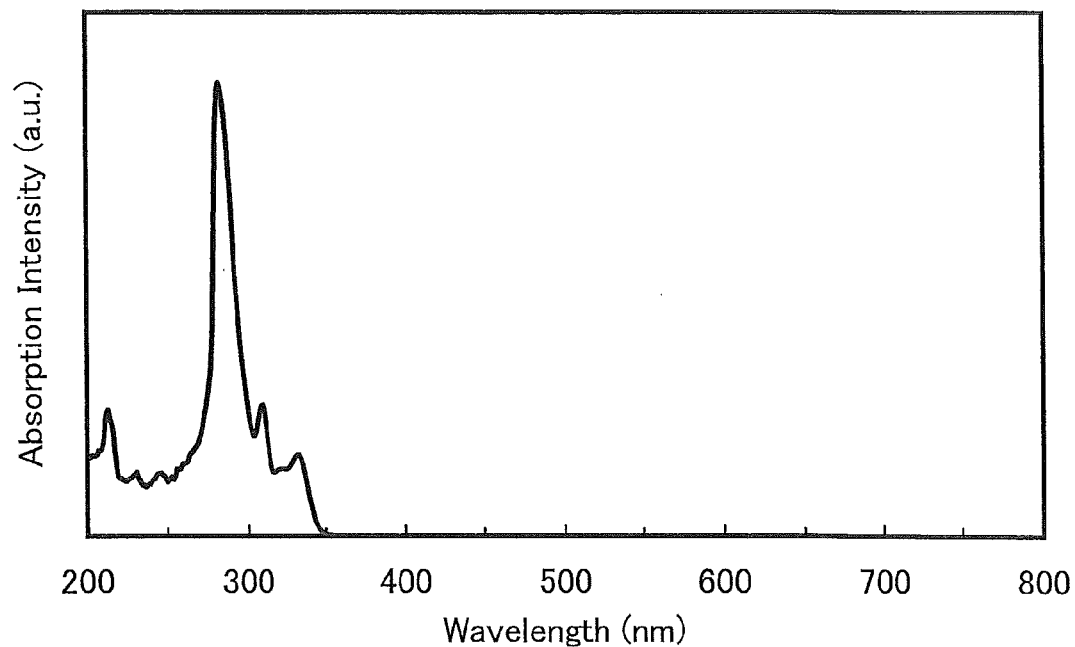
FIGS. 28A and 28B show an absorption spectrum and an emission spectrum of mmDBTFLBi-II in a toluene solution of mmDBTFLBi-II.
Figure 28B:
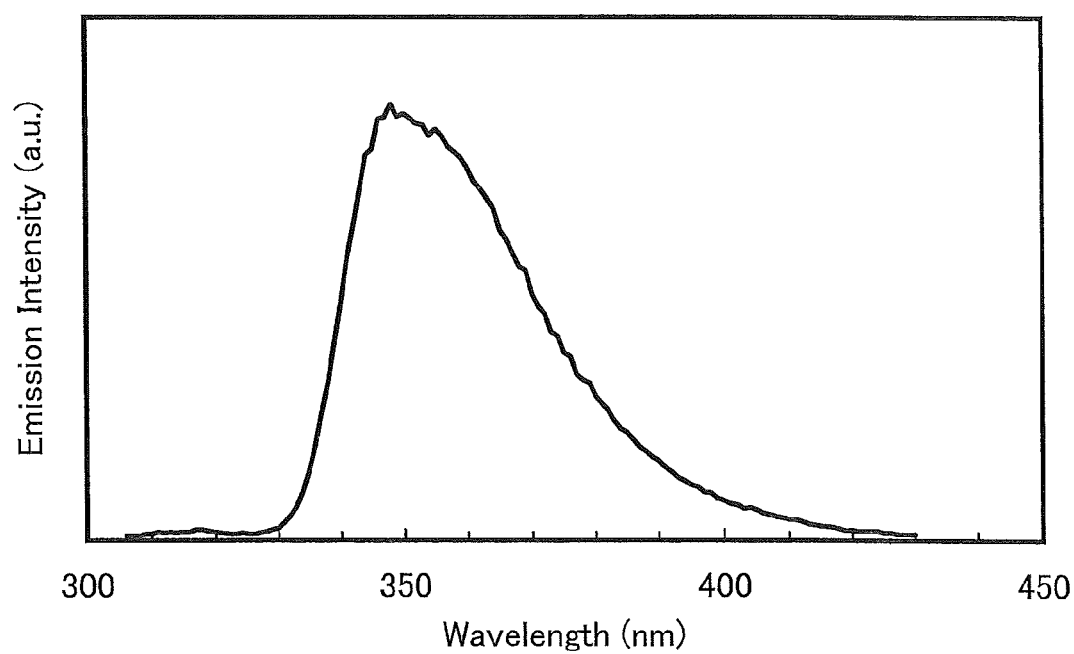

Further, FIG. 28A shows the absorption spectrum of mmDBTFLBi-II in a toluene solution of mmDBTFLBi-II, and FIG. 28B shows the emission spectrum thereof. An ultraviolet-visible spectrophotometer (V-550, manufactured by JASCO Corporation) was used for the measurements. A sample was prepared in such a way that the solution was put in a quartz cell. Here is shown the absorption spectrum which was obtained by subtracting the absorption spectra of quartz and toluene from those of quartz and the solution. In FIG. 28A, the horizontal axis represents wavelength (nm) and the vertical axis represents absorption intensity (arbitrary unit). In FIG. 28B, the horizontal axis represents wavelength (nm) and the vertical axis represents emission intensity (arbitrary unit). As shown in FIGS. 28A and 28B, an absorption peak was found at around 330 nm and a peak of the emission wavelength was at 348 nm (at an excitation wavelength of 290 nm). FIG. 28A shows that mmDBTFLBi-II is a substance having weak absorption in the visible region. In other words, it is suggested that in the case where mmDBTFLBi-II which is a fluorene compound of one embodiment of the present invention is used for a light-emitting element, visible light emitted is unlikely to be reabsorbed, and thus the element is unlikely to have a decrease in light extraction efficiency.

It is also found that mmDBTFLBi-II has a peak of the emission spectrum at a very short wavelength and thus can be used as a host material of a light-emitting layer or used for a carrier-transport layer adjacent to the light-emitting layer in a fluorescent element which emits visible light.

EXAMPLE 8

Synthesis Example 5

This example gives descriptions of a method of synthesizing 4-(3-{9-[4-(9-phenylanthracen-10-yl)phenyl]-9H-fluoren-9-yl}phenyl)dibenzofuran (abbreviation: mDBF-FLPPhA-II), which is a fluorene compound of one embodiment of the present invention, represented by the structural formula (231) in Embodiment 1, and organic compounds of one embodiment of the present invention, which are represented by the structural formulae (700), (720), and (740).

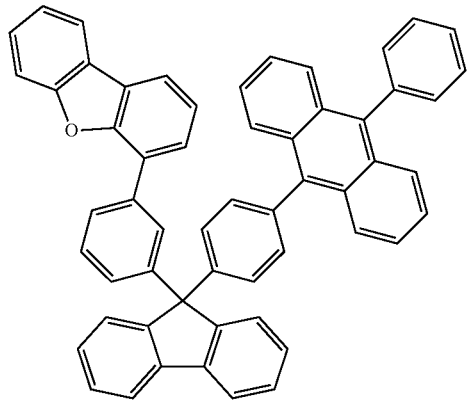

mDBFFLPPhA-II

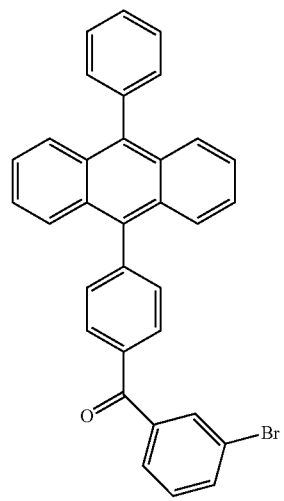

(700)

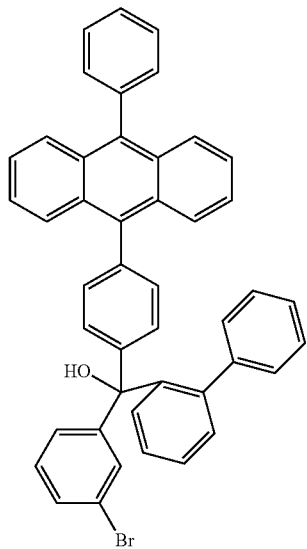

(720)

(740)

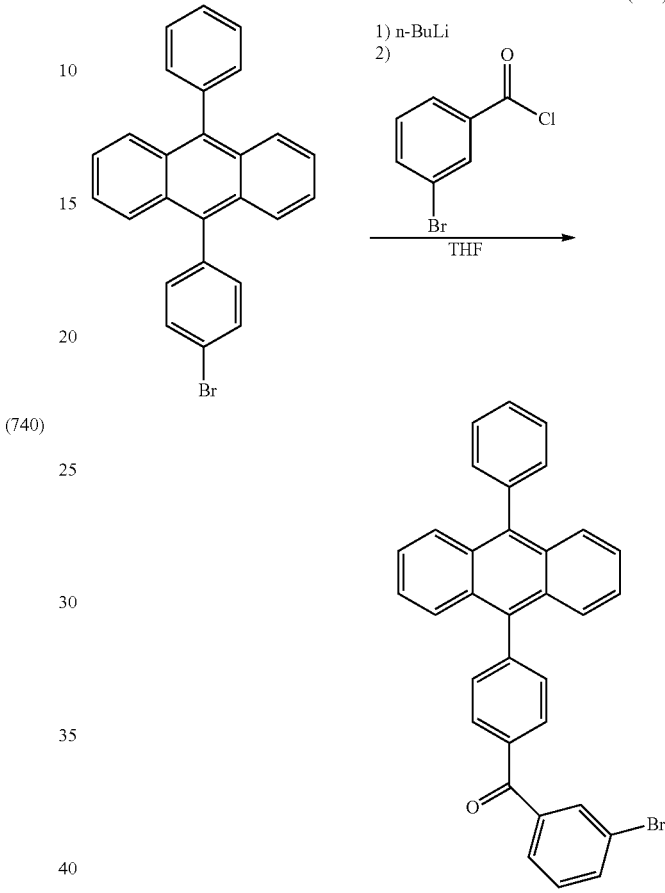

Step 1: Synthesis of 3-bromo-4'-(9-phenylanthracen-10-yl)benzophenone

To a 200 mL three-neck flask was added 5.0 g (12 mmol) of 9-(4-bromophenyl)-10-phenylanthracene. The air in the flask was replaced with nitrogen. Then, 65 mL of tetrahydrofuran was added thereto, and the temperature of the mixture was set to −80° C. Into this solution was dripped 8.1 mL (13 mmol) of n-butyllithium (a 1.6 mol/L hexane solution) with a syringe. After that, this solution was stirred at the same temperature for 1 hour. Then, 2.8 g (13 mmol) of 3-bromobenzoyl chloride was added to this solution, and the mixture was stirred for 18 hours while its temperature was returned to room temperature. Then, an organic substance was extracted from the aqueous layer of this mixture with ethyl acetate, and the solution of the extract and the organic layer were combined and washed with a saturated aqueous sodium chloride solution. The organic layer was dried with magnesium sulfate. Then, this mixture was gravity filtered. The obtained filtrate was concentrated to give a solid. The obtained solid was purified by silica gel column chromatography (with a developing solvent of hexane and toluene in a 5:1 ratio) to give 1.8 g of a light-yellow solid in a yield of 28%. A reaction scheme of the above synthesis method is illustrated in the following (H-1).

Step 2: Synthesis of (2-biphenyl)-(3-bromophenyl)-4-(9-phenylanthracen-10-yl)phenylmethanol)

The air in a 100 mL three-neck flask was replaced with nitrogen, and then 20 mL of tetrahydrofuran and 0.57 mL (3.4 mmol) of 2-bromobiphenyl were put in the flask. The temperature of the mixture was set to −80° C. To this mixture was added 2.3 mL (3.8 mmol) of n-butyllithium, and the mixture was stirred for 1 hour. After that, 1.8 g (3.4 mol) of 3-bromo-4'-(9-phenylanthracen-10-yl)benzophenone was added to the mixture, the temperature of the mixture was set to room temperature, and the mixture was stirred overnight. After that, about 20 mL of diluted hydrochloric acid (1.0 mol/L) was added to this solution. The organic layer and the aqueous layer of this mixture were separated. An organic substance was extracted from the aqueous layer with ethyl acetate and combined with the organic layer, and the mixture was washed with a saturated aqueous sodium chloride solution. The organic layer was dried with magnesium sulfate. After drying, this mixture was gravity filtered. The obtained filtrate was concentrated to give a solid which was the object of the synthesis. The obtained solid was dissolved in toluene, and the solution was suction filtered through Celite (manufactured by Wako Pure Chemical Industries, Ltd., Catalog No. 531-16855), alumina, and Florisil (manufactured by Wako Pure Chemical Industries, Ltd., Catalog No. 540-00135). The filtrate was concentrated to give a white solid. The obtained solid was recrystallized with toluene and hexane to give 1.4 g of a white solid in a yield of 59%. A reaction scheme of the above synthesis method is illustrated in the following (H-2).

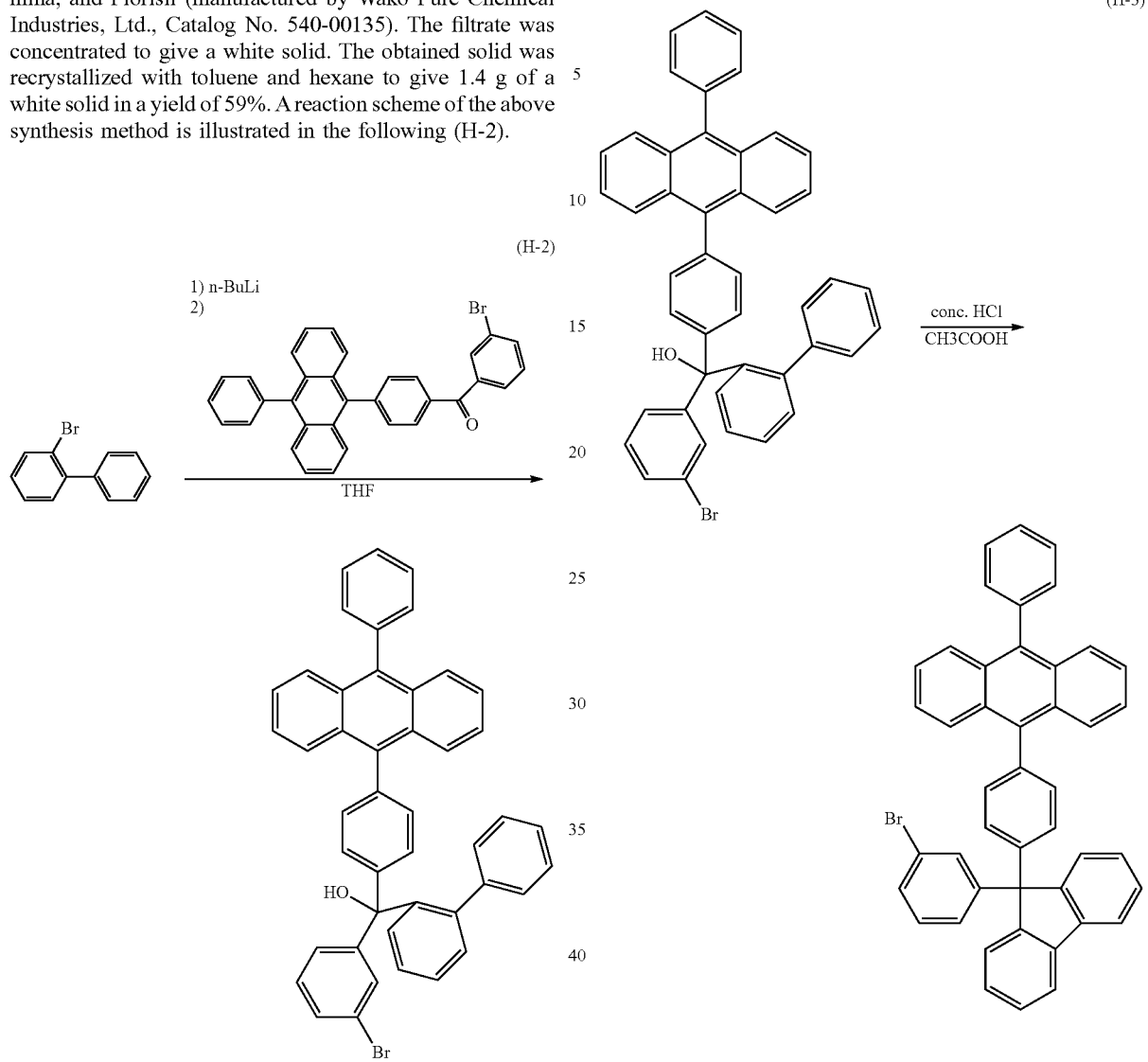

Step 3: Synthesis of 9-phenyl-10-{4-[9-(3-bromophenyl)-9H-fluoren-9-yl]}phenylanthracene To a 300 mL recovery flask were added 1.4 g (2.0 mmol) of (2-biphenyl)-(3-bromophenyl)-4-(9-phenylanthracen-10-yl)phenylmethanol, 100 mL of glacial acetic acid, and 1 mL of hydrochloric acid, and the mixture was stirred for 4 days. After that, an organic substance was extracted from the aqueous layer of the mixture and combined with the organic layer, and the mixture was sequentially washed with water, a saturated aqueous sodium hydrogen carbonate solution, and a saturated aqueous sodium chloride solution. The organic layer was dried with magnesium sulfate. After drying, this mixture was gravity filtered. The obtained filtrate was concentrated to give a solid. The obtained solid was recrystallized with toluene and ethanol to give 0.92 g of a light-yellow solid in a yield of 69%. A reaction scheme of the above synthesis method is illustrated in the following (H-3).

Step 4: Synthesis of 4-(3-{9-[4-(9-phenylanthracen-10-yl)phenyl]-9H-fluoren-9-yl}phenyl)dibenzofuran (abbreviation: mDBFFLPPhA-II))

To a 50 mL three-neck flask were added 1.6 g (2.5 mmol) of 9-phenyl-10-{4-[9-(3-bromophenyl)-9H-fluoren-9-yl]} phenylanthracene, 0.57 g (2.7 mmol) of dibenzofuran-4-boronic acid, and 216 mg (0.071 mmol) of tri(ortho-tolyl) phosphine. The air in the flask was replaced with nitrogen. To this mixture were added 10 mL of toluene, 10 mL of ethanol, and 4 mL of a 2.0 M aqueous sodium carbonate solution. While the pressure was reduced, this mixture was degassed by being stirred. To this mixture was added 6 mg (0.025 mmol) of palladium(II) acetate, and the mixture was stirred under a nitrogen stream at 80° C. for 13 hours. After that, the mixture was filtered to collect a solid. Toluene was added to the obtained solid, and the solution was suction filtered through Celite (manufactured by Wako Pure Chemical Industries, Ltd., Catalog No. 531-16855), alumina, and Florisil (manufactured by Wako Pure Chemical Industries, Ltd., Catalog No. 540-00135). The filtrate was concentrated to give a solid. The obtained solid was recrystallized with toluene.

The recrystallized filtrate was purified by high performance liquid column chromatography (abbreviation: HPLC) (a developing solvent: chloroform). The obtained fraction was concentrated to give a light-yellow solid. The substances obtained by recrystallization and purified by high performance liquid column chromatography were combined to give 1.3 g of a light-yellow solid in a yield of 69%.

The obtained light-yellow solid was sublimated and purified by a train sublimation method. In the sublimation purification, the light-yellow solid was heated at 300° C. under a pressure of 2.5 Pa with a flow rate of argon gas of 5 mL/min. After the sublimation purification, a light-yellow solid was obtained in a yield of 94%. A reaction scheme of the above synthesis method is illustrated in the following (H-4).

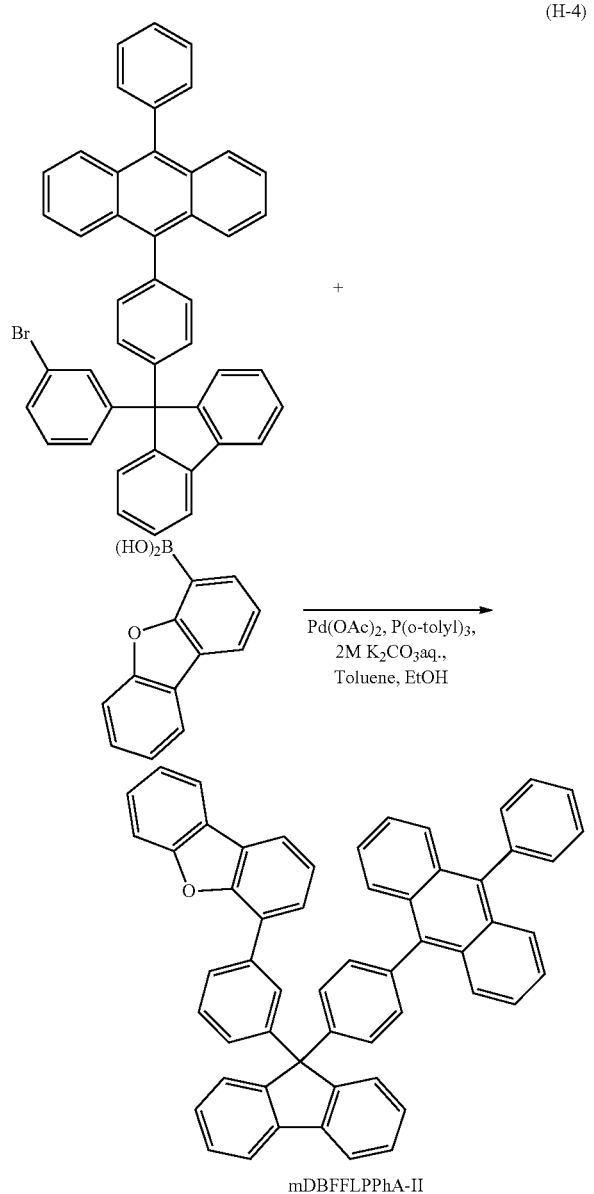

(H-4)

mDBFFLPPhA-II

This compound was identified as mDBFFLPPhA-II, which was the object of the synthesis, by nuclear magnetic resonance (NMR) spectroscopy.

$^1$H NMR data of the obtained compound are as follows: $^1$H NMR (CDCl$_3$, 300 MHz): δ=7.20-7.63 (m, 24H), 7.65-7.74 (m, 6H), 7.78 (d, J1=7.8 Hz, 1H), 7.85-7.86 (m, 1H), 7.87 (d, J1=2.1 Hz, 1H), 7.78 (dd, J1=1.5 Hz, J2=7.8 Hz, 1H), 7.96-7.99 (m, 1H), 8.05 (t, J1=2.1 Hz, 1H).

Figure 29A:
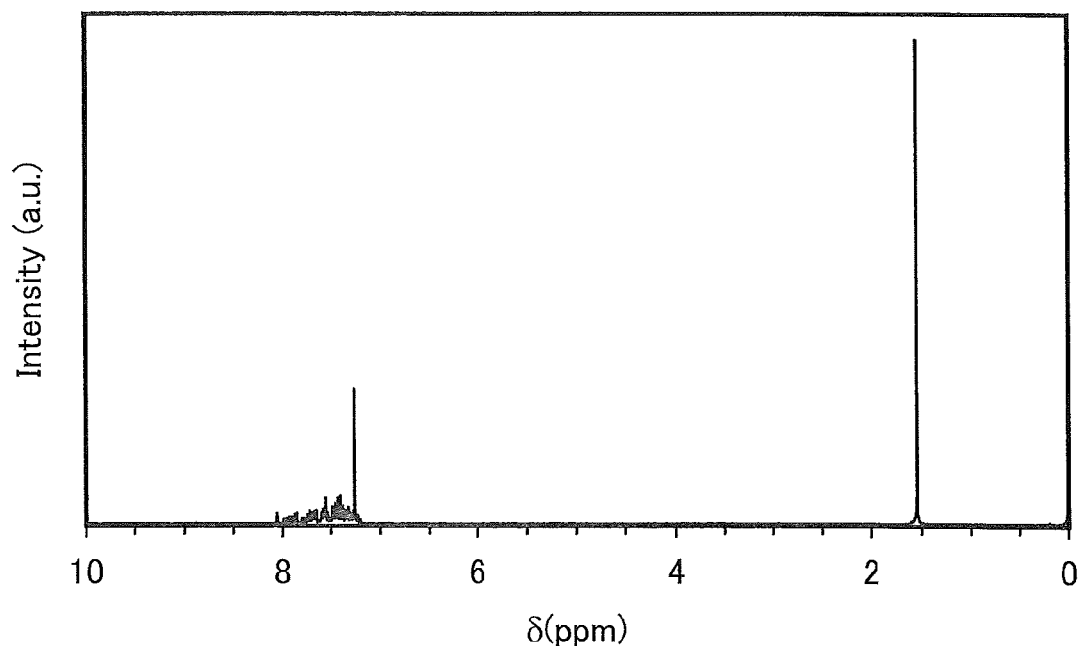
FIGS. 29A and 29B show $^1$H NMR charts of mDBFFLP-PhA-II.
Figure 29B:
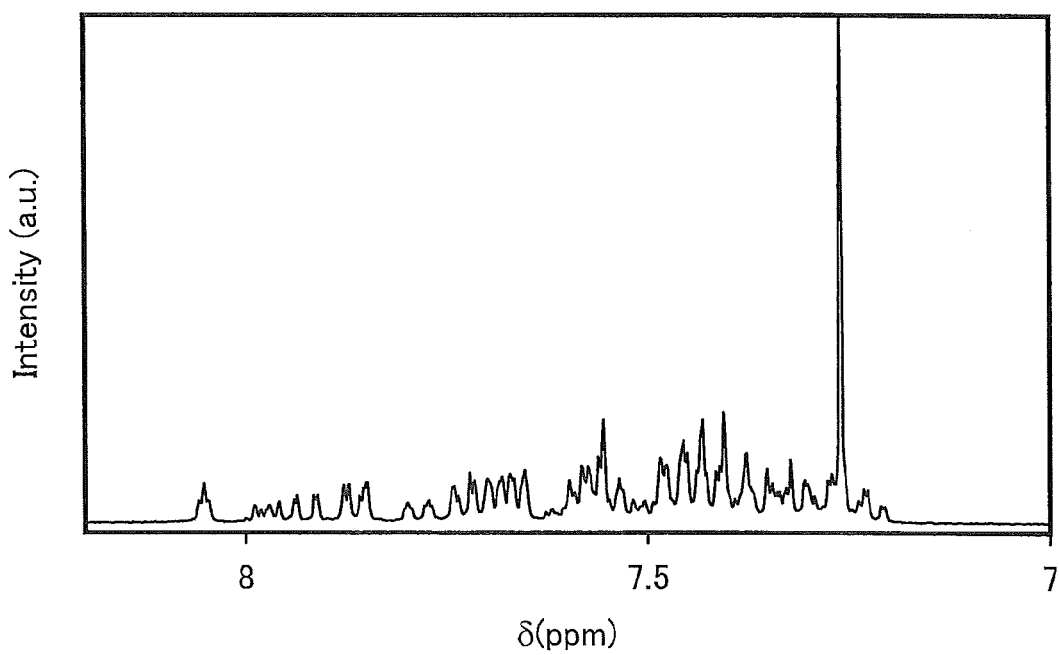

Further, the $^1$H NMR charts are shown in FIGS. 29A and 29B. Note that FIG. 29B is a chart where the range of from 7.0 ppm to 8.2 ppm in FIG. 29A is enlarged.

Figure 30A:
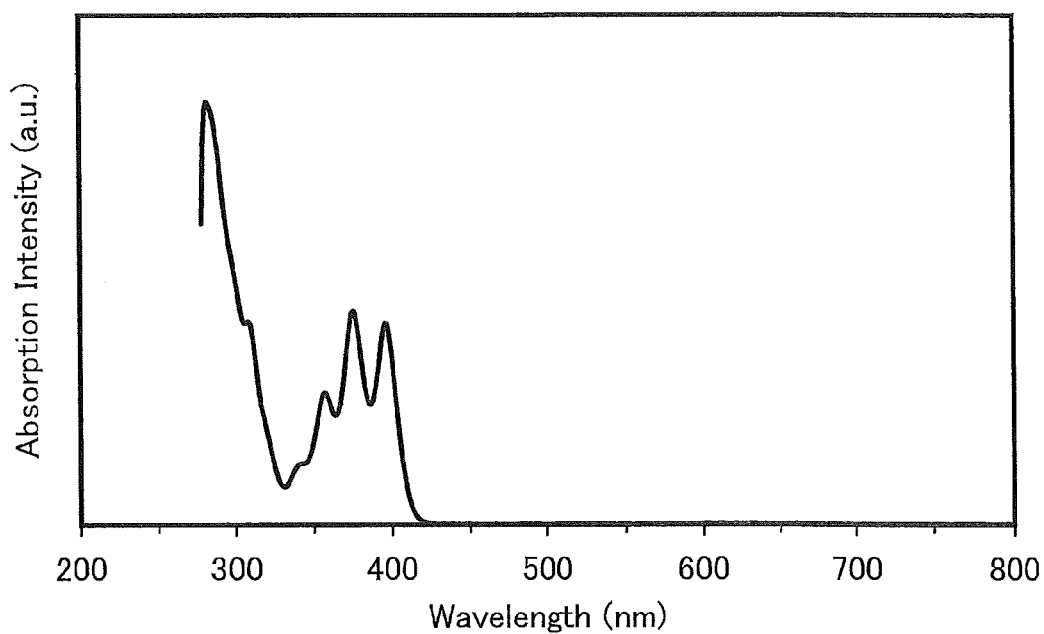
FIGS. 30A and 30B show an absorption spectrum and an emission spectrum of mDBFFLPPhA-II in a toluene solution of mDBFFLPPhA-II.
Figure 30B:
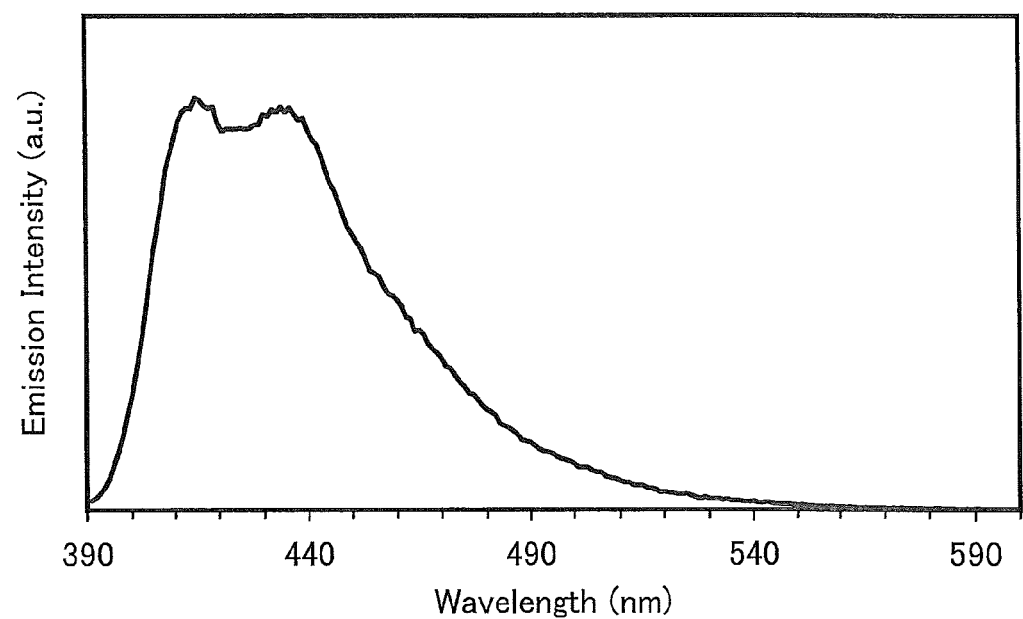
Figure 31A:
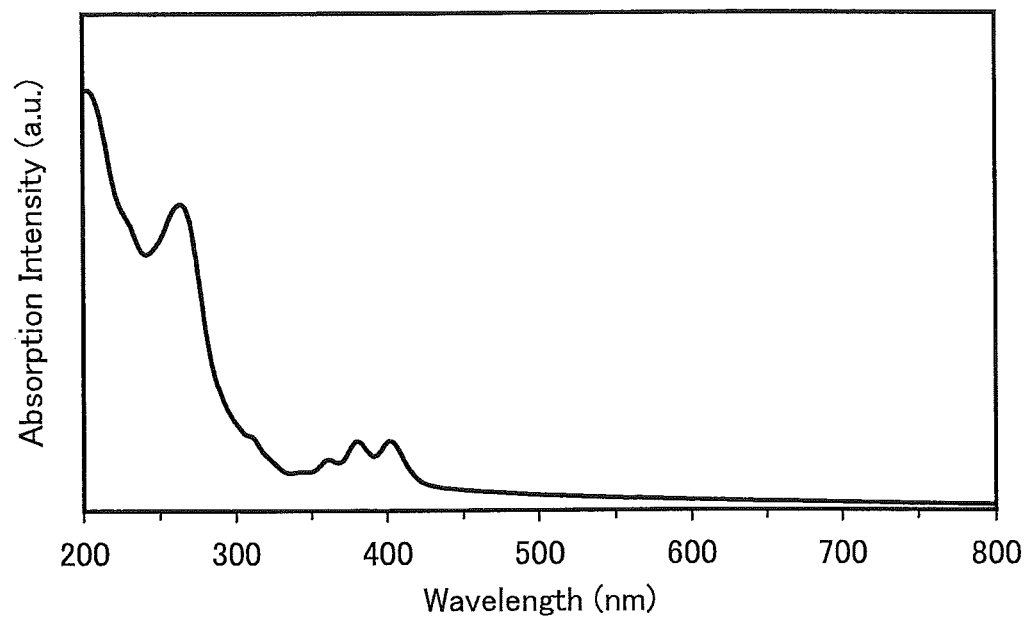
FIGS. 31A and 31B show an absorption spectrum and an emission spectrum of a thin film of mDBFFLPPhA-II.
Figure 31B:
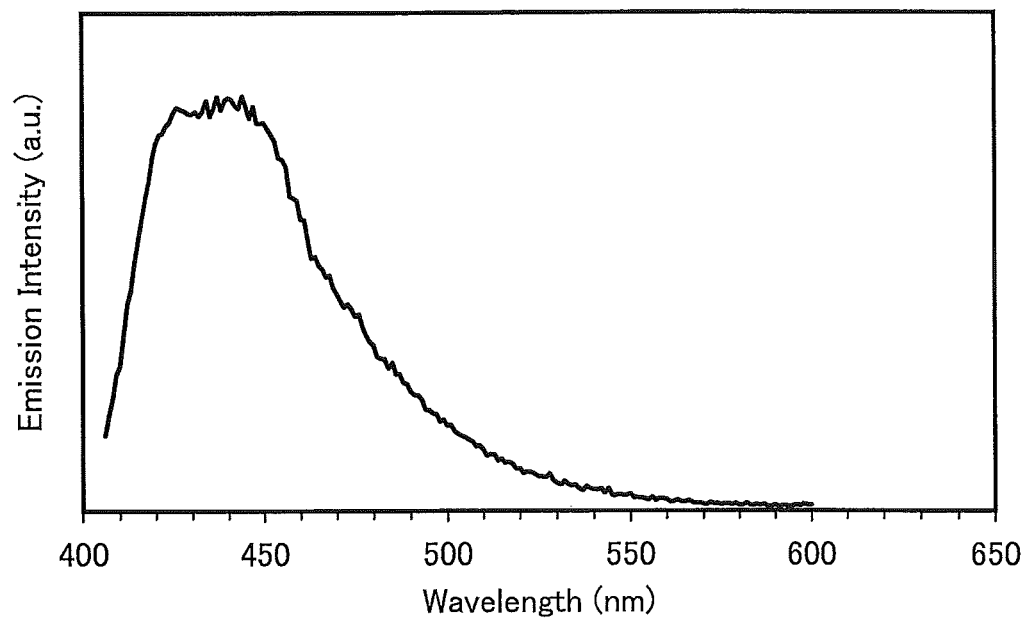

Further, FIG. 30A shows the absorption spectrum of mDBFFLPPhA-II in a toluene solution of mDBFFLPPhA-II, and FIG. 30B shows the emission spectrum thereof. In addition, FIG. 31A shows the absorption spectrum of a thin film of mDBFFLPPhA-II, and FIG. 31B shows the emission spectrum thereof. An ultraviolet-visible spectrophotometer (V-550, manufactured by JASCO Corporation) was used for the measurements. Samples were prepared in such a way that the solution was put in a quartz cell and the thin film was formed on a quartz substrate by evaporation. Here are shown the absorption spectrum for the solution which was obtained by subtracting the absorption spectra of quartz and toluene from those of quartz and the solution, and the absorption spectrum for the thin film which was obtained by subtracting the absorption spectrum of the quartz substrate from those of the quartz substrate and the thin film. In FIG. 30A and FIG. 31A, the horizontal axis represents wavelength (nm) and the vertical axis represents absorption intensity (arbitrary unit). In FIG. 30B and FIG. 31B, the horizontal axis represents wavelength (nm) and the vertical axis represents emission intensity (arbitrary unit). In the case of the solution, absorption peaks were found at around 282 nm, 308 nm, 357 nm, 376 nm, and 396 nm, and peaks of the emission wavelength were at 416 nm and 434 nm (at an excitation wavelength of 376 nm). In the case of the thin film, absorption peaks were found at around 203 nm, 225 nm, 264 nm, 309 nm, 342 nm, 362 nm, 381 nm, and 402 nm, and peaks of the emission wavelength were at 427 nm and 440 nm (at an excitation wavelength of 401 nm). FIG. 30A and FIG. 31A show that mDBFFLPPhA-II is a substance having weak absorption in the visible region. In other words, it is suggested that in the case where mDBFFLPPhA-II which is a fluorene compound of one embodiment of the present invention is used for a light-emitting element, visible light emitted is unlikely to be reabsorbed, and thus the element is unlikely to have a decrease in light extraction efficiency.

It is also found that mDBFFLPPhA-II has a peak of the emission spectrum at a very short wavelength and thus can be used as a host material of a light-emitting layer or used for a carrier-transport layer adjacent to the light-emitting layer in a fluorescent element which emits visible light.

It is also found that mDBFFLPPhA-II has high emission intensity and can be used as a light-emitting material.

A thin film of mDBFFLPPhA-II was formed by vacuum evaporation. This thin film was not a white and opaque film but a transparent film. This also suggests that mDBFFLPPhA-II is a substance which is unlikely to be crystallized.

EXAMPLE 9

In this example, a light-emitting element of one embodiment of the present invention will be described with reference to FIG. 13A. The chemical formulae of materials used in this example are illustrated below. Note that the chemical formulae of materials which are already illustrated will be omitted.

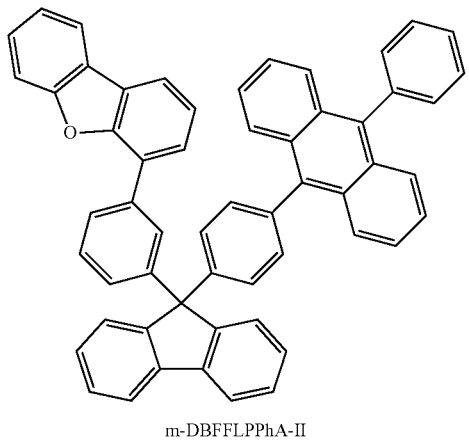 [SMILES: c1ccc(-c2c3ccccc3c(-c3ccc(C4(c5cccc(-c6cccc7c6oc6ccccc67)c5)c5ccccc5-c5ccccc54)cc3)c3ccccc23)cc1]

m-DBFFLPPhA-II

A method for manufacturing Light-Emitting Element 6 of this example will be described below.

(Light-Emitting Element 6)

First, a film of ITSO was formed over a glass substrate 1100 by a sputtering method, so that a first electrode 1101 was formed. Note that the thickness was set to 110 nm and the electrode area was set to 2 mm×2 mm.

In pretreatment for forming the light-emitting element over the substrate 1100, UV ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about $10^{-4}$ Pa. Then, PCzPA and molybdenum(VI) oxide were co-evaporated to form a hole-injection layer 1111 over the first electrode 1101. The thickness of the hole-injection layer 1111 was set to 50 nm, and the weight ratio of PCzPA to molybdenum(VI) oxide was adjusted to 4:2 (=PCzPA:molybdenum oxide).

Next, over the hole-injection layer 1111, a PCzPA film was formed to a thickness of 10 nm to form a hole-transport layer 1112.

Then, 4-(3-{9-[4-(9-phenylanthracen-10-yl)phenyl]-9H-fluoren-9-yl}phenyl)dibenzofuran (abbreviation: mDBF-FLPPhA-II) synthesized in Example 8 and 1,6FLPAPrn were co-evaporated to form a light-emitting layer 1113 oer the hole-transport layer 1112. Here, the weight ratio of mDBFFLPPhA-II to 1,6FLPAPrn was adjusted to 1:0.03 (=mDBFFLPPhA-II:1,6FLPAPrn). In addition, the thickness of the light-emitting layer 1113 was set to 30 nm.

Next, over the light-emitting layer 1113, a film of Alq was formed to a thickness of 10 nm to form a first electron-transport layer 1114a.

Then, over the first electron-transport layer 1114a, a BPhen film was formed to a thickness of 15 nm to form a second electron-transport layer 1114b.

Further, over the second electron-transport layer 1114b, a LiF film was formed by evaporation to a thickness of 1 nm to form an electron-injection layer 1115.

Lastly, an aluminum film was formed by evaporation to a thickness of 200 nm as a second electrode 1103 functioning as a cathode. Thus, Light-Emitting Element 6 of this example was fabricated.

Note that, in the above evaporation steps, evaporation was all performed by a resistance heating method.

Table 7 shows an element structure of Light-Emitting Element 6 obtained as described above.

TABLE 7

| | First electrode | Hole injection layer | Hole transport layer | Light-emitting layer | First electron transport layer | Second electron transport layer | Electron injection layer | Second electrode |
|---|---|---|---|---|---|---|---|---|
| Light emitting element 6 | ITSO 110 nm | PCzPA:MoOx (=4:2) 50 nm | PCzPA 10 nm | mDBFFLPPhA-II:1,6FLPAPrn (=1:0.03) 30 nm | Alq 10 nm | BPhen 15 nm | LiF 1 nm | Al 200 nm |

In a glove box containing a nitrogen atmosphere, Light-Emitting Element 6 was sealed so as not to be exposed to air. Then, operation characteristics of Light-Emitting Element 6 were measured. Note that the measurements were carried out at room temperature (in the atmosphere kept at 25° C.).

Figure 32:
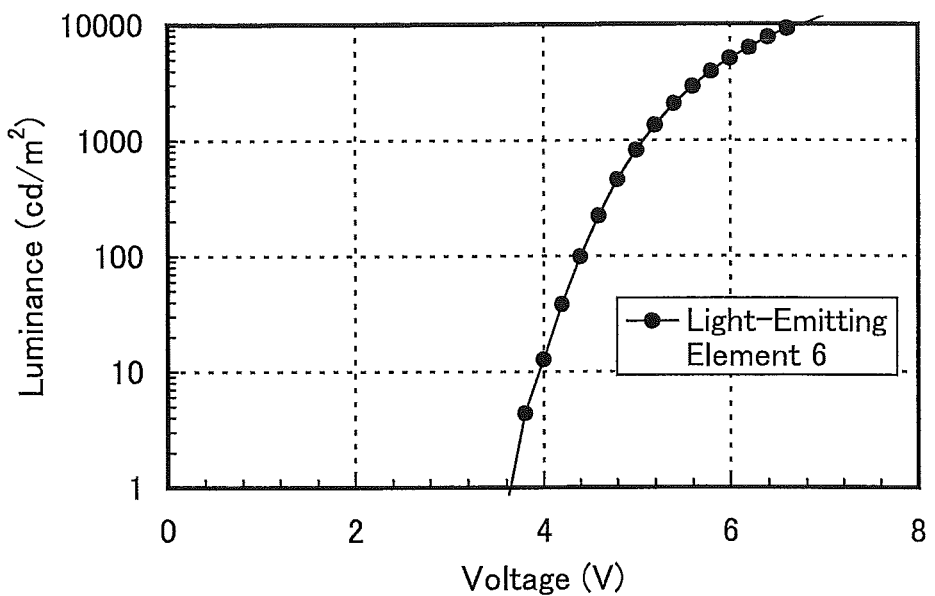
FIG. 32 shows voltage-luminance characteristics of a light-emitting element of Example 9.
Figure 33:
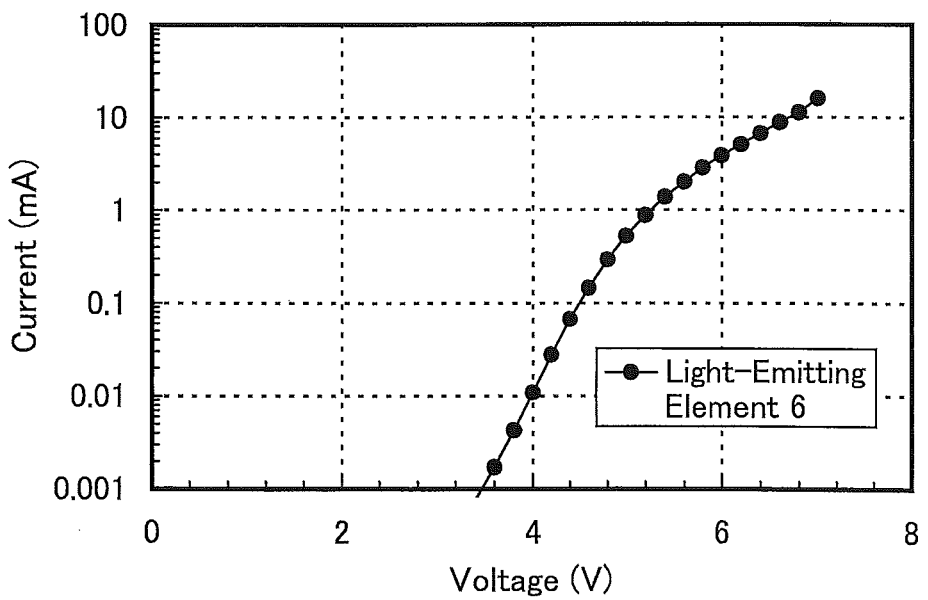
FIG. 33 shows voltage-current characteristics of a light-emitting element of Example 9.
Figure 34:
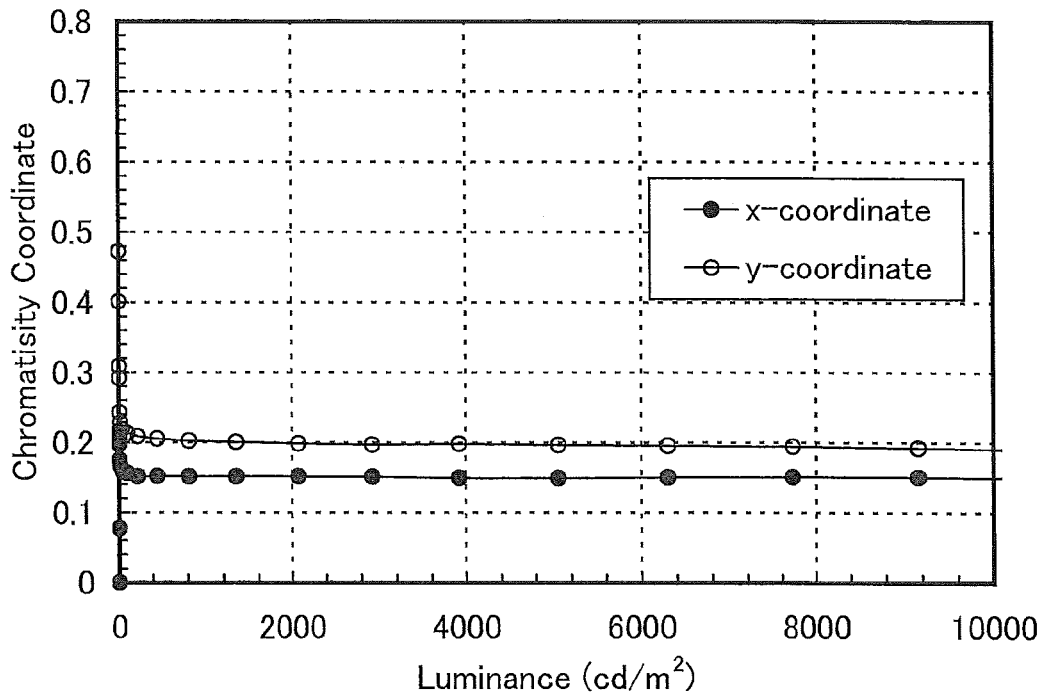
FIG. 34 shows luminance-chromaticity coordinate characteristics of a light-emitting element of Example 9.
Figure 35:
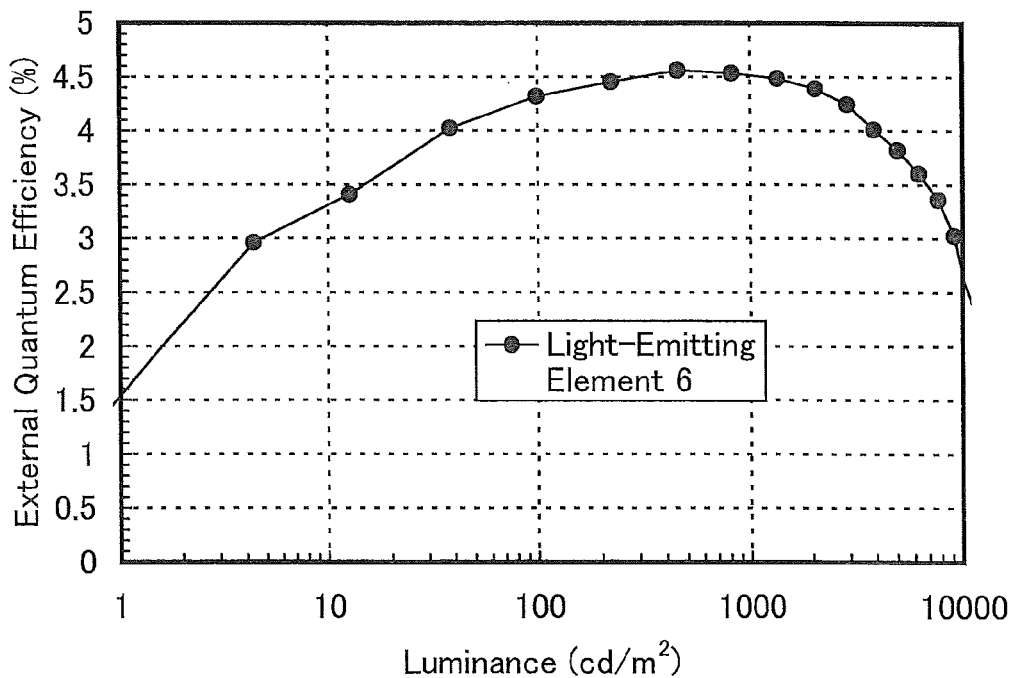
FIG. 35 shows luminance-external quantum efficiency characteristics of a light-emitting element of Example 9.

FIG. 32 shows the voltage-luminance characteristics of Light-Emitting Element 6. In FIG. 32, the horizontal axis represents voltage (V) and the vertical axis represents luminance (cd/m$^2$). FIG. 33 shows the voltage-current efficiency characteristics. In FIG. 33, the horizontal axis represents voltage (V) and the vertical axis represents current (mA). FIG. 34 shows the luminance-chromaticity coordinate characteristics. In FIG. 34, the horizontal axis represents luminance (cd/m$^2$) and the vertical axis represents chromaticity coordinate (the x-coordinate or the y-coordinate). In addition, FIG. 35 shows the luminance-external quantum efficiency characteristics. In FIG. 35, the horizontal axis represents luminance (cd/m$^2$) and the vertical axis represents external quantum efficiency (%). Further, Table 8 shows the voltage (V), current density (mA/cm$^2$), CIE chromaticity coordinates (x, y), luminance (cd/m$^2$), current efficiency (cd/A), power efficiency (lm/W), and external quantum efficiency (%) of Light-Emitting Element 6 at a luminance of 820 cd/m$^2$.

TABLE 8

|  | Voltage | Current density | Chromaticity coordinate | | Current efficiency | Power efficiency | External quantum |
| --- | --- | --- | --- | --- | --- | --- | --- |
|  | (V) | (mA/cm$^2$) | x | y | (cd/A) | (lm/W) | efficiency (%) |
| Light emitting element 6 | 5.0 | 13 | 0.15 | 0.20 | 6.2 | 3.9 | 4.5 |

Figure 36:
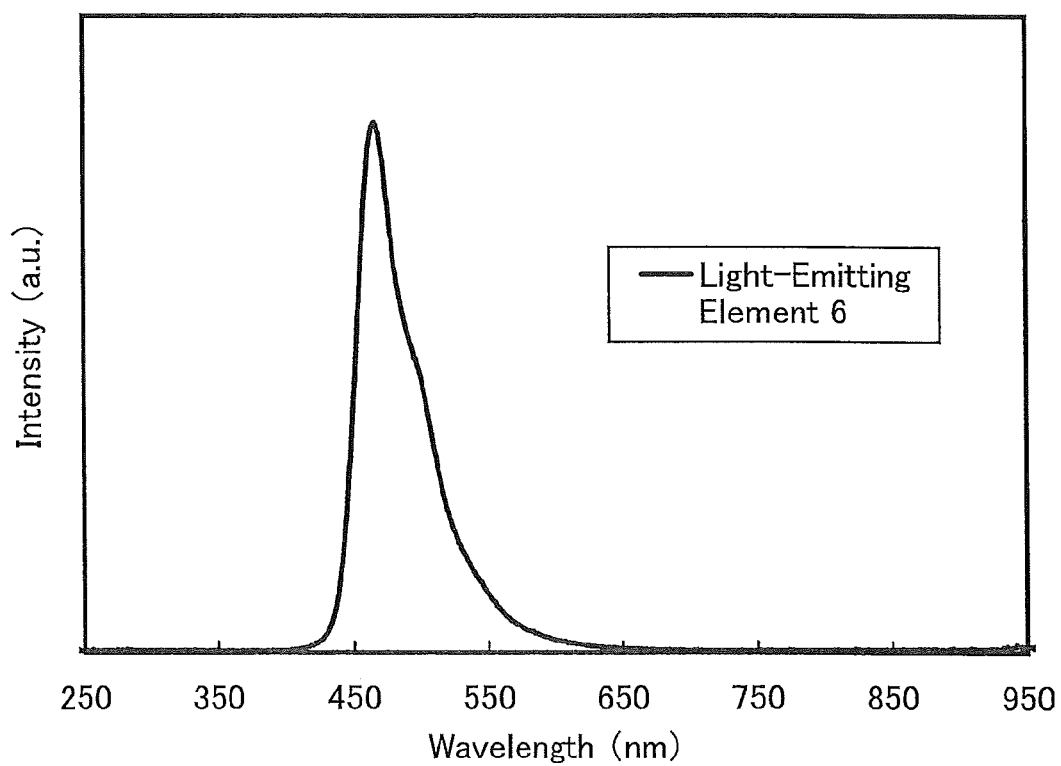
FIG. 36 shows an emission spectrum of a light-emitting element of Example 9.

FIG. 36 shows the emission spectrum of Light-Emitting Element 6 which was obtained by applying a current at a current density of 1 mA/cm$^2$. In FIG. 36, the horizontal axis represents wavelength (nm) and the vertical axis represents intensity (arbitrary unit). As shown in FIG. 36, the emission spectrum of Light-Emitting Element 6 has a peak at around 466 nm. In addition, as shown in Table 8, the CIE chromaticity coordinates of Light-Emitting Element 6 were (x, y) (0.15, 0.20) at a luminance of 820 cd/m$^2$. These results show that blue light emission originating from 1,6FLPAPm was obtained from Light-Emitting Element 6.

Table 8, FIG. 32, FIG. 33, and FIG. 35 show that Light-Emitting Element 6 has high emission efficiency, low driving voltage, and low power consumption. In addition, FIG. 34 shows that Light-Emitting Element 6 has a small change in chromaticity according to luminance and has excellent carrier balance.

Figure 37:
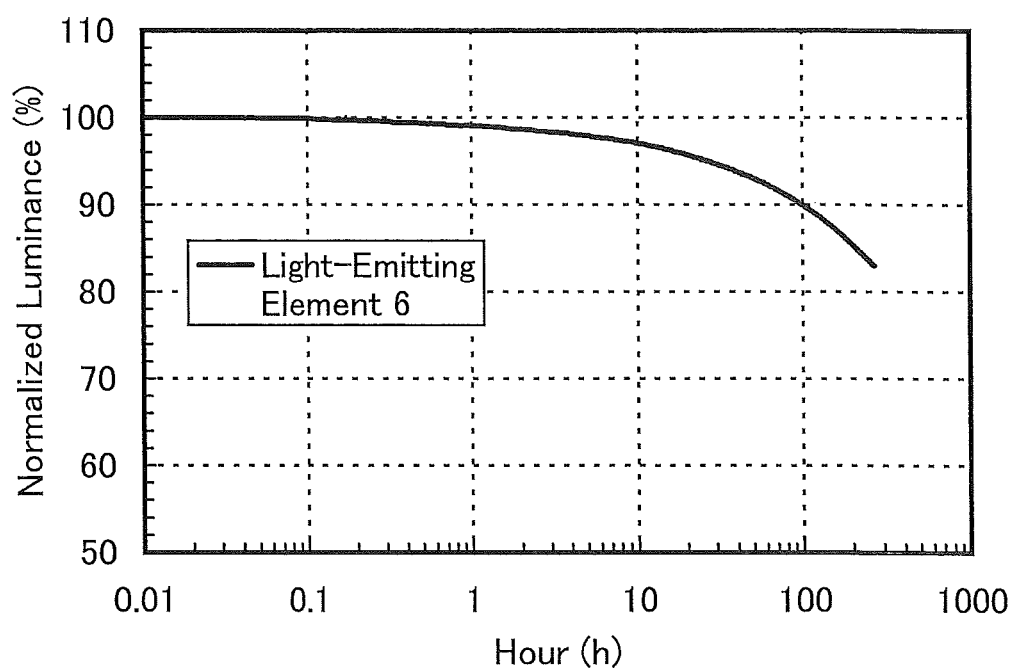
FIG. 37 shows results of reliability tests of a light-emitting element of Example 9.

Next, Light-Emitting Element 6 was subjected to reliability tests. Results of the reliability tests are shown in FIG. 37. In FIG. 37, the vertical axis represents normalized luminance (%) with an initial luminance of 100%, and the horizontal axis represents driving time (h) of the element.

In the reliability tests, Light-Emitting Element 6 was driven under the conditions where the initial luminance was set to 1000 cd/m$^2$ and the current density was constant.

FIG. 37 shows that Light-Emitting Element 6 kept 83% of the initial luminance after the driving for 270 hours. It is found that Light-Emitting Element 6 according to one embodiment of the present invention has long lifetime and high reliability.

The above results suggest that an element having high emission efficiency can be realized by use of a fluorene compound of one embodiment of the present invention for a host material of a light-emitting layer. The above results also show the possibilities of realizing an element having a low driving voltage, an element having low power consumption, and an element having high reliability.

In addition, a fluorene compound of one embodiment of the present invention is found suitable for a host material of a light-emitting layer which emits blue light. Thus, a fluorene compound of one embodiment of the present invention is found to have a sufficiently high S1 level (which is at least higher than that of a blue light-emitting material).

EXAMPLE 10

Figure 13B:
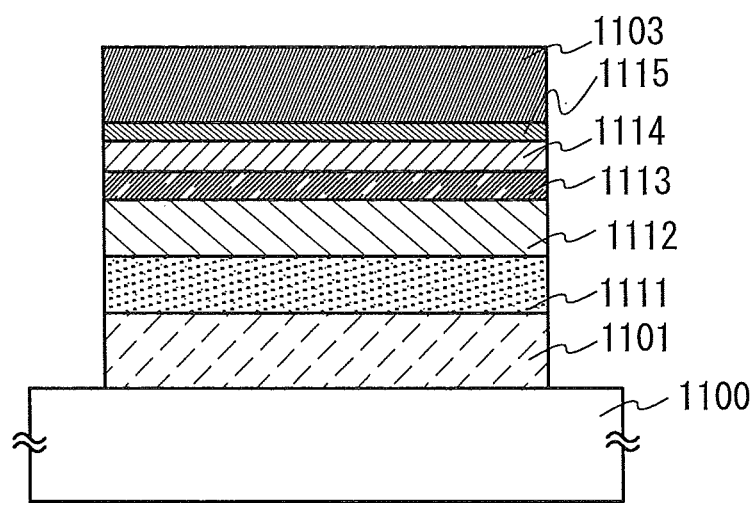

In this example, a light-emitting element of one embodiment of the present invention will be described with reference to FIG. 13B. The materials used in this example are used in the above examples, and therefore the chemical formulae thereof are omitted here.

A method for manufacturing Light-Emitting Element 7 of this example will be described below.

(Light-Emitting Element 7)

First, a first electrode 1101, a hole-injection layer 1111, a hole-transport layer 1112, and a light-emitting layer 1113 were formed over a glass substrate 1100 under the same conditions as those of Light-Emitting Element 6 described in Example 9.

Then, over the light-emitting layer 1113, a film of BPhen was formed to a thickness of 25 nm to form an electron-transport layer 1114.

After that, over the electron-transport layer 1114, a LiF film was formed by evaporation to a thickness of 1 urn to form an electron-injection layer 1115.

Lastly, an aluminum film was formed by evaporation to a thickness of 200 nm as a second electrode 1103 functioning as a cathode. Thus, Light-Emitting Element 7 of this example was fabricated.

Note that, in the above evaporation steps, evaporation was all performed by a resistance heating method.

Table 9 shows an element structure of Light-Emitting Element 7 obtained as described above.

TABLE 9

|  | First electrode | Hole injection layer | Hole transport layer | Light-emitting layer | Electoron transport layer | Electron injection layer | Second electrode |
| --- | --- | --- | --- | --- | --- | --- | --- |
| Light emitting element 7 | ITSO 110 nm | PCzPA:MoOx (=4:2) 50 nm | PCzPA 10 nm | mDBFFLPPhA-II:1,6FLPAPrn (=1:0.03) 30 nm | BPhen 25 nm | LiF 1 nm | Al 200 nm |

In a glove box containing a nitrogen atmosphere, Light-Emitting Element 7 was sealed so as not to be exposed to air. Then, operation characteristics of Light-Emitting Element 7 were measured. Note that the measurements were carried out at room temperature (in the atmosphere kept at 25° C.).

Figure 38:
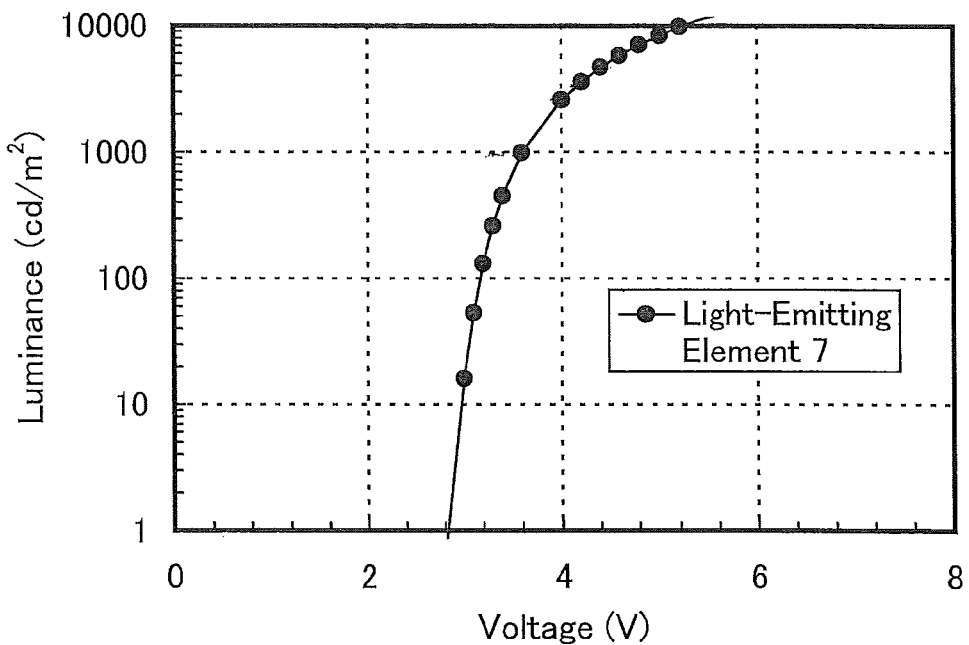
FIG. 38 shows voltage-luminance characteristics of a light-emitting element of Example 10.
Figure 39:
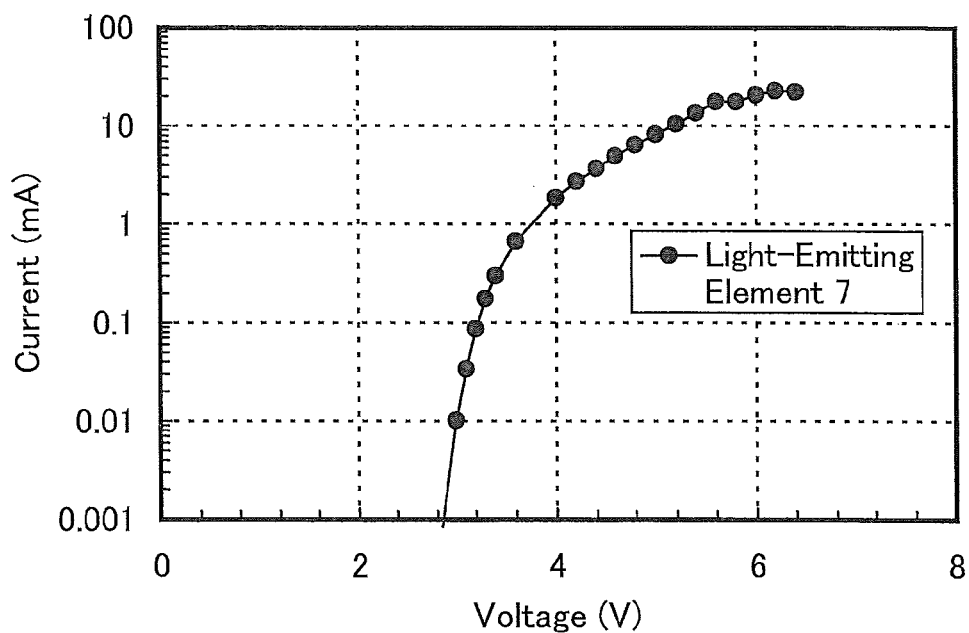
FIG. 39 shows voltage-current characteristics of a light-emitting element of Example 10.
Figure 40:
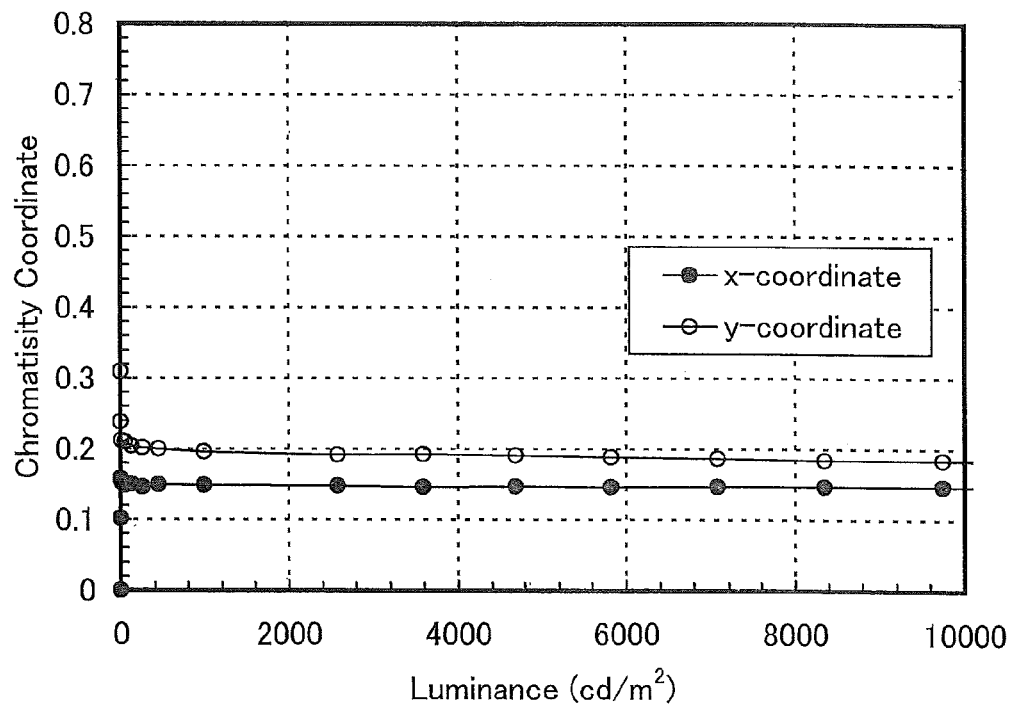
FIG. 40 shows luminance-chromaticity coordinate characteristics of a light-emitting element of Example 10.
Figure 41:
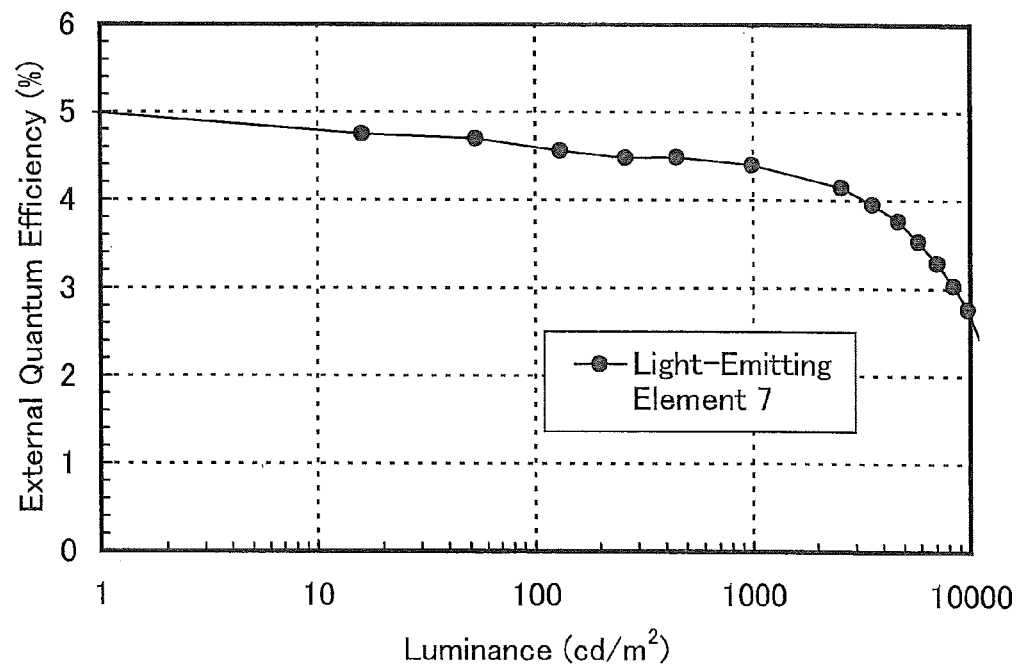
FIG. 41 shows luminance-external quantum efficiency characteristics of a light-emitting element of Example 10.

FIG. 38 shows the voltage-luminance characteristics of Light-Emitting Element 7. In FIG. 38, the horizontal axis represents voltage (V) and the vertical axis represents luminance (cd/m$^2$). FIG. 39 shows the voltage-current characteristics. In FIG. 39, the horizontal axis represents voltage (V) and the vertical axis represents current (mA). FIG. 40 shows the luminance-chromaticity coordinate characteristics. In FIG. 40, the horizontal axis represents luminance (cd/m$^2$) and the vertical axis represents chromaticity coordinate (the x-coordinate or the y-coordinate). In addition, FIG. 41 shows the luminance-external quantum efficiency characteristics. In FIG. 41, the horizontal axis represents luminance (cd/m$^2$) and the vertical axis represents external quantum efficiency (%). Further, Table 10 shows the voltage (V), current density (mA/cm$^2$), CIE chromaticity coordinates (x, y), luminance (cd/m$^2$), current efficiency (cd/A), power efficiency (lm/W), and external quantum efficiency (%) of Light-Emitting Element 7 at a luminance of 990 cd/m$^2$.

TABLE 10

| | Voltage (V) | Current density (mA/cm$^2$) | Chromaticity coordinate | | Current efficiency (cd/A) | Power efficiency (lm/W) | External quantum efficiency (%) |
|---|---|---|---|---|---|---|---|
| | | | x | y | | | |
| Light emitting element 7 | 3.6 | 17 | 0.15 | 0.20 | 5.9 | 5.1 | 4.4 |

Figure 42:
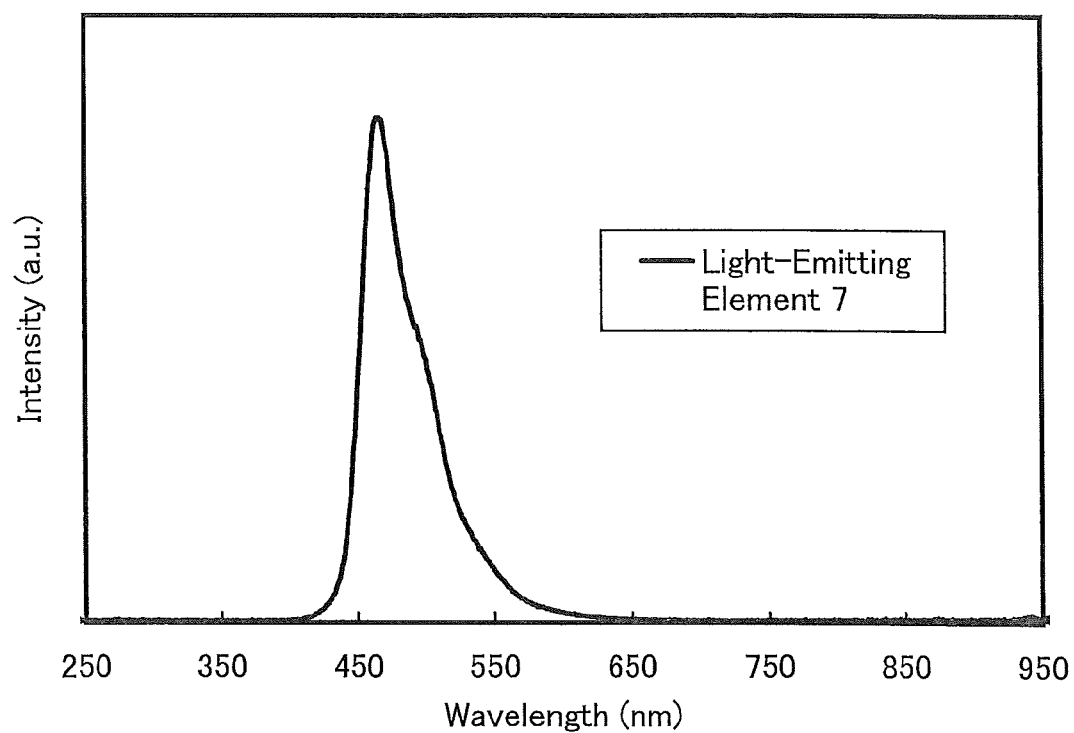
FIG. 42 shows an emission spectrum of a light-emitting element of Example 10.

FIG. 42 shows the emission spectrum of Light-Emitting Element 7 which was obtained by applying a current at a current density of 1 mA/cm$^2$. In FIG. 42, the horizontal axis represents wavelength (nm) and the vertical axis represents intensity (arbitrary unit). As shown in FIG. 42, the emission spectrum of Light-Emitting Element 7 has a peak at around 466 nm. In addition, as shown in Table 10, the CIE chromaticity coordinates of Light-Emitting Element 7 were (x, y)=(0.15, 0.20) at a luminance of 990 cd/m$^2$. These results show that blue light emission originating from 1,6FLPAPm was obtained from Light-Emitting Element 7.

Table 10, FIG. 38, FIG. 39, and FIG. 41 show that Light-Emitting Element 7 has high emission efficiency, low driving voltage, and low power consumption. In addition, FIG. 40 shows that Light-Emitting Element 7 has a small change in chromaticity according to luminance and has excellent carrier balance.

The above results suggest that an element having high emission efficiency can be realized by use of a fluorene compound of one embodiment of the present invention for a host material of a light-emitting layer. The above results also show the possibilities of realizing an element having a low driving voltage and an element having low power consumption.

In addition, a fluorene compound of one embodiment of the present invention is found suitable for a host material of a light-emitting layer which emits blue light. Thus, a fluorene compound of one embodiment of the present invention is found to have a sufficiently high S1 level (which is at least higher than that of a blue light-emitting material).

REFERENCE EXAMPLE 1

A synthesis example of manufacturing N,N'-bis[4-(9-phenyl-9H-fluoren-9-yl)phenyl]-N,N'-diphenylpyrene-1,6-diamine (abbreviation: 1,6FLPAPrn) used in the above examples will be described.

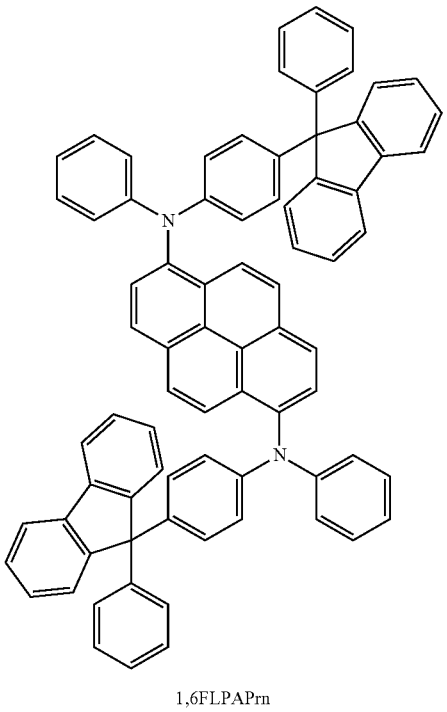 [SMILES: c1ccc(N(c2ccc(C3(c4ccccc4)c4ccccc4-c4ccccc43)cc2)c2ccc3ccc4c(N(c5ccccc5)c5ccc(C6(c7ccccc7)c7ccccc7-c7ccccc76)cc5)ccc5ccc2c3c54)cc1]

1,6FLPAPrn

In a 300 mL three-neck flask were put 3.0 g (8.3 mmol) of 1,6-dibromopyrene and 6.8 g (17 mmol) of 4-(9-phenyl-9H-fluoren-9-yl)diphenylamine (abbreviation: FLPA). The air in the flask was replaced with nitrogen. To this mixture were added 100 mL of toluene, 0.10 mL of a 10 wt % hexane solution of tri(tert-butyl)phosphine, and 2.4 g (25 mmol) of sodium tert-butoxide. This mixture was degassed while being stirred under reduced pressure. This mixture was heated at 80° C., and after the confirmation that the material was dissolved, 48 mg (0.083 mmol) of bis(dibenzylideneacetone)palladium(0) was added. This mixture was stirred at 80° C. for 1.5 hours. After the stirring, the precipitated yellow solid was collected through suction filtration without cooling the mixture. The obtained solid was suspended in 3 L of toluene and heated at 110° C. This suspension was suction filtered through alumina, Celite, and Florisil while the temperature of the suspension was kept at 110° C. Further, the suspension was processed with 200 mL of toluene which had been heated to 110° C. The resulting filtrate was concentrated to about 300 mL, which was then recrystallized. Accordingly, 5.7 g of a substance which was the object of the synthesis was obtained in a yield of 67%.

By a train sublimation method, 3.56 g of the obtained yellow solid was purified. Under a pressure of 5.0 Pa with a flow rate of argon at 5.0 mL/min, the sublimation purification was carried out at 353° C. After the sublimation purification, 2.54 g of a yellow solid, which was the object of the synthesis, was obtained in a yield of 71%. A reaction scheme of the above synthesis method is illustrated in the following (x-1).

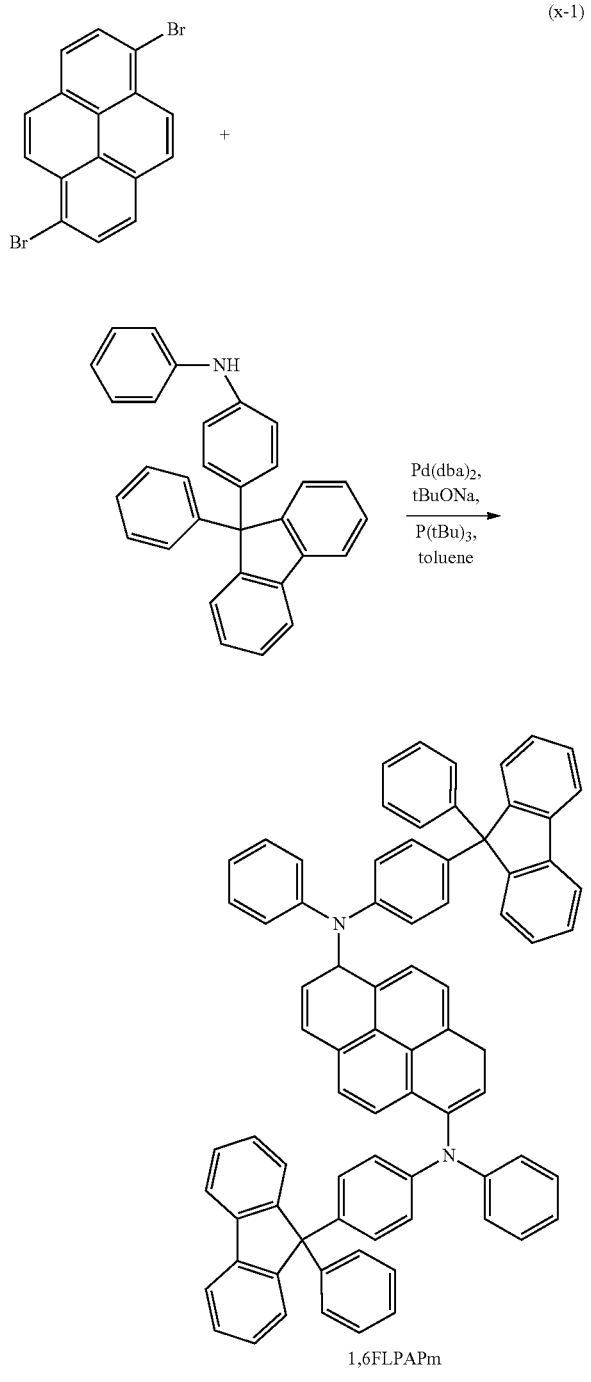

1,6FLPAPm

The obtained compound was identified as N,N'-bis[4-(9-phenyl-9H-fluoren-9-yl)phenyl]-N,N-diphenylpyrene-1,6-diamine (abbreviation: 1,6FLPAPm) by nuclear magnetic resonance (NMR) spectroscopy.

$^1$H NMR data of the compound obtained in the above synthesis example are as follows: $^1$H NMR (CDCl$_3$, 300 MHz): δ=6.88-6.91 (m, 6H), 7.00-7.03 (m, 8H), 7.13-7.40 (m, 26H), 7.73-7.80 (m, 6H), 7.87 (d, J=9.0 Hz, 2H), 8.06-8.09 (m, 4H).

This application is based on Japanese Patent Application serial no. 2010-200522 filed with Japan Patent Office on Sep. 8, 2010 and Japanese Patent Application serial no. 2011-122811 filed with Japan Patent Office on May 31, 2011, the entire contents of which are hereby incorporated by reference.

What is claimed is:

1. An organic compound represented by a general formula (G2),

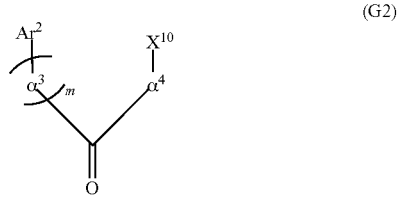

(G2)

wherein α$^3$ and α$^4$ separately represent a substituted or unsubstituted arylene group having 6 to 13 carbon atoms, wherein Ar$^2$ represents a substituted or unsubstituted aryl group having 14 carbon atoms, a substituted or unsubstituted 4-dibenzothiophenyl group, or a substituted or unsubstituted 4-dibenzofuranyl group, wherein m represents 0 or 1, and wherein X$^{10}$ represents chlorine, bromine, or iodine.

2. The organic compound according to claim 1, wherein the organic compound is represented by a general formula (G3),

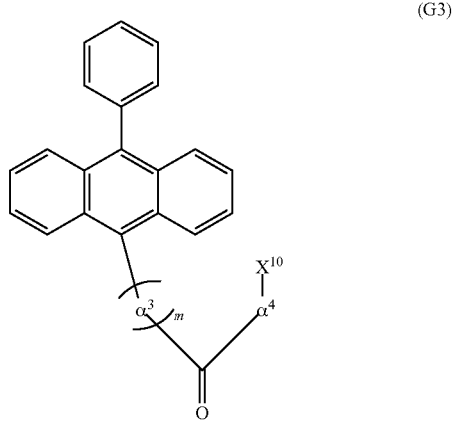

(G3)

wherein α$^3$ and α$^4$ represent a substituted or unsubstituted arylene group having 6 to 13 carbon atoms, wherein m represents 0 or 1, and wherein X$^{10}$ represents chlorine, bromine, or iodine.

3. The organic compound according to claim 1, wherein the organic compound is represented by a structural formula (700),

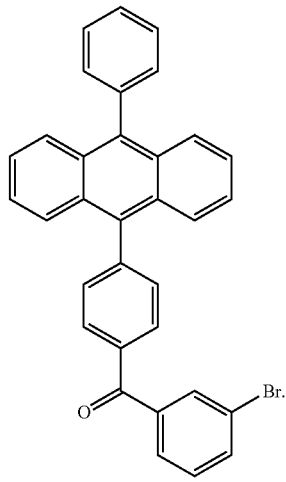
(700)

4. An organic compound represented by a general formula (G4),

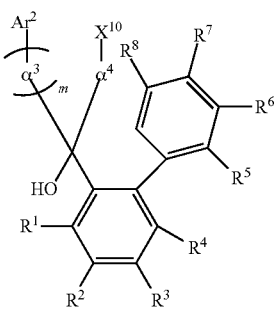
(G4)

wherein α³ and α⁴ separately represent a substituted or unsubstituted arylene group having 6 to 13 carbon atoms, wherein Ar² represents a substituted or unsubstituted aryl group having 14 carbon atoms, a substituted or unsubstituted 4-dibenzothiophenyl group, or a substituted or unsubstituted 4-dibenzofuranyl group, wherein m represents 0 or 1, wherein $X^{10}$ represents chlorine, bromine, or iodine, and wherein $R^1$ to $R^8$ separately represent hydrogen, an alkyl group having 1 to 12 carbon atoms, or an aryl group having 6 to 14 carbon atoms.

5. The organic compound according to claim 4, wherein the organic compound is represented by a general formula (G5),

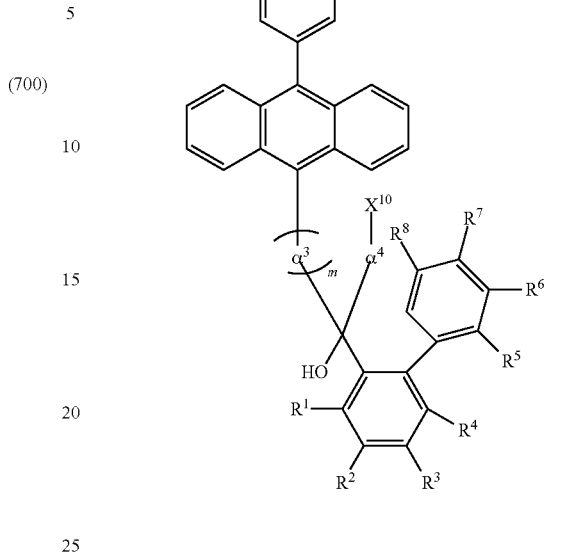
(G5)

wherein α³ and α⁴ separately represent a substituted or unsubstituted arylene group having 6 to 13 carbon atoms, wherein m represents 0 or 1, wherein $X^{10}$ represents chlorine, bromine, or iodine, and wherein $R^1$ to $R^8$ separately represent hydrogen, an alkyl group having 1 to 12 carbon atoms, or an aryl group having 6 to 14 carbon atoms.

6. The organic compound according to claim 4, wherein the organic compound is represented by a structural formula (720),

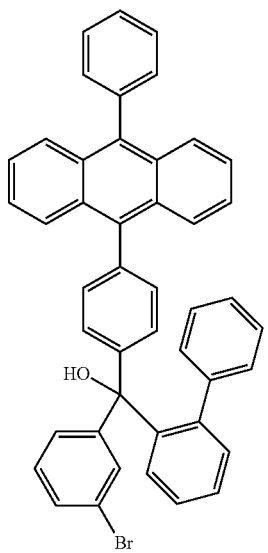
(720)

7. The organic compound according to claim 4, wherein the organic compound is represented by any one of formulae (721) to (723) and (728) to (730), (721)
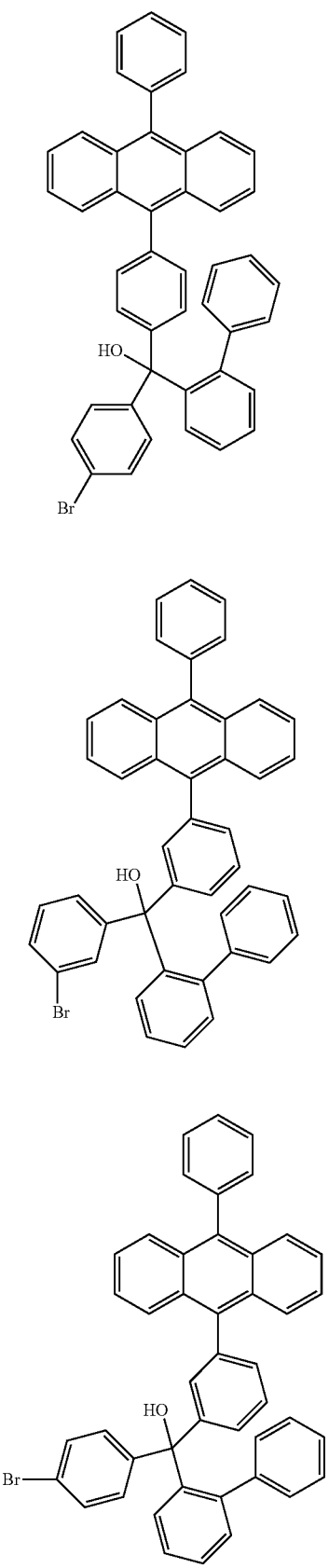
(722)
(723)
-continued
(728)
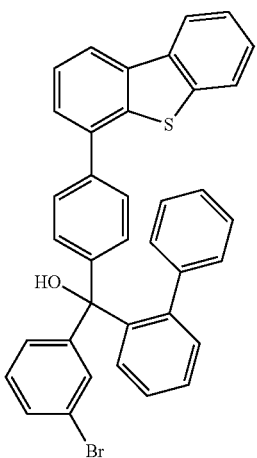
(729)
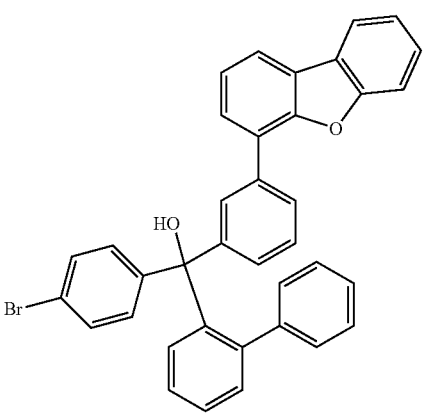
(730)
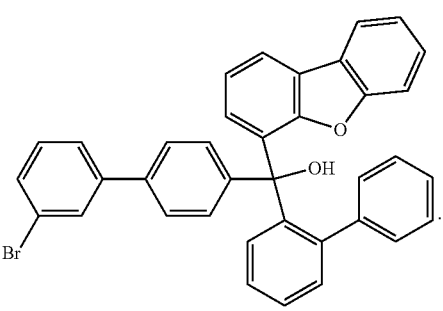
8. An organic compound represented by a general formula (G6),
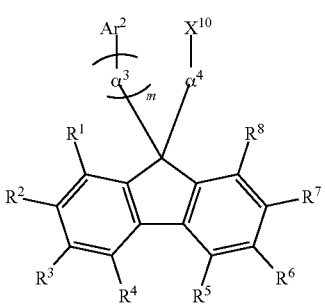
(G6)

wherein α³ and α⁴ separately represent a substituted or unsubstituted arylene group having 6 to 13 carbon atoms, wherein Ar² represents a substituted or unsubstituted aryl group having 14 carbon atoms, a substituted or unsubstituted 4-dibenzothiophenyl group, or a substituted or unsubstituted 4-dibenzofuranyl group, wherein m represents 0 or 1, wherein $X^{10}$ represents chlorine, bromine, or iodine, and wherein $R^1$ to $R^8$ separately represent hydrogen, an alkyl group having 1 to 12 carbon atoms, or an aryl group having 6 to 14 carbon atoms.

9. The organic compound according to claim 8, wherein the organic compound is represented by a general formula (G7), (G7)

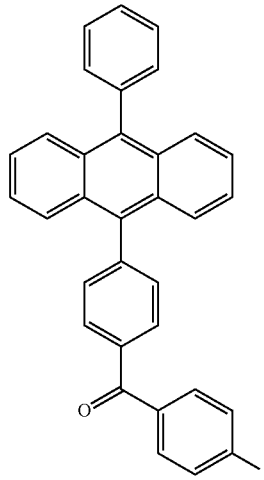

wherein α³ and α⁴ separately represent a substituted or unsubstituted arylene group having 6 to 13 carbon atoms, wherein m represents 0 or 1, wherein $X^{10}$ represents chlorine, bromine, or iodine, and wherein $R^1$ to $R^8$ separately represent hydrogen, an alkyl group having 1 to 12 carbon atoms, or an aryl group having 6 to 14 carbon atoms.

10. The organic compound according to claim 8, wherein the organic compound is represented by a structural formula (740), (740)

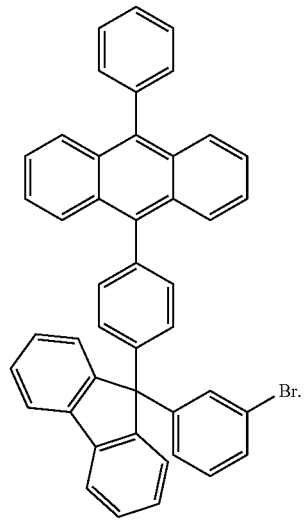

11. The organic compound according to claim 1, wherein the organic compound is represented by any one of formulae (701) to (703) and (708) to (710), (701)

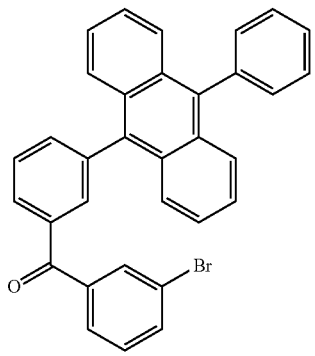

(702)

(703) 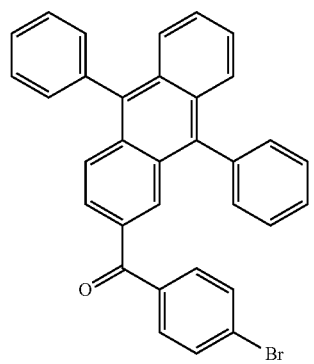
(708) 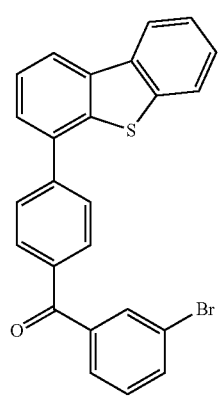
(709) 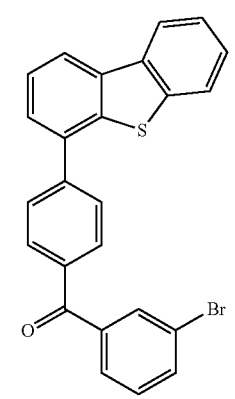
(710) 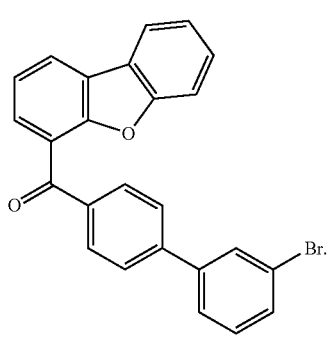
(741) 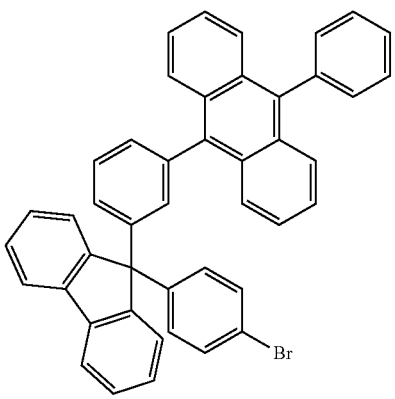
(742) 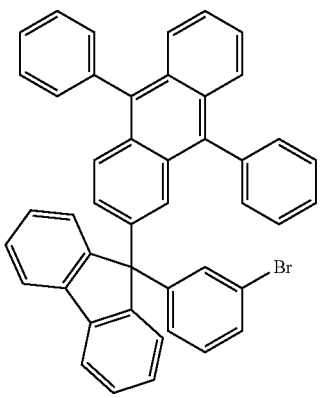
(746) 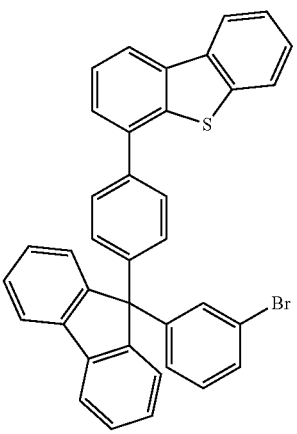
(747) 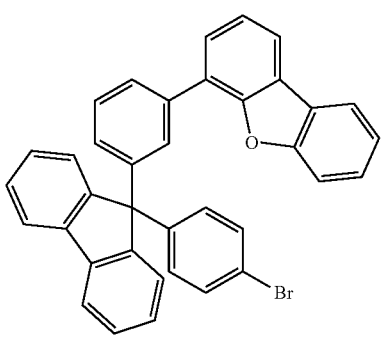
12. The organic compound according to claim 8, wherein the organic compound is represented by any one of formulae (741) to (742) and (746) to (748), (748)
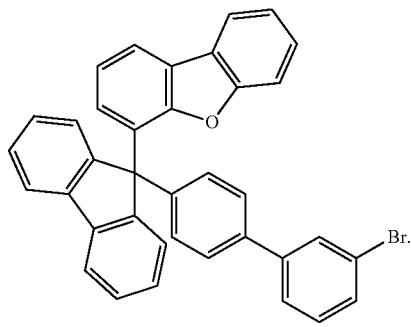
* * * * *

UNITED STATES PATENT AND TRADEMARK OFFICE
CERTIFICATE OF CORRECTION

Page 1 of 3

PATENT NO. : 9,564,597 B2
APPLICATION NO. : 14/668239
DATED : February 7, 2017
INVENTOR(S) : Harue Osaka et al.

It is certified that error appears in the above-identified patent and that said Letters Patent is hereby corrected as shown below:

In the Specification

Column 2, Line 63; Change "element Another" to --element. Another--.

Column 12, Line 36; Change "does' not" to --does not--.

Column 69, Line 39; Change "scheme A-l)," to --scheme (A-l),--.

Column 78, Line 44; Change "group; or" to --group, or--.

Column 80, Line 57; Change "Embodiment (2)" to --(Embodiment 2)--.

Column 81, Line 49; Change "found" to --formed--.

Column 81, Line 51; Change "found" to --formed--.

Column 82, Line 15; Change "a. layer" to --a layer--.

Column 82, Line 48; Change ")-N,N-bis" to --)-N,N'-bis--.

Column 84, Lines 14 to 15; Change "anthryptriphenylamine" to --anthryl)triphenylamine--.

Column 84, Line 24; Change "N,N,N" to --N,N',N'--.

Column 84, Line 40; Change "difluorophenyepyridinato" to --difluorophenyl)pyridinato--.

Column 84, Line 43; Change "FIrpic)," to --FIrpic),--.

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,564,597 B2

Column 85, Line 3; Change "(ace tylacetonato)" to --(acetylacetonato)--.

Column 85, Line 7; Change "[4,5-c]" to --[4,5-α]--.

Column 85, Line 31; Change "diocVlfluorene" to --dioctylfluorene--.

Column 85, Line 32; Change "poly[9,9-" to --poly[(9,9- --.

Column 85, Line 48; Change "(N,N-" to --(N,N'- --.

Column 86, Line 5; Change "(Si" to --(S1--.

Column 87, Line 2; Change "beryilium" to --beryillium--.

Column 89, Line 53; Change "fainted" to --formed--.

Column 90, Line 29; Change "Embodiment (3)" to --(Embodiment 3)--.

Column 91, Line 22; Change "tetrafiuoroquinodimethane" to --tetrafluoroquinodimethane--.

Column 91, Line 43; Change "cm$^2$IVs" to --cm$^2$/Vs--.

Column 92, Line 21; Change "Embodiment (4)" to --(Embodiment 4)--.

Column 93, Line 14; Change "faulted" to --formed--.

Column 94, Line 37; Change "Embodiment (5)" to --(Embodiment 5)--.

Column 99, Line 50; Change "cycles: This" to --cycles. This--.

Column 100, Line 9; Change "Zaiiyou" to --Zairyou--.

Column 100, Line 43; Change "$E_{pc}$ ($E_{pa}$" to --$E_{pc}$, ($E_{pa}$--.

Column 105, Lines 30 to 31; Change "phenyldibenzo thiophene" to --phenyldibenzothiophene--.

Column 105, Line 42; Change "fainted" to --formed--.

Column 109, Line 15; Change "50 mn," to --50 nm,--.

Column 111, Line 25; Change "l,6FLPAPm" to --l,6FLPAPrn--.

Column 111, Line 57; Change "(Si level)" to --(S1 level)--.
Column 113, Line 44; Change "formed" to --form--.

CERTIFICATE OF CORRECTION (continued)
U.S. Pat. No. 9,564,597 B2

Column 113, Line 53; Change "l,6FLPAPm" to --l,6FLPAPrn--.

Column 117, Line 61; Change "nm at" to --nm (at--.

Column 129, Lines 18 to 19; Change "(x, y) (0.15, 0.20)" to --(x, y)=(0.15, 0.20)--.

Column 129, Line 20; Change "l,6FLPAPm" to --l,6FLPAPrn--.

Column 130, Line 25; Change "1 urn" to --1 nm--.

Column 131, Line 25; Change "l,6FLPAPm" to --l,6FLPAPrn--.

Column 133, Line 65; Change "N,N" to --N,N'--.

Column 133, Line 66; Change "l,6FLPAPm)" to --l,6FLPAPrn)--.

In the Claims

Column 134, Line 64, Claim 2; Change "$\alpha^4$ represent" to --$\alpha^4$ separately represent--.